(12) United States Patent
Manoharan et al.

(10) Patent No.: US 9,476,045 B2
(45) Date of Patent: *Oct. 25, 2016

(54) IRNA AGENTS WITH BIOCLEAVABLE TETHERS

(71) Applicant: Alnylam Pharmaceuticals, Inc., Cambridge, MA (US)

(72) Inventors: Muthiah Manoharan, Cambridge, MA (US); Kallanthottathil G. Rajeev, Cambridge, MA (US)

(73) Assignee: Alnylam Pharmaceuticals, Inc., Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/485,255

(22) Filed: Sep. 12, 2014

(65) Prior Publication Data

US 2015/0073133 A1   Mar. 12, 2015

Related U.S. Application Data

(63) Continuation of application No. 13/849,017, filed on Mar. 22, 2013, now Pat. No. 8,865,677, which is a continuation of application No. 12/724,267, filed on Mar. 10, 2010, now Pat. No. 8,426,377, which is a continuation of application No. 10/985,426, filed on Nov. 9, 2004, now Pat. No. 7,723,509, which is a continuation-in-part of application No. 10/916,185, filed on Aug. 10, 2004, now Pat. No. 7,745,608, which is a continuation-in-part of application No. PCT/US2004/011829, filed on Apr. 16, 2004.

(60) Provisional application No. 60/493,986, filed on Aug. 8, 2003, provisional application No. 60/494,597, filed on Aug. 11, 2003, provisional application No. 60/506,341, filed on Sep. 26, 2003, provisional application No. 60/518,453, filed on Nov. 7, 2003, provisional application No. 60/463,772, filed on Apr. 17, 2003, provisional application No. 60/465,802, filed on Apr. 25, 2003, provisional application No. 60/469,612, filed on May 9, 2003, provisional application No. 60/510,246, filed on Oct. 9, 2003, provisional application No. 60/510,318, filed on Oct. 10, 2003, provisional application No. 60/503,414, filed on Sep. 15, 2003, provisional application No. 60/465,665, filed on Apr. 25, 2003.

(51) Int. Cl.
  *C12N 15/113* (2010.01)
  *C12N 15/11* (2006.01)

(52) U.S. Cl.
  CPC ........... *C12N 15/113* (2013.01); *C12N 15/111* (2013.01); *C12N 2310/14* (2013.01); *C12N 2310/323* (2013.01); *C12N 2320/51* (2013.01)

(58) Field of Classification Search
  None
  See application file for complete search history.

(56) References Cited

U.S. PATENT DOCUMENTS

| 4,572,912 | A | 2/1986 | Yoshioka et al. |
|---|---|---|---|
| 5,328,470 | A | 7/1994 | Nabel et al. |
| 5,519,134 | A | 5/1996 | Acevedo et al. |
| 5,646,126 | A | 7/1997 | Cheng et al. |
| 5,714,606 | A | 2/1998 | Acevedo et al. |
| 5,994,517 | A * | 11/1999 | Ts'o ............ A61K 47/48092 530/391.7 |
| 6,147,204 | A | 11/2000 | Gold et al. |
| 6,239,107 | B1 | 5/2001 | Gozes et al. |
| 6,509,323 | B1 | 1/2003 | Davis et al. |
| 2002/0016285 | A1 | 2/2002 | Bhatt et al. |
| 2002/0086356 | A1 | 7/2002 | Tuschl et al. |
| 2003/0008818 | A1 | 1/2003 | Pun et al. |
| 2003/0170891 | A1 | 9/2003 | McSwiggen |
| 2005/0107325 | A1 | 5/2005 | Manoharan et al. |
| 2005/0119214 | A1 | 6/2005 | Manoharan et al. |
| 2005/0164235 | A1 | 7/2005 | Manoharan et al. |
| 2006/0058266 | A1 | 3/2006 | Manoharan et al. |
| 2007/0179100 | A1 | 8/2007 | Manoharan et al. |
| 2007/0275914 | A1 | 11/2007 | Manoharan et al. |
| 2010/0240881 | A1 | 9/2010 | Manoharan et al. |

FOREIGN PATENT DOCUMENTS

| EP | 0023725 A1 | 2/1981 |
|---|---|---|
| WO | 9203464 A1 | 3/1992 |

(Continued)

OTHER PUBLICATIONS

Amosova et al., "Effect of the 1-(2'-deoxy-beta-D-ribofuranosyl) 3-nitropyrrole residue on the stability of DNA duplexes and triplexes," Nucleic Acids Res. 25:1930-1934 (1997).

An et al., "Synthesis of Novel 3'-C-MethyleneThymidine and 5-Methyluridine/Cytidine H-Phosphonates and Phosphonamidites for New Backbone Modification of Oligonucleotides," J. Org. Chem. 66:2789-2801 (2001).

Ausin et al., "Synthesis of Amino-and Guanidino-G-Clamp PNA Monomers," Organic Letters 4:4073-4075 (2002).

(Continued)

*Primary Examiner* — Tracy Vivlemore
(74) *Attorney, Agent, or Firm* — Jeffrey N. Townes; LeClairRyan

(57) ABSTRACT

The invention relates to iRNA agents, which preferably include a monomer in which the ribose moiety has been replaced by a moiety other than ribose that further includes a tether having one or more linking groups, in which at least one of the linking groups is a cleavable linking group. The tether in turn can be connected to a selected moiety, e.g., a ligand, e.g., a targeting or delivery moiety, or a moiety which alters a physical property. The cleavable linking group is one which is sufficiently stable outside the cell such that it allows targeting of a therapeutically beneficial amount of an iRNA agent (e.g., a single stranded or double stranded iRNA agent), coupled by way of the cleavable linking group to a targeting agent—to targets cells, but which upon entry into a target cell is cleaved to release the iRNA agent from the targeting agent.

16 Claims, 15 Drawing Sheets

(56) References Cited

FOREIGN PATENT DOCUMENTS

| | | |
|---|---|---|
| WO | 9518792 A1 | 7/1995 |
| WO | 0044895 A1 | 8/2000 |
| WO | 0044914 A1 | 8/2000 |
| WO | 0136646 A1 | 5/2001 |
| WO | 0175164 A2 | 10/2001 |
| WO | 0198273 A1 | 12/2001 |
| WO | 0244321 A2 | 6/2002 |
| WO | 02094185 A2 | 11/2002 |
| WO | 03012052 A2 | 2/2003 |
| WO | 03051839 A1 | 6/2003 |
| WO | 2004065601 A2 | 8/2004 |
| WO | 2004080406 A2 | 9/2004 |
| WO | 2004090108 A2 | 10/2004 |
| WO | 2004091515 A2 | 10/2004 |
| WO | 2004094345 A2 | 11/2004 |
| WO | 2005061499 A1 | 7/2005 |

OTHER PUBLICATIONS

Aoki et al., "Potential tumor-targeting peptide vector of histidylated oligolysine conjugated to a tumor-homing RGD MOTIF," Cancer Gene Therapy 8:783-787 (2001).
Basbaum et al., "Focalized proteolysis: spatial and temporal regulation of extra cellular matrix degradation at the cell surface," Curr. Opin. Cell Biol. 8:731-738 (1996).
Benezra et al., "The Id proteins and angiogenesis," Oncogene 20(58):8334-8341 (2001).
Berger el al., "Universal bases for hybridization, replication and chain termination," Nucleic Acids Res. 28:2911-2914 (2000).
Bergstrom et al., "Synthesis, Structure, and Deoxyribonucleic Acid Sequencing with a Universal Nucleoside: 1-(2'-Deoxy-(B-D-ribofuranosyl)-3-nitropyrrole," Ant. Chem. Soc. 117:1201-1209 (1995).
Bernstein et al., "Role for a bidentate ribonucicase in the initiation step of RNA interference," Nature 409:363-366 (2001).
Birkedal-Hansen et al., "Matrix Metalloproteinases: A Review," Crit. Rev. Oral Biol. Med. 4:197-250(1993).
Boyd, "Invasion and metastasis," Cancer Metastasis Rev. 15(1):77-89 (1996).
Brinckerhoff et al., "Matrix metalloproteinases: a tail of a frog that became a prince," Nature Reviews 3:207-214 (2002).
Brotsehi et al., "A Stable DNA Duplex Containing a Non-Hydrogen-Bonding and Non-Shape-Complementary Base Couple: Interstrand Stacking as the Stability Determining Factor," Agnew Chem. Int. Ed. 40:3012-3014 (2001).
Chaloin et al., "Design of Carrier Peptide-Oligonucleotide Conjugates with Rapid Membrane Translocation and Nuclear Localization Properties," Biochem. Biophys. Res. Commun. 243:601-608 (1998).
Chao et al., "BCL-2 Family: Regulators of Cell Death," Annu. Rev. Immunol. 16:395-419 (1998).
Chen et al., "Gene therapy for brain tumors: regression of experimental gliomas by adenovirus-mediated gene transfer in vivo," Proc. Natl. Acad. Sci. USA 91:3054-3057 (1994).
Childs et al., "The MDR Superfamily of Genes and Its Biological Implications," Imp. Adv. Oncol. 21-36 (1994).
Chothia et al., "The Molecular Structure of Cell Adhesion Molecules," Anna. Rev. Binchem. 66:823-862 (1997).
Colledge et al., "Disruption of C-MOS causes parthenogenetic development of unfertilized mouse eggs," Nature 370: 65-68 (1994).
Corey et al., "Protection of Hydroxyl Groups as tert-Butyldimcthylsilyl Derivatives," J. Am. Chem. Soc. 94:6190-6191 (1972).
Cormier et al., "Synthesis of hexanucleotide analogues containing diisopropylsilyl internucleotide linkages," Nucleic Acids Res. 16:4583-4594 (1988).
Cosstick et al, "Solid Phase Synthesis of Oligonucleotides Containing 3'-Thiothymidine," Tetrahedron Lett. 30 (35):4693-4696 (1989).
D'Ari, "Cycle-regulated genes and cell cycle regulation," Bioassays 23(7):563-565 (2001).
De et al., "Structure-Activity Relationships for Antiplasmodial Activity among 7-Substituted 4-Aminoquinolines," J. Med. Chem. 41:4918-4926 (1998).
Deller et al., "Cell surface receptors," Curr. Opin. Struct. Biol. 10(2):213-219 (2000).
Derossi et al, "The Third Helix of the Antennapedia Homeodomain Translocates through Biological Membranes," J. Biol. Chem. 269(14):10444-10450 (1994).
Eckstein, "Oligonucleotides and Analogues, A practical approach," Table of Contents IRL Press (1991).
Edge et al., "Synthetic Analogues of Polynucleotides. Part VIII. Analogues of Oligonucleotides containing Carboxymethylthymidine," J. Chem. Soc. Perkin Trans. 1:1991-1996 (1972).
Elbashir el al., "RNA interference is mediated by 21-and 22-nucleotide RNAs," Genes and Dev. 15:188-200 (2001).
Elmquist et al., "VE-Cadherin-Derived Cell-Penetrating Peptide, pVEC, with Carrier Functions," Exp. Cell Res. 269:237-244 (2001).
Fang et al., "Fluoride-cleavable biotinylation phosphoramidite for 5'-end-labeling and affinity purification of synthetic oligonucleotides," Nucleic Acids Res. 31(2):708-715 (2003).
Fire et al., "Potent specific genetic interference by double-stranded RNA in Caenorhabditis elegans," Nature 391:806-811 (1998).
Fischer et al., "Cellular delivery of impermeable effector molecules in the form of conjugates with peptides capable of mediating membrane translocation" Bioconjugate Chem. 12:825-841 (2001).
Flanagan et al., "A cytosine analog that confers enhanced potency to antisense oligonucleotides," Proc. Natl. Acad. Sci. USA 96:3513-3518 (1999).
Fotedar et al., "Apoptosis and the cell cycle," Prog. Cell Cycle Res. 2:147-163 (1996).
Gante, "Azapeptides," Synthesis 405-413 (1989).
Gould et al., "Angiogenesis: An Expanding Universe," Hum. Pathol. 33(11):1061-1063 (2002).
Guckian et al., "Structure and Base Pairing Properties of a Replicable Nonpolar Isostere for Deoxyadenosine," J. Org. Chem. 63:9652-9656 (1998).
Hammond, "Argonaute2, a link between genetic and biochemical analyses of RNAi," Science 293:1146-1150 (2001).
Hashimoto et al., "Parthenogenetic activation of oocytes in c-mos-deficient mice," Nature 370:68-71 (1994).
Hanahan et al., "The Hallmarks of Cancer," Cell 100:57-70 (2000).
Haubner et al., "Glycosylated RGD-Containing Peptides: Tracer for Tumor Targeting and Angiogenesis Imaging with Improved Biokinetics," J. Nucl. Med. 42(2):326-336 (2001).
Holmes et al., "Steric inhibition of human immunodeficiency virus type-1 Tat-dependent trans-activation in vitro and in cells by oligonucleotides containing 2'-O-methyl G-clamp ribonucleoside analogues," Nucleic Acids Res. 31:2759-2768 (2003).
Holmes et al., "The Synthesis of 2'-O-Methyl G-Clamp Containing Oligonucleotides and Their Inhibition of the HIV-1 Tat-TAR Interaction," Nucleosides, Nucleotides & Nucleic Acids 22:1259-1262 (2003).
Hyrup et al., "Peptide Nucleic Acids (PNA): Synthesis, Properties and Potential Applications," Bioorganic & Medicinal Chemistry 4:5-23 (1996).
Iyer et al, "3H-1,2-Benzodithiole-3-one 1,1-Dioxide as an Improved Sulfurizing Reagent in the Solid-Phase Synthesis of Oligodeoxyribonucleoside Phosphorothioates," J. Am. Chem. Soc., 112:1253-1254 (1990).
Katajisto et al., "Solid-Phase Synthesis of Multiantennary Oligonucleotide Glycoconjugates Utilizing On-Support Oximation," Bioconjugate Chem. 15:890-896 (2004).
Kawasaki et al., "Uniformly Modified 2'-Deoxy-2'-fluoro Phosphorothioate Oligonucleotides as Nuclease-Resistant Antisense Compounds with High Affinity and Specificity for RNA Targets," J. Med. Chem. 36:831-841 (1993).
Ketting et al., "Dicer functions ill RNA interference and in synthesis of small RNA involved in developmental timing in C. elegans," Genes Dev. 15(20):2654-2659 (2001).

(56) References Cited

OTHER PUBLICATIONS

Krepela, "Cysteine proteinases in tumor cell growth and apoptosis," Neoplasma 48(5):332-349 (2001).
Kumar et al., "Express Protocol for Functionalization of Polymer Supports for Oligonucleotide Synthesis," Nucleosides & Nucleotides 15(4):879-888 (1996).
Lam et al., "A new type of synthetic peptide library for identifying ligand-binding activity," Nature 354:82-84 (1991).
Lan et al., "Minor Groove Hydration is Critical to the Stability of DNA Duplexes," J. Am. Chem. Soc. 122:6512-6513 (2000).
Larock, "Table of Contents from Comprehensive Organic Transformation," VCH Publishers, Inc. (1989).
Levin et al., "Rapid, One-Pot Conversion of Aryl Fluorides into Phenols with 2-Butyn-1-OL and Potassium t-Butoxide in Dmso," Synthetic Communications 32(9):1401-1406 (2002).
Limbach et al. "Summary: the modified nucleosides of RNA," Nucleic Acids Res. 22:2183-2196 (1994).
Lindgren et al., "Cell-penetrating peptides," Tips 21:99-103 (2000).
Liu et al., "Bi-stranded, multisite replication of a base pair between difluorotoluene and adenine: confirmation by 'inverse' sequencing," Chem. Biol. 4:919-926 (1997).
Loakes, "The applications of universal DNA base analogues," NAR 29:2437-2447 (2001).
Loakes, "Survey and Summary: The Applications of Universal DNA base analogues" Nucleic Acid Res. 29:2437-2117 (2001).
Maier et al., "Nuclease resistance of oligonucleotides containing the tricyclic cytosine analogues phenoxazine and 9(2-aminoethoxy)-phenoxazine ("G-clamp") and origins of their nuclease resistance properties" Biochem. 41:1323-1327 (2002).
Manoharan, "Oligonucleotide Conjugates as Potential Antisense Drugs with Improved Uptake, Biodistribution, Targeted Delivery, and Mechanism of Action," Antisense Nucleic Acid Drug Devel. 12:103-128 (2002).
Martin, "Stereoselektive Synthese von 2'-0-(2-Methoxyethyl)ribonucleosiden: Nachbargruppenbeteiligung der methyoxyethosy-Gruppe bei der Ribosylierung von Heterocyclen," Helv. Chim. Acta 79:1930-1938 (1996) (English abstract only).
Matray et al., "Selective and Stable DNA Base Pairing without Hydrogen Bonds," J. Am. Chem. Soc. 120:6191-6192 (1998).
Matrisian, "Cancer biology: Extracellular proteinases in malignancy," Curr. Biol. 9(20):R776-778 (1999).
McMinn et al., "Efforts toward Expansion of the Genetic Alphabet; DNA Polymerase Recognition of a Highly Stable, Self-Pairing Hydrophobic Base," J. Am. Chem. Soc. 121:11585-11586 (1999).
Mendelsohn et al., "The EGF receptor family as target for cancer therapy," Oncogene, 19(56):6550-6565 (2000).
Mi et al. "Characterization of a Class of Cationic Peptides Able to Facilitate Efficient Protein Transduction in Vitro and in Vivo," Mol. Ther. 2(4):339-347 (2000).
Mignatti et al., "Biology and Biochemistry of proteinases in Tumor Invasion," Physiol. Rev. 73:161-195 (1993).
Mitchell et al., "Polyarginine enters cells more efficiently than other polycationic homopolymers," J. Pept. Res. 56:318-325 (2000).
Morales et al., "Importance of Terminal Base Pair Hydrogen-Bonding in 3'-End Proofreading by the Klenow Fragment of DNA Polymerase I," Biochem. 39:2626-2632 (2000).
Moran et al., "Difluorotoluene, a Nonpolar Isostere for Thymine, Codes Specifically and Efficiently for Adenine in DNA Replication," J. Am. Chem. Soc. 119:2056-2057 (1997).
Mullauer et al., "Mutations in apoptosis genes; a pathogenetic factor for human disease," Mutat. Res. 488(3):211-231 (2001).
Nakata et al., "A Formal Total Synthesis of Erythromycin A. 2. A Convergent Synthesis of Woodward's Caramate Intermediate," Tetrahedron Lett. 29(18):2223-2226 (1988).
Noguchi et al., "Total Synthesis of Analogs of Topostin B, A DNA Topoisomerase I Inhibitor. Part 1. Synthesis of Fragments of Topostin B-1 Analogs," Tetrahedron 51:10531-10544 (1995).
Nakatani et al., "Recognition of a Single Guanine Bulge by 2-Acylamino-1, 8-naphthyridine," J. Am. Chem. Soc. 122:2172-2177 (2000).

Nakatani et al., "Specific binding of 2-amino-1,8-naphthyridine into a single guanine bulge as evidenced by photooxidation of GG doublet," Bioorg. Med. Chem. Lett. 11:335-337 (2001).
Normanno et al., "The role of EGF-Related Peptides in Tumor Growth," Front. Biosci. 6:D685-707 (2001).
Nykanen et al., "ATP requirements and small interfering RNA structure in the RNA interference pathway," Cell 107:309-321 (2001).
Norton, "ID helix-loop-helix proteins in cell growth, differentiation and tumorigenesis," J. Cell Sci. 113(22):3897-3905 (2000).
Ogawa et al., "Efforts toward the Expansion of the Genetic Alphabet Information Storage and Replication with Unnatural Hydrophobic Base Pairs," J. Am. Chem. Soc. 122:3274-3287 (2000).
Ogawa et al., "Rational Design of an Unnatural Base Pair with Increased Kinetic Selectivity," J. Am. Chem. Soc. 122:8803-8804 (2000).
Oliver et al., "Effect of the universal base 3-nitropyrrole on the selectivity of neighboring natural bases" Organic Lett. 3:1977-1980 (2001).
Opalinska et al., "Nucleic-Acid Therapeutic: Basic Principles and Recent Applications," Nature Reviews Drug Discovery, 1:503-514 (2002).
Parise et al., New aspects of integrin signaling in cancer, Semin. Cancer Biol. 10(6):407-414 (2000).
Patri et al., "Dendritic polymer macromolecular carriers for drug delivery," Curr. Opin. Chem. Biol. 6:466-471 (2002).
Pooga et al., "Cell penetration by transportation," FASEB J. 12:67-77 (2000).
Pirrung et al., "A universal, photocleavable DNA base: nitropiperonyl 2'-deoxyriboside," J. Org. Chem. 66:2067-2071 (2001).
Prakash et al., "Synthesis of 2'-O'[2-[(N,N-Dimethylamino)oxy]ethyl]Modified Nucleosides and Oligonucleotides," J. Org. Chem. 67:357-369 (2002).
Prusiner et al., "Prion Protein Biology," Cell 93(3):337-348 (1998).
Quintana et al., "Design and Function of a Dendrimer-Based Therapeutic Nanodevice Targeted to Tumor Cells Through the Folate Receptor," Pharma Res. 19(9):1310-1316 (2002).
Rajeev el al., "High-Affinity Peptide Nucleic Acid Oligomers Containing Tricyclic Cytosine Analogues," Organic Letters 4:4395-4398 (2002).
Rajeev et al., "2'-Modified-2-thiothymidine Oligonucleotides," Org. Lett. 5(17):3005-3008 (2003).
Reed, "Mechanisms of Apoptosis" Am. J. Pathol. 157(5):1415-1430 (2000).
Rogers et al. "Mild conversion of electron deficient aryl fluorides to phenols using 2-(rnethylsulfonyl)ethanol," Tetrahedron Lett. 43:3585-3587 (2002).
Rubinstein et al., "Recent Advances in Cytokines, Cytokine Receptors and Signal Transduction," Cytokine Growth Factor Rev. 9(2):175-181 (1998).
Rump et al., "Preparation of Conguates of Oligodeoxynucleotides and Lipid Structures and their Interaction with Low-Density Lipoprotein," Bioconjugate Chem. 9(3):341-349 (1998).
Safar et al., "Molecular studies of prion diseases," Prog. Brain Res. 117:421-434 (1998).
Sajiki et al, "Highly chemoselective Hydrogenation with retention of the epoxide function using a heterogeneous Pd/C—Ethylenediamine catalyst and THF," Chem. Eur. J. 6(12):2200-2204 (2000).
Simeoni et al., "Insight into the mechanism of the peptide-based gene delivery system MPG: implications for delivery of siRNA into mammalian cells," Nucl. Acids Res. 31(11):2717-2724 (2003).
Sproat et al., "Synthesis of Modified Building Blocks Containing Amino or Thiol Moieties: Application of Modified oligodeoxyribonucleotides," Nucleosides Nucleotides 7:651-653 (1988).
Stetler-Stevenson et al., "Tumor Cell Interactions with the Extracellular Matrix During Invasion and Metastasis," Annu. Rev. Cell Biol. 9:541-573 (1993).
Stirchak, "Uncharged stereoregular nucleic acid analogs: 2. Morpholino nucleoside oligomers with carbamate internucleoside linkages," Nucleic Acids Res. 17:6129-6141 (1989).

(56) References Cited

OTHER PUBLICATIONS

Strasser et al., "Apoptosis Signaling," Annu. Rev. Biochem. 69:217-245 (2000).
Tae et al., "Efforts toward expansion of the genetic alphabet: replication of DNA with three base pairs," J. Am. Chem. Soc. 123:7439-7440 (2001).
Takeda et al., "Convenient Methods for Syntheses of Active Carbamates, Ureas and Nitrosoureas Using N,N'-disuccinimido Carbonate (DSC)," Tetrahedron Lett. 24(42):4569-4572 (1983).
Tittensor, "The Preparation of Nucleoside Carbonates," J. Chem. Soc. (C), 2656-2662 (1971).
Truffert et al., "Synthesis, Purification and Characterization of Two Peptide-Oligonucleotide Conjugates as Potential Artificial Nucleases," Tetrahedron 52(8):3005-3016 (1996).
Valentijn et al., "Solid-phase Synthesis of Lysine-based Cluster Galactosides with High Affinity for the Asialoglycoprotein Receptor," Tetrahedron 3:759-770 (1997).
Verma et al., "Modified Oligonucleotides: Synthesis and Strategy for Users," Annu. Rev. Biochem. 67:99-134 (1998).
Vives et al., "A Truncated HIV-1 Tat Protein Basic Domain Rapidly Translocates through the Plasma Membrane and Accumulates in the Cell Nucleus," J. Biol. Chem. 272(25):16010-16017 (1997).
Weizman et al., "2,2'-Bipyridine ligandoside: a novel building block for modifying DNA with intra-duplex metal complexes," J. Am. Chem. Soc. 123:3375-3376 (2001).
Wender et al., "Oligocarbamate Molecular Transporters: Design, Synthesis, and Biological Evaluation of a New Class of Transporters for Drug Delivery," J. Am. Chem. Soc. 124:13382-13383 (2002).
Wengel, "Synthesis of 3'-C- and 4' C-Branched Oligodeoxynucicotides and the Development of Locked Nucleic Acid (LNA)," Acc. Chem. Res. 32:301-310 (1999).
Wijsman et al., "Solid-support synthesis of di- and tetramannosylated tetrathymidylic acid," Recl. Tray. Chim. Pays-Bas. 115:397-401 (1996).
Wilds et al., "Structural basis for recognition of guanosine by a synthetic tricyclic cytosine analogue: Guanidinium G-clamp," Helvetica Chimica Acta 86:966-978 (2003).
Wincott et al., "Synthesis, deprotection, analysis and purification of RNA and ribozymes," Nucleic Acids Res. 23 (14):2677-2684 (1995).
Wirz et al., "Facile chemoenzymic preparation of enantiomerically pure 2-methylglycerol derivatives as versatile trifunctional C4-synthons," J. Org. Chem. 58:3980-3984 (1993).
Witzeman et al., "Transacetoacetylation with ten-Butyl Acetoacetate: Synthetic Applications," J. Org. Chem. 56:1713-1718 (1991).
Wu et al., "Efforts toward Expansion of the Genetic Alphabet: Optimization of Interbase Hydrophobic Interactions," J Am. Chem. Soc. 122:7621-7632 (2000).
Yokota, "Tumor progression and metastasis," Carcinogenesis 21:497-503 (2000).
Zhou et al., "Lipophilic polylysines mediate efficient DNA transfection in mammalian cells," J. of Controlled Release 19:269-274 (1992).
Zimmerman et al., "Model Studies Directed toward a General Triplex DNA Recognition Scheme: A Novel DNA Base That Binds a CG Base-Pair in an Organic Solvent," J. Am. Chem. Soc. 117:10769-10770 (1995).
Zitzmann et al., "Arginine-Glycine-Aspartic Acid (RGD)-Peptide Binds to Both Tumor and Tumor-Endothelial Cells in Vivo," Cancer Res. 62:5139-5143 (2002).
Amarzguioui et al., "Tolerance for Mutations and Chemical Modifications in a siRNA," Nucleic Acids Research 31 (2):589-595 (2003).
Schwarz et al., "Asymmetry in the Assembly of the RNAi Enzyme Complex," Cell 115:199-208 (2003).
Reed et al., "Structure-Activity Relationships of Cytotoxic Cholesterol-Modified DNA Duplexes," J. Med. Chem. 38: 4587-4596 (1995).
Zhang et al., "RNA interface in mammalian cells by siRNAs modified with morpholino nucleoside analogues," Bioorganic & Medicinal Chemistry 17: 2441-2446 (2009).
Lorenz et al., "Steroid and lipid conjugates of siRNAS to enhance cellular uptake and gene silencing in liver cells," Bioorganic & Medicinal Chemistry Letters 14: 4975-4977 (2004).
Oishi et al., "Lactosylated Poly(ethylene glycol)- siRNA Conjugate through Acid-Labile β-Thiopropionate Linkage to Construct pH-Sensitive Polyion Complex Micelles Achieving Enchanced Gene Silencing in Hepatoma Cells," JACS 127: 1624-1625 (2005).

* cited by examiner

Synthesis of Ant and Tat Peptides. Synthesis of Ant and Tat Peptides could be Obtained With Respective Sequences.

```
SEQUENCE LISTING

<160> NUMBER OF SEQ ID NOS: 29

<210> SEQ ID NO 1
<211> LENGTH: 16
<212> TYPE: PRT
<213> ORGANISM: Artificial Sequence
<220> FEATURE:
<223> OTHER INFORMATION: Exemplary Cell Permeation Peptide

<400> SEQUENCE: 1

Arg Gln Ile Lys Ile Trp Phe Gln Asn Arg Arg Met Lys Trp Lys Lys
1               5                   10                  15

<210> SEQ ID NO 2
<211> LENGTH: 14
<212> TYPE: PRT
<213> ORGANISM: Artificial Sequence
<220> FEATURE:
<223> OTHER INFORMATION: Exemplary Cell Permeation Peptide

<400> SEQUENCE: 2

Gly Arg Lys Lys Arg Arg Gln Arg Arg Arg Pro Pro Gln Cys
1               5                   10

<210> SEQ ID NO 3
<211> LENGTH: 27
<212> TYPE: PRT
<213> ORGANISM: Artificial Sequence
<220> FEATURE:
<223> OTHER INFORMATION: Exemplary Cell Permeation Peptide

<400> SEQUENCE: 3

Gly Ala Leu Phe Leu Gly Trp Leu Gly Ala Ala Gly Ser Thr Met Gly
```

```
                1               5                  10                 15
Ala Trp Ser Gln Pro Lys Lys Lys Arg Lys Val
                20                  25

<210> SEQ ID NO 4
<211> LENGTH: 18
<212> TYPE: PRT
<213> ORGANISM: Artificial Sequence
<220> FEATURE:
<223> OTHER INFORMATION: Exemplary Cell Permeation Peptide

<400> SEQUENCE: 4

Leu Leu Ile Ile Leu Arg Arg Arg Ile Arg Lys Gln Ala His Ala His
1               5                   10                  15

Ser Lys

<210> SEQ ID NO 5
<211> LENGTH: 26
<212> TYPE: PRT
<213> ORGANISM: Artificial Sequence
<220> FEATURE:
<223> OTHER INFORMATION: Exemplary Cell Permeation Peptide

<400> SEQUENCE: 5

Gly Trp Thr Leu Asn Ser Ala Gly Tyr Leu Leu Lys Ile Asn Leu Lys
1               5                   10                  15

Ala Leu Ala Ala Leu Ala Lys Lys Ile Leu
                20                  25

<210> SEQ ID NO 6
<211> LENGTH: 18
<212> TYPE: PRT
<213> ORGANISM: Artificial Sequence
<220> FEATURE:
<223> OTHER INFORMATION: Amphiphilic model peptide

<400> SEQUENCE: 6

Lys Leu Ala Leu Lys Leu Ala Leu Lys Ala Leu Lys Ala Ala Leu Lys
1               5                   10                  15

Leu Ala

<210> SEQ ID NO 7
<211> LENGTH: 9
<212> TYPE: PRT
<213> ORGANISM: Artificial Sequence
<220> FEATURE:
<223> OTHER INFORMATION: Exemplary Cell Permeation Peptide

<400> SEQUENCE: 7

Arg Arg Arg Arg Arg Arg Arg Arg Arg
1               5

<210> SEQ ID NO 8
<211> LENGTH: 10
<212> TYPE: PRT
<213> ORGANISM: Artificial Sequence
<220> FEATURE:
<223> OTHER INFORMATION: Exemplary Cell Permeation Peptide

<400> SEQUENCE: 8

Lys Phe Phe Lys Phe Phe Lys Phe Phe Lys
1               5                   10

<210> SEQ ID NO 9
```

```
<211> LENGTH: 37
<212> TYPE: PRT
<213> ORGANISM: Artificial Sequence
<220> FEATURE:
<223> OTHER INFORMATION: Exemplary Cell Permeation Peptides

<400> SEQUENCE: 9

Leu Leu Gly Asp Phe Phe Arg Lys Ser Lys Glu Lys Ile Gly Lys Glu
 1               5                  10                  15

Phe Lys Arg Ile Val Gln Arg Ile Lys Asp Phe Leu Arg Asn Leu Val
            20                  25                  30

Pro Arg Thr Glu Ser
        35

<210> SEQ ID NO 10
<211> LENGTH: 31
<212> TYPE: PRT
<213> ORGANISM: Artificial Sequence
<220> FEATURE:
<223> OTHER INFORMATION: Exemplary Cell Permeation Peptides

<400> SEQUENCE: 10

Ser Trp Leu Ser Lys Thr Ala Lys Lys Leu Glu Asn Ser Ala Lys Lys
 1               5                  10                  15

Arg Ile Ser Glu Gly Ile Ala Ile Ala Ile Gln Gly Gly Pro Arg
            20                  25                  30

<210> SEQ ID NO 11
<211> LENGTH: 30
<212> TYPE: PRT
<213> ORGANISM: Artificial Sequence
<220> FEATURE:
<223> OTHER INFORMATION: Exemplary Cell Permeation Peptides

<400> SEQUENCE: 11

Ala Cys Tyr Cys Arg Ile Pro Ala Cys Ile Ala Gly Glu Arg Arg Tyr
 1               5                  10                  15

Gly Thr Cys Ile Tyr Gln Gly Arg Leu Trp Ala Phe Cys Cys
            20                  25                  30

<210> SEQ ID NO 12
<211> LENGTH: 36
<212> TYPE: PRT
<213> ORGANISM: Artificial Sequence
<220> FEATURE:
<223> OTHER INFORMATION: Exemplary Cell Permeation Peptides

<400> SEQUENCE: 12

Asp His Tyr Asn Cys Val Ser Ser Gly Gly Gln Cys Leu Tyr Ser Ala
 1               5                  10                  15

Cys Pro Ile Phe Thr Lys Ile Gln Gly Thr Cys Tyr Arg Gly Lys Ala
            20                  25                  30

Lys Cys Cys Lys
        35

<210> SEQ ID NO 13
<211> LENGTH: 12
<212> TYPE: PRT
<213> ORGANISM: Artificial Sequence
<220> FEATURE:
<223> OTHER INFORMATION: Exemplary Cell Permeation Peptides

<400> SEQUENCE: 13

Arg Lys Cys Arg Ile Val Val Ile Arg Val Cys Arg
```

```
<210> SEQ ID NO 14
<211> LENGTH: 42
<212> TYPE: PRT
<213> ORGANISM: Artificial Sequence
<220> FEATURE:
<223> OTHER INFORMATION: Exemplary Cell Permeation Peptides

<400> SEQUENCE: 14

Arg Arg Arg Pro Arg Pro Pro Tyr Leu Pro Arg Pro Arg Pro Pro
 1               5                  10                  15

Phe Phe Pro Pro Arg Leu Pro Pro Arg Ile Pro Pro Gly Phe Pro Pro
            20                  25                  30

Arg Phe Pro Pro Arg Phe Pro Gly Lys Arg
        35                  40

<210> SEQ ID NO 15
<211> LENGTH: 13
<212> TYPE: PRT
<213> ORGANISM: Artificial Sequence
<220> FEATURE:
<223> OTHER INFORMATION: Exemplary Cell Permeation Peptides

<400> SEQUENCE: 15

Ile Leu Pro Trp Lys Trp Pro Trp Trp Pro Trp Arg Arg
 1               5                  10

<210> SEQ ID NO 16
<211> LENGTH: 16
<212> TYPE: PRT
<213> ORGANISM: Artificial Sequence
<220> FEATURE:
<223> OTHER INFORMATION: Synthetically generated peptide

<400> SEQUENCE: 16

Ala Ala Val Ala Leu Leu Pro Ala Val Leu Leu Ala Leu Leu Ala Pro
 1               5                  10                  15

<210> SEQ ID NO 17
<211> LENGTH: 11
<212> TYPE: PRT
<213> ORGANISM: Artificial Sequence
<220> FEATURE:
<223> OTHER INFORMATION: Synthetically generated peptide

<400> SEQUENCE: 17

Ala Ala Leu Leu Pro Val Leu Leu Ala Ala Pro
 1               5                  10

<210> SEQ ID NO 18
<211> LENGTH: 13
<212> TYPE: PRT
<213> ORGANISM: Human immunodeficiency virus

<400> SEQUENCE: 18

Gly Arg Lys Lys Arg Arg Gln Arg Arg Pro Pro Gln
 1               5                  10

<210> SEQ ID NO 19
<211> LENGTH: 16
<212> TYPE: PRT
<213> ORGANISM: Drosophila Antennapedia

<400> SEQUENCE: 19
```

```
Arg Gln Ile Lys Ile Trp Phe Gln Asn Arg Arg Met Lys Trp Lys Lys
 1               5                   10                  15
```

<210> SEQ ID NO 20
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: misc_ feature
<222> LOCATION: 20, 21
<223> OTHER INFORMATION: n =deoxythymidine

<400> SEQUENCE: 20
cuuacgcuga guacuucgan n                                            21

<210> SEQ ID NO 21
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 20, 21
<223> OTHER INFORMATION: n = dT= deoxythymidine

<400> SEQUENCE: 21
ucgaaguacu cagcguaagn n                                            21

<210> SEQ ID NO 22
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20
<223> OTHER INFORMATION: n = deoxythymidine
<220> FEATURE:
<221> NAME/KEY: misc_feature
<222> LOCATION: 21
<223> OTHER INFORMATION: n = deoxythymidine cholesterol 6-aminohexanoic
      acid with trans-4-hydroxy-L-prolinol linker

<400> SEQUENCE: 22
cuuacgcuga guacuucgan n                                            21

<210> SEQ ID NO 23
<211> LENGTH: 21
<212> TYPE: RNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20
<223> OTHER INFORMATION: n = dT= deoxythymidine
<220> FEATURE:
<221> NAME/KEY: misc_feature
<222> LOCATION: 21
<223> OTHER INFORMATION: n = deoxythymidine cholesterol 6-aminohexanoic
      acid with trans-4-hydroxy-L-prolinol linker

<400> SEQUENCE: 23
ucgaaguacu cagcguaagn n                                            21

<210> SEQ ID NO 24

```
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 1
<223> OTHER INFORMATION: n = cytosine cholesterol 6-aminohexanoic acid
      with trans-4-hydroxy-L-prolinol linker
<220> FEATURE:
<221> NAME/KEY: misc_feature
<222> LOCATION: 20, 21
<223> OTHER INFORMATION: n = deoxythymidine

<400> SEQUENCE: 24
nuuacgcuga guacuucgan n                                              21

<210> SEQ ID NO 25
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 1
<223> OTHER INFORMATION: n = uridine cholesterol 6-aminohexanoic acid
      with trans-4-hydroxy-L-prolinol linker
<220> FEATURE:
<221> NAME/KEY: misc_feature
<222> LOCATION: 20, 21
<223> OTHER INFORMATION: n = deoxythymidine

<400> SEQUENCE: 25
ncgaaguacu cagcguaagn n                                              21

<210> SEQ ID NO 26
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20
<223> OTHER INFORMATION: n = deoxythymidine
<220> FEATURE:
<221> NAME/KEY: misc_feature
<222> LOCATION: 21
<223> OTHER INFORMATION: n = deoxythymidine thiocholesterol with
      trans-4-hydroxy-L-prolinol linker

<400> SEQUENCE: 26
cuuacgcuga guacuucgan n                                              21

<210> SEQ ID NO 27
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 20
<223> OTHER INFORMATION: n = deoxythymidine
<220> FEATURE:
<221> NAME/KEY: misc_feature
<222> LOCATION: 21
<223> OTHER INFORMATION: n = deoxythymidine thiocholesterol with
      trans-4-hydroxy-L-prolinol linker

<400> SEQUENCE: 27
```

```
ucgaaguacu cagcguaagn n                                            21

<210> SEQ ID NO 28
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 1
<223> OTHER INFORMATION: n = cytosine thiocholesterol with
      trans-4-hydroxy-L-prolinol linker
<220> FEATURE:
<221> NAME/KEY: misc_feature
<222> LOCATION: 20, 21
<223> OTHER INFORMATION: n = dT = deoxythymidine

<400> SEQUENCE: 28
nuuacgcuga guacuucgan n                                            21

<210> SEQ ID NO 29
<211> LENGTH: 21
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: misc_feature
<222> LOCATION: 1
<223> OTHER INFORMATION: n = uridine thiocholesterol with
      trans-4-hydroxy-L-prolinol linker
<220> FEATURE:
<221> NAME/KEY: misc_feature
<222> LOCATION: 20, 21
<223> OTHER INFORMATION: n =deoxythymidine

<400> SEQUENCE: 29
ncgaaguacu cagcguaagn n                                            21
```

IRNA AGENTS WITH BIOCLEAVABLE TETHERS

CROSS-REFERENCE TO RELATED APPLICATIONS

This application is a continuation of U.S. application Ser. No. 13/849,017, filed Mar. 22, 2013, which is a continuation of U.S. application Ser. No. 12/724,267, filed Mar. 10, 2010, now U.S. Pat. No. 8,426,377, which is a continuation of application Ser. No. 10/985,426, filed Nov. 9, 2004, now U.S. Pat. No. 7,723,509, which is a continuation-in-part application of U.S. application Ser. No. 10/916,185, filed Aug. 10, 2004, now U.S. Pat. No. 7,745,608, which is a continuation-in-part of International Application No. PCT/US2004/011829, filed on Apr. 16, 2004, which claims the benefit of U.S. Provisional Application No. 60/493,986, filed on Aug. 8, 2003; U.S. Provisional Application No. 60/494,597, filed on Aug. 11, 2003; U.S. Provisional Application No. 60/506,341, filed on Sep. 26, 2003; U.S. Provisional Application No. 60/518,453, filed on Nov. 7, 2003; U.S. Provisional Application No. 60/463,772, filed on Apr. 17, 2003; U.S. Provisional Application No. 60/465,802, filed on Apr. 25, 2003; U.S. Provisional Application No. 60/469,612, filed on May 9, 2003; U.S. Provisional Application No. 60/510,246, filed on Oct. 9, 2003; U.S. Provisional Application No. 60/510,318, filed on Oct. 10, 2003; U.S. Provisional Application No. 60/503,414, filed on Sep. 15, 2003; U.S. Provisional Application No. 60/465,665, filed on Apr. 25, 2003; International Application No.: PCT/US04/07070, filed on Mar. 8, 2004; International Application No.: PCT/US2004/10586, filed on Apr. 5, 2004; International Application No.: PCT/US2004/11255, filed on Apr. 9, 2004; and International Application No.: PCT/US2004/011822, filed on Apr. 16, 2004. The contents of all of these prior applications are hereby incorporated by reference in their entireties.

TECHNICAL FIELD

The invention relates to iRNA agents, which preferably include a monomer in which the ribose moiety has been replaced by a moiety other than ribose. The monomer can be used to attach a ligand, e.g., a lipophilic moiety, such as cholesterol, directly or indirectly to the iRNA agent via a tether that includes a cleavable linking group. The invention also relates to methods of making and using such modified iRNA agents.

BACKGROUND

RNA interference or "RNAi" is a term initially coined by Fire and co-workers to describe the observation that double-stranded RNA (dsRNA) can block gene expression when it is introduced into worms (Fire et al. (1998) *Nature* 391, 806-811). Short dsRNA directs gene-specific, post-transcriptional silencing in many organisms, including vertebrates, and has provided a new tool for studying gene function. RNAi may involve mRNA degradation.

SUMMARY

The inventor has discovered, inter alia, that the ribose sugar of one or more ribonucleotide subunits of an iRNA agent can be replaced with another moiety, e.g., a non-carbohydrate (preferably cyclic) carrier that further includes a tether having one or more linking groups, in which at least one of the linking groups is a cleavable linking group. The tether in turn can be connected to a selected moiety, e.g., a ligand, e.g., a targeting or delivery moiety, or a moiety which alters a physical property. The cleavable linking group is one which is sufficiently stable outside the cell such that it allows targeting of a therapeutically beneficial amount of an iRNA agent (e.g., a single stranded or double stranded iRNA agent), coupled by way of the cleavable linking group to a targeting agent—to targets cells, but which upon entry into a target cell is cleaved to release the iRNA agent from the targeting agent.

A ribonucleotide subunit in which the ribose sugar of the subunit has been so replaced is referred to herein as a ribose replacement modification subunit (RRMS). A cyclic carrier may be a carbocyclic ring system, i.e., all ring atoms are carbon atoms, or a heterocyclic ring system, i.e., one or more ring atoms may be a heteroatom, e.g., nitrogen, oxygen, sulfur. The cyclic carrier may be a monocyclic ring system, or may contain two or more rings, e.g. fused rings. The cyclic carrier may be a fully saturated ring system, or it may contain one or more double bonds.

The carriers further include (i) at least two "backbone attachment points" and (ii) at least one "tethering attachment point." A "backbone attachment point" as used herein refers to a functional group, e.g. a hydroxyl group, or generally, a bond available for, and that is suitable for incorporation of the carrier into the backbone, e.g., the phosphate, or modified phosphate, e.g., sulfur containing, backbone, of a ribonucleic acid. A "tethering attachment point" in some embodiments refers to a constituent ring atom of the cyclic carrier, e.g., a carbon atom or a heteroatom (distinct from an atom which provides a backbone attachment point), that connects the tethers described above or a tethered moiety, e.g., a ligand, e.g., a targeting or delivery moiety, or a moiety which alters a physical property. One of the most preferred tethered moieties is a moiety which promotes entry into a cell, e.g., a lipophilic moiety, e.g., cholesterol. While not wishing to be bound by theory it is believed the attachment of a lipohilic agent increases the lipophilicity of an iRNA agent. Optionally, the selected moiety is connected by an intervening tether to the cyclic carrier. Thus, it will often include a functional group, e.g., an amino group, or generally, provide a bond, that is suitable for incorporation or tethering of another chemical entity, e.g., a ligand to the constituent ring.

Incorporation of one or more ligand conjugated monomer subunits (sometimes referred to herein as ribose replacement monomer subunits, RRMSs) described herein into an RNA agent, e.g., an iRNA agent, particularly when tethered to an appropriate entity, can confer one or more new properties to the RNA agent and/or alter, enhance or modulate one or more existing properties in the RNA molecule. E.g., it can alter one or more of lipophilicity or nuclease resistance. Incorporation of one or more RRMSs described herein into an iRNA agent can, particularly when the RRMS is tethered to an appropriate entity, modulate, e.g., increase, binding affinity of an iRNA agent to a target mRNA, change the geometry of the duplex form of the iRNA agent, alter distribution or target the iRNA agent to a particular part of the body, or modify the interaction with nucleic acid binding proteins (e.g., during RISC formation and strand separation).

Accordingly, in one aspect, the invention features, an iRNA agent preferably comprising a first strand and option ally a second strand, wherein at least one subunit having a formula (I) is incorporated into at least one of said strands:

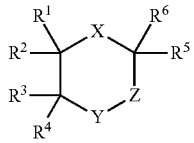

(I)

wherein:

X is N(CO)R$^7$, NR$^7$ or CH$_2$;

Y is NR$^8$, O, S, CR$^9$R$^{10}$, or absent;

Z is CR$^{11}$R$^{12}$ or absent;

Each of R$^1$, R$^2$, R$^3$, R$^4$, R$^9$, and R$^{10}$ is, independently, H, OR$^a$, OR$^b$, (CH$_2$)$_n$OR$^a$, or (CH$_2$)$_n$OR$^b$, provided that at least one of R$^1$, R$^2$, R$^3$, R$^4$, R$^9$, and R$^{10}$ is OR$^a$ or OR$^b$ and that at least one of R$^1$, R$^2$, R$^3$, R$^4$, R$^9$, and R$^{10}$ is (CH$_2$)$_n$OR$^a$, or (CH$_2$)$_n$OR$^b$ (when the RRMS is terminal, one of R$^1$, R$^2$, R$^3$, R$^4$, R$^9$, and R$^{10}$ will include R$^a$ and one will include R$^b$; when the RRMSS is internal, two of R$^1$, R$^2$, R$^3$, R$^4$, R$^9$, and R$^{10}$ will each include an R$^b$); further provided that preferably OR$^a$ may only be present with (CH$_2$)$_n$OR$^b$ and (CH$_2$)$_n$OR$^a$ may only be present with OR$^b$;

Each of R$^5$, R$^6$, R$^{11}$, and R$^{12}$ is, independently, H, C$_1$-C$_6$ alkyl optionally substituted with 1-3 R$^{13}$, or C(O)NHR$^7$; or R$^5$ and R$^{11}$ together are C$_3$-C$_8$ cycloalkyl optionally substituted with R$^{14}$;

R$^7$ can be T-R$^d$, in which T is a tether having one or more linking groups, wherein at least one of the linking groups is cleavable; and R$^d$ can be H or a ligand e.g., a lipophilic ligand, e.g., cholesterol;

R$^8$ is C$_1$-C$_6$ alkyl;

R$^{13}$ is hydroxy, C$_1$-C$_4$ alkoxy, or halo;

R$^{14}$ is NR$^c$R$^7$;

R$^a$ is H or:

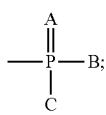

R$^b$ is H or:

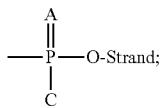

Each of A and C is, independently, O or S;

B is OH, O$^-$, or

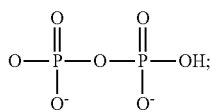

R$^c$ is H or C$_1$-C$_6$ alkyl; and n is 1-4; provided that X is N(CO)R$^7$ or NR$^7$; or one of R$^5$, R$^6$, R$^{11}$, and R$^{12}$ is C(O)NHR$^7$; or R$^{14}$ is present.

Embodiments can include one or more of the following features.

The linking groups can be cleaved at least about 100 times (e.g., about 90 times faster, about 80 times faster, about 70 times faster, about 60 times faster, about 50 times faster, about 40 times faster, about 30 times faster, about 20 times faster, about 10 times faster) faster in intracellular media (e.g., under conditions chosen to mimic intracellular media) than in extracellular media (e.g., under conditions chosen to mimic extracellular media).

In some embodiments, at least one of the linking groups can be a redox cleavable linking group, an acid cleavable linking group, an esterase cleavable linking group, a phosphatase cleavable linking group, or a peptidase cleavable linking group.

In some embodiments, at least one of the linking groups can be a reductively cleavable linking group (e.g., a disulfide group).

In some embodiments, at least one of the linking groups can be an acid cleavable linking group (e.g., a hydrazone group or an ester group).

In some embodiments, at least one of the linking groups can be an esterase cleavable linking group (e.g., an ester group).

In some embodiments, at least one of the linking groups can be a phosphatase cleavable linking group (e.g., a phosphate group).

In some embodiments, at least one of the linking groups can be an peptidase cleavable linking group (e.g., a peptide bond).

T can include a terminal linking group (e.g., a terminal linking group that links the tether to the ligand or a terminal linking group that links the tether to the nitrogen atom of X or R$^{14}$ in formula (I), or the nitrogen atom of CONHR$^7$ when R$^8$, R$^6$, R$^{11}$, or R$^{12}$ is CONHR$^7$ in formula (I).

T can include a terminal linking group that links the tether to the ligand and a terminal linking group that links the tether to the nitrogen atom of X or R$^{14}$ in formula (I), or the nitrogen atom of CONHR$^7$ when R$^8$, R$^6$, R$^{11}$, or R$^{12}$ is CONHR$^7$ in formula (I).

T can include one or more internal linking groups (e.g., 1-20 internal linking groups, 1-15 internal linking groups, 1-10 internal linking groups, 1-5 internal linking groups, 1-3 internal linking groups, 1-2 linking groups).

T can include a terminal linking group (e.g., a terminal linking group that links the tether to the ligand and/or a terminal linking group that links the tether to the nitrogen atom of X or R$^{14}$ in formula (I), or the nitrogen atom of CONHR$^7$ when R$^5$, R$^6$, R$^{11}$, or R$^{12}$ is CONHR$^7$ in formula (I)) and one or more internal linking groups (e.g., 1-5, e.g., 1, 2, 3, 4, or 5 internal linking groups).

The terminal linking group can be a cleavable linking group.

T can include at least one internal linking group that is cleavable.

T can include a cleavable terminal linking group that links the tether to the ligand and/or a cleavable terminal linking group links the tether to the nitrogen atom of X or R$^{14}$ in formula (I), or the nitrogen atom of CONHR$^7$ when R$^5$, R$^6$, R$^{11}$, or R$^{12}$ is CONHR$^7$ in formula (I), and/or at least one internal linking group that is cleavable.

The terminal linking group that links the tether to the ligand can be cleavable.

The terminal linking group that links the tether to the nitrogen atom of X or R$^{14}$ in formula (I), or the nitrogen atom of CONHR$^7$ when R$^5$, R$^6$, R$^{11}$, or R$^{12}$ is CONHR$^7$ in formula (I) can be cleavable.

T can include at least one internal linking group that is cleavable.

R⁷ can have the formula $R^d$-(E')$_s$-Δ-(E'')$_t$—;
wherein:
each of E' and E'' is a terminal linking group; and
Δ is a hydrocarbon chain that optionally includes one or more internal linking groups, G;
each of s and t is, independently, 0 or 1;
provided that one of s or t is 1, or Δ includes at least one G;
s can be 1 and t can be 0.
s can be 0, and t can be 1.
s and t can both be 1.
Each of E', E'', and G can be, independently,
—NR$^k$C(O)—, —C(O)NR$^k$—, —OC(O)NR$^k$—, —NR$^k$C(O)O—, —O—, —S—, —SS—, —S(O)—, —S(O₂)—, —NR$^k$C(O)NR$^k$—, —NR$^k$C(S)NR$^k$—, —C(O)O—, —OC(O)—, —NR$^k$C(S)—, —NR$^k$C(S)O—, —C(S)NR$^k$—, —OC(S)NR$^k$—, —NR$^k$C(S)O—, —O—P(O)(OR$^k$)—O—, —O—P(S)(OR$^k$)—O—, —O—P(S)(SR$^k$)—O—, —S—P(O)(OR$^k$)—O—, —O—P(O)(OR$^k$)—S—, —S—P(O)(OR$^k$)—S—, —O—P(S)(OR$^k$)—S—, —S—P(S)(OR$^k$)—O—, —O—P(O)(R$^k$)—O—, —O—P(S)(R$^k$)—O—, —S—P(O)(R$^k$)—O—, —S—P(S)(R$^k$)—O—, —S—P(O)(R$^k$)—S—, —O—P(S)(R$^k$)—S—, —C(O)—, —NR$^k$—, —R$^k$C=NNR$^k$—, —NHCHR$^{k'}$C(O)NHCHR$^{k''}$C(O)—, or —NHCHR$^{k'}$NHC(O)CHR$^{k''}$C(O)—; in which
R$^k$ at each occurrence can be, independently, C1-C20 alkyl, C1-C20 haloalkyl, C6-C10 aryl, C7-C12 aralkyl; and
each of R$^{k'}$ and R$^{k''}$ can be, independently of one another, an amino acid sidechain.

In certain embodiments, at least one of E', E'', and G can be —SS—, —O—P(O)(OR$^k$)—O—, —O—P(S)(OR$^k$)—O—, —O—P(S)(SR$^k$)—O—, —S—P(O)(OR$^k$)—O—, —O—P(O)(OR$^k$)—S—, —S—P(O)(OR$^k$)—S—, —O—P(S)(OR$^k$)—S—, —S—P(S)(OR$^k$)—O—, —O—P(O)(R$^k$)—O—, —O—P(S)(R$^k$)—O—, —S—P(O)(R$^k$)—O—, —S—P(S)(R$^k$)—O—, —S—P(O)(R$^k$)—S—, —O—P(S)(R$^k$)—S—, —C(O)O—, —OC(O)—, —R$^k$C=NNR$^k$—, —NHCHR$^{k'}$C(O)NHCHR$^{k''}$C(O)—, or —NHCHR$^{k'}$NHC(O)CHR$^{k''}$C(O)—; and the others can each be, independently, NR$^k$C(O)—, —C(O)NR$^k$—, —OC(O)NR$^k$—, —NR$^k$C(O)O—, —O—, —S—, NR$^k$C(O)NR$^k$—, —NR$^k$C(S)NR$^k$—, —NR$^k$C(S)—, —NR$^k$C(S)O—, —C(S)NR$^k$—, —OC(S)NR$^k$—, —NR$^k$C(S)O, —C(O)—, —NR$^k$—.

In certain embodiments, at least one G can be —SS—, —O—P(O)(OR$^k$)—O—, —O—P(S)(OR$^k$)—O—, —O—P(S)(SR$^k$)—O—, —S—P(O)(OR$^k$)—O—, —O—P(O)(OR$^k$)—S—, —S—P(O)(OR$^k$)—S—, —O—P(S)(OR$^k$)—S—, —S—P(S)(OR$^k$)—O—, —O—P(O)(R$^k$)—O—, —O—P(S)(R$^k$)—O—, —S—P(O)(R$^k$)—O—, —S—P(S)(R$^k$)—O—, —S—P(O)(R$^k$)—S—, —O—P(S)(R$^k$)—S—, —C(O)O—, —OC(O)—, or —R$^k$C=NNR$^k$—, —NHCHR$^{k'}$C(O)NHCHR$^{k''}$C(O)—, or —NHCHR$^{k'}$NHC(O)CHR$^{k''}$C(O)—.

In certain embodiments, at least one G can be —SS—.

In certain embodiments, at least one G can be —C(O)O—, or —OC(O)—.

In certain embodiments, at least one G can be —R$^k$C=NNR$^k$—.

In certain embodiments, at least one G can be —NHCHR$^{k'}$C(O)NHCHR$^{k''}$C(O)—, or —NHCHR$^{k'}$NHC(O)CHR$^{k''}$C(O)—.

In certain embodiments, at least one G can be —O—P(O)(OR$^k$)—O—, —O—P(S)(OR$^k$)—O—, —O—P(S)(SR$^k$)—O—, —S—P(O)(OR$^k$)—O—, —O—P(O)(OR$^k$)—S—, —S—P(O)(OR$^k$)—S—, —O—P(S)(OR$^k$)—S—, —S—P(S)(OR$^k$)—O—, —O—P(O)(R$^k$)—O—, —O—P(S)(R$^k$)—O—, —S—P(O)(R$^k$)—O—, —S—P(S)(R$^k$)—O—, —S—P(O)(R$^k$)—S—, —O—P(S)(R$^k$)—S—.

Δ can be C1-100 alkylene, alkenylene, or alkynylene having at least one G.

Δ can be C1-20 alkylene, alkenylene, or alkynylene having at least one G.

Δ can be C1-20 alkylene, alkenylene, or alkynylene having 1, 2, 3, 4, or 5 G.

Δ can be C1-20 alkylene having at least one G.

Δ can be C16 alkylene, C14 alkylene, or C12 alkylene having 1, 2, 3, or 4 G.

Δ can be C9 alkylene chain having 1, 2, or 3 G.

Δ can be a C5 alkylene having 1 or 2 G.

Δ can be C18 alkylene chain having 1, 2, 3, 4, or 5 G.

-(E')$_s$-Δ-(E'')$_t$— can be

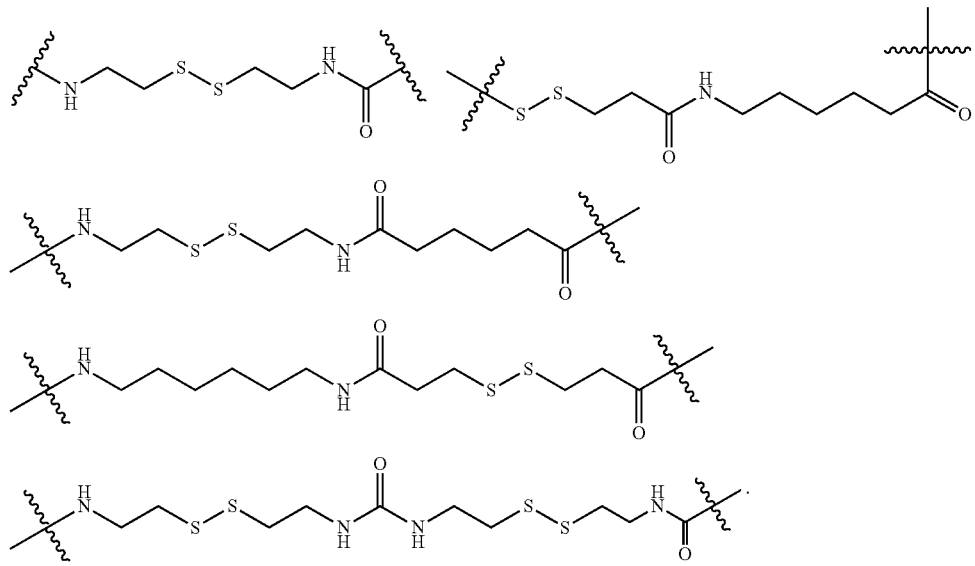

The iRNA agent can be 21 nucleotides in length and there can be a duplex region of about 19 pairs.

The iRNA agent can include a duplex region between 17 and 23 pairs in length.

$R^1$ can be $CH_2OR^a$ and $R^3$ can be $OR^b$; or $R^1$ can be $CH_2OR^a$ and $R^9$ can be $OR^b$; or $R^1$ can be $CH_2OR^a$ and $R^2$ can be $OR^b$.

$R^1$ can be $CH_2OR^b$ and $R^3$ can be $OR^b$; or $R^1$ can be $CH_2OR^b$ and $R^9$ can be $OR^b$; or $R^1$ can be $CH_2OR^b$ and $R^2$ can be $OR^b$; or $R^1$ can be $CH_2OR^b$ and $R^3$ can be $OR^a$; or $R^1$ can be $CH_2OR^b$ and $R^9$ can be $OR^a$; or $R^1$ can be $CH_2OR^b$ and $R^2$ can be $OR^a$.

$R^1$ can be $OR^a$ and $R^3$ can be $CH_2OR^b$; or $R^1$ can be $OR^a$ and $R^9$ can be $CH_2OR^b$; or $R^1$ can be $OR^a$ and $R^2$ can be $CH_2OR^b$.

$R^1$ can be $OR^b$ and $R^3$ can be $CH_2OR^b$; or $R^1$ can be $OR^b$ and $R^9$ can be $CH_2OR^b$; or $R^1$ can be $OR^b$ and $R^2$ can be $CH_2OR^b$; or $R^1$ can be $OR^b$ and $R^3$ can be $CH_2OR^a$; or $R^1$ can be $OR^b$ and $R^9$ can be $CH_2OR^a$; or $R^1$ can be $OR^b$ and $R^2$ can be $CH_2OR^a$.

$R^3$ can be $CH_2OR^a$ and $R^9$ can be $OR^b$; or $R^3$ can be $CH_2OR^a$ and $R^4$ can be $OR^b$.

$R^3$ can be $CH_2OR^b$ and $R^9$ can be $OR^b$; or $R^3$ can be $CH_2OR^b$ and $R^4$ can be $OR^b$; or $R^3$ can be $CH_2OR^b$ and $R^9$ can be $OR^a$; or $R^3$ can be $CH_2OR^b$ and $R^4$ can be $OR^a$.

$R^3$ can be $OR^b$ and $R^9$ can be $CH_2OR^a$; or $R^3$ can be $OR^b$ and $R^4$ can be $CH_2OR^a$; or $R^3$ can be $OR^b$ and $R^9$ can be $CH_2OR^b$; or $R^3$ can be $OR^b$ and $R^4$ can be $CH_2OR^b$.

$R^3$ can be $OR^a$ and $R^9$ can be $CH_2OR^b$; or $R^3$ can be $OR^a$ and $R^4$ can be $CH_2OR^b$.

$R^9$ can be $CH_2OR^a$ and $R^{10}$ can be $OR^b$.

$R^9$ can be $CH_2OR^b$ and $R^{10}$ can be $OR^b$; or $R^9$ can be $CH_2OR^b$ and $R^{10}$ can be $OR^a$.

In a preferred embodiment the ribose is replaced with a pyrroline scaffold or with a 4-hydroxyproline-derived scaffold, and X is $N(CO)R^7$ or $NR^7$, Y is $CR^9R^{10}$, and Z is absent.

$R^1$ and $R^3$ can be cis or $R^1$ and $R^3$ can be trans.

n can be 1.

A can be O or S.

$R^1$ can be $(CH_2)_nOR^b$ and $R^3$ can be $OR^b$; or $R^1$ can be $(CH_2)_nOR^a$ and $R^3$ can be $OR^b$.

$R^7$ can be can be $T-R^d$, in which T is a tether having one or more linking groups, wherein at least one of the linking groups is cleavable; and $R^d$ can be H or a ligand, e.g., $R^d$ can be chosen from a folic acid radical; a cholesterol radical; a carbohydrate radical; a vitamin A radical; a vitamin E radical; a vitamin K radical. Preferably, $R^d$ is a cholesterol radical.

$R^1$ can be $OR^b$ and $R^3$ can be $(CH_2)_nOR^b$; or $R^1$ can be $OR^b$ and $R^3$ can be $(CH_2)_nOR^a$; or $R^1$ can be $OR^a$ and $R^3$ can be $(CH_2)_nOR^b$; or $R^1$ can be $(CH_2)_nOR^b$ and $R^9$ can be $OR^a$.

$R^1$ and $R^9$ can be cis or $R^1$ and $R^9$ can be trans.

$R^1$ can be $OR^a$ and $R^9$ can be $(CH_2)_nOR^b$; or $R^1$ can be $(CH_2)_nOR^b$ and $R^9$ can be $OR^b$; or $R^1$ can be $(CH_2)_nOR^a$ and $R^9$ can be $OR^b$; or $R^1$ can be $OR^b$ and $R^9$ can be $(CH_2)_nOR^b$; or $R^1$ can be $OR^b$ and $R^9$ can be $(CH_2)_nOR^a$.

$R^3$ can be $(CH_2)_nOR^b$ and $R^9$ can be $OR^a$; or $R^3$ can be $(CH_2)_nOR^b$ and $R^9$ can be $OR^b$; or $R^3$ can be $(CH_2)_nOR^a$ and $R^9$ can be $OR^b$; or $R^3$ can be $OR^a$ and $R^9$ can be $(CH_2)_nOR^b$; $R^3$ can be $OR^b$ and $R^9$ can be $(CH_2)_nOR^b$; or $R^3$ can be $OR^b$ and $R^9$ can be $(CH_2)_nOR^a$.

$R^3$ and $R^9$ can be cis or $R^3$ and $R^9$ can be trans.

In other preferred embodiments the ribose is replaced with a piperidine scaffold, and X is $N(CO)R^7$ or $NR^7$, Y is $CR^9R^{10}$, and Z is $CR^{11}R^{12}$.

$R^9$ can be $(CH_2)_nOR^b$ and $R^{10}$ can be $OR^a$.

n can be 1 or 2.

$R^9$ can be $(CH_2)_nOR^b$ and $R^{10}$ can be $OR^b$; or $R^9$ can be $(CH_2)_nOR^a$ and $R^{10}$ can be $OR^b$.

A can be O or S.

$R^7$ can be can be $T-R^d$, in which T is a tether having one or more linking groups, wherein at least one of the linking groups is cleavable; and $R^d$ can be H or a ligand, e.g., $R^d$ can be chosen from a folic acid radical; a cholesterol radical; a carbohydrate radical; a vitamin A radical; a vitamin E radical; a vitamin K radical. Preferably, $R^d$ is a cholesterol radical.

$R^3$ can be $(CH_2)_nOR^b$ and $R^4$ can be $OR^a$; or $R^3$ can be $(CH_2)_nOR^b$ and $R^4$ can be $OR^b$; or $R^3$ can be $(CH_2)_nOR^a$ and $R^4$ can be $OR^b$.

$R^1$ can be $(CH_2)_nOR^b$ and $R^2$ can be $OR^a$; or $R^1$ can be $(CH_2)_nOR^b$ and $R^2$ can be $OR^b$; or $R^1$ can be $(CH_2)_nOR^a$ and $R^2$ can be $OR^b$.

$R^3$ can be $(CH_2)_nOR^b$ and $R^9$ can be $OR^a$.

$R^3$ and $R^9$ can be cis, or $R^3$ and $R^9$ can be trans.

$R^3$ can be $(CH_2)_nOR^b$ and $R^9$ can be $OR^b$; or $R^3$ can be $(CH_2)_nOR^b$ and $R^9$ can be $OR^a$; or $R^3$ can be $(CH_2)_nOR^a$ and $R^9$ can be $OR^b$.

$R^1$ can be $(CH_2)_nOR^b$ and $R^3$ can be $OR^a$.

$R^1$ and $R^3$ can be cis, or $R^1$ and $R^3$ can be trans.

$R^3$ can be $OR^a$ and $R^9$ can be $(CH_2)_nOR^b$.

$R^1$ can be $OR^a$ and $R^3$ can be $(CH_2)_nOR^b$.

In other preferred embodiments the ribose is replaced with a piperazine scaffold, and X is $N(CO)R^7$ or $NR^7$, Y is $NR^8$, and Z is $CR^{11}R^{12}$.

$R^1$ can be $(CH_2)_nOR^b$ and $R^3$ can be $OR^a$.

$R^1$ and $R^3$ can be cis or $R^1$ and $R^3$ can be trans.

n can be 1.

$R^1$ can be $(CH_2)_nOR^b$ and $R^3$ can be $OR^b$; or $R^1$ can be $(CH_2)_nOR^a$ and $R^3$ can be $OR^b$.

A can be O or S, preferably S.

$R^7$ can be can be $T-R^d$, in which T is a tether having one or more linking groups, wherein at least one of the linking groups is cleavable; and $R^d$ can be H or a ligand, e.g., $R^d$ can be chosen from a folic acid radical; a cholesterol radical; a carbohydrate radical; a vitamin A radical; a vitamin E radical; a vitamin K radical. Preferably, $R^d$ is a cholesterol radical.

$R^8$ can be $CH_3$.

$R^1$ can be $OR^a$ and $R^3$ can be $(CH_2)_nOR^b$.

In other preferred embodiments the ribose is replaced with a morpholino scaffold, and X is $N(CO)R^7$ or $NR^7$, Y is O, and Z is $CR^{11}R^{12}$.

$R^1$ can be $(CH_2)_nOR^b$ and $R^3$ can be $OR^a$.

$R^1$ and $R^3$ can be cis, or $R^1$ and $R^3$ can be trans.

n can be 1.

$R^1$ can be $(CH_2)_nOR^b$ and $R^3$ can be $OR^b$; of $R^1$ can be $(CH_2)_nOR^a$ and $R^3$ can be $OR^b$.

A can be O or S.

$R^7$ can be can be $T-R^d$, in which T is a tether having one or more linking groups, wherein at least one of the linking groups is cleavable; and $R^d$ can be H or a ligand, e.g., $R^d$ can be chosen from a folic acid radical; a cholesterol radical; a carbohydrate radical; a vitamin A radical; a vitamin E radical; a vitamin K radical. Preferably, $R^d$ is a cholesterol radical.

$R^8$ can be $CH_3$.

$R^1$ can be $OR^a$ and $R^3$ can be $(CH_2)_nOR^b$.

In other preferred embodiments the ribose is replaced with a decalin scaffold, and X is $CH_2$; Y is $CR^9R^{10}$; and Z is $CR^{11}R^{12}$; and $R^5$ and $R^{11}$ together are $C^6$ cycloalkyl.

$R^6$ can be $C(O)NHR^7$.

$R^{12}$ can be hydrogen.

$R^6$ and $R^{12}$ can be trans.

$R^3$ can be $OR^a$ and $R^9$ can be $(CH_2)_nOR^b$.

$R^3$ and $R^9$ can be cis, or $R^3$ and $R^9$ can be trans.

n can be 1 or 2.

$R^3$ can be $OR^b$ and $R^9$ can be $(CH_2)_nOR^b$; or $R^3$ can be $OR^b$ and $R^9$ can be $(CH_2)_nOR^a$.

A can be O or S.

$R^7$ can be can be T-$R^d$, in which T is a tether having one or more linking groups, wherein at least one of the linking groups is cleavable; and $R^d$ can be H or a ligand, e.g., $R^d$ can be chosen from a folic acid radical; a cholesterol radical; a carbohydrate radical; a vitamin A radical; a vitamin E radical; a vitamin K radical. Preferably, $R^d$ is a cholesterol radical.

In other preferred embodiments the ribose is replaced with a decalin/indane scaffold, e.g., X is $CH_2$; Y is $CR^9R^{10}$; and Z is $CR^{11}R^{12}$; and $R^5$ and $R^{11}$ together are $C^5$ cycloalkyl.

$R^6$ can be $CH_3$.

$R^{12}$ can be hydrogen.

$R^6$ and $R^{12}$ can be trans.

$R^3$ can be $OR^a$ and $R^9$ can be $(CH_2)_nOR^b$.

$R^3$ and $R^9$ can be cis, or $R^3$ and $R^9$ can be trans.

n can be 1 or 2.

$R^3$ can be $OR^b$ and $R^9$ can be $(CH_2)_nOR^a$; or $R^3$ can be $OR^b$ and $R^9$ can be $(CH_2)_nOR^a$.

A can be O or S.

$R^{14}$ can be $N(CH3)R^7$. $R^7$ can be can be T-$R^d$, in which T is a tether having one or more linking groups, wherein at least one of the linking groups is cleavable; and $R^d$ can be H or a ligand, e.g., $R^d$ can be chosen from a folic acid radical; a cholesterol radical; a carbohydrate radical; a vitamin A radical; a vitamin E radical; a vitamin K radical. Preferably, $R^d$ is a cholesterol radical.

In another aspect, this invention features an iRNA agent comprising a first strand and a second strand, wherein at least one subunit having a formula (II) is incorporated into at least one of said strands:

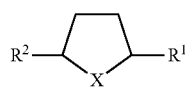

(II)

X is $N(CO)R^7$ or $NR^7$;

Each of $R^1$ and $R^2$ is, independently, $OR^a$, $OR^b$, $(CH_2)_nOR^a$, or $(CH_2)_nOR^b$, provided that one of $R^1$ and $R^2$ is $OR^a$ or $OR^b$ and the other is $(CH_2)_nOR^a$ or $(CH_2)_nOR^b$ (when the RRMS is terminal, one of $R^1$ or $R^2$ will include $R^a$ and one will include $R^b$; when the RRMSS is internal, both $R^1$ and $R^2$ will each include an $R^b$); further provided that preferably $OR^a$ may only be present with $(CH_2)_nOR^b$ and $(CH_2)_nOR^a$ may only be present with $OR^b$;

$R^7$ is $R^7$ can be can be T-$R^d$, in which T is a tether having one or more linking groups, wherein at least one of the linking groups is cleavable; and $R^d$ can be H or a ligand, e.g., $R^d$ can be chosen from a folic acid radical; a cholesterol radical; a carbohydrate radical; a vitamin A radical; a vitamin E radical; a vitamin K radical. Preferably, $R^d$ is a cholesterol radical;

$R^8$ is $C_1$-$C_6$ alkyl;

$R^{13}$ is hydroxy, $C_1$-$C_4$ alkoxy, or halo;

$R^{14}$ is $NR^cR^7$;

$R^a$ is H or:

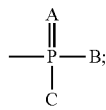

$R^b$ is H or:

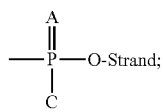

Each of A and C is, independently, O or S;
B is OH, O⁻, or

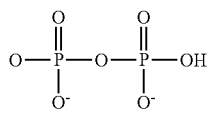

$R^c$ is H or $C_1$-$C_6$ alkyl; and n is 1-4.

Embodiments can include one or more of the features described above.

In a further aspect, this invention features an iRNA agent having a first strand and a second strand, wherein at least one subunit having a formula (I) or formula (II) is incorporated into at least one of said strands.

In one aspect, this invention features an iRNA agent having a first strand and a second strand, wherein at least two subunits having a formula (I) and/or formula (II) are incorporated into at least one of said strands.

In another aspect, this invention provides a method of making an iRNA agent described herein having a first strand and a second strand in which at least one subunit of formula (I) and/or (II) is incorporated in the strands. The method includes contacting the first strand with the second strand.

In a further aspect, this invention provides a method of modulating expression of a target gene, the method includes administering an iRNA agent described herein having a first strand and a second strand in which at least one subunit of formula (I) and/or (II) is incorporated in the strands. to a subject.

In one aspect, this invention features a pharmaceutical composition having an iRNA agent described herein having a first strand and a second strand in which at least one subunit of formula (I) and/or (II) is incorporated in the strands and a pharmaceutically acceptable carrier.

RRMSs described herein may be incorporated into any double-stranded RNA-like molecule described herein, e.g., an iRNA agent. An iRNA agent may include a duplex comprising a hybridized sense and antisense strand, in which the antisense strand and/or the sense strand may include one or more of the RRMSs described herein. An RRMS can be introduced at one or more points in one or both strands of a double-stranded iRNA agent. An RRMS can be placed at or near (within 1, 2, or 3 positions) of the 3' or 5' end of the sense strand or at near (within 2 or 3 positions of) the 3' end of the antisense strand. In some embodiments it is preferred to not have an RRMS at or near (within 1, 2, or 3 positions of) the 5' end of the antisense strand. An RRMS can be internal, and will preferably be positioned in regions not critical for antisense binding to the target.

In an embodiment, an iRNA agent may have an RRMS at (or within 1, 2, or 3 positions of) the 3' end of the antisense strand. In an embodiment, an iRNA agent may have an RRMS at (or within 1, 2, or 3 positions of) the 3' end of the antisense strand and at (or within 1, 2, or 3 positions of) the 3' end of the sense strand. In an embodiment, an iRNA agent may have an RRMS at (or within 1, 2, or 3 positions of) the 3' end of the antisense strand and an RRMS at the 5' end of the sense strand, in which both ligands are located at the same end of the iRNA agent.

In certain embodiments, two ligands are tethered, preferably, one on each strand and are hydrophobic moieties. While not wishing to be bound by theory, it is believed that pairing of the hydrophobic ligands can stabilize the iRNA agent via intermolecular van der Waals interactions.

In an embodiment, an iRNA agent may have an RRMS at (or within 1, 2, or 3 positions of) the 3' end of the antisense strand and an RRMS at the 5' end of the sense strand, in which both RRMSs may share the same ligand (e.g., cholic acid) via connection of their individual tethers to separate positions on the ligand. A ligand shared between two proximal RRMSs is referred to herein as a "hairpin ligand."

In other embodiments, an iRNA agent may have an RRMS at the 3' end of the sense strand and an RRMS at an internal position of the sense strand. An iRNA agent may have an RRMS at an internal position of the sense strand; or may have an RRMS at an internal position of the antisense strand; or may have an RRMS at an internal position of the sense strand and an RRMS at an internal position of the antisense strand.

In preferred embodiments the iRNA agent includes a first and second sequences, which are preferably two separate molecules as opposed to two sequences located on the same strand, have sufficient complementarity to each other to hybridize (and thereby form a duplex region), e.g., under physiological conditions, e.g., under physiological conditions but not in contact with a helicase or other unwinding enzyme.

It is preferred that the first and second sequences be chosen such that the ds iRNA agent includes a single strand or unpaired region at one or both ends of the molecule. Thus, a ds iRNA agent contains first and second sequences, preferable paired to contain an overhang, e.g., one or two 5' or 3' overhangs but preferably a 3' overhang of 2-3 nucleotides. Most embodiments will have a 3' overhang. Preferred sRNA agents will have single-stranded overhangs, preferably 3' overhangs, of 1 or preferably 2 or 3 nucleotides in length at each end. The overhangs can be the result of one strand being longer than the other, or the result of two strands of the same length being staggered. 5' ends are preferably phosphorylated.

Other modifications to sugars, bases, or backbones described herein can be incorporated into the iRNA agents.

The iRNA agents can take an architecture or structure described herein. The iRNA agents can be palindromic, or double targeting, as described herein.

The iRNA agents can have a sequence such that a non-cannonical or other than cannonical Watson-Crick structure is formed between two monomers of the iRNA agent or between a strand of the iRNA agent and another sequence, e.g., a target or off-target sequence, as is described herein.

The iRNA agent can be selected to target any of a broad spectrum of genes, including any of the genes described herein.

In a preferred embodiment the iRNA agent has an architecture (architecture refers to one or more of overall length, length of a duplex region, the presence, number, location, or length of overhangs, single strand versus double strand form) described herein. E.g., the iRNA agent can be less than 30 nucleotides in length, e.g., 21-23 nucleotides. Preferably, the iRNA is 21 nucleotides in length and there is a duplex region of about 19 pairs. In one embodiment, the iRNA is 21 nucleotides in length, and the duplex region of the iRNA is 19 nucleotides. In another embodiment, the iRNA is greater than 30 nucleotides in length.

In some embodiment the duplex region of the iRNA agent will have, mismatches. Preferably it will have no more than 1, 2, 3, 4, or 5 bases, which do not form canonical Watson-Crick pairs or which do not hybridize. Overhangs are discussed in detail elsewhere herein but are preferably about 2 nucleotides in length. The overhangs can be complementary to the gene sequences being targeted or can be other sequence. TT is a preferred overhang sequence. The first and second iRNA agent sequences can also be joined, e.g., by additional bases to form a hairpin, or by other non-base linkers.

In addition of the RRMS-containing bases the iRNA agents described herein can include nuclease resistant monomers (NRMs).

In another aspect, the invention features an iRNA agent to which is conjugated a lipophilic moiety, e.g., cholesterol, e.g., by conjugation to an RRMS of an iRNA agent. In a preferred embodiment, the lipophilic moiety enhances entry of the iRNA agent into a cell. In a preferred embodiment, the cell is part of an organism, tissue, or cell line, e.g., a primary cell line, immortalized cell line, or any type of cell line disclosed herein. Thus, the conjugated iRNA agent an be used to silence a target gene in an organism, e.g., a mammal, e.g., a human, or to silence a target gene in a cell line or in cells which are outside an organism.

The lipophilic moiety can be chosen, for example, from the group consisting of a lipid, cholesterol, oleyl, retinyl, cholesteryl residues, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine. A preferred lipophilic moiety is cholesterol.

The iRNA agent can have a first strand and a second strand, wherein at least one subunit having formula (I) or formula (II) is incorporated into at least one of the strands. The iRNA agent can have one or more of any of the features described herein. For example, when the subunit is of formula (I), $R^d$ can be cholesterol; X can be $N(CO)R^7$ or $NR^7$, Y can be $CR^9R^{10}$, and Z can be absent, and $R^1$ can be $(CH_2)_nOR^b$ and $R^3$ can be $OR^a$; X can be $N(CO)R^7$ or $NR^7$, Y can be $CR^9R^{10}$, and Z can be $CR^{11}R^{12}$, and $R^9$ can be $(CH_2)_nOR^b$ and $R^{10}$ can be $OR^a$; X can be $N(CO)R^7$ or $NR^7$, Y can be $NR^8$, and Z can be $CR^{11}R^{12}$, and $R^1$ can be $(CH_2)_nOR^b$ and $R^3$ can be $OR^a$; X can be $CH_2$; Y can be $CR^9R^{10}$; and Z can be $CR^{11}R^{12}$, in which $R^6$ can be $C(O)NHR^7$; or X can be $CH_2$; Y can be $CR^9R^{10}$; and Z can be $CR^{11}R^{12}$, in which $R^{11}$ or $R^{12}$ can be $C(O)NHR^7$ or $R^8$ and $R^{11}$ together can be $C_5$ or $C_6$ cycloalkyl substituted with $N(CH3)R^7$.

In a preferred embodiment, the lipophilic moiety, e.g., a cholesterol, enhances entry of the iRNA agent into a synoviocyte, myocyte, keratinocyte, hepatocyte, leukocyte, endothelial cell (e.g., a kidney cell), B-cell, T-cell, epithelial cell, mesodermal cell, myeloid cell, neural cell, neoplastic cell, mast cell, or fibroblast cell. In certain aspects, a myocyte can be a smooth muscle cell or a cardiac myocyte, a fibroblast cell can be a dermal fibroblast, and a leukocyte can be a monocyte. In another preferred embodiment, the cell can be from an adherent tumor cell line derived from a tissue, such as bladder, lung, breast, cervix, colon, pancreas, prostate, kidney, liver, skin, or nervous system (e.g., central nervous system).

In a preferred embodiment, the iRNA agent targets a protein tyrosine phosphatase (PTP-1B) gene or a MAP kinase gene, such as ERK1, ERK2, JNK1, JNK2, or p38. In a preferred embodiment, these iRNA agents are used to silence genes in a fibroblast cell.

In a preferred embodiment, the iRNA agent targets an MDR, Myc, Myb, c-Myc, N-Myc, L-Myc, c-Myb, a-Myb, b-Myb, v-Myb, cyclin D1, Cyclin D2, cyclin E, CDK4, cdc25A, CDK2, or CDK4 gene. In a preferred embodiment, these iRNA agents are used to silence genes in an epithelial cell or mesodermal cell.

In a preferred embodiment, the iRNA agent targets a G72 or DAAO gene. In a preferred embodiment, these iRNA agents are used to silence genes in a neural cell.

In a preferred embodiment, the iRNA agent targets a gene of the telomerase pathway, such as a TERT or TR/TERC. In a preferred embodiment, these iRNA agents are used to silence genes in a keratinocyte.

In a preferred embodiment, the iRNA agent targets an interleukin gene, such as IL-1, IL-2, IL-5, IL-8, IL-10, IL-15, IL-16, IL-17, or IL-18. In another preferred embodiment, the iRNA agent targets an interleukin receptor gene, or a chromosomal translocation, such as BCR-ABL, TEL-AML-1, EWS-FLI1, EWS-ERG, TLS-FUS, PAX3-FKHR, or AML-ETO. In a preferred embodiment, these iRNA agents are used to silence genes in a lymphoma or a leukemia cell.

In a preferred embodiment, the iRNA agent targets a GRB2 associated binding protein. In a preferred embodiment, these iRNA agents are used to silence genes in a mast cell.

In a preferred embodiment, the iRNA agent targets a growth factor or growth factor receptor, such as a TGFbeta or TGFbeta Receptor; PDGF or PDGFR; VEGF or VEGFr1, VEGFr2, or VEGFr3; or IGF-1R, DAF-2, or InR. In another preferred embodiment, the iRNA agent targets PRL1, PRL2, PRL3, protein kinase C (PKC), PKC receptor, MDR1, TERT, TR/TERC, cyclin D1, NF-KappaB, REL-A, REL-B, PCNA, CHK-1, c-fos, jun, or BCL-2. In a preferred embodiment, these iRNA agents are used to silence genes in an adherent tumor cell line.

In a preferred embodiment, the iRNA agent targets an exogenous gene of a genetically modified cell. An exogenous gene can be, for example, a viral or bacterial gene that derives from an organism that has invaded or infected the cell, or the exogenous gene can be any gene introduced into the cell by natural or artificial means, such as by a genetic recombination event. An iRNA agent can target a viral gene, for example, such as a hepatitis viral gene (e.g., a gene of an HAV, HBV, or HCV). Alternatively, or in addition, the iRNA agent can silence a reporter gene, such as GFP or beta galactosidase and the like. These iRNA agents can be used to silence exogenous genes in an adherent tumor cell line.

In a preferred embodiment, the iRNA agent to which the lipophilic moiety is conjugated silences at least one gene, e.g., any gene described herein, in any one of a number of cell lines including, but not limited to, a 3T3, DLD2, THP1, Raw264.7, IC21, P388D1, U937, HL60, SEM-K2, WEHI-231, HB56, TIB55, Jurkat, J45.01, K562, EL4, LRMB, Bcl-1, BC-3, TF1, CTLL-2, C1R, Rat6, VERO, MRC5, CV1, Cos7, RPTE, A10, T24, J82, A549, A375, ARH-77, Calu1, SW480, SW620, SKOV3, SK-UT, CaCo2, A375, C8161, CCRF-CEM, MCF-7, MDA-MB-231, MOLT, mIMCD-3, NHDF, HeLa, HeLa-S3, Huh1, Huh4, Huh7, HUVEC, HASMC, HEKn, HEKa, MiaPaCell, Panc1, PC-3, LNCaP, HepG2, or U87 cell line. Cell lines are available from a variety of sources known to those with skill in the art (see, e.g., the American Type Culture Collection (ATCC) (Manassas, Va.)).

In another aspect, the invention provides, methods of silencing a target gene by providing an iRNA agent to which a lipophilic moiety is conjugated, e.g., a lipophilic conjugated iRNA agent described herein, to a cell. In a preferred embodiment the conjugated iRNA agent an be used to silence a target gene in an organism, e.g., a mammal, e.g., a human, or to silence a target gene in a cell line or in cells which are outside an organism. In the case of a whole organism, the method can be used to silence a gene, e.g., a gene described herein, and treat a condition mediated by the gene. In the case of use on a cell which is not part of an organism, e.g., a primary cell line, secondary cell line, tumor cell line, or transformed or immortalized cell line, the iRNA agent to which a lipophilic moiety is conjugated can be used to silence a gene, e.g., one described herein. Cells which are not part of a whole organism can be used in an initial screen to determine if an iRNA agent is effective in silencing a gene. A test in cells which are not part of a whole organism can be followed by testing the iRNA agent in a whole animal. In preferred embodiments, the iRNA agent which is conjugated to a lipophilic moiety is administered to an organism, or contacted with a cell which is not part of an organism, in the absence of (or in a reduced amount of) other reagents that facilitate or enhance delivery, e.g., a compound which enhances transit through the cell membrane. (A reduced amount can be an amount of such reagent which is reduced in comparison to what would be needed to get an equal amount of nonconjugated iRNA agent into the target cell). E.g., the iRNA agent which is conjugated to a lipophilic moiety is administered to an organism, or contacted with a cell which is not part of an organism, in the absence (or reduced amount) of: an additional lipophilic moiety; a transfection agent, e.g., concentrations of an ion or other substance which substantially alters cell permeability to an iRNA agent; a transfecting agent such as Lipofectamine™ (Invitrogen, Carlsbad, Calif.), Lipofectamine 2000™, TranslT-TKO™ (Minis, Madison, Wis.), FuGENE 6 (Roche, Indianapolis, Ind.), polyethylenimine, X-tremeGENE Q2 (Roche, Indianapolis, Ind.), DOTAP, DOSPER, Metafectene™ (Biontex, Munich, Germany), and the like.

In a preferred embodiment the iRNA agent is suitable for delivery to a cell in vivo, e.g., to a cell in an organism. In another aspect, the iRNA agent is suitable for delivery to a cell in vitro, e.g., to a cell in a cell line.

An iRNA agent to which a lipophilic moiety is attached can target any gene described herein and can be delivered to any cell type described herein, e.g., a cell type in an organism, tissue, or cell line. Delivery of the iRNA agent can be in vivo, e.g., to a cell in an organism, or in vitro, e.g., to a cell in a cell line.

In another aspect, the invention provides compositions of iRNA agents described herein, and in particular compositions of an iRNA agent to which a lipophilic moiety is conjugated, e.g., a lipophilic conjugated iRNA agent described herein. In a preferred embodiment the composition is a pharmaceutically acceptable composition.

In preferred embodiments, the composition, e.g., pharmaceutically acceptable composition, is free of, has a reduced amount of, or is essentially free of other reagents that facilitate or enhance delivery, e.g., compounds which enhance transit through the cell membrane. (A reduced amount can be an amount of such reagent which is reduced in comparison to what would be needed to get an equal amount of nonconjugated iRNA agent into the target cell). E.g., the composition is free of, has a reduced amount of, or is essentially free of: an additional lipophilic moiety; a transfection agent, e.g., concentrations of an ion or other substance which substantially alters cell permeability to an iRNA agent; a transfecting agent such as Lipofectamine™ (Invitrogen, Carlsbad, Calif.), Lipofectamine 2000™, TransIT-TKO™ (Minis, Madison, Wis.), FuGENE 6 (Roche, Indianapolis, Ind.), polyethylenimine, X-tremeGENE Q2 (Roche, Indianapolis, Ind.), DOTAP, DOSPER, Metafectene™ (Biontex, Munich, Germany), and the like.

In a preferred embodiment the composition is suitable for delivery to a cell in vivo, e.g., to a cell in an organism. In another aspect, the iRNA agent is suitable for delivery to a cell in vitro, e.g., to a cell in a cell line.

The RRMS-containing iRNA agents can be used in any of the methods described herein, e.g., to target any of the genes described herein or to treat any of the disorders described herein. They can be incorporated into any of the formulations, modes of delivery, delivery modalities, kits or preparations, e.g., pharmaceutical preparations, described herein. E.g., a kit which includes one or more of the iRNA agents described herein, a sterile container in which the iRNA agent is disclosed, and instructions for use.

The methods and compositions of the invention, e.g., the RRSM-containing iRNA agents described herein, can be used with any of the iRNA agents described herein. In addition, the methods and compositions of the invention can be used for the treatment of any disease or disorder described herein, and for the treatment of any subject, e.g., any animal, any mammal, such as any human.

The methods and compositions of the invention, e.g., the RRMS-containing iRNA agents described herein, can be used with any dosage and/or formulation described herein, as well as with any route of administration described herein.

The non-ribose scaffolds, as well as monomers and dimers of the RRMSs described herein are within the invention The details of one or more embodiments of the invention are set forth in the accompanying drawings and the description below. Other features and advantages of the invention will be apparent from the description and drawings, and from the claims. This application incorporates all cited references, patents, and patent applications by references in their entirety for all purposes.

DESCRIPTION OF DRAWINGS

FIG. 3A (Panel 1) shows pyrroline-based RRMSs; FIG. 3B (panel 2) shows 3-hydroxyproline-based RRMSs; FIG. 3C (panel 3) shows piperidine-based RRMSs; FIG. 3D (panel 4) shows morpholine and piperazine-based RRMSs; and FIG. 3E (panel 5) shows decalin-based RRMSs. $R_1$ is succinate or phosphoramidate and $R_2$ is H or a conjugate ligand.

DETAILED DESCRIPTION

Figure 1:
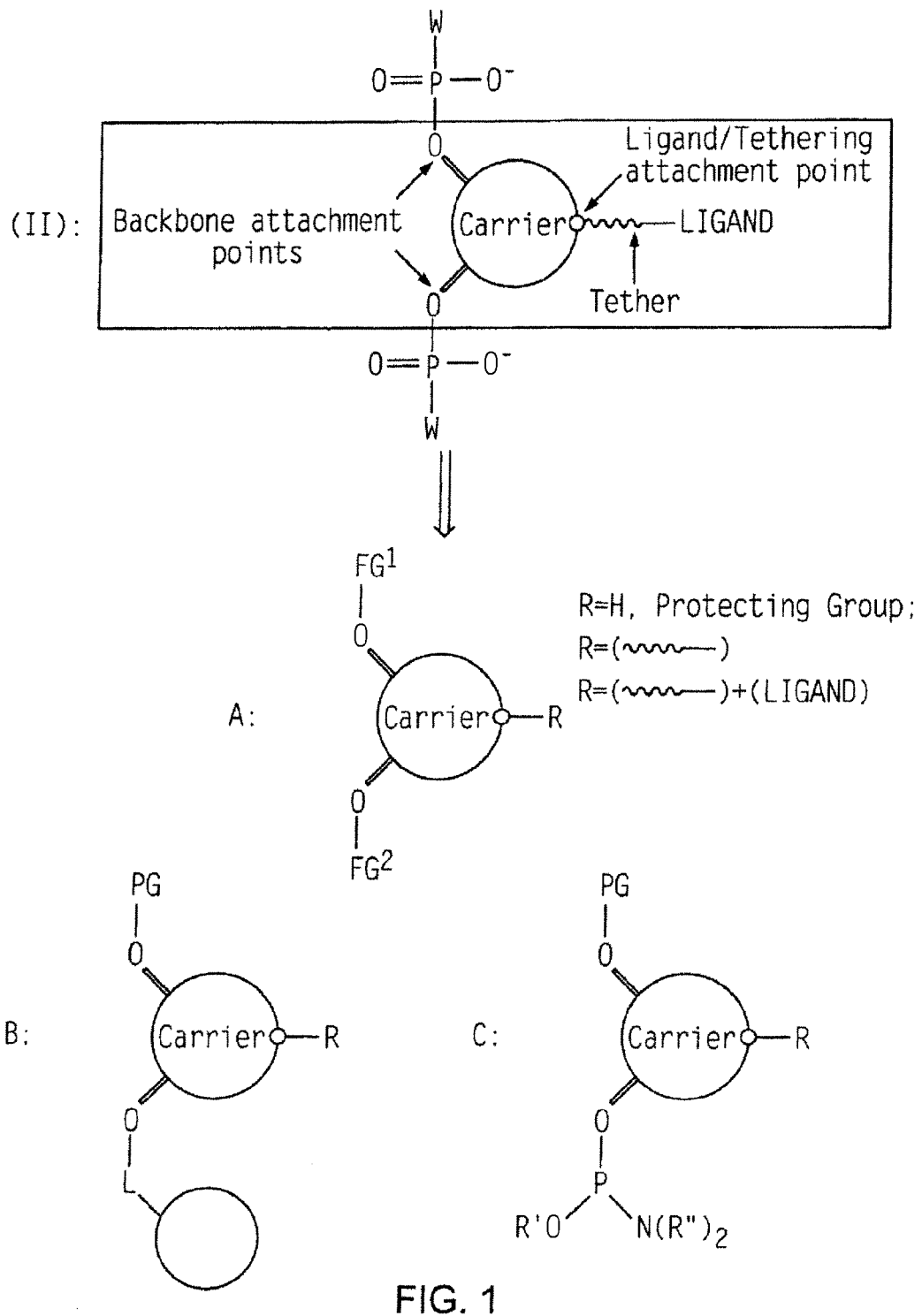
FIG. 1 a general synthetic scheme for incorporation of RRMS monomers into an oligonucleotide.

Double-stranded (dsRNA) directs the sequence-specific silencing of mRNA through a process known as RNA interference (RNAi). The process occurs in a wide variety of organisms, including mammals and other vertebrates.

It has been demonstrated that 21-23 nt fragments of dsRNA are sequence-specific mediators of RNA silencing, e.g., by causing RNA degradation. While not wishing to be bound by theory, it may be that a molecular signal, which may be merely the specific length of the fragments, present in these 21-23 nt fragments recruits cellular factors that mediate RNAi. Described herein are methods for preparing and administering these 21-23 nt fragments, and other iRNAs agents, and their use for specifically inactivating gene function. The use of iRNAs agents (or recombinantly produced or chemically synthesized oligonucleotides of the same or similar nature) enables the targeting of specific mRNAs for silencing in mammalian cells. In addition, longer dsRNA agent fragments can also be used, e.g., as described below.

Although, in mammalian cells, long dsRNAs can induce the interferon response which is frequently deleterious, sRNAs do not trigger the interferon response, at least not to an extent that is deleterious to the cell and host. In particular, the length of the iRNA agent strands in an sRNA agent can be less than 31, 30, 28, 25, or 23 nt, e.g., sufficiently short to avoid inducing a deleterious interferon response. Thus, the administration of a composition of sRNA agent (e.g., formulated as described herein) to a mammalian cell can be used to silence expression of a target gene while circumventing the interferon response. Further, use of a discrete species of iRNA agent can be used to selectively target one allele of a target gene, e.g., in a subject heterozygous for the allele.

Moreover, in one embodiment, a mammalian cell is treated with an iRNA agent that disrupts a component of the interferon response, e.g., double stranded RNA (dsRNA)-activated protein kinase PKR. Such a cell can be treated with a second iRNA agent that includes a sequence complementary to a target RNA and that has a length that might otherwise trigger the interferon response.

As used herein, a "subject" refers to a mammalian organism undergoing treatment for a disorder mediated by unwanted target gene expression. The subject can be any mammal, such as a cow, horse, mouse, rat, dog, pig, goat, or a primate. In the preferred embodiment, the subject is a human.

Because iRNA agent mediated silencing persists for several days after administering the iRNA agent composition, in many instances, it is possible to administer the composition with a frequency of less than once per day, or, for some instances, only once for the entire therapeutic regimen. For example, treatment of some cancer cells may be mediated by a single bolus administration, whereas a chronic viral infection may require regular administration, e.g., once per week or once per month.

A number of exemplary routes of delivery are described that can be used to administer an iRNA agent to a subject. In addition, the iRNA agent can be formulated according to an exemplary method described herein.

Ligand-Conjugated Monomer Subunits and Monomers for Oligonucleotide Synthesis

DEFINITIONS

The term "halo" refers to any radical of fluorine, chlorine, bromine or iodine.

The term "alkyl" refers to a hydrocarbon chain that may be a straight chain or branched chain, containing the indicated number of carbon atoms. For example, $C_1$-$C_{12}$ alkyl indicates that the group may have from 1 to 12 (inclusive) carbon atoms in it. The term "haloalkyl" refers to an alkyl in which one or more hydrogen atoms are replaced by halo, and includes alkyl moieties in which all hydrogens have been replaced by halo (e.g., perfluoroalkyl). Alkyl and haloalkyl groups may be optionally inserted with O, N, or S. The terms "aralkyl" refers to an alkyl moiety in which an alkyl hydrogen atom is replaced by an aryl group. Aralkyl includes groups in which more than one hydrogen atom has been replaced by an aryl group. Examples of "aralkyl" include benzyl, 9-fluorenyl, benzhydryl, and trityl groups.

The term "alkenyl" refers to a straight or branched hydrocarbon chain containing 2-8 carbon atoms and characterized in having one or more double bonds. Examples of a typical alkenyl include, but not limited to, allyl, propenyl, 2-butenyl, 3-hexenyl and 3-octenyl groups. The term "alkynyl" refers to a straight or branched hydrocarbon chain containing 2-8 carbon atoms and characterized in having one or more triple bonds. Some examples of a typical alkynyl are ethynyl, 2-propynyl, and 3-methylbutynyl, and propargyl. The $sp^2$ and $sp^3$ carbons may optionally serve as the point of attachment of the alkenyl and alkynyl groups, respectively.

The terms "alkylamino" and "dialkylamino" refer to —NH(alkyl) and —N(alkyl)$_2$ radicals respectively. The term "aralkylamino" refers to a —NH(aralkyl) radical. The term "alkoxy" refers to an —O-alkyl radical, and the terms "cycloalkoxy" and "aralkoxy" refer to an —O-cycloalkyl and O-aralkyl radicals respectively. The term "siloxy" refers to a $R_3SiO$— radical. The term "mercapto" refers to an SH radical. The term "thioalkoxy" refers to an —S-alkyl radical.

The term "alkylene" refers to a divalent alkyl (i.e., —R—), e.g., —CH$_2$—, —CH$_2$CH$_2$—, and —CH$_2$CH$_2$CH$_2$—. The term alkenylene refers to a divalent alkenyl (e.g., —CH$_2$CH═CH—, polyalkenyl). The term alkynylene refers to a divalent alkynyl (e.g., propargyl, polyalkynyl). The term "alkylenedioxo" refers to a divalent species of the structure —O—R—O—, in which R represents an alkylene.

The term "aryl" refers to an aromatic monocyclic, bicyclic, or tricyclic hydrocarbon ring system, wherein any ring atom can be substituted. Examples of aryl moieties include, but are not limited to, phenyl, naphthyl, anthracenyl, and pyrenyl.

The term "cycloalkyl" as employed herein includes saturated cyclic, bicyclic, tricyclic, or polycyclic hydrocarbon groups having 3 to 12 carbons, wherein any ring atom can be substituted. The cycloalkyl groups herein described may also contain fused rings. Fused rings are rings that share a common carbon-carbon bond or a common carbon atom (e.g., spiro-fused rings). Examples of cycloalkyl moieties include, but are not limited to, cyclohexyl, adamantyl, and norbornyl.

The term "heterocyclyl" refers to a nonaromatic 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein any ring atom can be substituted. The heterocyclyl groups herein described may also contain fused rings. Fused rings are rings that share a common carbon-carbon bond or a common carbon atom (e.g., spiro-fused rings). Examples of heterocyclyl include, but are not limited to tetrahydrofuranyl, tetrahydropyranyl, piperidinyl, morpholino, pyrrolinyl and pyrrolidinyl.

The term "cycloalkenyl" as employed herein includes partially unsaturated, nonaromatic, cyclic, bicyclic, tricyclic, or polycyclic hydrocarbon groups having 5 to 12 carbons, preferably 5 to 8 carbons, wherein any ring atom can be substituted. The cycloalkenyl groups herein described may also contain fused rings. Fused rings are rings that share a common carbon-carbon bond or a common carbon atom (e.g., spiro-fused rings). Examples of cycloalkenyl moieties include, but are not limited to cyclohexenyl, cyclohexadienyl, or norbornenyl.

The term "heterocycloalkenyl" refers to a partially saturated, nonaromatic 5-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein any ring atom can be substituted. The heterocycloalkenyl groups herein described may also contain fused rings. Fused rings are rings that share a common carbon-carbon bond or a common carbon atom (e.g., spiro-fused rings). Examples of heterocycloalkenyl include but are not limited to tetrahydropyridyl and dihydropyran.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein any ring atom can be substituted. The heteroaryl groups herein described may also contain fused rings that share a common carbon-carbon bond.

The term "oxo" refers to an oxygen atom, which forms a carbonyl when attached to carbon, an N-oxide when attached to nitrogen, and a sulfoxide or sulfone when attached to sulfur.

The term "acyl" refers to an alkylcarbonyl, cycloalkylcarbonyl, arylcarbonyl, heterocyclylcarbonyl, or heteroaryl carbonyl substituent, any of which may be further substituted by substituents.

The term "substituents" refers to a group "substituted" on an alkyl, cycloalkyl, alkenyl, alkynyl, heterocyclyl, heterocycloalkenyl, cycloalkenyl, aryl, or heteroaryl group at any atom of that group. Suitable substituents include, without limitation, alkyl, alkenyl, alkynyl, alkoxy, halo, hydroxy, cyano, nitro, amino, $SO_3H$, sulfate, phosphate, perfluoroalkyl, perfluoroalkoxy, methylenedioxy, ethylenedioxy, carboxyl, oxo, thioxo, imino (alkyl, aryl, aralkyl), $S(O)_n$alkyl (where n is 0-2), $S(O)_n$ aryl (where n is 0-2), $S(O)_n$ heteroaryl (where n is 0-2), $S(O)_n$ heterocyclyl (where n is 0-2), amine (mono-, di-, alkyl, cycloalkyl, aralkyl, heteroaralkyl, and combinations thereof), ester (alkyl, aralkyl, heteroaralkyl), amide (mono-, di-, alkyl, aralkyl, heteroaralkyl, and combinations thereof), sulfonamide (mono-, di-, alkyl, aralkyl, heteroaralkyl, and combinations thereof), unsubstituted aryl, unsubstituted heteroaryl, unsubstituted heterocyclyl, and unsubstituted cycloalkyl. In one aspect, the substituents on a group are independently any one single, or any subset of the aforementioned substituents.

The terms "adeninyl, cytosinyl, guaninyl, thyminyl, and uracilyl" and the like refer to radicals of adenine, cytosine, guanine, thymine, and uracil.

A "protected" moiety refers to a reactive functional group, e.g., a hydroxyl group or an amino group, or a class of molecules, e.g., sugars, having one or more functional groups, in which the reactivity of the functional group is temporarily blocked by the presence of an attached protecting group. Protecting groups useful for the monomers and methods described herein can be found, e.g., in Greene, T. W., *Protective Groups in Organic Synthesis* (John Wiley and Sons: New York), 1981, which is hereby incorporated by reference.

General

An RNA agent, e.g., an iRNA agent, containing a preferred, but nonlimiting ligand-conjugated monomer subunit is presented as formula (II) below and in the scheme in FIG. 1. The carrier (also referred to in some embodiments as a "linker") can be a cyclic or acyclic moiety and includes two "backbone attachment points" (e.g., hydroxyl groups) and a ligand. The ligand can be directly attached (e.g., conjugated) to the carrier or indirectly attached (e.g., conjugated) to the carrier by an inter8-29vening tether (e.g., an acyclic chain of one or more atoms; or a nucleobase, e.g., a naturally occurring nucleobase optionally having one or more chemical modifications, e.g., an unusual base; or a universal base). The carrier therefore also includes a "ligand or tethering attachment point" for the ligand and tether/tethered ligand, respectively.

The ligand-conjugated monomer subunit may be the 5' or 3' terminal subunit of the RNA molecule, i.e., one of the two "W" groups may be a hydroxyl group, and the other "W" group may be a chain of two or more unmodified or modified ribonucleotides. Alternatively, the ligand-conjugated monomer subunit may occupy an internal position, and both "W" groups may be one or more unmodified or modified ribonucleotides. More than one ligand-conjugated monomer subunit may be present in a RNA molecule, e.g., an iRNA agent. Preferred positions for inclusion of a tethered ligand-conjugated monomer subunits, e.g., one in which a lipophilic moiety, e.g., cholesterol, is tethered to the carrier are at the 3' terminus, the 5' terminus, or an internal position of the sense strand.

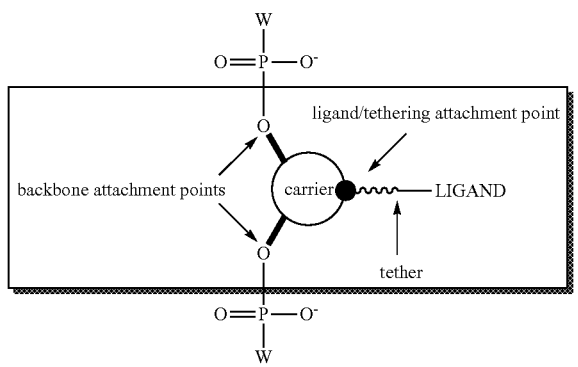

(II)

The modified RNA molecule of formula (II) can be obtained using oligonucleotide synthetic methods known in the art. In a preferred embodiment, the modified RNA molecule of formula (II) can be prepared by incorporating one or more of the corresponding monomer compounds (see, e.g., A, B, and C below and in the scheme in FIG. 1) into a growing sense or antisense strand, utilizing, e.g., phosphoramidite or H-phosphonate coupling strategies.

The monomers, e.g., a ligand-conjugated monomer, generally include two differently functionalized hydroxyl groups ($OFG^1$ and $OFG^2$), which are linked to the carrier molecule (see A below and in FIG. 1), and a ligand/tethering attachment point. As used herein, the term "functionalized hydroxyl group" means that the hydroxyl proton has been replaced by another substituent. As shown in representative structures B and C below and in FIG. 1, one hydroxyl group ($OFG^1$) on the carrier is functionalized with a protecting group (PG). The other hydroxyl group ($OFG^2$) can be functionalized with either (1) a liquid or solid phase synthesis support reagent (solid circle) directly or indirectly through a linker, L, as in B, or (2) a phosphorus-containing moiety, e.g., a phosphoramidite as in C. The tethering attachment point may be connected to a hydrogen atom, a suitable protecting group, a tether, or a tethered ligand at the time that the monomer is incorporated into the growing sense or antisense strand (see variable "R" in A below). Thus, the tethered ligand can be, but need not be attached to the monomer at the time that the monomer is incorporated into the growing strand. In certain embodiments, the tether, the ligand or the tethered ligand may be linked to a "precursor" ligand-conjugated monomer subunit after a "precursor" ligand-conjugated monomer subunit has been incorporated into the strand. The wavy line used below (and elsewhere herein) refers to a connection, and can represent a direct bond between the moiety and the attachment point or a tethering molecule which is interposed between the moiety and the attachment point. Directly tethered means the moiety is bound directly to the attachment point. Indirectly tethered means that there is a tether molecule interposed between the attachment point and the moiety.

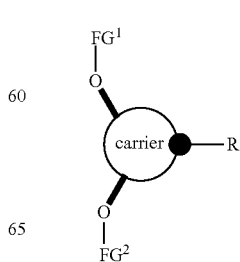

A

-continued

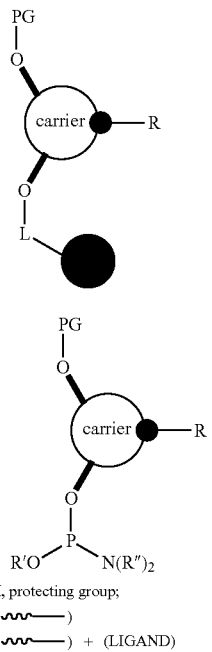

R = H, protecting group;
R = (∿∿—)
R = (∿∿—) + (LIGAND)

The (OFG$^1$) protecting group may be selected as desired, e.g., from T. W. Greene and P. G. M. Wuts, *Protective Groups in Organic Synthesis,* 2d. Ed., John Wiley and Sons (1991). The protecting group is preferably stable under amidite synthesis conditions, storage conditions, and oligonucleotide synthesis conditions. Hydroxyl groups, —OH, are nucleophilic groups (i.e., Lewis bases), which react through the oxygen with electrophiles (i.e., Lewis acids). Hydroxyl groups in which the hydrogen has been replaced with a protecting group, e.g., a triarylmethyl group or a trialkylsilyl group, are essentially unreactive as nucleophiles in displacement reactions. Thus, the protected hydroxyl group is useful in preventing e.g., homocoupling of compounds exemplified by structure C during oligonucleotide synthesis. In some embodiments, a preferred protecting group is the dimethoxytrityl group. In other embodiments, a preferred protecting group is a silicon-based protecting group having the formula below:

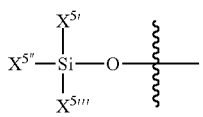

Figure 2A:
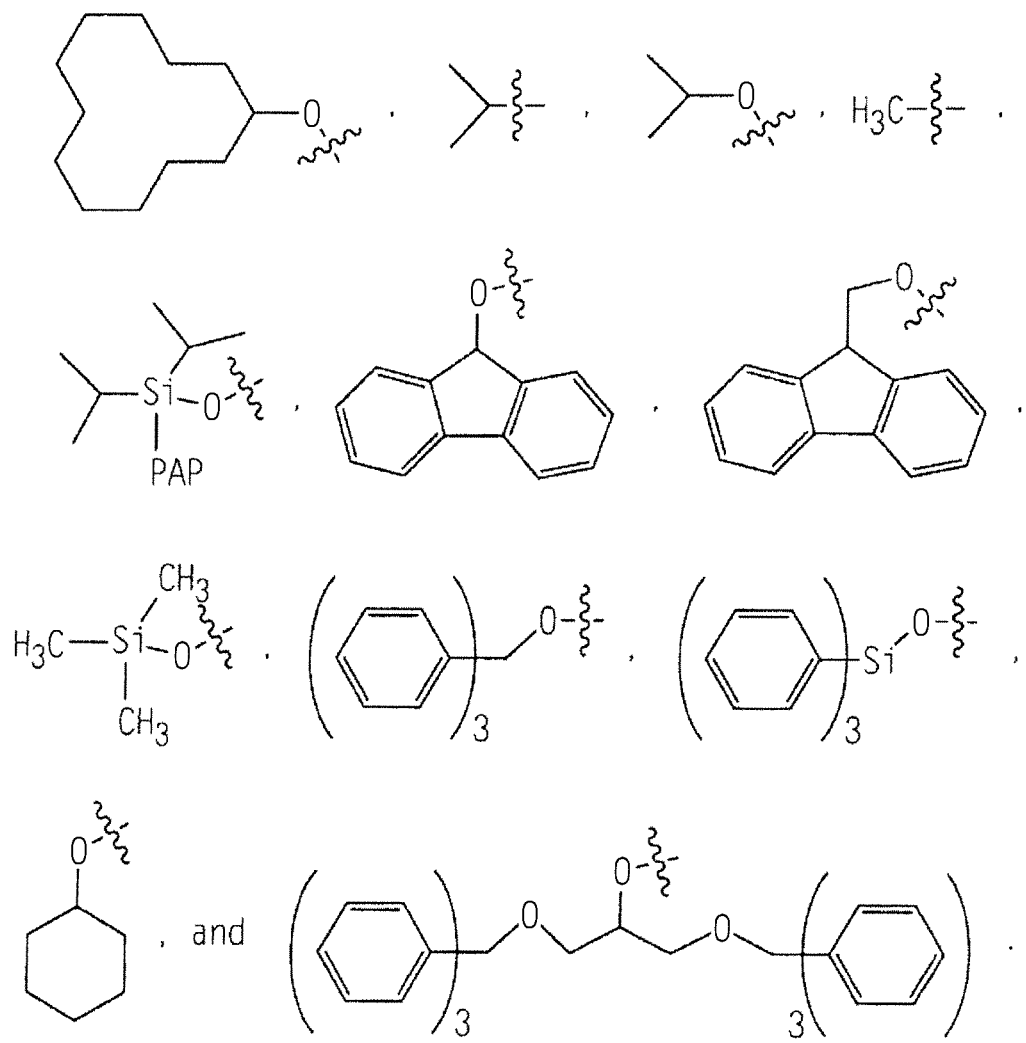
FIG. 2A is a list of substituents that may be present on silicon in OFG[1].

X5', X5", and X5''' can be selected from substituted or unsubstituted alkyl, cycloalkyl, aryl, araklyl, heteroaryl, alkoxy, cycloalkoxy, aralkoxy, aryloxy, heteroaryloxy, or siloxy (i.e., R$_3$SiO—, the three "R" groups can be any combination of the above listed groups). X$^{5'}$, X$^{5''}$, and X$^{5'''}$ may all be the same or different; also contemplated is a combination in which two of X$^{5'}$, X$^{5''}$, and X$^{5'''}$ are identical and the third is different. In certain embodiments X$^{5'}$, X$^{5''}$, and X$^{5'''}$ include at least one alkoxy or siloxy groups and may be any one of the groups listed in FIG. 2A, a preferred combination includes X$^{5'}$, X$^{5''}$=trimethylsiloxy and X$^{5'''}$=1,3-tri-2-propoxy or cyclododecyloxy.

Other preferred combinations of X$^{5'}$, X$^{5''}$, and X$^{5'''}$ include those that result in OFG$^1$ groups that meet the deprotection and stability criteria delineated below. The group is preferably stable under amidite synthesis conditions, storage conditions, and oligonucleotide synthesis conditions. Rapid removal, i.e., less than one minute, of the silyl group from e.g., a support-bound oligonucleotide is desirable because it can reduce synthesis times and thereby reduce exposure time of the growing oligonucleotide chain to the reagents. Oligonucleotide synthesis can be improved if the silyl protecting group is visible during deprotection, e.g., from the addition of a chromophore silyl substituent.

Selection of silyl protecting groups can be complicated by the competing demands of the essential characteristics of stability and facile removal, and the need to balance these competitive goals. Most substituents that increase stability can also increase the reaction time required for removal of the silyl group, potentially increasing the level of difficulty in removal of the group.

The addition of alkoxy and siloxy substituents to OFG$^1$ silicon-containing protecting groups increases the susceptibility of the protecting groups to fluoride cleavage of the silylether bonds. Increasing the steric bulk of the substituents preserves stability while not decreasing fluoride lability to an equal extent. An appropriate balance of substituents on the silyl group makes a silyl ether a viable nucleoside protecting group.

Candidate OFG$^1$ silicon-containing protecting groups may be tested by exposing a tetrahydrofuran solution of a preferred carrier bearing the candidate OFG$^1$ group to five molar equivalents of tetrahydrofuran at room temperature. The reaction time may be determined by monitoring the disappearance of the starting material by thin layer chromatography.

When the OFG$^2$ in B includes a linker, e.g., a relatively long organic linker, connected to a soluble or insoluble support reagent, solution or solid phase synthesis techniques can be employed to build up a chain of natural and/or modified ribonucleotides once OFG$^1$ is deprotected and free to react as a nucleophile with another nucleoside or monomer containing an electrophilic group (e.g., an amidite group). Alternatively, a natural or modified ribonucleotide or oligoribonucleotide chain can be coupled to monomer C via an amidite group or H-phosphonate group at OFG$^2$. Subsequent to this operation, OFG$^1$ can be deblocked, and the restored nucleophilic hydroxyl group can react with another nucleoside or monomer containing an electrophilic group. R' can be substituted or unsubstituted alkyl or alkenyl. In preferred embodiments, R' is methyl, allyl or 2-cyanoethyl. R" may a C$_1$-C$_{10}$ alkyl group, preferably it is a branched group containing three or more carbons, e.g., isopropyl.

OFG$^2$ in B can be hydroxyl functionalized with a linker, which in turn contains a liquid or solid phase synthesis support reagent at the other linker terminus. The support reagent can be any support medium that can support the monomers described herein. The monomer can be attached to an insoluble support via a linker, L, which allows the monomer (and the growing chain) to be solubilized in the solvent in which the support is placed. The solubilized, yet immobilized, monomer can react with reagents in the surrounding solvent; unreacted reagents and soluble by-products can be readily washed away from the solid support to which the monomer or monomer-derived products is attached. Alternatively, the monomer can be attached to a soluble support moiety, e.g., polyethylene glycol (PEG) and liquid phase synthesis techniques can be used to build up the chain. Linker and support medium selection is within skill of the art. Generally the linker may be —C(O)(CH$_2$)$_q$C(O)—, or —C(O)(CH$_2$)$_q$S—, in which q can be 0, 1, 2, 3, or 4;

preferably, it is oxalyl, succinyl or thioglycolyl. Standard control pore glass solid phase synthesis supports can not be used in conjunction with fluoride labile 5' silyl protecting groups because the glass is degraded by fluoride with a significant reduction in the amount of full-length product. Fluoride-stable polystyrene based supports or PEG are preferred.

The ligand/tethering attachment point can be any divalent, trivalent, tetravalent, pentavalent or hexavalent atom. In some embodiments, ligand/tethering attachment point can be a carbon, oxygen, nitrogen or sulfur atom. For example, a ligand/tethering attachment point precursor functional group can have a nucleophilic heteroatom, e.g., —SH, —NH$_2$, secondary amino, ONH$_2$, or NH$_2$NH$_2$. As another example, the ligand/tethering attachment point precursor functional group can be an olefin, e.g., —CH=CH$_2$, and the precursor functional group can be attached to a ligand, a tether, or tethered ligand using, e.g., transition metal catalyzed carbon-carbon (for example olefin metathesis) processes or cycloadditions (e.g., Diels-Alder). As a further example, the ligand/tethering attachment point precursor functional group can be an electrophilic moiety, e.g., an aldehyde. When the carrier is a cyclic carrier, the ligand/tethering attachment point can be an endocyclic atom (i.e., a constituent atom in the cyclic moiety, e.g., a nitrogen atom) or an exocyclic atom (i.e., an atom or group of atoms attached to a constituent atom in the cyclic moiety).

The carrier can be any organic molecule containing attachment points for OFG$^1$, OFG$^2$, and the ligand. In certain embodiments, carrier is a cyclic molecule and may contain heteroatoms (e.g., O, N or S). E.g., carrier molecules may include aryl (e.g., benzene, biphenyl, etc.), cycloalkyl (e.g., cyclohexane, cis or trans decalin, etc.), or heterocyclyl (piperazine, pyrrolidine, etc.). In other embodiments, the carrier can be an acyclic moiety, e.g., based on serinol. Any of the above cyclic systems may include substituents in addition to OFG$^1$, OFG$^2$, and the ligand.

Sugar-Based Monomers

In some embodiments, the carrier molecule is an oxygen containing heterocycle. Preferably the carrier is a ribose sugar as shown in structure LCM-I. In this embodiment, the monomer, e.g., a ligand-conjugated monomer is a nucleoside.

LCM-I

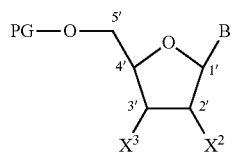

"B" represents a nucleobase, e.g., a naturally occurring nucleobase optionally having one or more chemical modifications, e.g., and unusual base; or a universal base.

As used herein, an "unusual" nucleobase can include any one of the following:

2-methyladeninyl,
N6-methyladeninyl,
2-methylthio-N6-methyladeninyl,
N6-isopentenyladeninyl,
2-methylthio-N6-isopentenyladeninyl,
N6-(cis-hydroxyisopentenyl)adeninyl,
2-methylthio-N6-(cis-hydroxyisopentenyl)adeninyl,
N6-glycinylcarbamoyladeninyl,
N6-threonylcarbamoyladeninyl,
2-methylthio-N6-threonyl carbamoyladeninyl,
N6-methyl-N6-threonylcarbamoyladeninyl,
N6-hydroxynorvalylcarbamoyladeninyl,
2-methylthio-N6-hydroxynorvalyl carbamoyladeninyl,
N6,N6-dimethyladeninyl,
3-methylcytosinyl,
5-methylcytosinyl,
2-thiocytosinyl,
5-formylcytosinyl,

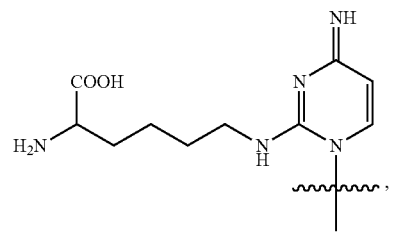 [SMILES: *n1ccc(=N)nc1NCCCCC(N)C(=O)O]

N4-methylcytosinyl,
5-hydroxymethylcytosinyl,
1-methylguaninyl,
N2-methylguaninyl,
7-methylguaninyl,
N2,N2-dimethylguaninyl,

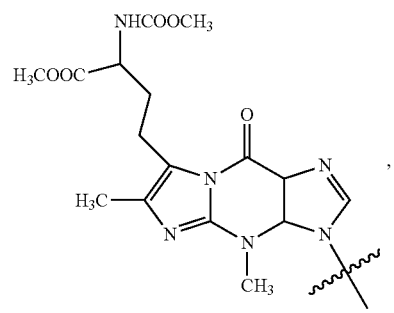

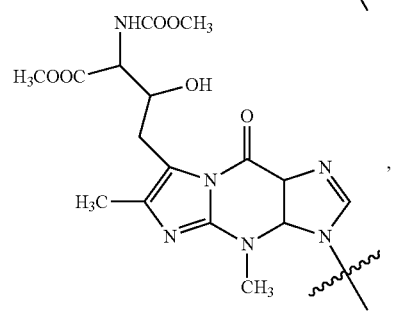

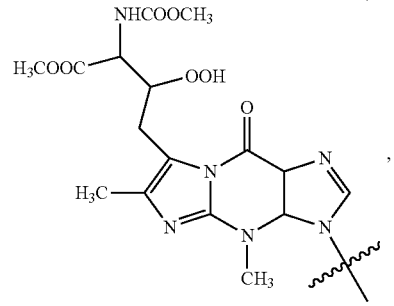

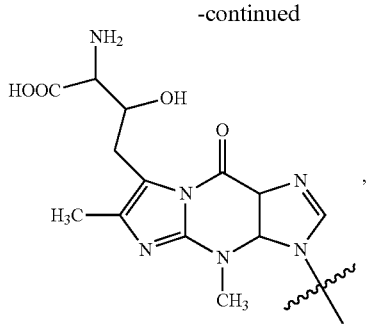
,

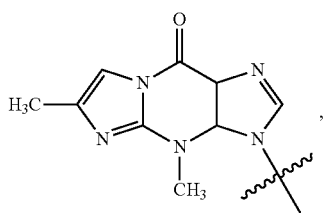
,

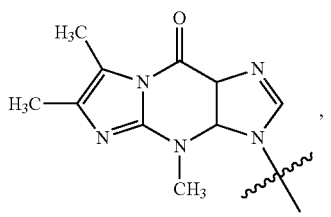
,

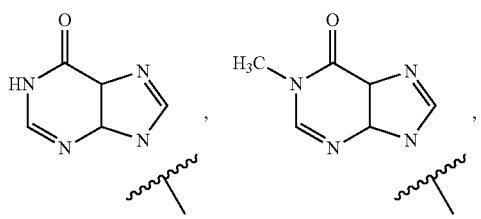
,

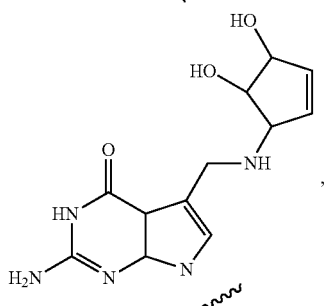
,

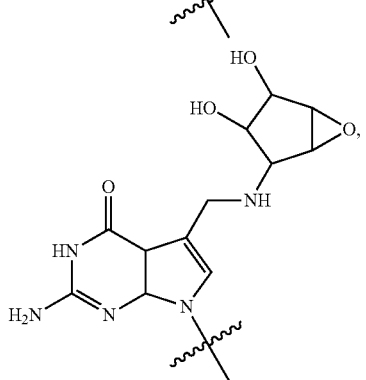

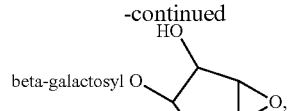
,

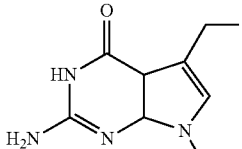
,

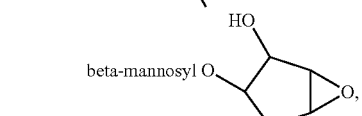
,

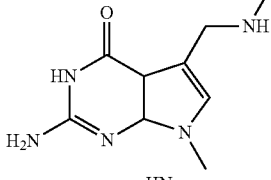
,

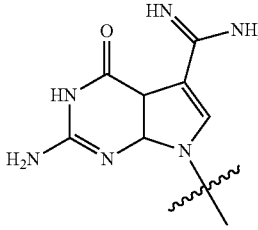

N2,7-dimethylguaninyl,
N2,N2,7-trimethylguaninyl,
1-methylguaninyl,
7-cyano-7-deazaguaninyl,
7-aminomethyl-7-deazaguaninyl,
pseudouracilyl,
dihydrouracilyl,
5-methyluracilyl,
1-methylpseudouracilyl,
2-thiouracilyl,
4-thiouracilyl,
2-thiothyminyl
5-methyl-2-thiouracilyl,
3-(3-amino-3-carboxypropyl)uracilyl,
5-hydroxyuracilyl,
5-methoxyuracilyl,
uracilyl 5-oxyacetic acid,
uracilyl 5-oxyacetic acid methyl ester,
5-(carboxyhydroxymethyl)uracilyl,
5-(carboxyhydroxymethyl)uracilyl methyl ester,
5-methoxycarbonylmethyluracilyl,
5-methoxycarbonylmethyl-2-thiouracilyl,
5-aminomethyl-2-thiouracilyl,
5-methylaminomethyluracilyl,
5-methylaminomethyl-2-thiouracilyl,
5-methylaminomethyl-2-selenouracilyl,
5-carbamoylmethyluracilyl,
5-carboxymethylaminomethyluracilyl,
5-carboxymethylaminomethyl-2-thiouracilyl,
3-methyluracilyl,
1-methyl-3-(3-amino-3-carboxypropyl)pseudouracilyl,
5-carboxymethyluracilyl,
5-methyldihydrouracilyl, or
3-methylpseudouracilyl.

A universal base can form base pairs with each of the natural DNA/RNA bases, exhibiting relatively little discrimination between them. In general, the universal bases are non-hydrogen bonding, hydrophobic, aromatic moieties which can stabilize e.g., duplex RNA or RNA-like molecules, via stacking interactions. A universal base can also include hydrogen bonding substituents. As used herein, a "universal base" can include anthracenes, pyrenes or any one of the following:

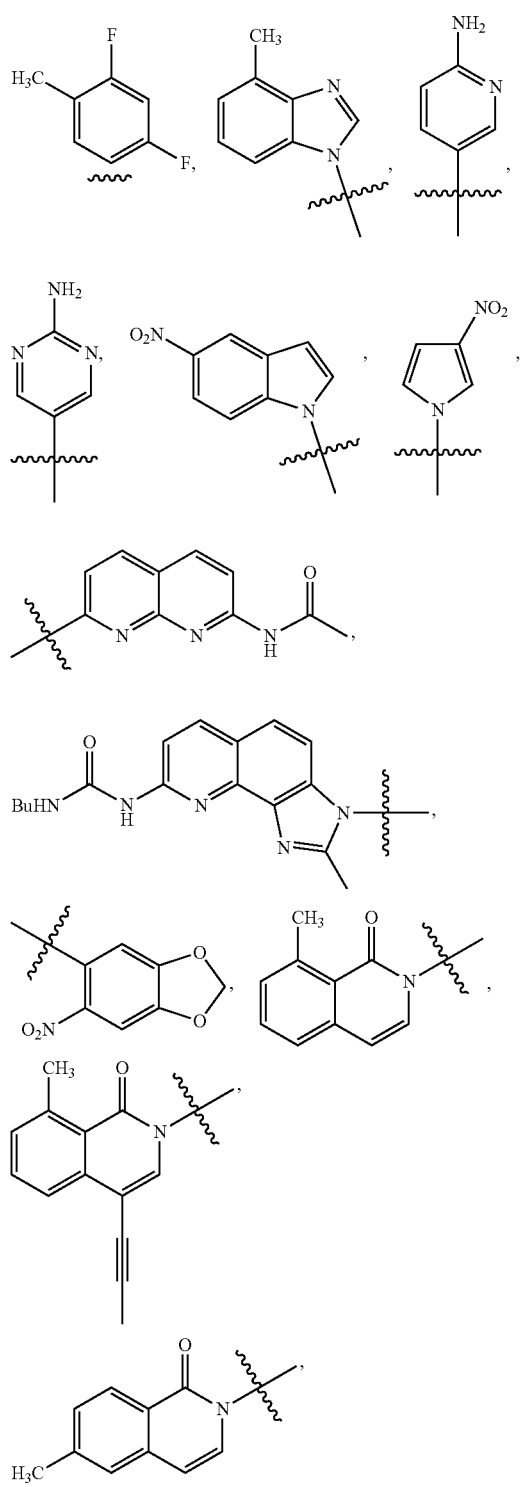

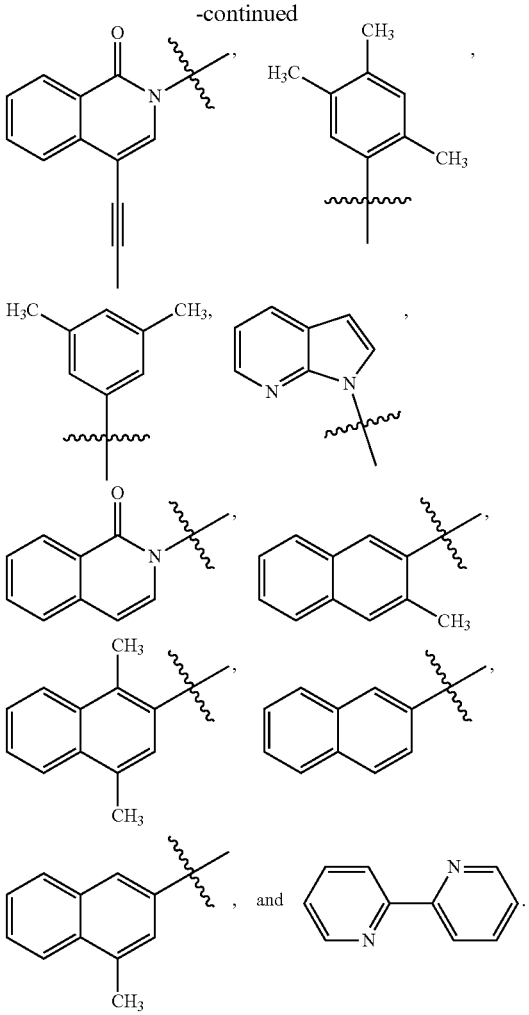

In some embodiments, B can form part of a tether that connects a ligand to the carrier. For example, the tether can be B—CH=CH—C(O)NH—(CH$_2$)$_5$—NHC(O)-LIGAND. In a preferred embodiment, the double bond is trans, and the ligand is a substituted or unsubstituted cholesterolyl radical (e.g., attached through the D-ring side chain or the C-3 hydroxyl); an aralkyl moiety having at least one sterogenic center and at least one substituent on the aryl portion of the aralkyl group; or a nucleobase. In certain embodiments, B, in the tether described above, is uracilyl or a universal base, e.g., an aryl moiety, e.g., phenyl, optionally having additional substituents, e.g., one or more fluoro groups. B can be substituted at any atom with the remainder of the tether.

$X^2$ can include "oxy" or "deoxy" substituents in place of the 2'-OH; or be a ligand or a tethered ligand.

Examples of "oxy"-substituents include alkoxy or aryloxy (OR, e.g., R=H, alkyl, cycloalkyl, aryl, aralkyl, heteroaryl, sugar, or protecting group); polyethyleneglycols (PEG), O(CH$_2$CH$_2$O)$_n$CH$_2$CH$_2$OR; "locked" nucleic acids (LNA) in which the 2' hydroxyl is connected, e.g., by a methylene bridge, to the 4' carbon of the same ribose sugar; O-PROTECTED AMINE (AMINE=NH$_2$; alkylamino, dialkylamino, heterocyclyl, arylamino, diaryl amino, heteroaryl amino, or diheteroaryl amino, ethylene diamine, polyamino) and aminoalkoxy, O(CH$_2$)$_n$PROTECTED AMINE, (e.g., AMINE=NH$_2$; alkylamino, dialkylamino, heterocyclyl, arylamino, diaryl amino, heteroaryl amino, or diheteroaryl amino, ethylene diamine, polyamino), and orthoester. Amine protecting groups can include formyl, amido, benzyl, allyl, etc.

Figure 2B:
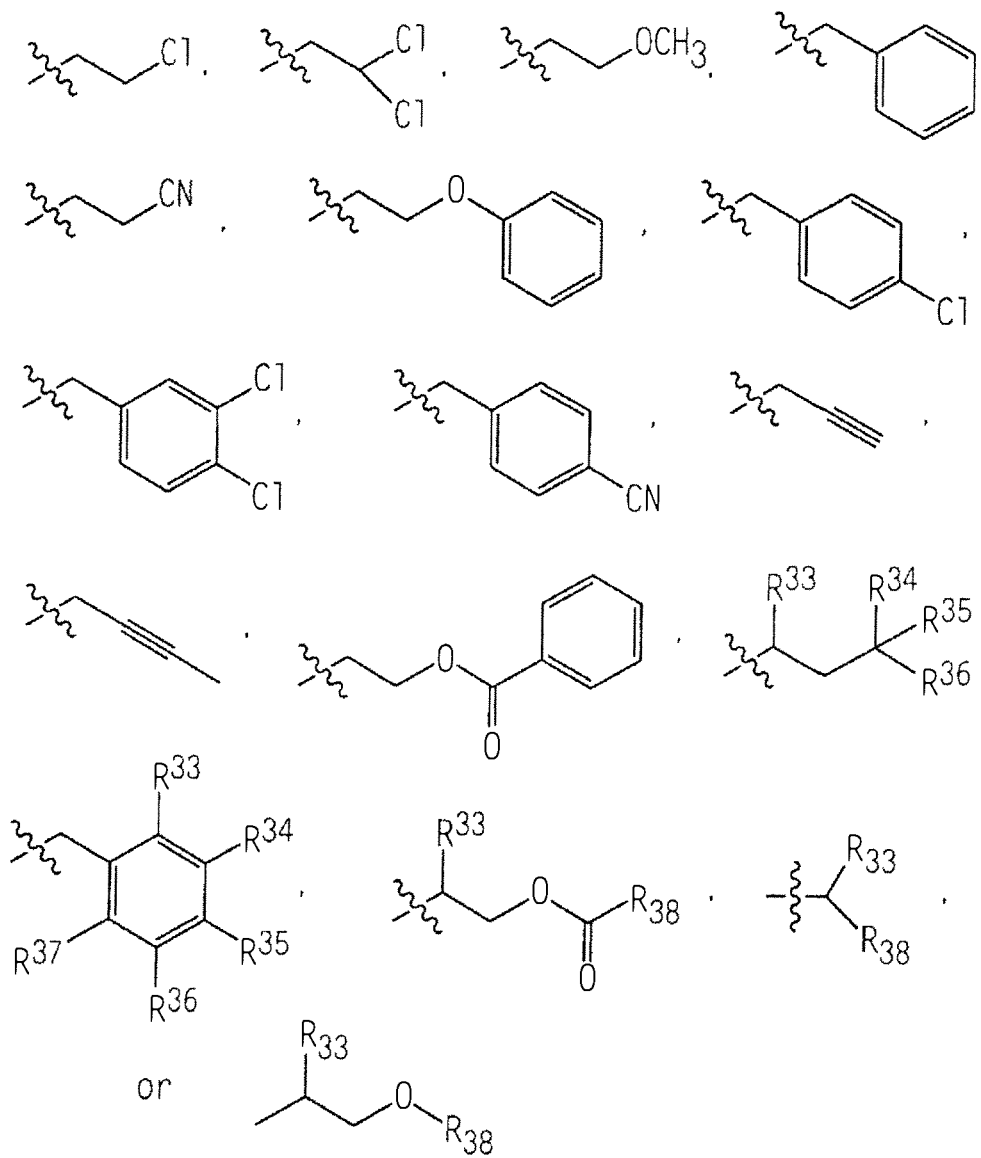
FIG. 2B is a list of substituents that may be present on the C2'-orthoester group.
Figure 3A:
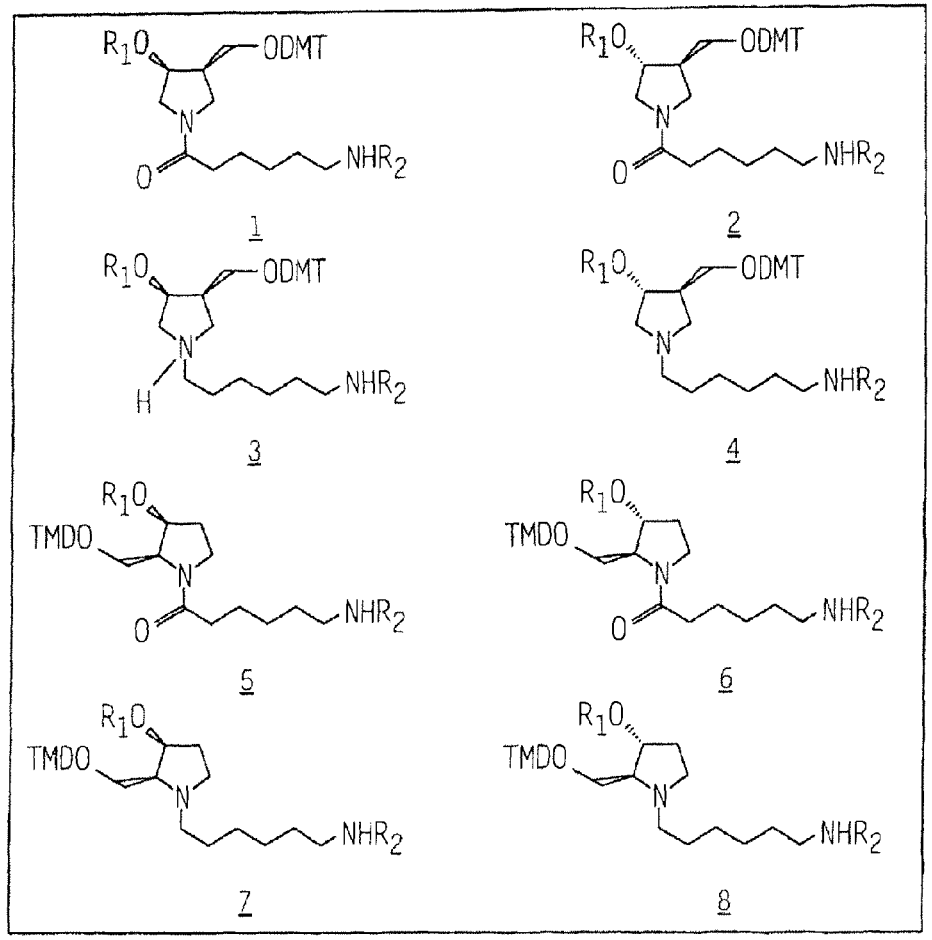
FIG. 3A-3E are a list of representative RRMS cyclic carriers.
Figure 3B:
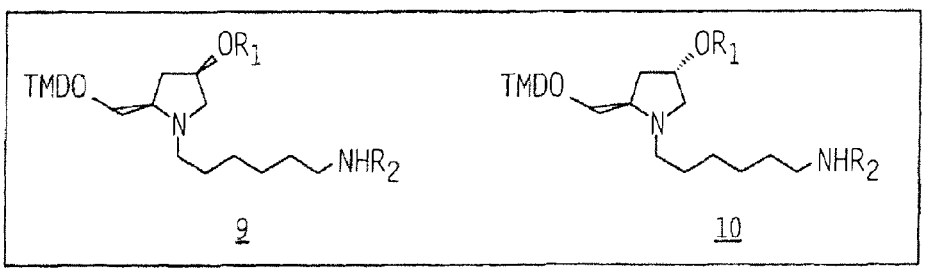
Figure 3C:
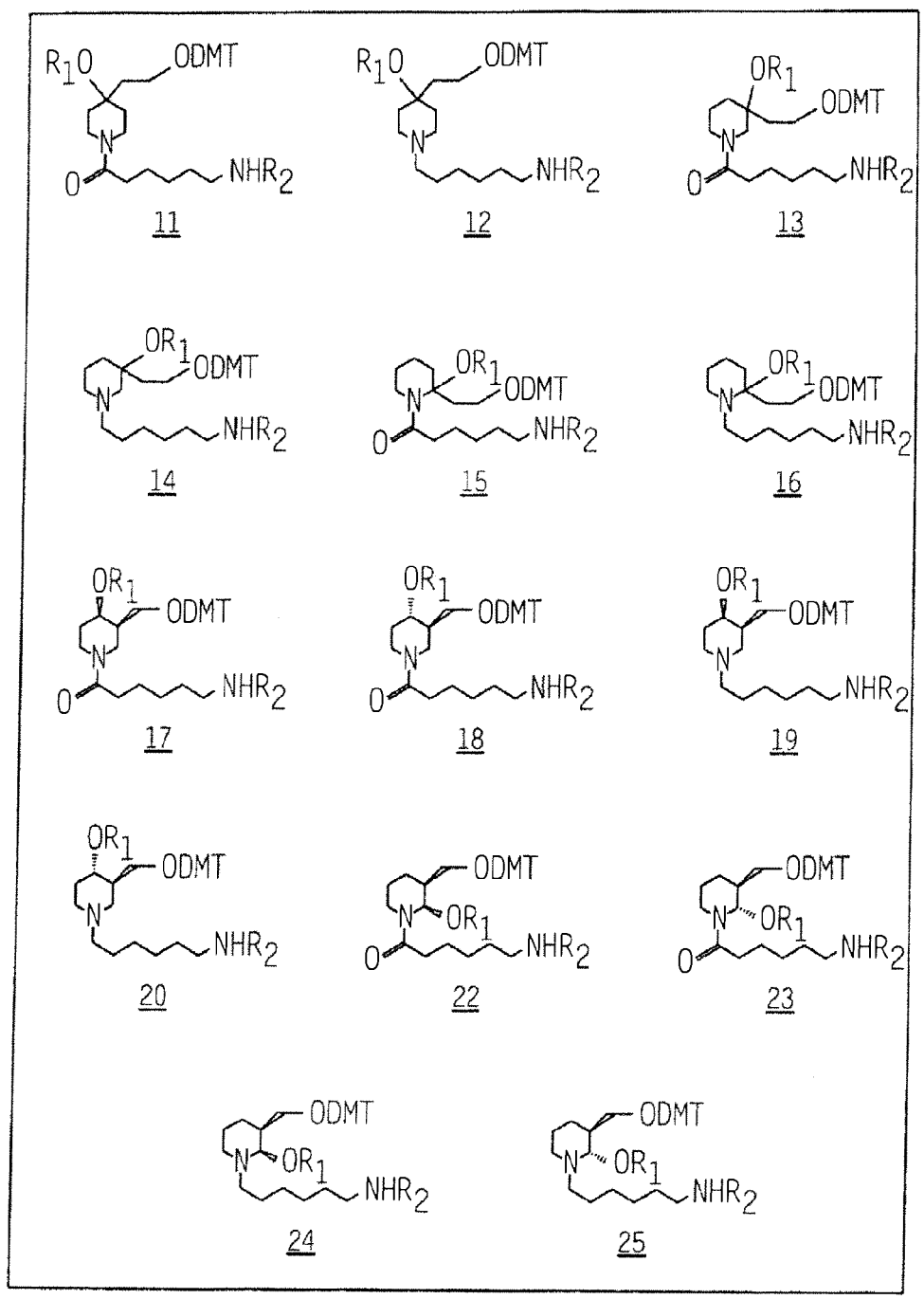
Figure 3D:
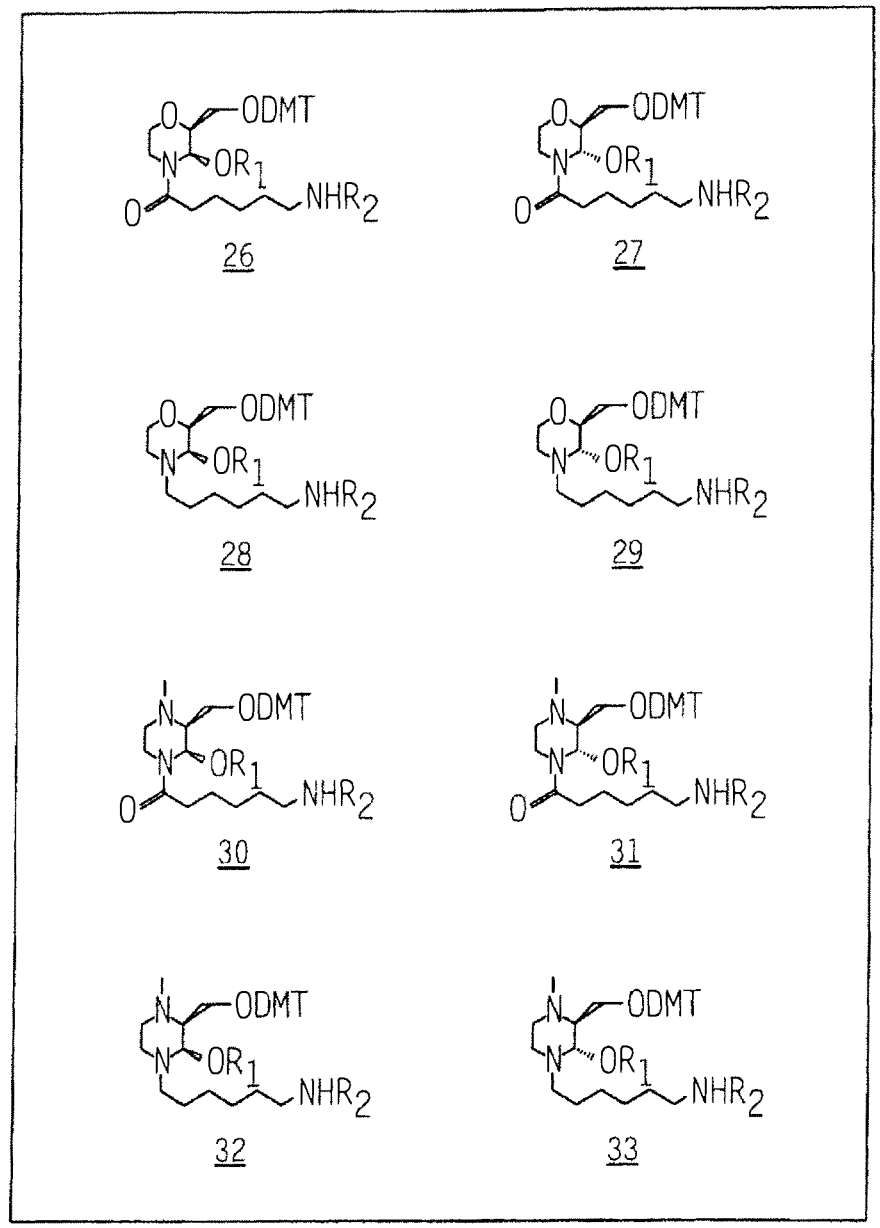
Figure 3E:
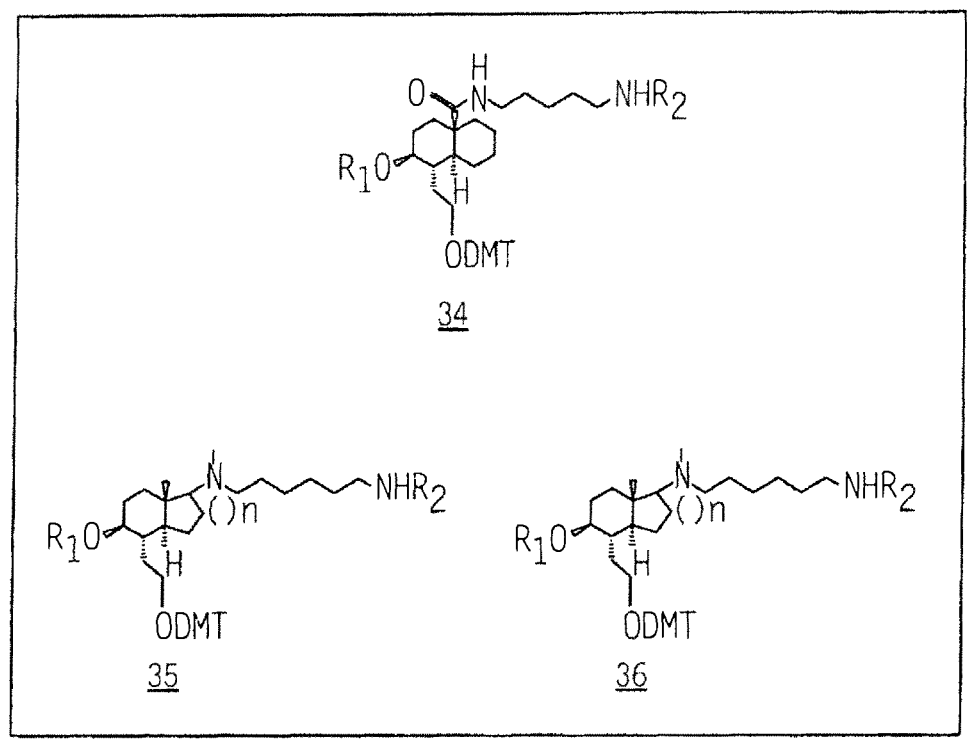

Preferred orthoesters have the general formula J. The groups $R^{31}$ and $R^{32}$ may be the same or different and can be any combination of the groups listed in FIG. 2B. A preferred orthoester is the "ACE" group, shown below as structure K.

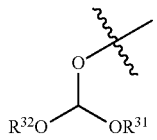

J

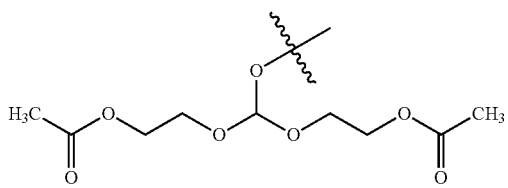

K

"Deoxy" substituents include hydrogen (i.e. deoxyribose sugars); halo (e.g., fluoro); protected amino (e.g. $NH_2$; alkylamino, dialkylamino, heterocyclyl, arylamino, diaryl amino, heteroaryl amino, diheteroaryl amino, or amino acid in which all amino are protected); fully protected polyamino (e.g., $NH(CH_2CH_2NH)_nCH_2CH_2$-AMINE, wherein AMINE=$NH_2$; alkylamino, dialkylamino, heterocyclyl, arylamino, diaryl amino, heteroaryl amino, or diheteroaryl amino and all amino groups are protected), —NHC(O)R (R=alkyl, cycloalkyl, aryl, aralkyl, heteroaryl or sugar), cyano; alkyl-thio-alkyl; thioalkoxy; and alkyl, cycloalkyl, aryl, alkenyl and alkynyl, which may be optionally substituted with e.g., a protected amino functionality. Preferred substitutents are 2'-methoxyethyl, 2'-OCH3, 2'-O-allyl, 2'-C-allyl, and 2'-fluoro.

$X^3$ is as described for $OFG^2$ above.

PG can be a triarylmethyl group (e.g., a dimethoxytrityl group) or $Si(X^{5'})(X^{5''})(X^{5'''})$ in which $(X^{5'})$, $(X^{5''})$, and $(X^{5'''})$ are as described elsewhere.

Sugar Replacement-Based Monomers, e.g., Ligand-Conjugated Monomers (Cyclic)

Cyclic sugar replacement-based monomers, e.g., sugar replacement-based ligand-conjugated monomers, are also referred to herein as ribose replacement monomer subunit (RRMS) monomer compounds. Preferred carriers have the general formula (LCM-2) provided below (In that structure preferred backbone attachment points can be chosen from $R^1$ or $R^2$; $R^3$ or $R^4$; or $R^9$ and $R^{10}$ if Y is $CR^9R^{10}$ (two positions are chosen to give two backbone attachment points, e.g., $R^1$ and $R^4$, or $R^4$ and $R^9$)). Preferred tethering attachment points include $R^7$; $R^5$ or $R^6$ when X is $CH_2$. The carriers are described below as an entity, which can be incorporated into a strand. Thus, it is understood that the structures also encompass the situations wherein one (in the case of a terminal position) or two (in the case of an internal position) of the attachment points, e.g., $R^1$ or $R^2$; $R^3$ or $R^4$; or $R^9$ or $R^{10}$ (when Y is $CR^9R^{10}$), is connected to the phosphate, or modified phosphate, e.g., sulfur containing, backbone. E.g., one of the above-named R groups can be —$CH_2$—, wherein one bond is connected to the carrier and one to a backbone atom, e.g., a linking oxygen or a central phosphorus atom.)

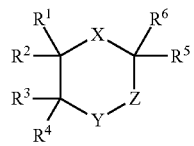

(LCM-2)

in which,
X is $N(CO)R^7$, $NR^7$ or $CH_2$;
Y is $NR^8$, O, S, $CR^9R^{10}$;
Z is $CR^{11}R^{12}$ or absent;
Each of $R^1$, $R^2$, $R^3$, $R^4$, $R^9$, and $R^{10}$ is, independently, H, $OR^a$, or $(CH_2)_nOR^b$, provided that at least two of $R^1$, $R^2$, $R^3$, $R^4$, $R^9$, and $R^{10}$ are $OR^a$ and/or $(CH_2)_nOR^b$;
Each of $R^5$, $R^6$, $R^{11}$, and $R^{12}$ is, independently, a ligand, H, $C_1$-$C_6$ alkyl optionally substituted with 1-3 $R^{13}$, or $C(O)NHR^7$; or $R^5$ and $R^{11}$ together are $C_3$-$C_8$ cycloalkyl optionally substituted with $R^{14}$;
$R^7$ can be a ligand, e.g., $R^7$ can be $R^d$, or $R^7$ can be a ligand tethered indirectly to the carrier, e.g., through a tethering moiety, e.g., $C_1$-$C_{20}$ alkyl substituted with $NR^cR^d$; or $C_1$-$C_{20}$ alkyl substituted with $NHC(O)R^d$;
$R^8$ is H or $C_1$-$C_6$ alkyl;
$R^{13}$ is hydroxy, $C_1$-$C_4$ alkoxy, or halo;
$R^{14}$ is $NR^cR^7$;
$R^{15}$ is $C_1$-$C_6$ alkyl optionally substituted with cyano, or $C_2$-$C_6$ alkenyl;
$R^{16}$ is $C_1$-$C_{10}$ alkyl;
$R^{17}$ is a liquid or solid phase support reagent;
L is —$C(O)(CH_2)_qC(O)$—, or —$C(O)(CH_2)_qS$—;
$R^a$ is a protecting group, e.g., $CAr_3$; (e.g., a dimethoxytrityl group) or $Si(X^{5'})(X^{5''})(X^{5'''})$ in which $(X^{5'})$, $(X^{5''})$, and $(X^{5'''})$ are as described elsewhere.
$R^b$ is $P(O)(O^-)H$, $P(OR^{15})N(R^{16})_2$ or $L$-$R^{17}$;
$R^c$ is H or $C_1$-$C_6$ alkyl;
$R^d$ is H or a ligand;
Each Ar is, independently, $C_6$-$C_{10}$ aryl optionally substituted with $C_1$-$C_4$ alkoxy;
n is 1-4; and q is 0-4.

Exemplary carriers include those in which, e.g., X is $N(CO)R^7$ or $NR^7$, Y is $CR^9R^{10}$, and Z is absent; or X is $N(CO)R^7$ or $NR^7$, Y is $CR^9R^{10}$, and Z is $CR^{11}R^{12}$; or X is $N(CO)R^7$ or $NR^7$, Y is $NR^8$, and Z is $CR^{11}R^{12}$; or X is $N(CO)R^7$ or $NR^7$, Y is O, and Z is $CR^{11}R^{12}$; or X is $CH_2$; Y is $CR^9R^{10}$; Z is $CR^{11}R^{12}$, and $R^5$ and $R^{11}$ together form $C_6$ cycloalkyl (H, z=2), or the indane ring system, e.g., X is $CH_2$; Y is $CR^9R^{10}$; Z is $CR^{11}R^{12}$, and $R^5$ and $R^{11}$ together form $C_5$ cycloalkyl (H, z=1).

In certain embodiments, the carrier may be based on the pyrroline ring system or the 4-hydroxyproline ring system, e.g., X is $N(CO)R^7$ or $NR^7$, Y is $CR^9R^{10}$, and Z is absent (D). $OFG^1$ is preferably attached to a primary carbon, e.g., an exocyclic alkylene

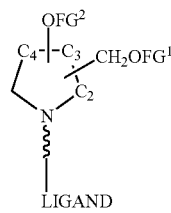

D group, e.g., a methylene group, connected to one of the carbons in the five-membered ring (—CH$_2$OFG$^1$ in D). OFG$^2$ is preferably attached directly to one of the carbons in the five-membered ring (—OFG$^2$ in D). For the pyrroline-based carriers, —CH$_2$OFG$^1$ may be attached to C-2 and OFG$^2$ may be attached to C-3; or —CH$_2$OFG$^1$ may be attached to C-3 and OFG$^2$ may be attached to C-4. In certain embodiments, CH$_2$OFG$^1$ and OFG$^2$ may be geminally substituted to one of the above-referenced carbons. For the 3-hydroxyproline-based carriers, —CH$_2$OFG$^1$ may be attached to C-2 and OFG$^2$ may be attached to C-4. The pyrroline- and 4-hydroxyproline-based monomers may therefore contain linkages (e.g., carbon-carbon bonds) wherein bond rotation is restricted about that particular linkage, e.g. restriction resulting from the presence of a ring. Thus, CH$_2$OFG$^1$ and OFG$^2$ may be cis or trans with respect to one another in any of the pairings delineated above Accordingly, all cis/trans isomers are expressly included. The monomers may also contain one or more asymmetric centers and thus occur as racemates and racemic mixtures, single enantiomers, individual diastereomers and diastereomeric mixtures. All such isomeric forms of the monomers are expressly included (e.g., the centers bearing CH$_2$OFG$^1$ and OFG$^2$ can both have the R configuration; or both have the S configuration; or one center can have the R configuration and the other center can have the S configuration and vice versa). The tethering attachment point is preferably nitrogen. Preferred examples of carrier D include the following:

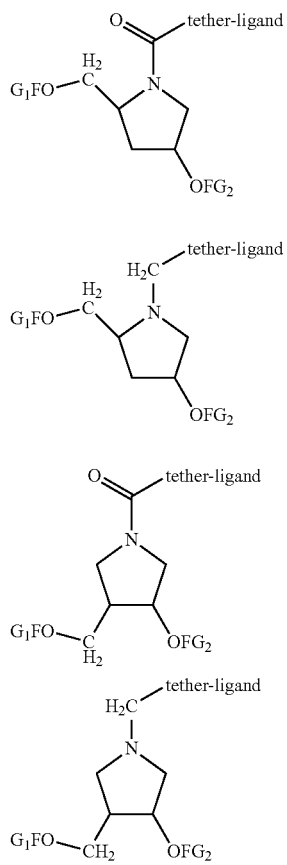

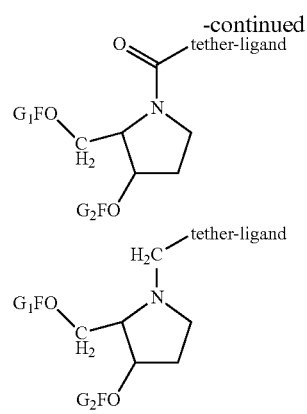

In certain embodiments, the carrier may be based on the piperidine ring system (E), e.g., X is N(CO)R$^7$ or NR$^7$, Y is CR$^9$R$^{10}$, and Z is CR$^{11}$R$^{12}$. OFG$^1$ is preferably

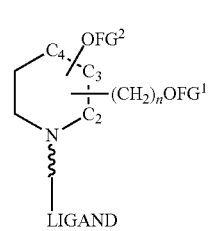

attached to a primary carbon, e.g., an exocyclic alkylene group, e.g., a methylene group (n=1) or ethylene group (n=2), connected to one of the carbons in the six-membered ring [—(CH$_2$)$_n$OFG$^1$ in E]. OFG$^2$ is preferably attached directly to one of the carbons in the six-membered ring (—OFG$^2$ in E). —(CH$_2$)$_n$OFG$^1$ and OFG$^2$ may be disposed in a geminal manner on the ring, i.e., both groups may be attached to the same carbon, e.g., at C-2, C-3, or C-4. Alternatively, —(CH$_2$)$_n$OFG$^1$ and OFG$^2$ may be disposed in a vicinal manner on the ring, i.e., both groups may be attached to adjacent ring carbon atoms, e.g., —(CH$_2$)$_n$OFG$^1$ may be attached to C-2 and OFG$^2$ may be attached to C-3; —(CH$_2$)$_n$OFG$^1$ may be attached to C-3 and OFG$^2$ may be attached to C-2; —(CH$_2$)$_n$OFG$^1$ may be attached to C-3 and OFG$^2$ may be attached to C-4; or —(CH$_2$)$_n$OFG$^1$ may be attached to C-4 and OFG$^2$ may be attached to C-3. The piperidine-based monomers may therefore contain linkages (e.g., carbon-carbon bonds) wherein bond rotation is restricted about that particular linkage, e.g. restriction resulting from the presence of a ring. Thus, —(CH$_2$)$_n$OFG$^1$ and OFG$^2$ may be cis or trans with respect to one another in any of the pairings delineated above. Accordingly, all cis/trans isomers are expressly included. The monomers may also contain one or more asymmetric centers and thus occur as racemates and racemic mixtures, single enantiomers, individual diastereomers and diastereomeric mixtures. All such isomeric forms of the monomers are expressly included (e.g., the centers bearing CH$_2$OFG$^1$ and OFG$^2$ can both have the R configuration; or both have the S configuration; or one center can have the R configuration and the other center can have the S configuration and vice versa). The tethering attachment point is preferably nitrogen.

In certain embodiments, the carrier may be based on the piperazine ring system (F), e.g., X is N(CO)R$^7$ or NR$^7$, Y is NR$^8$, and Z is CR$^{11}$R$^{12}$, or the morpholine ring system (G), e.g., X is N(CO)R$^7$ or NR$^7$, Y is O, and Z is CR$^{11}$R$^{12}$. OFG$^1$ is preferably

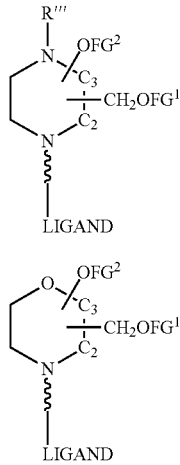

attached to a primary carbon, e.g., an exocyclic alkylene group, e.g., a methylene group, connected to one of the carbons in the six-membered ring (—CH$_2$OFG$^1$ in F or G). OFG$^2$ is preferably attached directly to one of the carbons in the six-membered rings (—OFG$^2$ in F or G). For both F and G, —CH$_2$OFG$^1$ may be attached to C-2 and OFG$^2$ may be attached to C-3; or vice versa. In certain embodiments, CH$_2$OFG$^1$ and OFG$^2$ may be geminally substituted to one of the above-referenced carbons. The piperazine- and morpholine-based monomers may therefore contain linkages (e.g., carbon-carbon bonds) wherein bond rotation is restricted about that particular linkage, e.g. restriction resulting from the presence of a ring. Thus, CH$_2$OFG$^1$ and OFG$^2$ may be cis or trans with respect to one another in any of the pairings delineated above. Accordingly, all cis/trans isomers are expressly included. The monomers may also contain one or more asymmetric centers and thus occur as racemates and racemic mixtures, single enantiomers, individual diastereomers and diastereomeric mixtures. All such isomeric forms of the monomers are expressly included (e.g., the centers bearing CH$_2$OFG$^1$ and OFG$^2$ can both have the R configuration; or both have the S configuration; or one center can have the R configuration and the other center can have the S configuration and vice versa). R''' can be, e.g., C$_1$-C$_6$ alkyl, preferably CH$_3$. The tethering attachment point is preferably nitrogen in both F and G.

In certain embodiments, the carrier may be based on the decalin ring system, e.g., X is CH$_2$; Y is CR$^9$R$^{10}$; Z is CR$^{11}$R$^{12}$, and R$^5$ and R$^{11}$ together form C$_6$ cycloalkyl (H, z=2), or the indane ring system, e.g., X is CH$_2$; Y is CR$^9$R$^{10}$; Z is CR$^{11}$R$^{12}$, and R$^5$ and R$^{11}$ together form C$_5$ cycloalkyl (H, z=1). OFG$^1$ is preferably attached to a primary carbon,

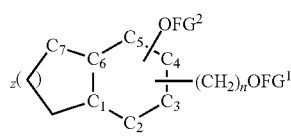

e.g., an exocyclic methylene group (n=1) or ethylene group (n=2) connected to one of C-2, C-3, C-4, or C-5 [—(CH$_2$)$_n$OFG$^1$ in H]. OFG$^2$ is preferably attached directly to one of C-2, C-3, C-4, or C-5 (—OFG$^2$ in H). —(CH$_2$)$_n$OFG$^1$ and OFG$^2$ may be disposed in a geminal manner on the ring, i.e., both groups may be attached to the same carbon, e.g., at C-2, C-3, C-4, or C-5. Alternatively, —(CH$_2$)$_n$OFG$^1$ and OFG$^2$ may be disposed in a vicinal manner on the ring, i.e., both groups may be attached to adjacent ring carbon atoms, e.g., —(CH$_2$)$_n$OFG$^1$ may be attached to C-2 and OFG$^2$ may be attached to C-3; —(CH$_2$)$_n$OFG$^1$ may be attached to C-3 and OFG$^2$ may be attached to C-2; —(CH$_2$)$_n$OFG$^1$ may be attached to C-3 and OFG$^2$ may be attached to C-4; or —(CH$_2$)$_n$OFG$^1$ may be attached to C-4 and OFG$^2$ may be attached to C-3; —(CH$_2$)$_n$OFG$^1$ may be attached to C-4 and OFG$^2$ may be attached to C-5; or —(CH$_2$)$_n$OFG$^1$ may be attached to C-5 and OFG$^2$ may be attached to C-4. The decalin or indane-based monomers may therefore contain linkages (e.g., carbon-carbon bonds) wherein bond rotation is restricted about that particular linkage, e.g. restriction resulting from the presence of a ring. Thus, —(CH$_2$)$_n$OFG$^1$ and OFG$^2$ may be cis or trans with respect to one another in any of the pairings delineated above. Accordingly, all cis/trans isomers are expressly included. The monomers may also contain one or more asymmetric centers and thus occur as racemates and racemic mixtures, single enantiomers, individual diastereomers and diastereomeric mixtures. All such isomeric forms of the monomers are expressly included (e.g., the centers bearing CH$_2$OFG$^1$ and OFG$^2$ can both have the R configuration; or both have the S configuration; or one center can have the R configuration and the other center can have the S configuration and vice versa). In a preferred embodiment, the substituents at C-1 and C-6 are trans with respect to one another. The tethering attachment point is preferably C-6 or C-7.

Other carriers may include those based on 3-hydroxyproline (J). Thus, —(CH$_2$)$_n$OFG$^1$ and OFG$^2$ may be cis or trans with respect to one another. Accordingly, all cis/trans isomers are expressly included. The monomers may also contain one or more asymmetric centers

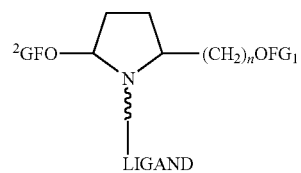

and thus occur as racemates and racemic mixtures, single enantiomers, individual diastereomers and diastereomeric mixtures. All such isomeric forms of the monomers are expressly included (e.g., the centers bearing CH$_2$OFG$^1$ and OFG$^2$ can both have the R configuration; or both have the S configuration; or one center can have the R configuration and the other center can have the S configuration and vice versa). The tethering attachment point is preferably nitrogen.

Representative cyclic, sugar replacement-based carriers are shown in FIG. 3A-3E.

Sugar Replacement-Based Monomers (Acyclic)

Acyclic sugar replacement-based monomers, e.g., sugar replacement-based ligand-conjugated monomers, are also referred to herein as ribose replacement monomer subunit (RRMS) monomer compounds. Preferred acyclic carriers can have formula LCM-3 or LCM-4 below.

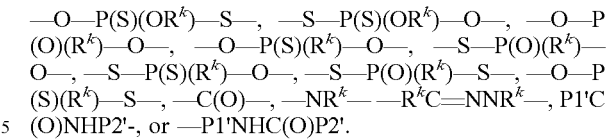

LCM-3

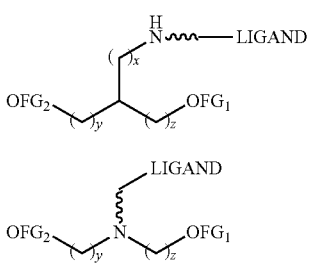

LCM-4

In some embodiments, each of x, y, and z can be, independently of one another, 0, 1, 2, or 3. In formula LCM-3, when y and z are different, then the tertiary carbon can have either the R or S configuration. In preferred embodiments, x is zero and y and z are each 1 in formula LCM-3 (e.g., based on serinol), and y and z are each 1 in formula LCM-3. Each of formula LCM-3 or LCM-4 below can optionally be substituted, e.g., with hydroxy, alkoxy, perhaloalkyl.

Tethers

In some embodiments, a moiety, e.g., a ligand may be connected indirectly to the carrier via the intermediacy of an intervening tether. Tethers are connected to the carrier at a tethering attachment point (TAP).

Tethers can include any C1-C100 carbon-containing moiety, (e.g. C1-C75, C1-C50, C1-C20, C1-C10; C1, C2, C3, C4, C5, C6, C7, C8, C9, or C10) and at least one linking group (e.g. at least two linking groups, at least three linking groups, at least four linking groups, at least five linking groups, at least six linking groups, at least seven linking groups, at least eight linking groups, at least nine linking groups, at least ten linking groups, at least eleven linking groups, at least twelve linking groups, at least thirteen linking groups, at least fourteen linking groups, at least fifteen linking groups, at least sixteen linking groups, at least seventeen linking groups, at least eighteen linking groups, at least nineteen linking groups, at least twenty linking groups). The linking group can be at one or both terminal positions of the tether (e.g., a terminal linking group can link the tether to the ligand or link the tether to the nitrogen atom of X or $R^{14}$ in formula (I), or the nitrogen atom of CONHR$^7$ when $R^5$, $R^6$, $R^{11}$, or $R^{12}$ is CONHR$^7$ in formula (I)) and/or at one or more internal positions of the tether (1 carbon from the end, 2 carbons from the end, 3 carbons from the end, 4 carbons from the end, 5 carbons from the end, 3 carbons from the end, etc.).

In general, the linking group can be any atom or group of atoms that includes as a linking atom a divalent, trivalent, tetravalent, pentavalent or hexavalent heteroatom, e.g. O, N, S, P. A carbon atom can be the linking atom of a linking group provided that the linking carbon atom is doubly bonded to a non-linking heteroatom (e.g., carbonyl, —C(O)—). Linking groups can include without limitation amides, ethers, esters, phosphates, carbamates, thioethers, disulphide, thioamide, thioester, thiocarbamate, thiophosphate, carbonyl, amino, and hydrazone. Exemplary linking groups could include without limitation —NR$^k$C(O)—, —C(O)NR$^k$—, —OC(O)NR$^k$—, —NR$^k$C(O)O—, —O—, —S—, —SS—, —S(O)—, —S(O$_2$)—, —NR$^k$C(O)NR$^k$—, —NR$^k$C(S)NR$^k$—, —C(O)O—, —OC(O)—, —NR$^k$C(S)—, —NR$^k$C(S)O—, —C(S)NR$^k$—, —OC(S)NR$^k$—, —NR$^k$C(S)O—, —O—P(O)(OR$^k$)—O—, —O—P(S)(OR$^k$)—O—, —O—P(S)(SR$^k$)—O—, —S—P(O)(OR$^k$)—O—, —O—P(O)(OR$^k$)—S—, —S—P(O)(OR$^k$)—S—, —O—P(S)(OR$^k$)—S—, —S—P(S)(OR$^k$)—O—, —O—P(O)(R$^k$)—O—, —O—P(S)(R$^k$)—O—, —S—P(O)(R$^k$)—O—, —S—P(S)(R$^k$)—O—, —S—P(O)(R$^k$)—S—, —O—P(S)(R$^k$)—S—, —C(O)—, —NR$^k$— —R$^k$C═NNR$^k$—, P1'C(O)NHP2'-, or —P1'NHC(O)P2'.

In general, at least one of the linking groups in the tether is a cleavable linking group. A cleavable linking group is one which is sufficiently stable outside the cell such that it allows targeting of a therapeutically beneficial amount of an iRNA agent (e.g., a single stranded or double stranded iRNA agent), coupled by way of the cleavable linking group to a targeting agent—to targets cells, but which upon entry into a target cell is cleaved to release the iRNA agent from the targeting agent. In a preferred embodiment, the cleavable linking group is cleaved at least 10 times or more, preferably at least 100 times faster in the target cell or under a first reference condition (which can, e.g., be selected to mimic or represent intracellular conditions) than in the blood of a subject, or under a second reference condition (which can, e.g., be selected to mimic or represent conditions found in the blood or serum).

Cleavable Linking Groups

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

A cleavable linkage group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some tethers will have a linkage group that is cleaved at a preferred pH, thereby releasing the iRNA agent from a ligand (e.g., a targeting or cell-permeable ligand, such as cholesterol) inside the cell, or into the desired compartment of the cell.

A chemical junction (e.g., a linking group) that links a ligand to an iRNA agent can include a disulfide bond. When the iRNA agent/ligand complex is taken up into the cell by endocytosis, the acidic environment of the endosome will cause the disulfide bond to be cleaved, thereby releasing the iRNA agent from the ligand (Quintana et al., *Pharm Res.* 19:1310-1316, 2002; Patri et al., *Curr. Opin. Curr. Biol.* 6:466-471, 2002). The ligand can be a targeting ligand or a second therapeutic agent that may complement the therapeutic effects of the iRNA agent.

A tether can include a linking group that is cleavable by a particular enzyme. The type of linking group incorporated into a tether can depend on the cell to be targeted by the iRNA agent. For example, an iRNA agent that targets an mRNA in liver cells can be conjugated to a tether that includes an ester group. Liver cells are rich in esterases, and therefore the tether will be cleaved more efficiently in liver cells than in cell types that are not esterase-rich. Cleavage of the tether releases the iRNA agent from a ligand that is attached to the distal end of the tether, thereby potentially enhancing silencing activity of the iRNA agent. Other cell-types rich in esterases include cells of the lung, renal cortex, and testis.

Tethers that contain peptide bonds can be conjugated to iRNA agents target to cell types rich in peptidases, such as liver cells and synoviocytes. For example, an iRNA agent targeted to synoviocytes, such as for the treatment of an inflammatory disease (e.g., rheumatoid arthritis), can be conjugated to a tether containing a peptide bond.

In general, the suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue, e.g., tissue the iRNA agent would be exposed to when administered to a subject. Thus one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It may be useful to make initial evaluations in cell-free or culture conditions and to confirm by further evaluations in whole animals. In preferred embodiments, useful candidate compounds are cleaved at least 2, 4, 10 or 100 times faster in the cell (or under in vitro conditions selected to mimic intracellular conditions) as compared to blood or serum (or under in vitro conditions selected to mimic extracellular conditions).

Redox Cleavable Linking Groups

One class of cleavable linking groups are redox cleavable linking groups that are cleaved upon reduction or oxidation. An example of reductively cleavable linking group is a disulphide linking group (—S—S—). To determine if a candidate cleavable linking group is a suitable "reductively cleavable linking group," or for example is suitable for use with a particular iRNA moiety and particular targeting agent one can look to methods described herein. For example, a candidate can be evaluated by incubation with dithiothreitol (DTT), or other reducing agent using reagents know in the art, which mimic the rate of cleavage which would be observed in a cell, e.g., a target cell. The candidates can also be evaluated under conditions which are selected to mimic blood or serum conditions. In a preferred embodiment, candidate compounds are cleaved by at most 10% in the blood. In preferred embodiments, useful candidate compounds are degraded at least 2, 4, 10 or 100 times faster in the cell (or under in vitro conditions selected to mimic intracellular conditions) as compared to blood (or under in vitro conditions selected to mimic extracellular conditions). The rate of cleavage of candidate compounds can be determined using standard enzyme kinetics assays under conditions chosen to mimic intracellular media and compared to conditions chosen to mimic extracellular media.

Phosphate-Based Cleavable Linking Groups

Phosphate-based linking groups are cleaved by agents that degrade or hydrolyze the phosphate group. An example of an agent that cleaves phosphate groups in cells are enzymes such as phosphatases in cells. Examples of phosphate-based linking groups are —O—P(O)(ORk)-O—, —O—P(S)(ORk)-O—, —O—P(S)(SRk)-O—, —S—P(O)(ORk)-O—, —O—P(O)(ORk)-S—, —S—P(O)(ORk)-S—, —O—P(S)(ORk)-S—, —S—P(S)(ORk)-O—, —O—P(O)(Rk)-O—, —O—P(S)(Rk)-O—, —S—P(O)(Rk)-O—, —S—P(S)(Rk)-O—, —S—P(O)(Rk)-S—, —O—P(S)(Rk)-S—. Preferred embodiments are —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, —O—P(S)(H)—S—. A preferred embodiment is —O—P(O)(OH)—O—. These candidates can be evaluated using methods analogous to those described above.

Acid Cleavable Linking Groups

Acid cleavable linking groups are linking groups that are cleaved under acidic conditions. In preferred embodiments acid cleavable linking groups are cleaved in an acidic environment with a pH of about 6.5 or lower (e.g., about 6.0, 5.5, 5.0, or lower), or by agents such as enzymes that can act as a general acid. In a cell, specific low pH organelles, such as endosomes and lysosomes can provide a cleaving environment for acid cleavable linking groups. Examples of acid cleavable linking groups include but are not limited to hydrazones, esters, and esters of amino acids. Acid cleavable groups can have the general formula —C=NN—, C(O)O, or —OC(O). A preferred embodiment is when the carbon attached to the oxygen of the ester (the alkoxy group) is an aryl group, substituted alkyl group, or tertiary alkyl group such as dimethyl pentyl or t-butyl. These candidates can be evaluated using methods analogous to those described above.

Ester-Based Linking Groups

Ester-based linking groups are cleaved by enzymes such as esterases and amidases in cells. Examples of ester-based cleavable linking groups include but are not limited to esters of alkylene, alkenylene and alkynylene groups. Ester cleavable linking groups have the general formula —C(O)O—, or —OC(O)—. These candidates can be evaluated using methods analogous to those described above.

Peptide-Based Cleaving Groups

Peptide-based linking groups are cleaved by enzymes such as peptidases and proteases in cells. Peptide-based cleavable linking groups are peptide bonds formed between amino acids to yield oligopeptides (e.g., dipeptides, tripeptides etc.) and polypeptides. Peptide-based cleavable groups do not include the amide group (—C(O)NH—). The amide group can be formed between any alkylene, alkenylene or alkynelene. A peptide bond is a special type of amide bond formed between amino acids to yield peptides and proteins. The peptide based cleavage group is generally limited to the peptide bond (i.e., the amide bond) formed between amino acids yielding peptides and proteins and does not include the entire amide functional group. Peptide cleavable linking groups have the general formula —NHCHR$^1$C(O)NHCHR$^2$C(O)—, where R$^1$ and R$^2$ are the R groups of the two adjacent amino acids. These candidates can be evaluated using methods analogous to those described above.

The carbon containing moiety (e.g., hydrocarbon moiety, partial or fully halocarbon moiety) can be cyclic or acyclic moiety or any combination thereof. In some embodiments, the carbon containing moiety can be saturated (e.g., alkylene) or unsaturated (e.g., alkenylene or alkynylene).

In certain embodiments, the saturated carbon containing moiety can be C1-C100 (e.g. C1-C75, C1-C50, C1-C20, C1-C10; C1, C2, C3, C4, C5, C6, C7, C8, C9, C10, C11, C12, C13, C14, C15, C16, C17, C18, C19, or C20) alkylene moiety, which may be straight chain or branched. In certain embodiments, the saturated carbon can be further substituted with halo, hydroxy or amino.

In certain embodiments, the unsaturated carbon containing moiety can be C1-C100 (e.g. C1-C75, C1-C50, C1-C20, C1-C10; C1, C2, C3, C4, C5, C6, C7, C8, C9, C10, C11, C12, C13, C14, C15, C16, C17, C18, C19, or C20) alkenylene moiety, which may be straight chain or branched. In certain embodiments, the alkenylene moieties can have one or more double bonds. In certain embodiments, the alkenylene moieties can have 1 to 60 double bonds (e.g., 1-50. 1-40, 1-30, 1-20, 1, 2, 3, 4, 5, 6, 7, 8, 9, 10, 11, 12, 13, 14, 15, 16, 17, 18, 19, or 20 double bonds). In general, each double bond can be independently of one another cis or trans or E or Z, or any combination thereof. In certain embodiments, the unsaturated carbon moiety can be $(CH_2)_{m1}(CH=CH)_{m2}(CH_2)m3$, in which each of m1, m2, or m3 is, independently of one another, 0-20 (e.g., 0, 1, 2, 3, 4, 5, 6, 7, 8, 9, 10, 11, 12, 13, 14, 15, 16, 17, 18, 19, or 20).

In certain embodiments, the unsaturated carbon containing moiety can be C1-C100 (e.g. C1-C75, C1-C50, C1-C20, C1-C10; C1, C2, C3, C4, C5, C6, C7, C8, C9, C10, C11, C12, C13, C14, C15, C16, C17, C18, C19, or C20) alkynylene moiety. In certain embodiments, the alkynylene moieties can have one or more triple bonds. In certain embodiments, the alkynylene moieties can have one to sixty triple bonds (e.g., 1-50. 1-40, 1-30, 1-20, 1, 2, 3, 4, 5, 6, 7, 8, 9, 10, 11, 12, 13, 14, 15, 16, 17, 18, 19, or 20 triple bonds). In certain embodiments, the carbon containing moiety can be substituted or unsubstituted. In certain embodiments, the carbon containing moiety can be straight or branched.

In certain embodiments, the unsaturated carbon containing moieties can be substituted or unsubstituted. In certain embodiments, the unsaturated carbon containing moiety can be straight or branched.

In certain embodiments, the carbon containing moiety can be cyclic or include a series of linked cyclic moieties. In certain embodiments, the cyclic moieties can be cycloalkyl groups. In certain embodiments, the cyclic moieties can be cycloalkenyl groups. In certain embodiments, the cyclic moieties can be cycloalkynyl groups. In certain embodiments, the cyclic moieties can be heterocyclyl groups. In certain embodiments, the cyclic moieties can be aryl groups. In certain embodiments, the cyclic moieties can be heteroaryl groups. In certain embodiments, the cyclic moieties can be phenyl, pyridinyl, pyranyl, or thiophenyl groups. In certain embodiments, the cyclic moieties can be carbohydrate or sugar groups. In certain embodiments, the carbohydrate moieties can be glucose, mannose or ribose groups.

In certain embodiments, the tether can have the formula shown below.

$$T=-(E')_s-\Delta-(E'')_t- \qquad \text{Formula } T_1'$$

In which, E' is a terminal linking group that is linking the tether to the ligand. E" is a tether linking group that links tether to the tethering attachment point (TAP); Δ is a hydrocarbon chain e.g. alkylene, alkenylene, or alkynylene that optionally has one or more internal linking groups G; and s and t can be 0 or 1. In all embodiments, one of s and t is one, or - includes at least one G, and at least one of the linking groups is a cleavable linking group.

When present, the terminal linking groups E' and E" can be selected as desired.

In certain embodiments, one or both of the terminal linking groups E' and E" can be cleavable linking groups (e.g., —SS—, —O—P(O)(OR$^k$)—O—, —O—P(S)(OR$^k$)—O—, —O—P(S)(SR$^k$)—O—, —S—P(O)(OR$^k$)—O—, —O—P(O)(OR$^k$)—S—, —S—P(O)(OR$^k$)—S—, —O—P(S)(OR$^k$)—S—, —S—P(S)(OR$^k$)—O—, —O—P(O)(R$^k$)—O—, —O—P(S)(R$^k$)—O—, —S—P(O)(R$^k$)—O—, —S—P(S)(R$^k$)—O—, —S—P(O)(R$^k$)—S—, —O—P(S)(R$^k$)—S—, —S—P(O)(R$^k$)—S—, —O—P(S)(R$^k$)—S—, —C(O)O—, —OC(O)—, —R$^k$C=NNR$^k$—, NHCHR$^{k'}$C(O)NHCHR$^{k''}$C(O)—, or —NHCHR$^k$NHC(O)CHR$^{k''}$C(O)—).

In some embodiments, s can be 0 and t can be 1, i.e. E" is present and E' is absent; and E" can be NR$^k$C(O)—, —C(O)NR$^k$—, —OC(O)NR$^k$—, —NR$^k$C(O)O—, —O—, —S—, —SS—, —S(O)—, —S(O$_2$)—, —NR$^k$C(O)NR$^k$—, —NR$^k$C(S)NR$^k$—, —C(O)O—, —OC(O)—, —NR$^k$C(S)—, —NR$^k$C(S)O—, —C(S)NR$^k$—, —OC(S)NR$^k$—, —NR$^k$C(S)O—, —O—P(O)(OR$^k$)—O—, —O—P(S)(OR$^k$)—O—, —O—P(S)(SR$^k$)—O—, —S—P(O)(OR$^k$)—O—, —O—P(O)(OR$^k$)—S—, —S—P(O)(OR$^k$)—S—, —O—P(S)(OR$^k$)—S—, —S—P(S)(OR$^k$)—O—, —O—P(O)(R$^k$)—O—, —O—P(S)(R$^k$)—O—, —S—P(O)(R$^k$)—O—, —S—P(S)(R$^k$)—O—, —S—P(O)(R$^k$)—S—, —O—P(S)(R$^k$)—S—, —C(O)—, —NR$^k$— —R$^k$C=NNR$^k$—, NHCHR$^{k'}$C(O)NHCHR$^{k''}$C(O)—, or —NHCHR$^k$NHC(O)CHR$^{k''}$C(O)—. In preferred embodiments, E" is C(O)NRk-, —NHC(O)—, —NHC(O)O—, OC(O)NRk- or —NHC(O)NRk-.

In some embodiments, s can be 1 and t can be 0, i.e., E' is present and E" is absent, and E' can be NR$^k$C(O)—, —C(O)NR$^k$—, —OC(O)NR$^k$—, —NR$^k$C(O)O—, —O—, —S—, —SS—, —S(O)—, —S(O$_2$)—, —NR$^k$C(O)NR$^k$—, —NR$^k$C(S)NR$^k$—, —C(O)O—, —OC(O)—, —NR$^k$C(S)—, —NR$^k$C(S)O—, —C(S)NR$^k$—, —OC(S)NR$^k$—, —NR$^k$C(S)O—, —O—P(O)(OR$^k$)—O—, —O—P(S)(OR$^k$)—O—, —O—P(S)(SR$^k$)—O—, —S—P(O)(OR$^k$)—O—, —O—P(O)(OR$^k$)—S—, —S—P(O)(OR$^k$)—S—, —O—P(S)(OR$^k$)—S—, —S—P(S)(OR$^k$)—O—, —O—P(O)(R$^k$)—O—, —O—P(S)(R$^k$)—O—, —S—P(O)(R$^k$)—O—, —S—P(S)(R$^k$)—O—, —S—P(O)(R$^k$)—S—, —O—P(S)(R$^k$)—S—, —C(O)—, —NR$^k$— —R$^k$C=NNR$^k$—, NHCHR$^{k'}$C(O)NHCHR$^{k''}$C(O)—, or —NHCHR$^k$NHC(O)CHR$^{k''}$C(O)—. In preferred embodiments, E' can be C(O)NH—, —NH—, OC(O)NRk- or —SS—.

In some embodiments, s and t can both be 1. In certain embodiments, one of E' and E" can be carbamates (—NHC(O)O—), ethers (—O—), amides (—C(O)NH—), thioethers (—S—), thioamide (—C(S)NH—), oxo (—C(O)—), amino (—NH—), and the other of E' and E" can be esters (—C(O)O—, —OC(O)—), phosphates (—O—P(O)(ORk)-O—, —O—P(S)(ORk)-O—, —O—P(S)(SRk)-O—, —S—P(O)(ORk)-O—, —O—P(O)(ORk)-S—, —S—P(O)(ORk)-S—, —O—P(S)(ORk)-S—, —S—P(S)(ORk)-O—, —O—P(O)(Rk)-O—, —O—P(S)(Rk)-O—, —S—P(O)(Rk)-O—, —S—P(S)(Rk)-O—, —S—P(O)(Rk)-S—, —O—P(S)(Rk)-S—), disulphide (—SS—), hydrazone (R$^k$C=NNR$^k$—), and peptides P1'C(O)NHP2'-, or —P1'NHC(O)P2'.

In a certain embodiment, one of E' and E" can be —C(O)NRk-, —NHC(O)—, —NHC(O)O—, —OC(O)NH— or —SS— and the other of E' and E" can be —C(O)NRk-, —NHC(O)—, —NHC(O)O—, or —NHC(O)NRk-.

- can be any hydrocarbon chain and can optionally have one or more internal groups, G. In some embodiments, - includes at least one internal linking group G.

As used herein, the term -=C4 alkylene having 1 G (and the like) can include for example and without limitation the moieties delineated in formulae T-2 and T-3:

—CH$_2$—CH$_2$—S—S—CH$_2$—CH$_2$—     T-2

—CH$_2$—CH$_2$—C(O)—CH$_2$—CH$_2$—,     T-3 in which G is —S—S— and —C(O)— in formulae T-2 and T-3 respectively.

In certain embodiments, Δ can be C1-C20 (e.g. C1, C2, C3, C4, C5, C6, C7, C8, C9, C10, C11, C12, C13, C14, C15, C16, C17, C18, C19, or C20) alkylene, alkenylene, or alkynylene and include 0 to 10 (e.g., 0, 1, 2, 3, 4, 5, 6, 7, 8, 9, or 10) G groups.

In certain embodiments, Δ can be C2-C20 (C2, C3, C4, C5, C6, C7, C8, C9, C10, C11, C12, C13, C14, C15, C16, C17, C18, C19, or C20) alkylene, having 1 to 10 (1, 2, 3, 4, 5, 6, 7, 8, 9, or 10) G groups.

In certain embodiments, Δ can be C2-C20 (C2, C3, C4, C5, C6, C7, C8, C9, C10, C11, C12, C13, C14, C15, C16, C17, C18, C19, or C20) alkenylene, having 1 to 10 (1, 2, 3, 4, 5, 6, 7, 8, 9, or 10) G groups.

In certain embodiments, Δ can be C2-C20 (C2, C3, C4, C5, C6, C7, C8, C9, C10, C11, C12, C13, C14, C15, C16, C17, C18, C19, or C20) alkynylene, having 1 to 10 (1, 2, 3, 4, 5, 6, 7, 8, 9, or 10) G groups.

In certain embodiments, Δ can be C2-C20 (e.g. C1, C2, C3, C4, C5, C6, C7, C8, C9, C10, C11, C12, C13, C14, C15, C16, C17, C18, C19, or C20) alkylene, alkenylene, or alkynylene and include 1 to 5 (e.g., 1, 2, 3, 4, or 5) G groups.

In certain embodiments, Δ can be C2-C20 (C2, C3, C4, C5, C6, C7, C8, C9, C10, C11, C12, C13, C14, C15, C16, C17, C18, C19, or C20) alkylene having 0-10 (0, 1, 2, 3, 4, 5, 6, 7, 8, 9, or 10) G groups. In certain embodiments, Δ can be $C_{1-6}$ alkylene having 1-4 (1, 2, 3, or 4) G groups, preferably 3 G groups. In certain embodiments, Δ can be $C_{1-4}$ alkylene having 1-4 (1, 2, 3, or 4) G groups, preferably 3 G groups. In certain embodiments, Δ can be $C_{1-2}$ alkylene having 1-4 (1, 2, 3, or 4) G groups, preferably 3 G groups. In certain embodiments, Δ can be C9 alkylene having 1-3 (1, 2, or 3) G groups, preferably 3 G groups. In certain embodiments, Δ can be C6 alkylene having 1-4 (1, 2, 3, or 4) G groups, preferably 3 G groups.

When present G can be selected as desired from e.g. —$NR^kC(O)$—, —$C(O)NR^k$—, —$OC(O)NR^k$—, —$NR^kC(O)O$—, —O—, —S—, —SS—, —S(O)—, —S(O$_2$)—, —$NR^kC(O)NR^k$—, —$NR^kC(S)NR^k$—, —$C(O)O$—, —OC(O)—, —$NR^kC(S)$—, —$NR^kC(S)O$—, —$C(S)NR^k$—, —$OC(S)NR^k$—, —$NR^kC(S)O$—, —O—P(O)(OR$^k$)—O—, —O—P(S)(OR$^k$)—O—, —O—P(S)(SR$^k$)—O—, —S—P(O)(OR$^k$)—O—, —O—P(O)(OR$^k$)—S—, —S—P(O)(OR$^k$)—S—, —O—P(S)(OR$^k$)—S—, —S—P(S)(OR$^k$)—O—, —O—P(O)(R$^k$)—O—, —O—P(S)(R$^k$)—O—, —S—P(O)(R$^k$)—O—, —S—P(S)(R$^k$)—O—, —S—P(O)(R$^k$)—S—, —O—P(S)(R$^k$)—S—, —C(O)—, —NR$^k$—, —$R^kC$=NNR$^k$—, NHCHR$^{k'}$C(O)NHCHR$^{k''}$C(O)—, or —NHCHR$^{k'}$NHC(O)CHR$^{k''}$C(O)—.

In some embodiments, G can be a cleavable internal linking group (e.g., disulphide, ester, hydrazone, peptide or phosphate, e.g., —SS—, —O—P(O)(OR$^k$)—O—, —O—P(S)(OR$^k$)—O—, —O—P(S)(SR$^k$)—O—, —S—P(O)(OR$^k$)—O—, —O—P(O)(OR$^k$)—S—, —S—P(O)(OR$^k$)—S—, —O—P(S)(OR$^k$)—S—, —S—P(S)(OR$^k$)—O—, —O—P(O)(R$^k$)—O—, —O—P(S)(R$^k$)—O—, —S—P(O)(R$^k$)—O—, —S—P(S)(R$^k$)—O—, —S—P(O)(R$^k$)—S—, —O—P(S)(R$^k$)—S—, —C(O)O—, —OC(O)—, —$R^kC$=NNR$^k$—, NHCHR$^{k'}$C(O)NHCHR$^{k''}$C(O)—, or —NHCHR$^{k'}$NHC(O)CHR$^{k''}$C(O)—).

In certain embodiments two or more (2, 3, 4, or 5) G groups can be present, and one G can be carbamates (—NHC(O)O—), ethers (—O—), amides (—C(O)NH—), thioethers (—S—), thioamide (—C(S)NH—), oxo (—C(O)—), amino (—NH—), and the remaining G groups can be esters (—C(O)O—, —OC(O)—), phosphates (—O—P(O)(ORk)-O—, —O—P(S)(ORk)-O—, —O—P(S)(SRk)-O—, —S—P(O)(ORk)-O—, —O—P(O)(ORk)-S—, —S—P(O)(ORk)-S—, —O—P(S)(ORk)-S—, —S—P(S)(ORk)-O—, —O—P(O)(Rk)-O—, —O—P(S)(Rk)-O—, —S—P(O)(Rk)-O—, —S—P(S)(Rk)-O—, —S—P(O)(Rk)-S—, —O—P(S)(Rk)-S—), disulphide (—SS—), hydrazone ($R^kC$=NNR$^k$—), and peptides NHCHR$^{k'}$C(O)NHCHR$^{k''}$C(O)—, or —NHCHR$^{k'}$NHC(O)CHR$^{k''}$C(O)—. Preferred G groups include —C(O)NH—, —SS—, —NHC(O)NH—, —C(O)N—, NHC(O)N, —NHC(O)—.

In certain embodiments, G can be an ether, amino, or thioether linking groups, and Δ can include a polyether or polyimino moiety (e.g., (CH2CH2O)m1(CH2)m2) or (CH2CH2NH)m1(CH2)m2) in which m1 and m2 can be 0-20.

In some embodiments, Δ can have the formula T-4 shown below:

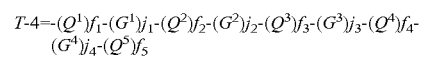

$$T\text{-}4 = -(Q^1)f_1 - (G^1)j_1 - (Q^2)f_2 - (G^2)j_2 - (Q^3)f_3 - (G^3)j_3 - (Q^4)f_4 - (G^4)j_4 - (Q^5)f_5$$

in which each of Q1, Q2, Q3, Q4, and Q5 independently of one another can be C1-C10, e.g. (C1, C2, C3, C4, C5, C6, C7, C8, C9, or C10) alkylene each of G1, G2, G3, and G4 can be, e.g., —SS—, —O—P(O)(OR$^k$)—O—, —O—P(S)(OR$^k$)—O—, —O—P(S)(SR$^k$)—O—, —S—P(O)(OR$^k$)—O—, —O—P(O)(OR$^k$)—S—, —S—P(O)(OR$^k$)—S—, —O—P(S)(OR$^k$)—S—, —S—P(S)(OR$^k$)—O—, —O—P(O)(R$^k$)—O—, —O—P(S)(R$^k$)—O—, —S—P(O)(R$^k$)—O—, —S—P(S)(R$^k$)—O—, —S—P(O)(R$^k$)—S—, —O—P(S)(R$^k$)—S—, —C(O)O—, —OC(O)—, —$R^kC$=NNR$^k$—, P1'C(O)NHP2'—, —P1'NHC(O)P2', NR$^k$C(O)—, —C(O)NR$^k$—, —OC(O)NR$^k$—, —NR$^k$C(O)O—, —O—, —S—, NR$^k$C(O)NR$^k$—, —NR$^k$C(S)NR$^k$—, —NR$^k$C(S)—, —NR$^k$C(S)O—, —C(S)NR$^k$—, —OC(S)NR$^k$—, —NR$^k$C(S)O, —C(O)—, or —NR$^k$—, where f and j can be 0 or 1.

In certain embodiments, $f_1$, $f_2$, $j_1$ can be 1 and, $f_3$, $f_4$, $f_5$, $j_2$, $j_3$, and $j_4$ can be 0, i.e., Q1-G1-Q2 are present. In certain embodiments each of Q1 and Q2 can be C1 to C5 (e.g. C1, C2, C3, C4, C5) alkylene, G1 can be selected from —SS—, —O—P(O)(OR$^k$)—O—, —O—P(S)(OR$^k$)—O—, —O—P(S)(SR$^k$)—O—, —S—P(O)(OR$^k$)—O—, —O—P(O)(OR$^k$)—S—, —S—P(O)(OR$^k$)—S—, —O—P(S)(OR$^k$)—S—, —S—P(S)(OR$^k$)—O—, —O—P(O)(R$^k$)—O—, —O—P(S)(R$^k$)—O—, —S—P(O)(R$^k$)—O—, —S—P(S)(R$^k$)—O—, —S—P(O)(R$^k$)—S—, —O—P(S)(R$^k$)—S—, —C(O)O—, —OC(O)—, —$R^kC$=NNR$^k$—, P1'C(O)NHP2'—, or —P1'NHC(O)P2'. In a preferred embodiment, each of Q1 and Q2 is C2 alkylene and G1 is —S—S—. In another preferred embodiment, each of Q1 and Q2 is C2 and C5 alkylene, respectively, and G1 is —NHC(O)—.

In certain embodiments, $f_1$, $f_2$, $f_3$, $f_4$, $j_1$, $j_2$, $j_3$ can be 1 and, $f_5$ and $j_4$ can be 0, i.e., Q1-G1-Q2-G2-Q3-G3-Q4 are present. In certain embodiments each of Q1, Q2, Q3, and Q4 can be C2 to C8 (e.g. C2, C3, C4, C5, C6, C7, C8) alkylene, G1, G2, and G3 is selected from —SS—, —O—P(O)(OR$^k$)—O—, —O—P(S)(OR$^k$)—O—, —O—P(S)(SR$^k$)—O—, —S—P(O)(OR$^k$)—O—, —O—P(O)(OR$^k$)—S—, —S—P(O)(OR$^k$)—S—, —O—P(S)(OR$^k$)—S—, —S—P(S)(OR$^k$)—O—, —O—P(O)(R$^k$)—O—, —O—P(S)(R$^k$)—O—, —S—P(O)(R$^k$)—O—, —S—P(S)(R$^k$)—O—, —S—P(O)(R$^k$)—S—, —O—P(S)(R$^k$)—S—, —C(O)O—, —OC(O)—, —$R^kC$=NNR$^k$—, P1'C(O)NHP2'—, —P1'NHC(O)P2', NR$^k$C(O)—, —C(O)NR$^k$—, —OC(O)NR$^k$—, —NR$^k$C(O)O—, —O—, —S—, NR$^k$C(O)NR$^k$—, —NR$^k$C(S)NR$^k$—, —NR$^k$C(S)—, —NR$^k$C(S)O—, —C(S)NR$^k$—, —OC(S)NR$^k$—, —NR$^k$C(S)O, —C(O)—, —NR$^k$—. In a preferred embodiment each of Q1, Q2, Q3, and Q4 is C2 alkylene and G1, G2 and G3 is —S—S— or —NHC(O)NH—.

In certain embodiments, $f_1$, $f_2$, $f_3$, $f_4$, $j_1$, $j_2$, $j_3$ can be 1 and $f_5$, and $j_4$ can be 0, i.e., Q1-G1-Q2-G2-Q3 are present. In certain embodiments each of Q1, Q2, and Q3, can be C1 to C8 (e.g. C1, C2, C3, C4, C5, C6, C7, C8) alkylene, G1, and G2, can be selected from —SS—, —O—P(O)(OR$^k$)—O—, —O—P(S)(OR$^k$)—O—, —O—P(S)(SR$^k$)—O—, —S—P(O)(OR$^k$)—O—, —O—P(O)(OR$^k$)—S—, —S—P(O)(OR$^k$)—S—, —O—P(S)(OR$^k$)—S—, —S—P(S)(OR$^k$)—O—, —O—P(O)(R$^k$)—O—, —O—P(S)(R$^k$)—O—, —S—P(O)(R$^k$)—O—, —S—P(S)(R$^k$)—O—, —S—P(O)(R$^k$)—S—, —O—P(S)(R$^k$)—S—, —C(O)O—, —OC(O)—, —R$^k$C=NNR$^k$—, P1'C(O)NHP2'-, —P1'NHC(O)P2', NR$^k$C(O)—, —C(O)NR$^k$—, —OC(O)NR$^k$—, —NR$^k$C(O)O—, —O—, —S—, NR$^k$C(O)NR$^k$—, —NR$^k$C(S)NR$^k$—, —NR$^k$C(S)—, —NR$^k$C(S)O—, —C(S)NR$^k$—, —OC(S)NR$^k$—, —NR$^k$C(S)O, —C(O)—, —NR$^k$—. In a preferred embodiment each of Q1, Q2, Q3, and Q4 is C2 or C6 alkylene and G1 or G2 is —S—S— or —NHC(O)—.

In certain embodiments, one of $G^1$ and $G^2$ can be —S—S—, —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, —O—P(S)(H)—S—, —C=NN—, C(O)O, —OC(O), P1'C(O)NHP2'-, or —P1'NHC(O)P2' and the other —NHC(O)O—, —O—, —C(O)NH—, —S—, —C(S)NH—, carbonyl, —C(O)—, or —NH—.

Exemplary tethers include after incorporation of the precursor monomer subunit into the strand, a ligand having an electrophilic group, e.g., a pentafluorophenyl ester or aldehyde group, can subsequently be attached to the precursor ligand-conjugated monomer by coupling the electrophilic group of the ligand with the terminal nucleophilic group of the precursor ligand-conjugated monomer subunit tether.

In preferred embodiments, a ligand alters the distribution, targeting or lifetime of an iRNA agent into which it is incorporated. In preferred embodiments a ligand provides an enhanced affinity for a selected target, e.g., molecule, cell or cell type, compartment, e.g., a cellular or organ compartment, tissue, organ or region of the body, as, e.g., compared to a species absent such a ligand.

Preferred ligands can improve transport, hybridization, and specificity properties and may also improve nuclease resistance of the resultant natural or modified oligoribonucleotide, or a polymeric molecule comprising any combination of monomers described herein and/or natural or modified ribonucleotides.

Ligands in general can include therapeutic modifiers, e.g., for enhancing uptake; diagnostic compounds or reporter groups e.g., for monitoring distribution; cross-linking agents; nuclease-resistance conferring moieties; and natural or unusual nucleobases. General examples include lipophiles, lipids, steroids (e.g., uvaol, hecigenin, diosgenin), terpenes (e.g., triterpenes, e.g., sarsasapogenin, Friedelin, epifriedelanol derivatized lithocholic acid), vitamins (e.g., folic acid, vitamin A, biotin, pyridoxal), carbohydrates, proteins, protein binding agents, integrin targeting molecules, polycationics, peptides, polyamines, and peptide mimics.

| E' | — | E" |
|---|---|---|
| —OC(O)NH— | —CH$_2$—CH$_2$—S—S—CH$_2$—CH$_2$— | —NHC(O)N— |
| —OC(O)NH— | —CH$_2$—CH$_2$—S—S—CH$_2$—CH$_2$—NHC(O)NH—CH$_2$—CH$_2$—S—S—CH$_2$—CH$_2$— | —NHC(O)N— |
| —OC(O)NH— | —CH$_2$—CH$_2$—S—S—CH$_2$—CH$_2$—NHC(O)—CH$_2$—CH$_2$—CH$_2$—CH$_2$— | —C(O)N— |
| —C(O)NH— | —CH$_2$—CH$_2$—CH$_2$—CH$_2$—CH$_2$—CH$_2$—NHC(O)—CH$_2$—CH$_2$—S—S—CH$_2$—CH$_2$— | —C(O)N— |
| —S—S— | —CH$_2$—CH$_2$—NHC(O)—CH$_2$—CH$_2$—CH$_2$—CH$_2$—CH$_2$— | —C(O)N— |

Tethered Ligands

A wide variety of entities, e.g., ligands, can be tethered to an iRNA agent, e.g., to the carrier of a ligand-conjugated monomer subunit. Examples are described below in the context of a ligand-conjugated monomer subunit but that is only preferred, entities can be coupled at other points to an iRNA agent.

Preferred moieties are ligands, which are coupled, preferably covalently, either directly or indirectly via an intervening tether, to the carrier. In preferred embodiments, the ligand is attached to the carrier via an intervening tether. As discussed above, the ligand or tethered ligand may be present on the ligand-conjugated monomer \ when the ligand-conjugated monomer is incorporated into the growing strand. In some embodiments, the ligand may be incorporated into a "precursor" ligand-conjugated monomer subunit after a "precursor" ligand-conjugated monomer subunit has been incorporated into the growing strand. For example, a monomer having, e.g., an amino-terminated tether, e.g., TAP—(CH$_2$)$_n$NH$_2$ may be incorporated into a growing sense or antisense strand. In a subsequent operation, i.e., Ligands can include a naturally occurring substance, (e.g., human serum albumin (HSA), low-density lipoprotein (LDL), or globulin); carbohydrate (e.g., a dextran, pullulan, chitin, chitosan, inulin, cyclodextrin or hyaluronic acid); amino acid, or a lipid. The ligand may also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly (2-ethylacrylic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic moieties, e.g., cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-gulucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, or an RGD peptide or RGD peptide mimetic.

Other examples of ligands include dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic molecules, e.g., cholesterol, cholic acid, adamantane acetic acid, 1-pyrene butyric acid, dihydrotestosterone, glycerol (e.g., esters and ethers thereof, e.g., $C_{10}$, $C_{11}$, $C_{12}$, $C_{13}$, $C_{14}$, $C_{15}$, $C_{16}$, $C_{17}$, $C_{18}$, $C_{19}$, or $C_{20}$ alkyl; e.g., 1,3-bis-O(hexadecyl)glycerol, 1,3-bis-O(octaadecyl)glycerol), geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Ligands can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as lipids, lectins, carbohydrates, vitamins, cofactors, multivalent lactose, multivalent galactose, N-acetyl-galactosamine, N-acetyl-glucosamine multivalent mannose, or multivalent fucose. The ligand can be, for example, a lipopolysaccharide, an activator of p38 MAP kinase, or an activator of NF-κB.

The ligand can be a substance, e.g., a drug, which can increase the uptake of the iRNA agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

The ligand can increase the uptake of the iRNA agent into the cell by activating an inflammatory response, for example. Exemplary ligands that would have such an effect include tumor necrosis factor alpha (TNFalpha), interleukin-1 beta, or gamma interferon.

In one aspect, the ligand is a lipid or lipid-based molecule. Such a lipid or lipid-based molecule preferably binds a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid based ligand can be used to modulate, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In a preferred embodiment, the lipid based ligand binds HSA. Preferably, it binds HSA with a sufficient affinity such that the conjugate will be preferably distributed to a non-kidney tissue. However, it is preferred that the affinity not be so strong that the HSA-ligand binding cannot be reversed.

In another preferred embodiment, the lipid based ligand binds HSA weakly or not at all, such that the conjugate will be preferably distributed to the kidney. Other moieties that target to kidney cells can also be used in place of or in addition to the lipid based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include are B vitamin, e.g., folic acid, B12, riboflavin, biotin, pyridoxal or other vitamins or nutrients taken up by cancer cells. Also included are HSA and low density lipoprotein (LDL).

In another aspect, the ligand is a cell-permeation agent, preferably a helical cell-permeation agent. Preferably, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

Peptides that target markers enriched in proliferating cells can be used. E.g., RGD containing peptides and petomimetics can target cancer cells, in particular cells that exhibit an $I_v\theta_3$ integrin. Thus, one could use RGD peptides, cyclic peptides containing RGD, RGD peptides that include D-amino acids, as well as synthetic RGD mimics. In addition to RGD, one can use other moieties that target the $I_v$-$\theta_3$ integrin ligand. Generally, such ligands can be used to control proliferating cells and angiogeneis. Preferred conjugates of this type include an iRNA agent that targets PECAM-1, VEGF, or other cancer gene, e.g., a cancer gene described herein.

The iRNA agents of the invention are particularly useful when targeted to the liver. An iRNA agent can be targeted to the liver by incorporation of a monomore derivitzed with a ligand which targets to the liver. For example, a liver-targeting agent can be a lipophilic moiety. Preferred lipophilic moieties include lipid, cholesterols, oleyl, retinyl, or cholesteryl residues. Other lipophilic moieties that can function as liver-targeting agents include cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl) lithocholic acid, O3-(oleoyl)cholenic acid, dimethoxytrityl, or phenoxazine.

An iRNA agent can also be targeted to the liver by association with a low-density lipoprotein (LDL), such as lactosylated LDL. Polymeric carriers complexed with sugar residues can also function to target iRNA agents to the liver.

A targeting agent that incorporates a sugar, e.g., galactose and/or analogues thereof, is particularly useful. These agents target, in particular, the parenchymal cells of the liver. For example, a targeting moiety can include more than one or preferably two or three galactose moieties, spaced about 15 angstroms from each other. The targeting moiety can alternatively be lactose (e.g., three lactose moieties), which is glucose coupled to a galactose. The targeting moiety can also be N-Acetyl-Galactosamine, N-Ac-Glucosamine. A mannose or mannose-6-phosphate targeting moiety can be used for macrophage targeting.

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to iRNA agents can affect pharmacokinetic distribution of the iRNA, such as by enhancing cellular recognition and absorption. The peptide or peptidomimetic moiety can be about 5-50 amino acids long, e.g., about 5, 10, 15, 20, 25, 30, 35, 40, 45, or 50 amino acids long (see Table 1, for example).

TABLE 1

Exemplary Cell Permeation Peptides.

| Cell Permeation Peptide | Amino acid Sequence | Reference |
| --- | --- | --- |
| Penetratin | RQIKIWFQNRRMKWKK (SEQ ID NO: 1) | Derossi et al., J. Biol. Chem. 269: 10444, 1994 |
| Tat fragment (48-60) | GRKKRRQRRRPPQC (SEQ ID NO: 2) | Vives et al., J. Biol. Chem., 272: 16010, 1997 |
| Signal Sequence-based peptide | GALFLGWLGAAGSTMGAWSQPK KKRKV (SEQ ID NO: 3) | Chaloin et al., Biochem. Biophys. Res. Commun., 243: 601, 1998 |
| PVEC | LLIILRRRIRKQAHAHSK (SEQ ID NO: 4) | Elmquist et al., Exp. Cell Res., 269: 237, 2001 |
| Transportan | GWTLNSAGYLLKINLKALAALA KKIL (SEQ ID NO: 5) | Pooga et al., FASEB J., 12: 67, 1998 |
| Amphiphilic model peptide | KLALKLALKALKAALKLA (SEQ ID NO: 6) | Oehlke et al., Mol. Ther., 2: 339, 2000 |
| $Arg_9$ | RRRRRRRRR (SEQ ID NO: 7) | Mitchell et al., J. Pept. Res., 56: 318, 2000 |
| Bacterial cell wall permeating | KFFKFFKFFK (SEQ ID NO: 8) | |
| LL-37 | LLGDFFRKSKEKIGKEFKRIVQ RIKDFLRNLVPRTES (SEQ ID NO: 9) | |

TABLE 1-continued

Exemplary Cell Permeation Peptides.

| Cell Permeation Peptide | Amino acid Sequence | Reference |
| --- | --- | --- |
| Cecropin P1 | SWLSKTAKKLENSAKKRISEGI AIAIQGGPR (SEQ ID NO: 10) | |
| α-defensin | ACYCRIPACIAGERRYGTCIYQ GRLWAFCC (SEQ ID NO: 11) | |
| b-defensin | DHYNCVSSGGQCLYSACPIFTK IQGTCYRGKAKCCK (SEQ ID NO: 12) | |
| Bactenecin | RKCRIVVIRVCR (SEQ ID NO: 13) | |
| PR-39 | RRRPRPPYLPRPRPPPFFPPRLP PRIPPGFPPRFPPRFPGKR-NH2 (SEQ ID NO: 14) | |
| Indolicidin | ILPWKWPWWPWRR-NH2 (SEQ ID NO: 15) | |

A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. In another alternative, the peptide moiety can include a hydrophobic membrane translocation sequence (MTS). An exemplary hydrophobic MTS-containing peptide is RFGF having the amino acid sequence AAVALLPAVLLALLAP (SEQ ID NO:16). An RFGF analogue (e.g., amino acid sequence AALLPV-LLAAP (SEQ ID NO:17)) containing a hydrophobic MTS can also be a targeting moiety. The peptide moiety can be a "delivery" peptide, which can carry large polar molecules including peptides, oligonucleotides, and protein across cell membranes. For example, sequences from the HIV Tat protein (GRKKRRQRRRPPQ (SEQ ID NO:18)) and the Drosophila Antennapedia protein (RQIKIWFQNRRMK-WKK (SEQ ID NO:19)) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., Nature, 354:82-84, 1991). Preferably the peptide or peptidomimetic tethered to an iRNA agent via an incorporated monomer unit is a cell targeting peptide such as an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized.

An RGD peptide moiety can be used to target a tumor cell, such as an endothelial tumor cell or a breast cancer tumor cell (Zitzmann et al., Cancer Res., 62:5139-43, 2002). An RGD peptide can facilitate targeting of an iRNA agent to tumors of a variety of other tissues, including the lung, kidney, spleen, or liver (Aoki et al., Cancer Gene Therapy 8:783-787, 2001). Preferably, the RGD peptide will facilitate targeting of an iRNA agent to the kidney. The RGD peptide can be linear or cyclic, and can be modified, e.g., glycosylated or methylated to facilitate targeting to specific tissues. For example, a glycosylated RGD peptide can deliver an iRNA agent to a tumor cell expressing $\alpha_v\beta_3$ (Haubner et al., Jour. Nucl. Med., 42:326-336, 2001).

Peptides that target markers enriched in proliferating cells can be used. E.g., RGD containing peptides and peptidomimetics can target cancer cells, in particular cells that exhibit an $I_v\theta_3$ integrin. Thus, one could use RGD peptides, cyclic peptides containing RGD, RGD peptides that include D-amino acids, as well as synthetic RGD mimics. In addition to RGD, one can use other moieties that target the $I_v$-$\theta_3$ integrin ligand. Generally, such ligands can be used to control proliferating cells and angiogenesis. Preferred conjugates of this type include an iRNA agent that targets PECAM-1, VEGF, or other cancer gene, e.g., a cancer gene described herein.

A "cell permeation peptide" is capable of permeating a cell, e.g., a microbial cell, such as a bacterial or fungal cell, or a mammalian cell, such as a human cell. A microbial cell-permeating peptide can be, for example, an α-helical linear peptide (e.g., LL-37 or Ceropin P1), a disulfide bond-containing peptide (e.g., α-defensin, β-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., Nucl. Acids Res. 31:2717-2724, 2003).

In one embodiment, a targeting peptide tethered to an ligand-conjugated monomer can be an amphipathic α-helical peptide. Exemplary amphipathic α-helical peptides include, but are not limited to, cecropins, lycotoxins, paradaxins, buforin, CPF, bombinin-like peptide (BLP), cathelicidins, ceratotoxins, S. clava peptides, hagfish intestinal antimicrobial peptides (HFIAPs), magainines, brevinins-2, dermaseptins, melittins, pleurocidin, $H_2A$ peptides, Xenopus peptides, esculentinis-1, and caerins. A number of factors will preferably be considered to maintain the integrity of helix stability. For example, a maximum number of helix stabilization residues will be utilized (e.g., leu, ala, or lys), and a minimum number helix destabilization residues will be utilized (e.g., proline, or cyclic monomeric units. The capping residue will be considered (for example Gly is an exemplary N-capping residue and/or C-terminal amidation can be used to provide an extra H-bond to stabilize the helix. Formation of salt bridges between residues with opposite charges, separated by i±3, or i±4 positions can provide stability. For example, cationic residues such as lysine, arginine, homo-arginine, ornithine or histidine can form salt bridges with the anionic residues glutamate or aspartate.

Peptide and peptidomimetic ligands include those having naturally occurring or modified peptides, e.g., D or L peptides; α, β, or γ peptides; N-methyl peptides; azapeptides; peptides having one or more amide, i.e., peptide, linkages replaced with one or more urea, thiourea, carbamate, or sulfonyl urea linkages; or cyclic peptides.

In some embodiments, the ligand can be any of the nucleobases described herein.

In some embodiments, the ligand can be a substituted amine, e.g. dimethylamino. In certain embodiments the substituted amine can be rendered cationic, e.g., by quaternization, e.g., protonation or alkylation. In certain embodiments, the substituted amine can be at the terminal position of a relatively hydrophobic chain, e.g., an alkylene chain.

In some embodiments, the ligand can be one of the following triterpenes:

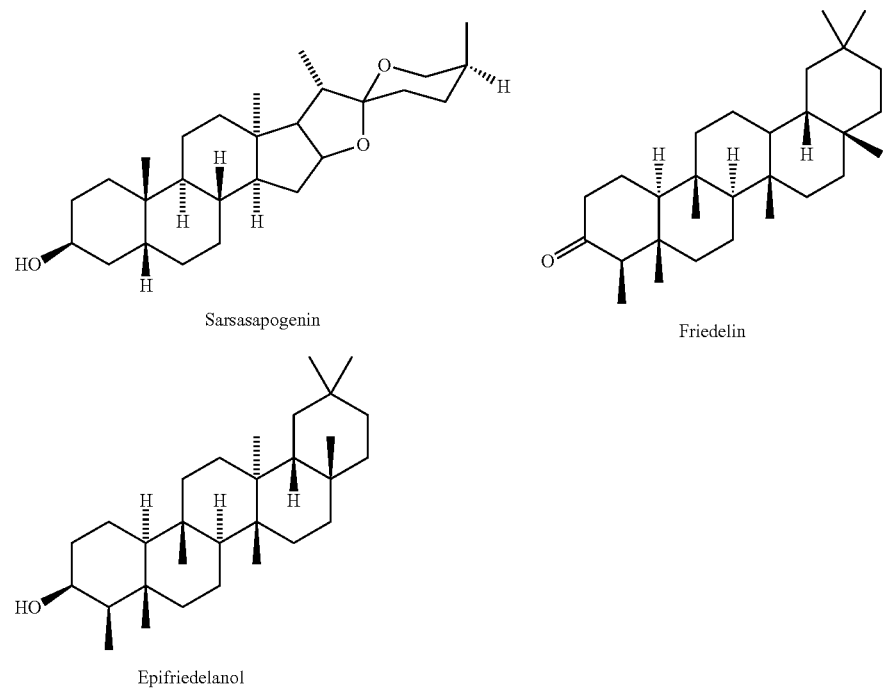

Sarsasapogenin

Friedelin

Epifriedelanol

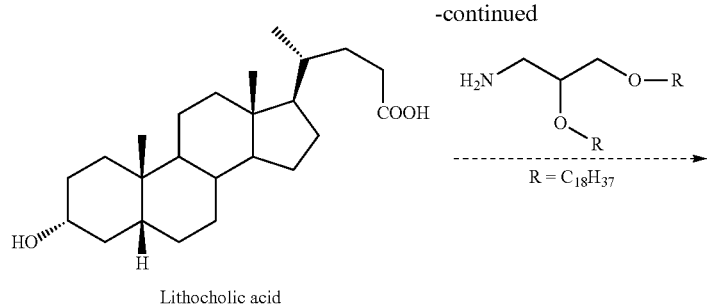

Lithocholic acid

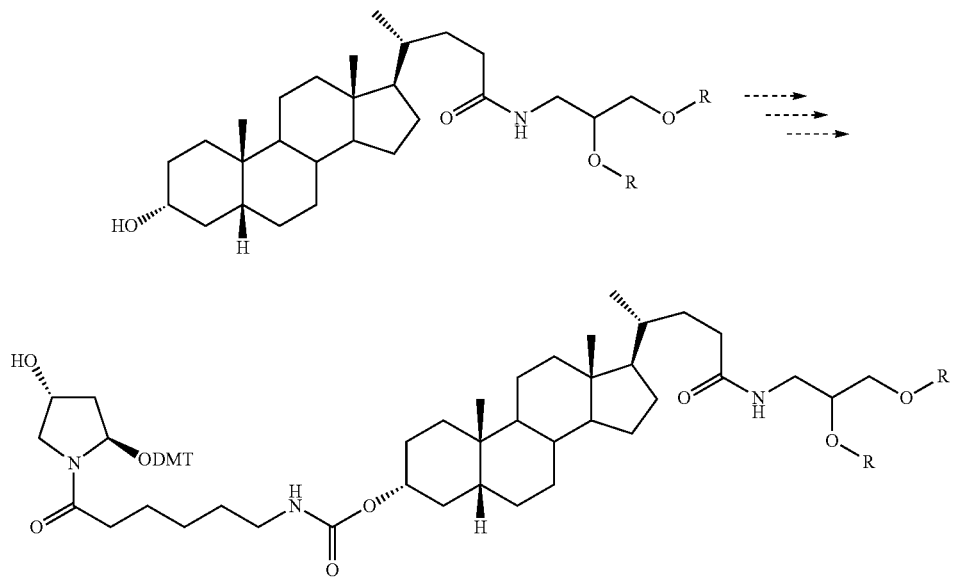

In some embodiments, the ligand can be substituted or unsubstituted cholesterol, or a stereoisomer thereof or one of the following steroids:

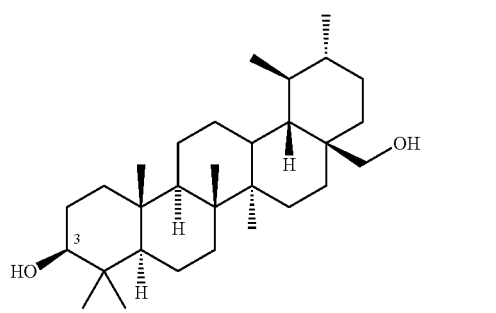

Uvaol

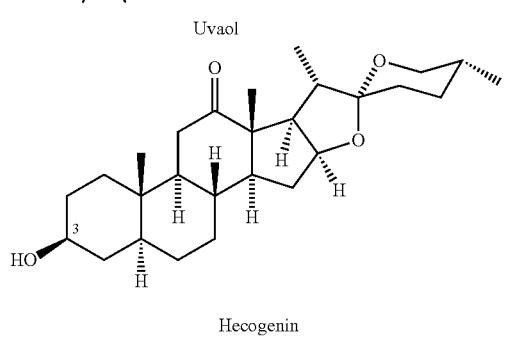

Hecogenin

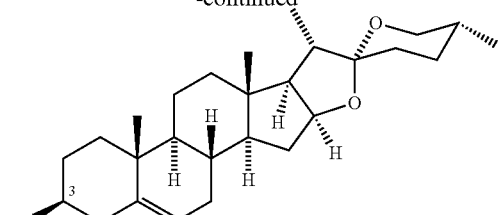

Diosgenin

Methods for Making iRNA Agents

A listing of ribonucleosides containing the unusual bases described herein are described online in "The RNA Modification Database" maintained by Pamela F. Crain, Jef Rozenski and James A. McCloskey; Departments of Medicinal Chemistry and Biochemistry, University of Utah, Salt Lake City, Utah 84112, USA.

The 5' silyl protecting group can be used in conjunction with acid labile orthoesters at the 2' position of ribonucleosides to synthesize oligonucleotides via phosphoramidite chemistry. Final deprotection conditions are known not to significantly degrade RNA products. Functional groups on the unusual and universal bases are blocked during oligonucleotide synthesis with protecting groups that are compatible with the operations being performed that are described herein. All syntheses can be can be conducted in any automated or manual synthesizer on large, medium, or small scale. The syntheses may also be carried out in multiple well plates or glass slides.

The 5'-O-silyl group can be removed via exposure to fluoride ions, which can include any source of fluoride ion, e.g., those salts containing fluoride ion paired with inorganic counterions e.g., cesium fluoride and potassium fluoride or those salts containing fluoride ion paired with an organic counterion, e.g., a tetraalkylammonium fluoride. A crown ether catalyst can be utilized in combination with the inorganic fluoride in the deprotection reaction. Preferred fluoride ion source are tetrabutylammonium fluoride or aminehydrofluorides (e.g., combining aqueous HF with triethylamine in a dipolar aprotic solvent, e.g., dimethylformamide).

The choice of protecting groups for use on the phosphite triesters and phosphotriesters can alter the stability of the triesters towards fluoride. Methyl protection of the phosphotriester or phosphitetriester can stabilize the linkage against fluoride ions and improve process yields.

Since ribonucleosides have a reactive 2' hydroxyl substituent, it can be desirable to protect the reactive 2' position in RNA with a protecting group that is compatible with a 5'-O-silyl protecting group, e.g. one stable to fluoride. Orthoesters meet this criterion and can be readily removed in a final acid deprotection step that can result in minimal RNA degradation.

Tetrazole catalysts can be used in the standard phosphoramidite coupling reaction. Preferred catalysts include e.g. tetrazole, S-ethyl-tetrazole, p-nitrophenyltetrazole.

The general process is as follows. Nucleosides are suitably protected and functionalized for use in solid-phase or solution-phase synthesis of RNA oligonucleotides. The 2'-hydroxyl group in a ribonucleotide can be modified using a tris orthoester reagent. The 2'-hydroxyl can be modified to yield a 2'-O-orthoester nucleoside by reacting the ribonucleoside with the tris orthoester reagent in the presence of an acidic catalyst, e.g., pyridinium p-toluene sulfonate. This reaction is known to those skilled in the art. The product can then be subjected to further protecting group reactions (e.g., 5'-O-silylation) and functionalizations (e.g., 3'-O-phosphitylation) to produce a desired reagent (e.g., nucleoside phosphoramidite) for incorporation within an oligonucleotide or polymer by reactions known to those skilled in the art.

Preferred orthoesters include those comprising ethylene glycol ligands which are protected with acyl or ester protecting groups. Specifically, the preferred acyl group is acetyl. The nucleoside reagents may then be used by those skilled in the art to synthesize RNA oligonucleotides on commercially available synthesizer instruments, e.g. Gene Assembler Plus (Pharmacia), 380B (Applied Biosystems). Following synthesis (either solution-phase or solid-phase) of an oligonucleotide or polymer, the product can be subjected to one or more reactions using non-acidic reagents. One of these reactions may be strong basic conditions, for example, 40% methylamine in water for 10 minutes at 55.degree. C., which will remove the acyl protecting groups from the ethylene glycol ligands but leave the orthoester moiety attached. The resultant orthoester may be left attached when the polymer or oligonucleotide is used in subsequent applications, or it may be removed in a final mildly-acidic reaction, for example, 10 minutes at 55.degree. C. in 50 mM acetic acid, pH 3.0, followed by addition of equal volume of 150 mM TRIS buffer for 10 minutes at 55.degree. C.

Universal bases are described in "Survey and Summary: The Applications of Universal DNA base analogues" Loakes, D., *Nucleic Acid Research* 2001, 29, 2437, which is incorporated by reference in its entirety. Specific examples are described in the following: Liu, D.; Moran, S.; Kool, E. T. *Chem. Biol.*, 1997, 4, 919-926; Morales, J. C.; Kool, E. T. *Biochemistry*, 2000, 39, 2626-2632; Matray, T, J.; Kool, E. T. *J. Am. Chem. Soc.*, 1998, 120, 6191-6192; Moran, S. Ren, R. X.-F.; Rumney IV, S.; Kool, E. T. *J. Am. Chem. Soc.*, 1997, 119, 2056-2057; Guckian, K. M.; Morales, J. C.; Kool, E. T. *J. Org. Chem.*, 1998, 63, 9652-9656; Berger, M.; Wu. Y.; Ogawa, A. K.; McMinn, D. L.; Schultz, P. G.; Romesberg, F. E. *Nucleic Acids Res.*, 2000, 28, 2911-2914; Ogawa, A. K.; Wu, Y.; McMinn, D. L.; Liu, J.; Schultz, P. G.; Romesberg, F. E. *J. Am. Chem. Soc.*, 2000, 122, 3274-3287; Ogawa, A. K.; Wu. Y.; Berger, M.; Schultz, P. G.; Romesberg, F. E. *J. Am. Chem. Soc.*, 2000, 122, 8803-8804; Tae, E. L.; Wu, Y.; Xia, G.; Schultz, P. G.; Romesberg, F. E. *J. Am. Chem. Soc.*, 2001, 123, 7439-7440; Wu, Y.; Ogawa, A. K.; Berger, M.; McMinn, D. L.; Schultz, P. G.; Romesberg, F. E. *J. Am. Chem. Soc.*, 2000, 122, 7621-7632; McMinn, D. L.; Ogawa. A. K.; Wu, Y.; Liu, J.; Schultz, P. G.; Romesberg, F. E. *J. Am. Chem. Soc.*, 1999, 121, 11585-11586; Brotschi, C.; Haberli, A.; Leumann, C, *J. Angew. Chem. Int. Ed.*, 2001, 40, 3012-3014; Weizman, H.; Tor, Y. *J. Am. Chem. Soc.*, 2001, 123, 3375-3376; Lan, T.; McLaughlin, L. W. *J. Am. Chem. Soc.*, 2000, 122, 6512-13.

As discussed above, the monomers and methods described herein can be used in the preparation of modified RNA molecules, or polymeric molecules comprising any combination of monomer compounds described herein and/or natural or modified ribonucleotides in which one or more subunits contain an unusual or universal base. Modified RNA molecules include e.g. those molecules containing a chemically or stereochemically modified nucleoside (e.g., having one or more backbone modifications, e.g., phosphorothioate or P-alkyl; having one or more sugar modifications, e.g., 2'-$OCH_3$ or 2'-F; and/or having one or more base modifications, e.g., 5-alkylamino or 5-allylamino) or a nucleoside surrogate.

Coupling of 5'-hydroxyl groups with phosphoramidites forms phosphite ester intermediates, which in turn are oxidized e.g., with iodine, to the phosphate diester. Alternatively, the phosphites may be treated with e.g., sulfur, selenium, amino, and boron reagents to form modified phosphate backbones. Linkages between the monomers described herein and a nucleoside or oligonucleotide chain can also be treated with iodine, sulfur, selenium, amino, and boron reagents to form unmodified and modified phosphate backbones respectively. Similarly, the monomers described herein may be coupled with nucleosides or oligonucleotides containing any of the modifications or nucleoside surrogates described herein.

Figure 4:
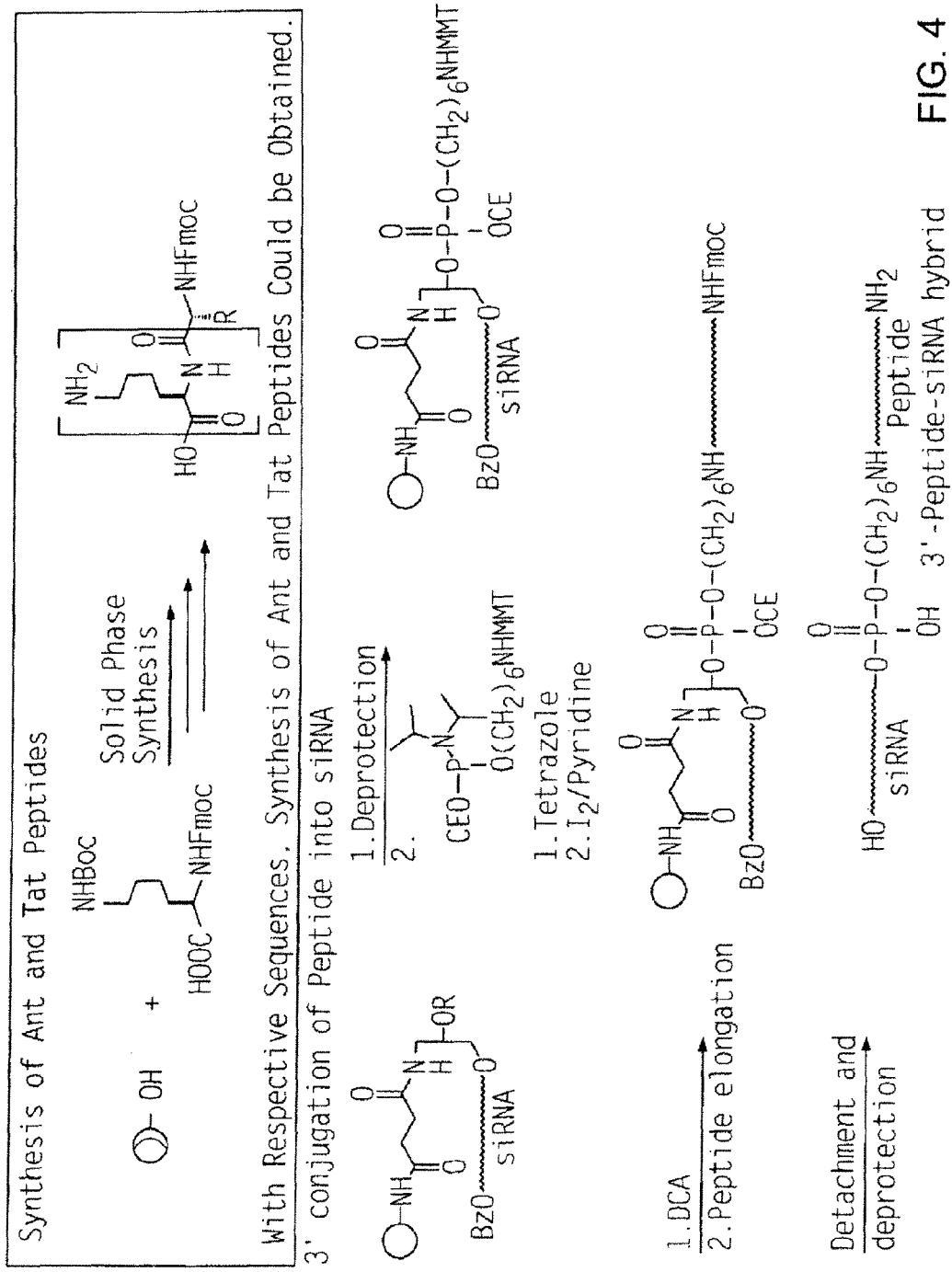
FIG. 4 is a general reaction scheme for 3' conjugation of peptide into iRNA.
Figure 5:
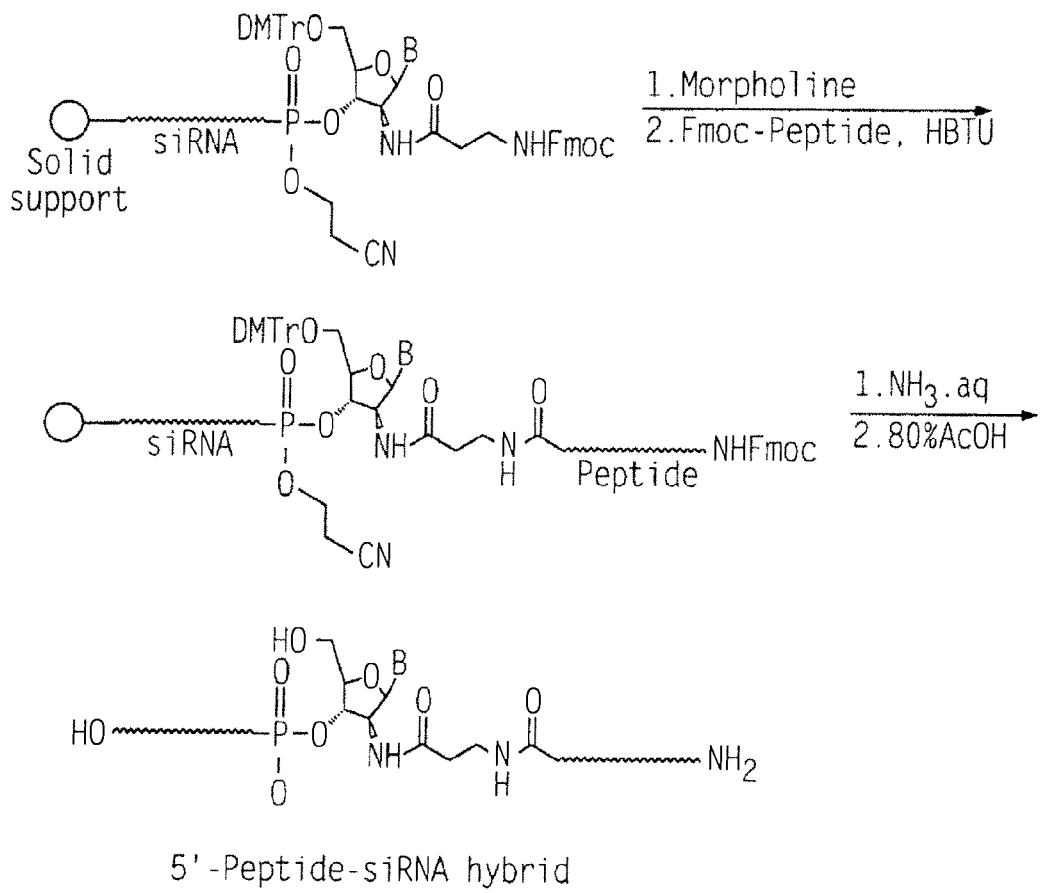
FIG. 5 is a general reaction scheme for 5' conjugation of peptide into iRNA.

The synthesis and purification of oligonucleotide peptide conjugates can be performed by established methods. See, for example, Trufert et al., Tetrahedron, 52:3005, 1996; and Manoharan, "Oligonucleotide Conjugates in Antisense Technology," in *Antisense Drug Technology*, ed. S. T. Crooke, Marcel Dekker, Inc., 2001. Exemplary methods are shown in FIGS. 4 and 5.

Figure 6:
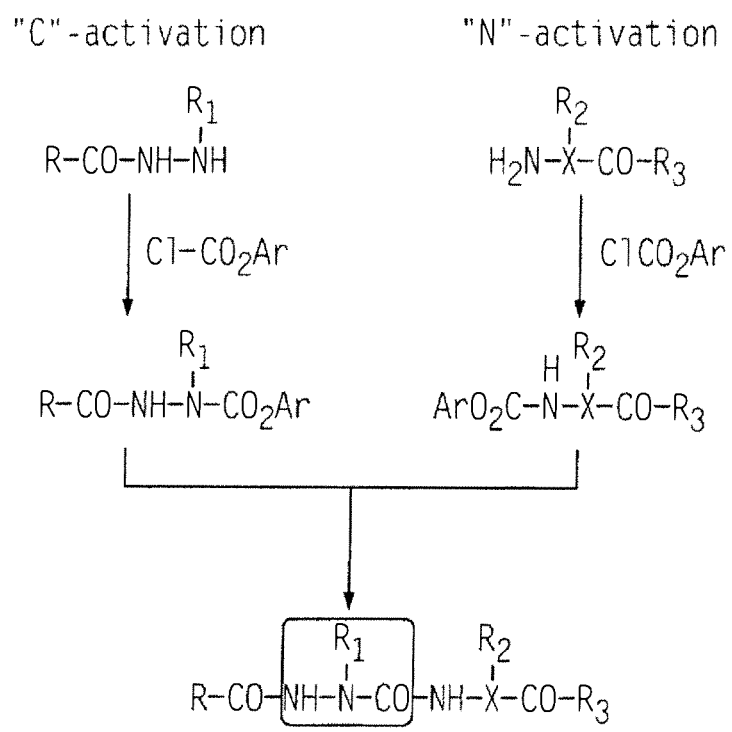
FIG. 6 is a general reaction scheme for the synthesis of aza-peptides.

In one embodiment of the invention, a peptidomimetic can be modified to create a constrained peptide that adopts a distinct and specific preferred conformation, which can increase the potency and selectivity of the peptide. For example, the constrained peptide can be an azapeptide (Gante, Synthesis, 405-413, 1989). An azapeptide is synthesized by replacing the α-carbon of an amino acid with a nitrogen atom without changing the structure of the amino acid side chain. For example, the azapeptide can be synthesized by using hydrazine in traditional peptide synthesis coupling methods, such as by reacting hydrazine with a "carbonyl donor," e.g., phenylchloroformate. A general azapeptide synthesis is shown in FIG. 6.

Figure 7:
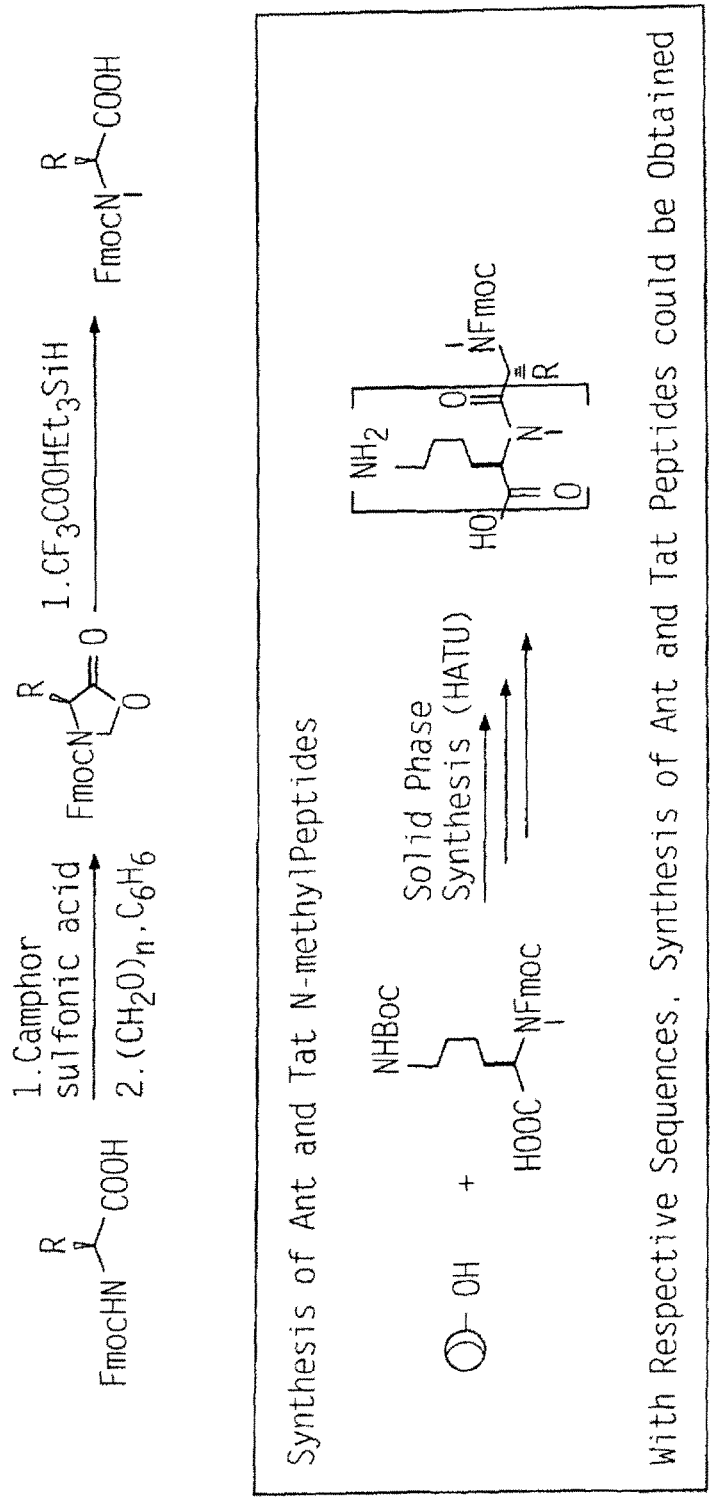
FIG. 7 is a general reaction scheme for the synthesis of N-methyl amino acids and peptides.

In one embodiment of the invention, a peptide or peptidomimetic (e.g., a peptide or peptidomimetic tethered to an ligand-conjugated monomer) can be an N-methyl peptide. N-methyl peptides are composed of N-methyl amino acids, which provide an additional methyl group in the peptide backbone, thereby potentially providing additional means of resistance to proteolytic cleavage. N-methyl peptides can by synthesized by methods known in the art (see, for example, Lindgren et al., Trends Pharmacol. Sci. 21:99, 2000; *Cell Penetrating Peptides: Processes and Applications*, Langel, ed., CRC Press, Boca Raton, Fla., 2002; Fische et al., Bioconjugate. Chem. 12: 825, 2001; Wander et al., J. Am. Chem. Soc., 124:13382, 2002). For example, an Ant or Tat peptide can be an N-methyl peptide. An exemplary synthesis is shown in FIG. 7.

Figure 8:
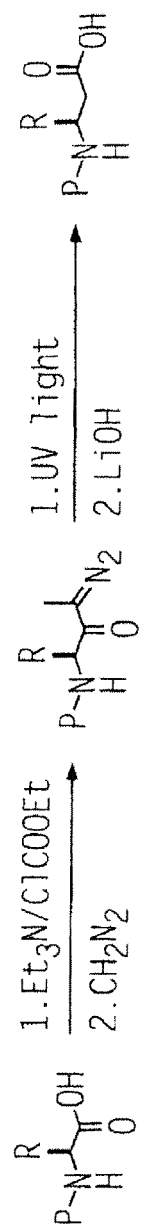
FIG. 8 is a general reaction scheme for the synthesis of β-methyl amino acids and Ant and Tat peptides.
Figure 8:
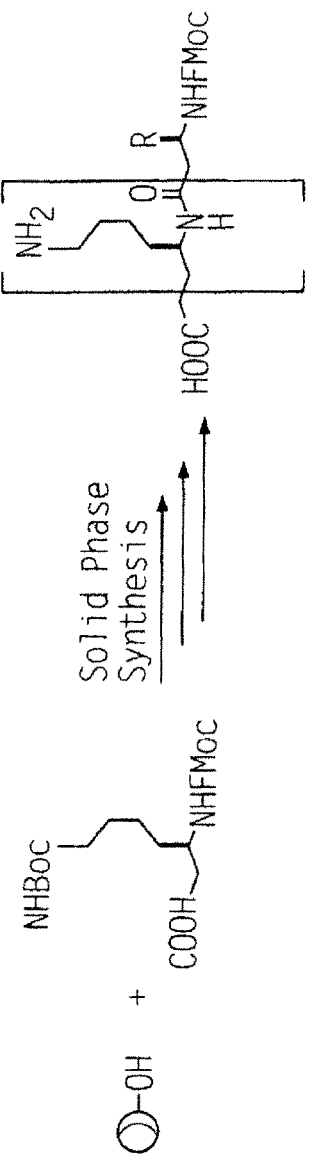

In one embodiment of the invention, a peptide or peptidomimetic (e.g., a peptide or peptidomimetic tethered to a ligand-conjugated monomer) can be a β-peptide. β-peptides form stable secondary structures such as helices, pleated sheets, turns and hairpins in solutions. Their cyclic derivatives can fold into nanotubes in the solid state. β-peptides are resistant to degradation by proteolytic enzymes. β-peptides can be synthesized by methods known in the art. For example, an Ant or Tat peptide can be a β-peptide. An exemplary synthesis is shown in FIG. 8.

Figure 9:
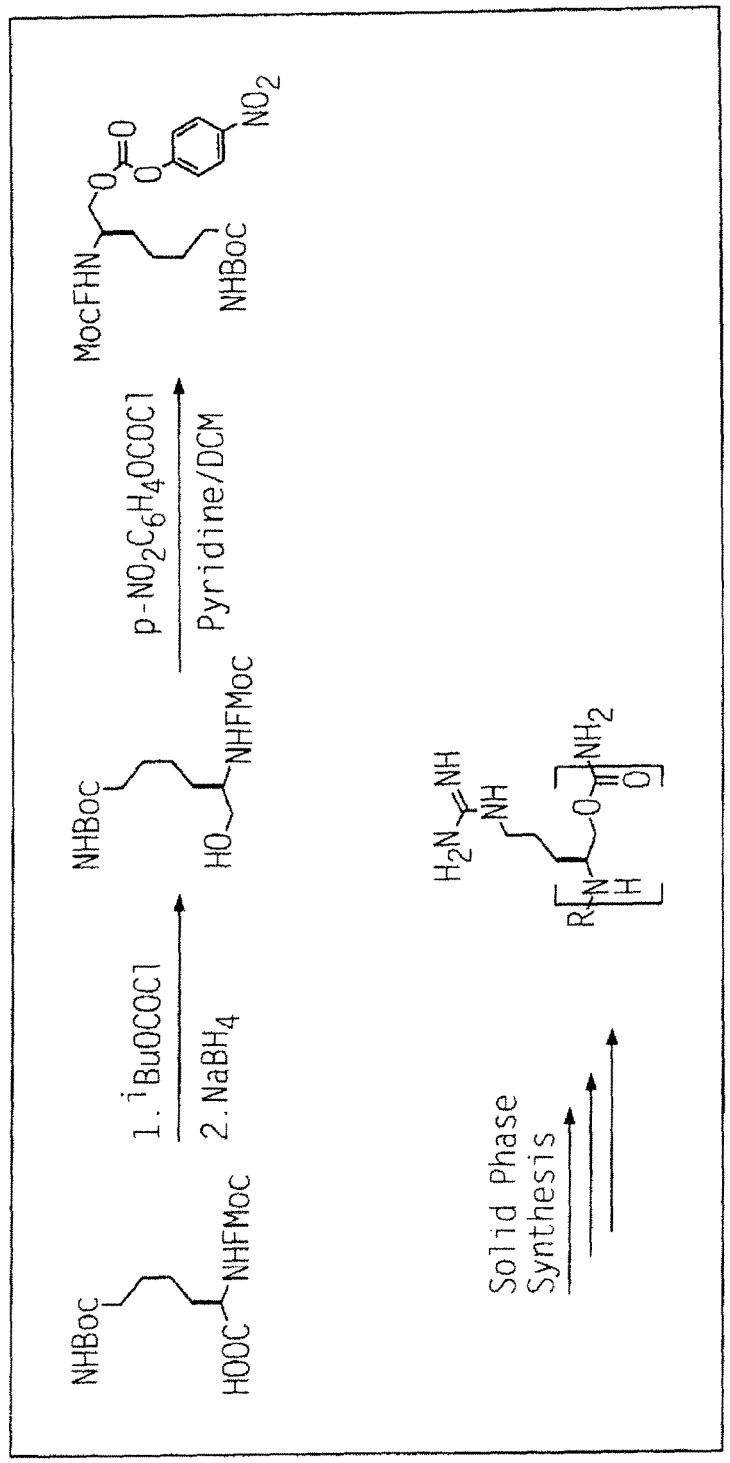
FIG. 9 is a general reaction scheme for the synthesis of Ant and Tat oligocarbamates.

In one embodiment of the invention, a peptide or peptidomimetic (e.g., a peptide or peptidomimetic tethered to a ligand-conjugated monomer) can be a oligocarbamate. Oligocarbamate peptides are internalized into a cell by a transport pathway facilitated by carbamate transporters. For example, an Ant or Tat peptide can be an oligocarbamate. An exemplary synthesis is shown in FIG. 9.

Figure 10:
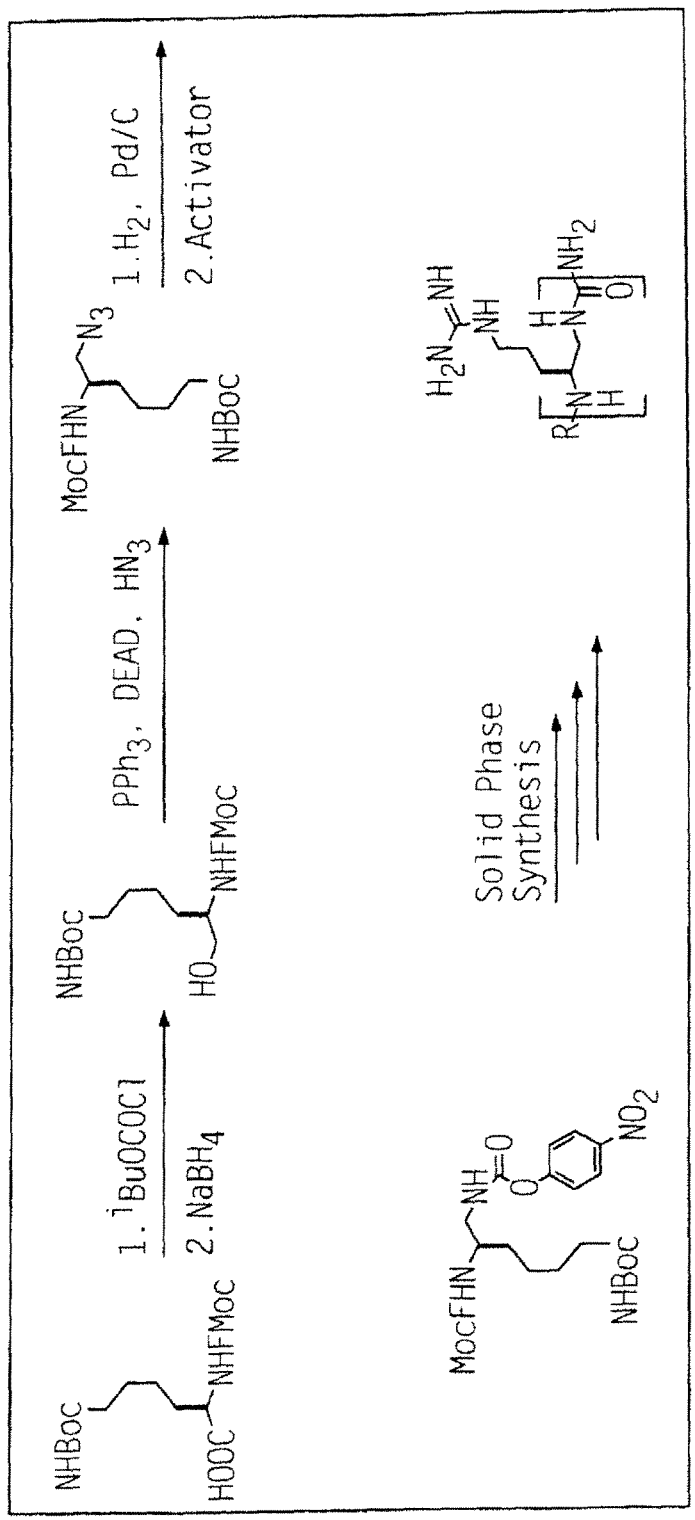
FIG. 10 is a general reaction scheme for the synthesis of Ant and Tat oligoureas.

In one embodiment of the invention, a peptide or peptidomimetic (e.g., a peptide or peptidomimetic tethered to a ligand-conjugated monomer) can be an oligourea conjugate (or an oligothiourea conjugate), in which the amide bond of a peptidomimetic is replaced with a urea moiety. Replacement of the amide bond provides increased resistance to degradation by proteolytic enzymes, e.g., proteolytic enzymes in the gastrointestinal tract. In one embodiment, an oligourea conjugate is tethered to an iRNA agent for use in oral delivery. The backbone in each repeating unit of an oligourea peptidomimetic can be extended by one carbon atom in comparison with the natural amino acid. The single carbon atom extension can increase peptide stability and lipophilicity, for example. An oligourea peptide can therefore be advantageous when an iRNA agent is directed for passage through a bacterial cell wall, or when an iRNA agent must traverse the blood-brain barrier, such as for the treatment of a neurological disorder. In one embodiment, a hydrogen bonding unit is conjugated to the oligourea peptide, such as to create an increased affinity with a receptor. For example, an Ant or Tat peptide can be an oligourea conjugate (or an oligothiourea conjugate). An exemplary synthesis is shown in FIG. 10.

The siRNA peptide conjugates of the invention can be affiliated with, e.g., tethered to, ligand-conjugated monomers occurring at various positions on an iRNA agent. For example, a peptide can be terminally conjugated, on either the sense or the antisense strand, or a peptide can be bisconjugated (one peptide tethered to each end, one conjugated to the sense strand, and one conjugated to the antisense strand). In another option, the peptide can be internally conjugated, such as in the loop of a short hairpin iRNA agent. In yet another option, the peptide can be affiliated with a complex, such as a peptide-carrier complex.

A peptide-carrier complex consists of at least a carrier molecule, which can encapsulate one or more iRNA agents (such as for delivery to a biological system and/or a cell), and a peptide moiety tethered to the outside of the carrier molecule, such as for targeting the carrier complex to a particular tissue or cell type. A carrier complex can carry additional targeting molecules on the exterior of the complex, or fusogenic agents to aid in cell delivery. The one or more iRNA agents encapsulated within the carrier can be conjugated to lipophilic molecules, which can aid in the delivery of the agents to the interior of the carrier.

Figure 11:
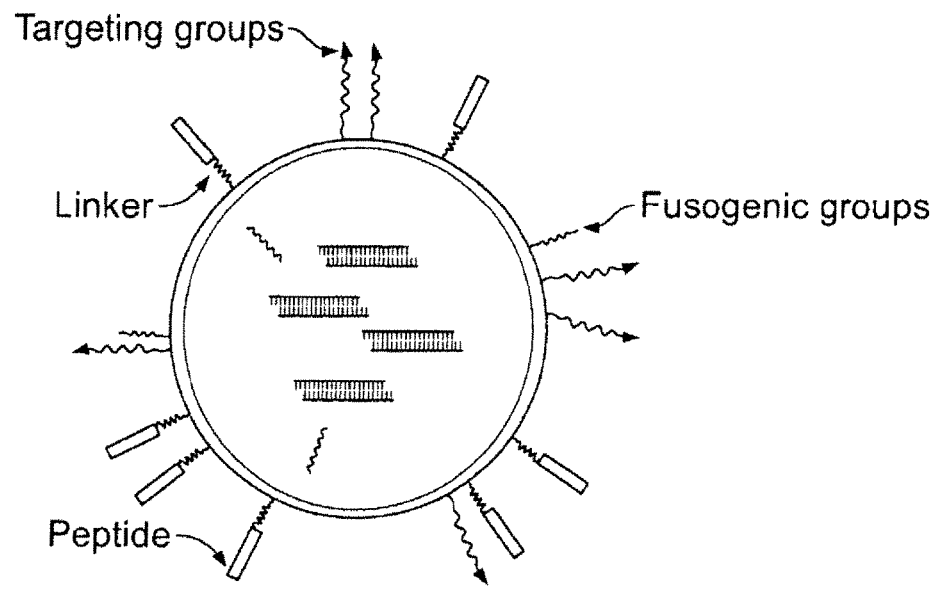
FIG. 11 is a schematic representation of peptide carriers.
Figure 11:
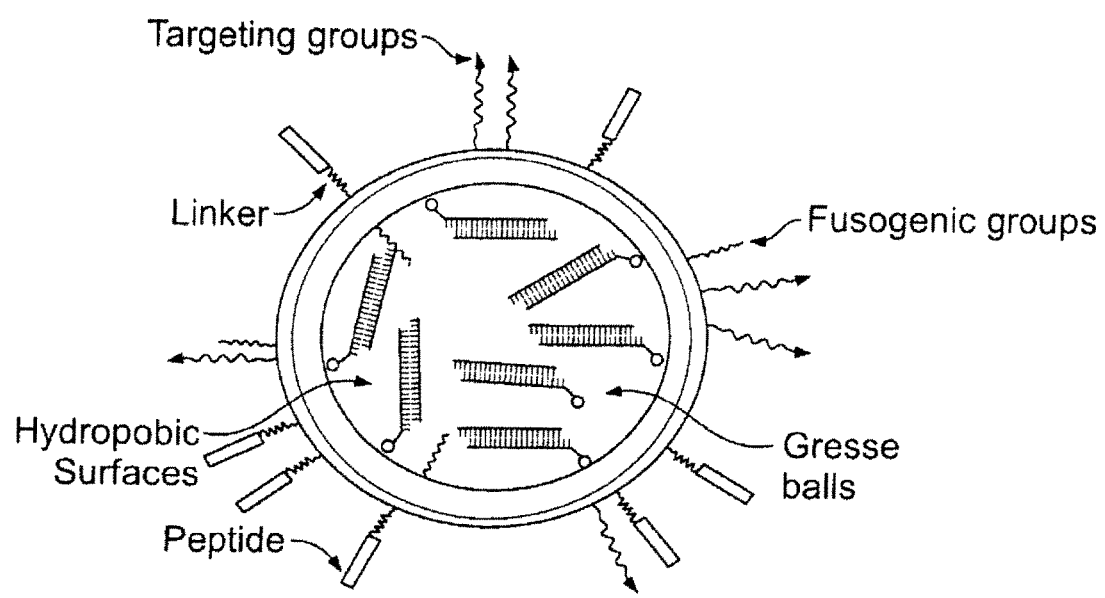

A carrier molecule or structure can be, for example, a micelle, a liposome (e.g., a cationic liposome), a nanoparticle, a microsphere, or a biodegradable polymer. A peptide moiety can be tethered to the carrier molecule by a variety of linkages, such as a disulfide linkage, an acid labile linkage, a peptide-based linkage, an oxyamino linkage or a hydrazine linkage. For example, a peptide-based linkage can be a GFLG peptide. Certain linkages will have particular advantages, and the advantages (or disadvantages) can be considered depending on the tissue target or intended use. For example, peptide based linkages are stable in the blood stream but are susceptible to enzymatic cleavage in the lysosomes. A schematic of preferred carriers is shown in FIG. 11.

The protected monomer compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Other synthetic chemistry transformations, protecting groups (e.g., for hydroxyl, amino, etc. present on the bases) and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The protected monomer compounds of this invention may contain one or more asymmetric centers and thus occur as racemates and racemic mixtures, single enantiomers, individual diastereomers and diastereomeric mixtures. All such isomeric forms of these compounds are expressly included in the present invention. The compounds described herein can also contain linkages (e.g., carbon-carbon bonds, carbon-nitrogen bonds, e.g., amides) or substituents that can restrict bond rotation, e.g. restriction resulting from the presence of a ring or double bond. Accordingly, all cis/trans, E/Z isomers, and rotational isomers (rotamers) are expressly included herein. The compounds of this invention may also be represented in multiple tautomeric forms, in such instances, the invention expressly includes all tautomeric forms of the compounds described herein (e.g., alkylation of a ring system may result in alkylation at multiple sites, the invention expressly includes all such reaction products). All such isomeric forms of such compounds are expressly included in the present invention. All crystal forms of the compounds described herein are expressly included in the present invention.

Representative ligand-conjugated monomers and typical syntheses for preparing ligand-conjugated monomers and related compounds are described in U.S. Ser. No. 10/916,185, filed Aug. 10, 2004, which is hereby incorporated by reference. As discussed elsewhere, protecting groups for ligand-conjugated monomer hydroxyl groups, e.g., $OFG^1$, include but are not limited to the dimethoxytrityl group (DMT). For example, it can be desirable in some embodiments to use silicon-based protecting groups as a protecting group for $OFG^1$. Silicon-based protecting groups can therefore be used in conjunction with or in place of the DMT group as necessary or desired. Thus, the ligand-conjugated monomers and syntheses delineated below, which feature the DMT protecting group as a protecting group for $OFG^1$, is not to be construed as limiting in any way to the invention.

Targeting

The iRNA agents of the invention are particularly useful when targeted to the liver. The chemical modifications described herein can be combined with the compounds and methods described in U.S. Provisional Application 60/462,097, filed on Apr. 9, 2003, which is hereby incorporated by reference; and U.S. Provisional Application 60/461,915, filed on Apr. 10, 2003, which is hereby incorporated by reference. For example, an iRNA agent can be targeted to the liver by incorporation of an RRMS containing a ligand that targets the liver, e.g., a lipophilic moiety. Preferred lipophilic moieties include lipid, cholesterols, oleyl, retinyl, or cholesteryl residues. Other lipophilic moieties that can function as liver-targeting agents include cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine.

An iRNA agent can also be targeted to the liver by association with a low-density lipoprotein (LDL), such as lactosylated LDL. Polymeric carriers complexed with sugar residues can also function to target iRNA agents to the liver.

Conjugation of an iRNA agent with a serum albumin (SA), such as human serum albumin, can also be used to target the iRNA agent to a non-kidney tissue, such as the liver.

An iRNA agent targeted to the liver by an RRMS targeting moiety described herein can target a gene expressed in the liver. For example, the iRNA agent can target p21 (WAF1/DIP1), P27(KIP1), the α-fetoprotein gene, beta-catenin, or c-MET, such as for treating a cancer of the liver. In another embodiment, the iRNA agent can target apoB-100, such as for the treatment of an HDL/LDL cholesterol imbalance; dyslipidemias, e.g., familial combined hyperlipidemia (FCHL), or acquired hyperlipidemia; hypercholesterolemia; statin-resistant hypercholesterolemia; coronary artery disease (CAD); coronary heart disease (CHD); or atherosclerosis. In another embodiment, the iRNA agent can target forkhead homologue in rhabdomyosarcoma (FKHR); glucagon; glucagon receptor; glycogen phosphorylase; PPAR-Gamma Coactivator (PGC-1); Fructose-1,6-bisphosphatase; glucose-6-phosphatase; glucose-6-phosphate translocator; glucokinase inhibitory regulatory protein; or phosphoenolpyruvate carboxykinase (PEPCK), such as to inhibit hepatic glucose production in a mammal, such as a human, such as for the treatment of diabetes. In another embodiment, an iRNA agent targeted to the liver can target Factor V, e.g., the Leiden Factor V allele, such as to reduce the tendency to form a blood clot. An iRNA agent targeted to the liver can include a sequence which targets hepatitis virus (e.g., Hepatitis A, B, C, D, E, F, G, or H). For example, an iRNA agent of the invention can target any one of the nonstructural proteins of HCV: NS3, 4A, 4B, 5A, or 5B. For the treatment of hepatitis B, an iRNA agent can target the protein X (HBx) gene, for example.

A targeting agent that incorporates a sugar, e.g., galactose and/or analogues thereof, can be useful. These agents target, for example, the parenchymal cells of the liver. For example, a targeting moiety can include more than one or preferably two or three galactose moieties, spaced about 15 angstroms from each other. The targeting moiety can alternatively be lactose (e.g., three lactose moieties), which is glucose coupled to a galactose. The targeting moiety can also be N-Acetyl-Galactosamine, N-Ac-Glucosamine. A mannose or mannose-6-phosphate targeting moiety can be used for macrophage targeting.

The iRNA agents of the invention are particularly useful when targeted to the kidney. The chemical modifications described herein can be combined with the compounds and methods described in U.S. Provisional Application 60/460,783, filed on Apr. 3, 2003, which is hereby incorporated by reference; and 60/503,414, filed on Sep. 15, 2003, which is hereby incorporated by reference. An iRNA agent can be targeted to the kidney by incorporation of an RRMS containing a ligand that targets the kidney.

An iRNA agent targeted to the kidney by an RRMS targeting moiety described herein can target a gene expressed in the kidney.

Ligands on RRMSs can include folic acid, glucose, cholesterol, cholic acid, Vitamin E, Vitamin K, or Vitamin A.

Conjugation with a Lipophilic Moiety which Promotes Entry into Cells

RNAi agents can be modified so as to enhance entry into cells, e.g., by conjugation with a lipophilic moiety. A lipophilic moiety can be attached to an RNAi agent in a number of ways but a preferred mode of attachment is by attachment to an RRMS, e.g., pyrroline-based RRMS. The lipohilic moiety can be attached at the N atom of a pyrroline-based RRMS. Examples of lipophilic moieties include cholesterols, lipid, oleyl, retinyl, or cholesteryl residues. Other lipophilic moieties include cholic acid, adamantane acetic acid, 1-pyrene butyric acid, dihydrotestosterone, 1,3-Bis-O (hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine. Cholesterol is a particularly preferred example.

The lipohilic moiety can be attached at the 3' terminus, the 5' terminus, or internally, preferably on the sense strand. The lipohilic moiety can be attached to an RRMS, e.g., a pyrroline-based RRMS which is at the 3' terminus, the 5' terminus, or internal, in the sense strand. The attachment can be direct or through a tethering molecule. Tethers, spacers or linkers discussed herein can be used to attach the moiety to the RRMS.

An iRNA agent to which one or more lipophilic (e.g., cholesterol) molecules is conjugated (referred to herein as an "iRNA-lipophilic conjugate") can be delivered in vivo, e.g., to a cell, such as a cell of a tissue in a subject, such as a mammalian subject (e.g., a human or mouse). Alternatively, or in addition, the iRNA agent can be delivered in vitro, e.g., to a cell in a cell line. Cell lines can be, for example, from a vertebrate organism, such as a mammal (e.g., a human or a mouse). Delivery of an iRNA-cholesterol conjugate to a cell line can be in the absence of other transfection reagents. For example, delivery of an iRNA-lipophilic conjugate to a cell can be in the absence of, or optionally, in the presence of, Lipofectamine™ (Invitrogen, Carlsbad, Calif.), Lipofectamine 2000™, TransIT-TKO™ (Mirus, Madison, Wis.), FuGENE 6 (Roche, Indianapolis, Ind.), polyethylenimine, X-tremeGENE Q2 (Roche, Indianapolis, Ind.), DOTAP, DOSPER, or Metafectene™ (Biontex, Munich, Germany), or another transfection reagent. Exemplary cell lines can be provided by the American Type Culture Collection (ATCC) (Manassas, Va.). An iRNA-lipophilic conjugate can be delivered to a cell line, such as any cell line described herein, to target a specific gene for downregulation.

In one example, an iRNA-lipophilic conjugate can be delivered to a primary cell line, e.g., a synoviocyte (such as type B), cardiac myocyte, keratinocyte, hepatocyte, smooth muscle cell, endothelial cell, or dermal fibroblast cell line.

In another example, an iRNA-lipophilic conjugate can be delivered to monocyte, or myeloid cell line, e.g., a THP1, Raw264.7, IC21, P388D1, U937, or HL60 cell line.

In another example, an iRNA-lipophilic conjugate can be delivered to lymphoma, or leukemia cell line, e.g., an SEM-K2, WEHI-231, HB56, TIB55, Jurkat, K562, EL4, LRMB, Bcl-1, or TF1 cell line. For example, an iRNA-lipophilic conjugate can be delivered to a lymphoma cell line to target a specific gene for down regulation. An iRNA-lipophilic agent can target (down-regulate) a gene in a Jurkat cell line, for example, that encodes an immune factor, such as an interleukin gene, e.g., IL-1, IL-2, IL-5, IL-6, IL-8, IL-10, IL-15, IL-16, IL-17, or IL-18. In another aspect, an iRNA-lipophilic conjugate can target a gene that encodes a receptor of an interleukin.

An iRNA-lipophilic conjugate can target a gene resulting from a chromosomal translocation, such as BCR-ABL, TEL-AML-1, EWS-FLI1, EWS-ERG, TLS-FUS, PAX3-FKHR, or AML1-ETO. For example, an iRNA-lipophilic conjugate that targets a gene resulting from a chromosomal translocation can be delivered to a leukemia cell line, e.g., any of the leukemia cell lines discussed above.

An iRNA-lipophilic conjugate can be delivered to an immortalized cell line, including immortalized cell lines from a variety of different tissue types, including but not limited to T-cells, fibroblast cells, epithelial cells (e.g., kidney epithelial cells) and muscle cells (e.g., smooth muscle cells). Exemplary immortalized cell lines are CTLL-2 (T-cell), Rat 6 (fibroblast), VERO (fibroblast), MRCS (fibroblast), CV1 (fibroblast), Cos7 (fibroblast), RPTE (kidney epithelial), and A10 (smooth muscle) cell lines.

An iRNA-lipophilic conjugate can be delivered to a mast cell line, for example. An iRNA-lipophilic conjugate delivered to a mast cell line can target, for example, a gene encoding a GRB2 associated binding protein (e.g., GAB2).

An iRNA-lipophilic conjugate can be delivered to an adherent tumor cell line, including tumor cell lines from a variety of different tissue types including but not limited to cancers of the bladder, lung, breast, cervix, colon, pancreas, prostate, and liver, melanomas, and glioblastomas. Exemplary tumor cell lines include the T24 (bladder), J82 (bladder), A549 (lung), Calu1 (lung), SW480 (colon), SW620 (colon), CaCo2 (colon), A375 (melanoma), C8161 (melanoma), MCF-7 (breast), MDA-MB-231 (breast), HeLa (cervical), HeLa S3 (cervical), MiaPaCaII (pancreas), Panc1 (pancreas), PC-3 (prostate), LNCaP (prostate), HepG2 (hepatocellular), and U87 (glioblastoma) cell lines. An iRNA-lipophilic conjugate that targets a specific gene can be delivered to an adherent tumor cell line. For example, an iRNA-lipophilic conjugate that targets a growth factor or growth factor receptor, such as a TGF-beta (e.g., TGF-beta 1) or TGF-beta receptor gene, can be delivered to an A549 or HepG2 cell line, a DLD2 colon carcinoma line, or a SKOV3 adenocarcinoma cell line. Other exemplary target growth factor genes include platelet derived growth factor (PDGF) and PDGF-Receptor (PDGFR), vascular endothelial growth factor (VEGF) and VEGF receptor genes (e.g., VEGFr1, VEGFr2, or VEGFr3), and insulin-growth factor receptors, such as type I insulin-growth factor (IGF) receptors, including IGF-1R, DAF-2 and InR.

In another example, an iRNA-lipophilic conjugate that targets one or more genes in a protein tyrosine phosphatase type IVA (PRL3, also called PTP4A3) gene family (e.g., PRL1, PRL2, or PRL3), or a gene in a PRL3 pathway, can be delivered to an A549 cell line, or to a cultured colorectal epithelial cell line.

In another example, an iRNA-lipophilic conjugate can target one or more protein kinase C genes in an adherent tumor cell line, such as in a mouse Lewis lung carcinoma, B16 melanoma, mouse mammary adenocarcinoma or fibrosarcoma; or a human lung carcinoma, bladder carcinoma, pancreatic cancer, gastric cancer, breast cancer, thyroid carcinoma, or melanoma. An iRNA-lipophilic conjugate can target a gene encoding a PKC isoforms, such as PKC-alpha, PKC beta I, PKC beta II, PKC gamma, PKC delta, PKC epsilon, and/or PKC zeta, or a gene encoding one or more receptors of a protein kinase C polypeptide.

In another example, an iRNA-lipophilic conjugate can target a gene encoding a P-glycoprotein, such as a gene in the multidrug resistance (MDR) gene family, e.g., MDR1. An iRNA-lipophilic conjugate that targets an MDR gene can be delivered, for example, to a human KB carcinoma cell line, a human leukemia or ovarian carcinoma cell line, or a lung carcinoma cell line such as A549.

In another example, an iRNA-lipophilic conjugate can target a gene encoding a gene in the telomerase pathway, such as TERT or the telomerase template RNA (TR/TERC). An iRNA-lipophilic conjugate that targets a gene in the telomerase pathway can be delivered, for example, to a human cancer cell line, e.g., a breast, cervical, endometrial, meningeal, lung, testicular, or ovarian cancer cell line.

In another example, an iRNA-lipophilic conjugate delivered to an adherent cell line (e.g., a HeLa, parathyroid adenoma, or A549 cell line) can target a cyclin gene, such as cyclin D1.

In another example, an iRNA-lipophilic conjugate delivered to an adherent cell line (e.g., a HeLa cell line) can target an NF-kappaB or REL-A gene, or a gene encoding a ligand or receptor of an NF-kappaB or REL-A polypeptide, or a gene encoding a subunit of NF-kappaB, such as REL-B, REL, NF-kappaB1 or NF-kappaB2.

In another example, an iRNA-lipophilic conjugate delivered to an adherent cell line (e.g., a HeLa or A549 cell line) can target a gene encoding proliferating cell nuclear antigen (PCNA), a checkpoint kinase gene (CHK-1), or a c-fos gene. Further, an iRNA-lipophilic conjugate can target any gene in a PCNA, CHK-1, or c-fos pathway. For example an iRNA-lipophilic conjugate can down-regulate a gene encoding jun, which is in the c-fos pathway.

In another example, an iRNA-lipophilic conjugate delivered to an adherent cell line (e.g., an A549, T24, or A375 cell line) can target a gene encoding BCL2.

The cell lines described herein can be used to test iRNA-lipophilic conjugates that target exogenous, such as pathogenic or viral, nucleic acids. For example, an iRNA-lipophilic conjugate that targets a hepatitis viral gene can be delivered to a human hepatoma cell line, such as a HepG2 or Huh cell line, e.g., Huh1, Huh4, Huh7, and the like, that has been infected with the virus (e.g., an HAV, HBV, or HCV). For example, an iRNA-lipophilic conjugate that targets an HCV gene, such as in an infected Huh cell line, can target a conserved region of the HCV genome, such as the 5'-non-coding region (NCR), the 5' end of the core protein coding region, or the 3'-NCR.

The cell lines described herein can be also be used to test iRNA-lipophilic conjugates that target exogenous recombinant nucleic acids, such as reporter genes (e.g., GFP, lacZ, beta-galactosidase, and the like), that are transfected (transiently or stably) into the cell lines.

In one aspect, an iRNA-lipophilic conjugate can be delivered to a B-cell line, e.g., BC-3, C1R, or ARH-77 cells. In another aspect, an iRNA-lipophilic conjugate can be delivered to T-cells, e.g., J45.01, MOLT, and CCRF-CEM cells. An iRNA-lipophilic conjugate can target an endogenous or exogenous nucleic acid. For example, development of an iRNA-lipophilic conjugate that targets an HIV gene can be tested against an exogenous HIV nucleic acid in a B cell or T cell line, or in a macrophage or endothelial cell culture system.

An iRNA-lipophilic conjugate can be delivered to cells derived from endoderm, epithelium, or mesoderm. For example, an iRNA-lipophilic conjugate can be delivered to cells of the HeLa or MCF7 epithelial cell lines, to cells of the HUVEC endothelial cell line, or to cells of an SK-UT or HASMC mesodermal cell line. In one example, an iRNA-lipophilic agent that targets a TGF-beta nucleic acid or TGF-beta receptor nucleic acid can be delivered to a vascular smooth muscle cell line, e.g., the kidney fibroblast 293 cell line. Other exemplary targets of iRNA-lipophilic conjugates delivered to fibroblast cells, such as 293 cells, included a protein tyrosine phosphatase-1B (PTP-1B) gene or MAP kinase gene (e.g., ERK1, ERK2, JNK1, JNK2, and p38). In another example, an iRNA-lipophilic conjugate that targets an MDR gene for down-regulation can be delivered to the human intestinal epithelial cell line, Caco-2.

In one example, an iRNA-lipophilic conjugate delivered to a cell line, such as an epithelial or mesodermal cell line (e.g., a HeLa or HASMC cell line, respectively), can target a gene encoding a Myc or Myb polypeptide, e.g., c-Myc, N-Myc, L-Myc, c-Myb, a-Myb, b-Myb, and v-Myb, or a gene in the Myc or Myb gene pathway, such as cyclin D1, cyclin D2, cyclin E, CDK4, cdc25A, CDK2, or CDK4.

In one example, an iRNA-lipophilic conjugate that targets a gene expressed in the nervous system, such as in the brain, e.g., a G72 or D-amino acid oxidase (DAAO) gene, can be delivered to a cultured neuronal cell line, such as an hNT cell line.

In another example, an iRNA-lipophilic conjugate can target a gene encoding a gene in the telomerase pathway, such as TERT or TR/TERC. An iRNA-lipophilic conjugate that targets a gene in the telomerase pathway can be delivered, for example, to a human keratinocyte cell line, such as a HEK cell line, e.g., HEKn or HEKa.

In another example, an iRNA-lipophilic conjugate delivered to a tissue-specific cell-line, such as a HEK (keratinocyte), HuVEC (endothelial), 3T3 (fibroblast), or NHDF (fibroblast) cell line, can target a gene encoding BCL-2, or VEGF or a VEGF receptor (e.g., VEGFr1, VEGFr2, or VEGFr3).

An iRNA-lipophilic conjugate can be delivered to a subgroup of cells derived from a particular tissue. For example, an iRNA-lipophilic conjugate can be delivered to a proximal tubular kidney cell line, such as the mouse cell line mIMCD-3. An iRNA-lipophilic conjugate that targets a TGF-beta nucleic acid or TGF-beta receptor nucleic acid, for example, can be delivered to a cell line derived from prostate tissue, e.g., a PC3 or RWPE prostate cell line. An iRNA-lipophilic conjugate delivered to a prostate tissue cell line can alternatively target a polycomb group gene, such as EZH2.

In another example, an iRNA-lipophilic conjugate can be delivered to pancreatic islet b-cells, where for example, it targets a gastric inhibitory polypeptide (GIP) gene, or a GIP-receptor gene.

The iRNA-lipophilic conjugates described herein are not limited in the cell lines to which they can be applied or to the nucleic acids to which they can target.

iRNA Agent Structure

The monomers described herein can be used to make oligonucleotides which are useful as iRNA agents, e.g., RNA molecules, (double-stranded; single-stranded) that mediate RNAi, e.g., with respect to an endogenous gene of a subject or to a gene of a pathogen. In most cases the iRNA agent will incorporate monomers described herein together with naturally occurring nucleosides or nucleotides or with other modified nucleosides or nucleotides. The modified monomers can be present at any position in the iRNA agent, e.g., at the termini or in the middle region of an iRNA agent or in a duplex region or in an unpaired region. In a preferred embodiment iRNA agent can have any architecture, e.g., architecture described herein. E.g., it can be incorporated into an iRNA agent having an overhang structure, a hairpin or other single strand structure or a two-strand structure, as described herein.

An "RNA agent" as used herein, is an unmodified RNA, modified RNA, or nucleoside surrogate, all of which are defined herein (see, e.g., the section below entitled RNA Agents). While numerous modified RNAs and nucleoside surrogates are described, preferred examples include those which have greater resistance to nuclease degradation than do unmodified RNAs. Preferred examples include those which have a 2' sugar modification, a modification in a single strand overhang, preferably a 3' single strand overhang, or, particularly if single stranded, a 5' modification which includes one or more phosphate groups or one or more analogs of a phosphate group.

An "iRNA agent" as used herein, is an RNA agent which can, or which can be cleaved into an RNA agent which can, down regulate the expression of a target gene, preferably an endogenous or pathogen target RNA. While not wishing to be bound by theory, an iRNA agent may act by one or more of a number of mechanisms, including post-transcriptional cleavage of a target mRNA sometimes referred to in the art as RNAi, or pre-transcriptional or pre-translational mechanisms. An iRNA agent can include a single strand or can include more than one strands, e.g., it can be a double stranded iRNA agent. For example, a single stranded iRNA agent can be a microRNA. If the iRNA agent is a single strand it is particularly preferred that it include a 5' modification which includes one or more phosphate groups or one or more analogs of a phosphate group.

The RRMS-containing iRNA agent should include a region of sufficient homology to the target gene, and be of sufficient length in terms of nucleotides, such that the iRNA agent, or a fragment thereof, can mediate down regulation of the target gene. It is not necessary that there be perfect complementarity between the iRNA agent and the target, but the correspondence must be sufficient to enable the iRNA agent, or a cleavage product thereof, to direct sequence specific silencing, e.g., by RNAi cleavage of the target RNA, e.g., mRNA.

Mismatches to the target mRNA sequence, particularly in the antisense strand of the iRNA agent, are most tolerated in the terminal regions and if present are preferably in a terminal region or regions, e.g., within 6, 5, 4, or 3 nucleotides of the 5' and/or 3' terminus, most preferably within 6, 5, 4, or 3 nucleotides of the 5' terminus of the sense strand or 3' terminus of the antisense strand. The sense strand need only be sufficiently complementary with the antisense strand to maintain the over all double strand character of the molecule.

As discussed elsewhere herein, an iRNA agent will often be modified or include nucleoside surrogates in addition to the ribose replacement modification subunit (RRMS). Single stranded regions of an iRNA agent will often be modified or include nucleoside surrogates, e.g., the unpaired region or regions of a hairpin structure, e.g., a region which links two complementary regions, can have modifications or nucleoside surrogates. Modification to stabilize one or more 3'- or 5'-terminus of an iRNA agent, e.g., against exonucleases, or to favor the antisense sRNA agent to enter into RISC are also favored. Modifications can include C3 (or C6, C7, C12) amino linkers, thiol linkers, carboxyl linkers, non-nucleotidic spacers (C3, C6, C9, C12, abasic, triethylene glycol, hexaethylene glycol), special biotin or fluorescein reagents that come as phosphoramidites and that have another DMT-protected hydroxyl group, allowing multiple couplings during RNA synthesis.

Although, in mammalian cells, long dsiRNA agents can induce the interferon response which is frequently deleterious, short ds iRNA agents do not trigger the interferon response, at least not to an extent that is deleterious to the cell and host. The iRNA agents featured in the present invention include molecules which are sufficiently short that they do not trigger the interferon response in mammalian cells. Thus, the administration of a composition of an iRNA agent (e.g., formulated as described herein) to a mammalian cell can be used to silence expression of the ApoB gene while circumventing the interferon response. Molecules that are short enough that they do not trigger an interferon response are termed sRNA agents or shorter iRNA agents herein. "sRNA agent or shorter iRNA agent" as used herein, refers to an iRNA agent, e.g., a double stranded RNA agent or single strand agent, that is sufficiently short that it does not induce a deleterious interferon response in a human cell, e.g., it has a duplexed region of less than 60 but preferably less than 50, 40, or 30 nucleotide pairs. The sRNA agent, or a cleavage product thereof, can down regulate a target gene, e.g., by inducing RNAi with respect to a target RNA, preferably an endogenous or pathogen target RNA.

In addition to homology to target RNA and the ability to down regulate a target gene, an iRNA agent will preferably have one or more of the following properties:

(1) it will be of the Formula 1, 2, 3, or 4 set out in the RNA Agent section below;

(2) if single stranded it will have a 5' modification which includes one or more phosphate groups or one or more analogs of a phosphate group;

(3) it will, despite modifications, even to a very large number, or all of the nucleosides, have an antisense strand that can present bases (or modified bases) in the proper three dimensional framework so as to be able to form correct base pairing and form a duplex structure with a homologous target RNA which is sufficient to allow down regulation of the target, e.g., by cleavage of the target RNA;

(4) it will, despite modifications, even to a very large number, or all of the nucleosides, still have "RNA-like" properties, i.e., it will possess the overall structural, chemical and physical properties of an RNA molecule, even though not exclusively, or even partly, of ribonucleotide-based content. For example, an iRNA agent can contain, e.g., a sense and/or an antisense strand in which all of the nucleotide sugars contain e.g., 2' fluoro in place of 2' hydroxyl. This deoxyribonucleotide-containing agent can still be expected to exhibit RNA-like properties. While not wishing to be bound by theory, the electronegative fluorine prefers an axial orientation when attached to the C2' position of ribose. This spatial preference of fluorine can, in turn, force the sugars to adopt a $C_{3'}$-endo pucker. This is the same puckering mode as observed in RNA molecules and gives rise to the RNA-characteristic A-family-type helix. Further, since fluorine is a good hydrogen bond acceptor, it can participate in the same hydrogen bonding interactions with water molecules that are known to stabilize RNA structures. (Generally, it is preferred that a modified moiety at the 2' sugar position will be able to enter into H-bonding which is more characteristic of the OH moiety of a ribonucleotide than the H moiety of a deoxyribonucleotide. A preferred iRNA agent will: exhibit a $C_{3'}$-endo pucker in all, or at least 50, 75, 80, 85, 90, or 95% of its sugars; exhibit a $C_{3'}$-endo pucker in a sufficient amount of its sugars that it can give rise to a the RNA-characteristic A-family-type helix; will have no more than 20, 10, 5, 4, 3, 2, or 1 sugar which is not a $C_{3'}$-endo pucker structure. These limitations are particularly preferably in the antisense strand;

(5) regardless of the nature of the modification, and even though the RNA agent can contain deoxynucleotides or modified deoxynucleotides, particularly in overhang or other single strand regions, it is preferred that DNA molecules, or any molecule in which more than 50, 60, or 70% of the nucleotides in the molecule, or more than 50, 60, or 70% of the nucleotides in a duplexed region are deoxyribonucleotides, or modified deoxyribonucleotides which are deoxy at the 2' position, are excluded from the definition of RNA agent.

A "single strand iRNA agent" as used herein, is an iRNA agent which is made up of a single molecule. It may include a duplexed region, formed by intra-strand pairing, e.g., it may be, or include, a hairpin or pan-handle structure. Single strand iRNA agents are preferably antisense with regard to the target molecule. In preferred embodiments single strand iRNA agents are 5' phosphorylated or include a phosphoryl analog at the 5' prime terminus. 5'-phosphate modifications include those which are compatible with RISC mediated gene silencing. Suitable modifications include: 5'-monophosphate ((HO)2(O)P—O-5); 5'-diphosphate ((HO)2(O)P—O—P(HO)(O)—O-5'); 5'-triphosphate ((HO)2(O)P—O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5'); 5'-adenosine cap (Appp), and any modified or unmodified nucleotide cap structure (N—O-5'-(HO)(O)P—O—(HO)(O)P—O—P(HO)(O)—O-5'); 5'-monothiophosphate (phosphorothioate; (HO)2(S)P—O-5'); 5'-monodithiophosphate (phosphorodithioate; (HO)(HS)(S)P—O-5'), 5'-phosphorothiolate ((HO)2(O)P—S-5'); any additional combination of oxygen/sulfur replaced monophosphate, diphosphate and triphosphates (e.g. 5'-alpha-thiotriphosphate, 5'-gamma-thiotriphosphate, etc.), 5'-phosphoramidates ((HO)2(O)P—NH-5', (HO)(NH2)(O)P—O-5'), 5'-alkylphosphonates (R=alkyl=methyl, ethyl, isopropyl, propyl, etc., e.g. RP(OH)(O)—O-5'-, (OH)2(O)P-5'-CH2-), 5'-alkyletherphosphonates (R=alkylether=methoxymethyl (MeOCH2-), ethoxymethyl, etc., e.g. RP(OH)(O)—O-5'—). (These modifications can also be used with the antisense strand of a double stranded iRNA.)

A "ds iRNA agent" (abbreviation for "double stranded iRNA agent") as used herein, is an iRNA agent which includes more than one, and preferably two, strands in which interchain hybridization can form a region of duplex structure.

The antisense strand of a double stranded iRNA agent should be equal to or at least, 14, 15, 16 17, 18, 19, 25, 29, 40, or 50 nucleotides in length. It should be equal to or less than 60, 50, 40, or 30, nucleotides in length. Preferred ranges are 15 to 30, 17 to 25, 19 to 23, and 19 to 21 nucleotides in length.

The sense strand of a double stranded iRNA agent should be equal to or at least 14, 15, 16 17, 18, 19, 25, 29, 40, or 50 nucleotides in length. It should be equal to or less than 60, 50, 40, or 30, nucleotides in length. Preferred ranges are 15 to 30, 17 to 25, 19 to 23, and 19 to 21 nucleotides in length.

The double strand portion of a double stranded iRNA agent should be equal to or at least 15, 16, 17, 18, 19, 20, 21, 22, 23, 24, 25, 29, 40, or 50 nucleotide pairs in length. It should be equal to or less than 60, 50, 40, or 30, nucleotides pairs in length. Preferred ranges are 15 to 30, 17 to 25, 19 to 23, and 19 to 21 nucleotides pairs in length.

It may be desirable to modify one or both of the antisense and sense strands of a double strand iRNA agent. In some cases they will have the same modification or the same class of modification but in other cases the sense and antisense strand will have different modifications, e.g., in some cases it is desirable to modify only the sense strand. It may be desirable to modify only the sense strand, e.g., to inactivate it, e.g., the sense strand can be modified in order to inactivate the sense strand and prevent formation of an active sRNA/protein or RISC. This can be accomplished by a modification which prevents 5'-phosphorylation of the sense strand, e.g., by modification with a 5'-O-methyl ribonucleotide (see Nykänen et al., (2001) ATP requirements and small interfering RNA structure in the RNA interference pathway. Cell 107, 309-321.) Other modifications which prevent phosphorylation can also be used, e.g., simply substituting the 5'-OH by H rather than O-Me. Alternatively, a large bulky group may be added to the 5'-phosphate turning it into a phosphodiester linkage, though this may be less desirable as phosphodiesterases can cleave such a linkage and release a functional sRNA 5'-end. Antisense strand modifications include 5' phosphorylation as well as any of the other 5' modifications discussed herein, particularly the 5' modifications discussed above in the section on single stranded iRNA molecules.

It is preferred that the sense and antisense strands be chosen such that the ds iRNA agent includes a single strand or unpaired region at one or both ends of the molecule. Thus, a ds iRNA agent contains sense and antisense strands, preferable paired to contain an overhang, e.g., one or two 5' or 3' overhangs but preferably a 3' overhang of 2-3 nucleotides. Most embodiments will have a 3' overhang. Preferred sRNA agents will have single-stranded overhangs, preferably 3' overhangs, of 1 to 4, or preferably 2 or 3 nucleotides in length at each end. The overhangs can be the result of one strand being longer than the other, or the result of two strands of the same length being staggered. 5' ends are preferably phosphorylated.

Preferred lengths for the duplexed region is between 15 and 30, most preferably 18, 19, 20, 21, 22, and 23 nucleotides in length, e.g., in the sRNA agent range discussed above. sRNA agents can resemble in length and structure the natural Dicer processed products from long dsRNAs. Embodiments in which the two strands of the sRNA agent are linked, e.g., covalently linked are also included. Hairpin, or other single strand structures which provide the required double stranded region, and preferably a 3' overhang are also within the invention.

As used herein, the phrase "mediates RNAi" refers to the ability of an agent to silence, in a sequence specific manner, a target gene. "Silencing a target gene" means the process whereby a cell containing and/or secreting a certain product of the target gene when not in contact with the agent, will contain and/or secret at least 10%, 20%, 30%, 40%, 50%, 60%, 70%, 80%, or 90% less of such gene product when contacted with the agent, as compared to a similar cell which has not been contacted with the agent. Such product of the target gene can, for example, be a messenger RNA (mRNA), a protein, or a regulatory element. While not wishing to be bound by theory, it is believed that silencing by the agents described herein uses the RNAi machinery or process and a guide RNA, e.g., an siRNA agent of 15 to 30 nucleotide pairs.

As used herein, the term "complementary" is used to indicate a sufficient degree of complementarity such that stable and specific binding occurs between a compound of the invention and a target RNA molecule. Specific binding requires a sufficient degree of complementarity to avoid non-specific binding of the oligomeric compound to non-target sequences under conditions in which specific binding is desired, i.e., under physiological conditions in the case of in vivo assays or therapeutic treatment, or in the case of in vitro assays, under conditions in which the assays are performed. The non-target sequences typically differ by at least 4 nucleotides.

As used herein, an iRNA agent is "sufficiently complementary" to a target RNA, e.g., a target mRNA, if the iRNA agent reduces the production of protein encoded by the target RNA in a cell. The iRNA agent may also be "exactly complementary" (excluding the RRMS containing subunit(s)) to a target RNA, e.g., the target RNA and the iRNA agent anneal, preferably to form a hybrid made exclusively of Watson-Crick basepairs in the region of exact complementarity. A "sufficiently complementary" target RNA can include an internal region (e.g., of at least 10 nucleotides) that is exactly complementary to a target RNA. Moreover, in some embodiments, the iRNA agent specifically discriminates a single-nucleotide difference. In this case, the iRNA agent only mediates RNAi if exact complementary is found in the region (e.g., within 7 nucleotides of) the single-nucleotide difference.

RNA agents discussed herein include otherwise unmodified RNA as well as RNA which have been modified, e.g., to improve efficacy, and polymers of nucleoside surrogates. Unmodified RNA refers to a molecule in which the components of the nucleic acid, namely sugars, bases, and phosphate moieties, are the same or essentially the same as that which occur in nature, preferably as occur naturally in the human body. The art has referred to rare or unusual, but naturally occurring, RNAs as modified RNAs, see, e.g., Limbach et al., (1994) Summary: the modified nucleosides of RNA, Nucleic Acids Res. 22: 2183-2196. Such rare or unusual RNAs, often termed modified RNAs (apparently because the are typically the result of a post transcriptionally modification) are within the term unmodified RNA, as used herein. Modified RNA as used herein refers to a molecule in which one or more of the components of the nucleic acid, namely sugars, bases, and phosphate moieties, are different from that which occur in nature, preferably different from that which occurs in the human body. While they are referred to as modified "RNAs," they will of course, because of the modification, include molecules which are not RNAs. Nucleoside surrogates are molecules in which the ribophosphate backbone is replaced with a non-ribophosphate construct that allows the bases to the presented in the correct spatial relationship such that hybridization is substantially similar to what is seen with a ribophosphate backbone, e.g., non-charged mimics of the ribophosphate backbone. Examples of all of the above are discussed herein.

Much of the discussion below refers to single strand molecules. In many embodiments of the invention a ds iRNA agent, e.g., a partially double stranded iRNA agent, is required or preferred. Thus, it is understood that double stranded structures (e.g. where two separate molecules are contacted to form the double stranded region or where the double stranded region is formed by intramolecular pairing (e.g., a hairpin structure)) made of the single stranded structures described below are within the invention. Preferred lengths are described elsewhere herein.

As nucleic acids are polymers of subunits or monomers, many of the modifications described below occur at a position which is repeated within a nucleic acid, e.g., a modification of a base, or a phosphate moiety, or the a non-linking O of a phosphate moiety. In some cases the modification will occur at all of the subject positions in the nucleic acid but in many, and in fact in most cases it will not. By way of example, a modification may only occur at a 3' or 5' terminal position, may only occur in a terminal regions, e.g. at a position on a terminal nucleotide or in the last 2, 3, 4, 5, or 10 nucleotides of a strand. A modification may occur in a double strand region, a single strand region, or in both. A modification may occur only in the double strand region of an RNA or may only occur in a single strand region of an RNA. E.g., a phosphorothioate modification at a non-linking O position may only occur at one or both termini, may only occur in a terminal regions, e.g., at a position on a terminal nucleotide or in the last 2, 3, 4, 5, or 10 nucleotides of a strand, or may occur in double strand and single strand regions, particularly at termini. Similarly, a modification may occur on the sense strand, antisense strand, or both. In some cases, the sense and antisense strand will have the same modifications or the same class of modifications, but in other cases the sense and antisense strand will have different modifications, e.g., in some cases it may be desirable to modify only one strand, e.g. the sense strand.

In some embodiments it is particularly preferred, e.g., to enhance stability, to include particular bases in overhangs, or to include modified nucleotides or nucleotide surrogates, in single strand overhangs, e.g., in a 5' or 3' overhang, or in both. E.g., it can be desirable to include purine nucleotides in overhangs. In some embodiments all or some of the bases in a 3' or 5' overhang will be modified, e.g., with a modification described herein. Modifications can include, e.g., the use of modifications at the 2' OH group of the ribose sugar, e.g., the use of deoxyribonucleotides, e.g., deoxythymidine, instead of ribonucleotides, and modifications in the phosphate group, e.g., phosphothioate modifications. Overhangs need not be homologous with the target sequence.

Modifications and nucleotide surrogates are discussed below.

FORMULA 1

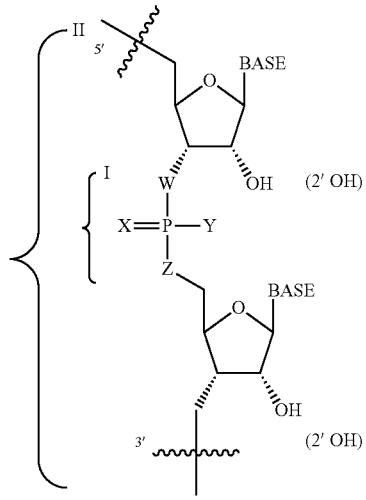

The scaffold presented above in Formula 1 represents a portion of a ribonucleic acid. The basic components are the ribose sugar, the base, the terminal phosphates, and phosphate internucleotide linkers. Where the bases are naturally occurring bases, e.g., adenine, uracil, guanine or cytosine, the sugars are the unmodified 2' hydroxyl ribose sugar (as depicted) and W, X, Y, and Z are all O, Formula 1 represents a naturally occurring unmodified oligoribonucleotide.

Unmodified oligoribonucleotides may be less than optimal in some applications, e.g., unmodified oligoribonucleotides can be prone to degradation by e.g., cellular nucleases. Nucleases can hydrolyze nucleic acid phosphodiester bonds. However, chemical modifications to one or more of the above RNA components can confer improved properties, and, e.g., can render oligoribonucleotides more stable to nucleases. Unmodified oligoribonucleotides may also be less than optimal in terms of offering tethering points for attaching ligands or other moieties to an iRNA agent.

Modified nucleic acids and nucleotide surrogates can include one or more of:

(i) alteration, e.g., replacement, of one or both of the non-linking (X and Y) phosphate oxygens and/or of one or more of the linking (W and Z) phosphate oxygens (When the phosphate is in the terminal position, one of the positions W or Z will not link the phosphate to an additional element in a naturally occurring ribonucleic acid. However, for simplicity of terminology, except where otherwise noted, the W position at the 5' end of a nucleic acid and the terminal Z position at the 3' end of a nucleic acid, are within the term "linking phosphate oxygens" as used herein.);

(ii) alteration, e.g., replacement, of a constituent of the ribose sugar, e.g., of the 2' hydroxyl on the ribose sugar, or wholesale replacement of the ribose sugar with a structure other than ribose, e.g., as described herein;

(iii) wholesale replacement of the phosphate moiety (bracket I) with "dephospho" linkers;

(iv) modification or replacement of a naturally occurring base;

(v) replacement or modification of the ribose-phosphate backbone (bracket II);

(vi) modification of the 3' end or 5' end of the RNA, e.g., removal, modification or replacement of a terminal phosphate group or conjugation of a moiety, e.g. a fluorescently labeled moiety, to either the 3' or 5' end of RNA.

The terms replacement, modification, alteration, and the like, as used in this context, do not imply any process limitation, e.g., modification does not mean that one must start with a reference or naturally occurring ribonucleic acid and modify it to produce a modified ribonucleic acid bur rather modified simply indicates a difference from a naturally occurring molecule.

It is understood that the actual electronic structure of some chemical entities cannot be adequately represented by only one canonical form (i.e. Lewis structure). While not wishing to be bound by theory, the actual structure can instead be some hybrid or weighted average of two or more canonical forms, known collectively as resonance forms or structures. Resonance structures are not discrete chemical entities and exist only on paper. They differ from one another only in the placement or "localization" of the bonding and nonbonding electrons for a particular chemical entity. It can be possible for one resonance structure to contribute to a greater extent to the hybrid than the others. Thus, the written and graphical descriptions of the embodiments of the present invention are made in terms of what the art recognizes as the predominant resonance form for a particular species. For example, any phosphoroamidate (replacement of a nonlinking oxygen with nitrogen) would be represented by X=O and Y=N in the above figure.

Specific modifications are discussed in more detail below.

The Phosphate Group

The phosphate group is a negatively charged species. The charge is distributed equally over the two non-linking oxygen atoms (i.e., X and Y in Formula 1 above). However, the phosphate group can be modified by replacing one of the oxygens with a different substituent. One result of this modification to RNA phosphate backbones can be increased resistance of the oligoribonucleotide to nucleolytic breakdown. Thus while not wishing to be bound by theory, it can be desirable in some embodiments to introduce alterations which result in either an uncharged linker or a charged linker with unsymmetrical charge distribution.

Examples of modified phosphate groups include phosphorothioate, phosphoroselenates, borano phosphates, borano phosphate esters, hydrogen phosphonates, phosphoroamidates, alkyl or aryl phosphonates and phosphotriesters. Phosphorodithioates have both non-linking oxygens replaced by sulfur. Unlike the situation where only one of X or Y is altered, the phosphorus center in the phosphorodithioates is achiral which precludes the formation of oligoribonucleotides diastereomers. Diastereomer formation can result in a preparation in which the individual diastereomers exhibit varying resistance to nucleases. Further, the hybridization affinity of RNA containing chiral phosphate groups can be lower relative to the corresponding unmodified RNA species. Thus, while not wishing to be bound by theory, modifications to both X and Y which eliminate the chiral center, e.g. phosphorodithioate formation, may be desirable in that they cannot produce diastereomer mixtures. Thus, X can be any one of S, Se, B, C, H, N, or OR (R is alkyl or aryl). Thus Y can be any one of S, Se, B, C, H, N, or OR (R is alkyl or aryl). Replacement of X and/or Y with sulfur is preferred.

The phosphate linker can also be modified by replacement of a linking oxygen (i.e., W or Z in Formula 1) with nitrogen (bridged phosphoroamidates), sulfur (bridged phosphorothioates) and carbon (bridged methylenephosphonates). The replacement can occur at a terminal oxygen (position W (3') or position Z (5'). Replacement of W with carbon or Z with nitrogen is preferred.

Candidate agents can be evaluated for suitability as described below.

The Sugar Group

A modified RNA can include modification of all or some of the sugar groups of the ribonucleic acid. E.g., the 2' hydroxyl group (OH) can be modified or replaced with a number of different "oxy" or "deoxy" substituents. While not being bound by theory, enhanced stability is expected since the hydroxyl can no longer be deprotonated to form a 2' alkoxide ion. The 2' alkoxide can catalyze degradation by intramolecular nucleophilic attack on the linker phosphorus atom. Again, while not wishing to be bound by theory, it can be desirable to some embodiments to introduce alterations in which alkoxide formation at the 2' position is not possible.

Examples of "oxy"-2' hydroxyl group modifications include alkoxy or aryloxy (OR, e.g., R=H, alkyl, cycloalkyl, aryl, aralkyl, heteroaryl or sugar); polyethyleneglycols (PEG), $O(CH_2CH_2O)_nCH_2CH_2OR$; "locked" nucleic acids (LNA) in which the 2' hydroxyl is connected, e.g., by a methylene bridge, to the 4' carbon of the same ribose sugar; O-AMINE (AMINE=$NH_2$; alkylamino, dialkylamino, heterocyclyl, arylamino, diaryl amino, heteroaryl amino, or diheteroaryl amino, ethylene diamine, polyamino) and aminoalkoxy, $O(CH_2)_n$AMINE, (e.g., AMINE=$NH_2$; alkylamino, dialkylamino, heterocyclyl, arylamino, diaryl amino, heteroaryl amino, or diheteroaryl amino, ethylene diamine, polyamino). It is noteworthy that oligonucleotides containing only the methoxyethyl group (MOE), ($OCH_2CH_2OCH_3$, a PEG derivative), exhibit nuclease stabilities comparable to those modified with the robust phosphorothioate modification.

"Deoxy" modifications include hydrogen (i.e. deoxyribose sugars, which are of particular relevance to the overhang portions of partially ds RNA); halo (e.g., fluoro); amino (e.g. $NH_2$; alkylamino, dialkylamino, heterocyclyl, arylamino, diaryl amino, heteroaryl amino, diheteroaryl amino, or amino acid); $NH(CH_2CH_2NH)_nCH_2CH_2$-AMINE (AMINE=$NH_2$; alkylamino, dialkylamino, heterocyclyl, arylamino, diaryl amino, heteroaryl amino, or diheteroaryl amino), —NHC(O)R (R=alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with e.g., an amino functionality. Preferred substitutents are 2'-methoxyethyl, 2'-OCH3, 2'-O-allyl, 2'-C— allyl, and 2'-fluoro.

The sugar group can also contain one or more carbons that possess the opposite stereochemical configuration than that of the corresponding carbon in ribose. Thus, a modified RNA can include nucleotides containing e.g., arabinose, as the sugar.

Modified RNAs can also include "abasic" sugars, which lack a nucleobase at C-1'. These abasic sugars can also be further contain modifications at one or more of the constituent sugar atoms.

To maximize nuclease resistance, the 2' modifications can be used in combination with one or more phosphate linker modifications (e.g., phosphorothioate). The so-called "chimeric" oligonucleotides are those that contain two or more different modifications.

The modification can also entail the wholesale replacement of a ribose structure with another entity at one or more sites in the iRNA agent. These modifications are described in section entitled Ribose Replacements for RRMSs.

Candidate modifications can be evaluated as described below.

Replacement of the Phosphate Group

The phosphate group can be replaced by non-phosphorus containing connectors (cf. Bracket I in Formula 1 above). While not wishing to be bound by theory, it is believed that since the charged phosphodiester group is the reaction center in nucleolytic degradation, its replacement with neutral structural mimics should impart enhanced nuclease stability. Again, while not wishing to be bound by theory, it can be desirable, in some embodiment, to introduce alterations in which the charged phosphate group is replaced by a neutral moiety.

Examples of moieties which can replace the phosphate group include siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino. Preferred replacements include the methylenecarbonylamino and methylenemethylimino groups.

Candidate modifications can be evaluated as described below.

Replacement of Ribophosphate Backbone

Oligonucleotide-mimicking scaffolds can also be constructed wherein the phosphate linker and ribose sugar are replaced by nuclease resistant nucleoside or nucleotide surrogates (see Bracket II of Formula 1 above). While not wishing to be bound by theory, it is believed that the absence of a repetitively charged backbone diminishes binding to proteins that recognize polyanions (e.g. nucleases). Again, while not wishing to be bound by theory, it can be desirable in some embodiment, to introduce alterations in which the bases are tethered by a neutral surrogate backbone.

Examples include the mophilino, cyclobutyl, pyrrolidine and peptide nucleic acid (PNA) nucleoside surrogates. A preferred surrogate is a PNA surrogate.

Candidate modifications can be evaluated as described below.

Terminal Modifications

The 3' and 5' ends of an oligonucleotide can be modified. Such modifications can be at the 3' end, 5' end or both ends of the molecule. They can include modification or replacement of an entire terminal phosphate or of one or more of the atoms of the phosphate group. E.g., the 3' and 5' ends of an oligonucleotide can be conjugated to other functional molecular entities such as labeling moieties, e.g., fluorophores (e.g., pyrene, TAMRA, fluorescein, Cy3 or Cy5 dyes) or protecting groups (based e.g., on sulfur, silicon, boron or ester). The functional molecular entities can be attached to the sugar through a phosphate group and/or a spacer. The terminal atom of the spacer can connect to or replace the linking atom of the phosphate group or the C-3' or C-5' O, N, S or C group of the sugar. Alternatively, the spacer can connect to or replace the terminal atom of a nucleotide surrogate (e.g., PNAs). These spacers or linkers can include e.g., —(CH$_2$)$_n$—, —(CH$_2$)$_n$N—, —(CH$_2$)$_n$O—, —(CH$_2$)$_n$S—, O(CH$_2$CH$_2$O)$_n$CH$_2$CH$_2$OH (e.g., n=3 or 6), abasic sugars, amide, carboxy, amine, oxyamine, oxyimine, thioether, disulfide, thiourea, sulfonamide, or morpholino, or biotin and fluorescein reagents. When a spacer/phosphate-functional molecular entity-spacer/phosphate array is interposed between two strands of iRNA agents, this array can substitute for a hairpin RNA loop in a hairpin-type RNA agent. The 3' end can be an —OH group. While not wishing to be bound by theory, it is believed that conjugation of certain moieties can improve transport, hybridization, and specificity properties. Again, while not wishing to be bound by theory, it may be desirable to introduce terminal alterations that improve nuclease resistance. Other examples of terminal modifications include dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic carriers (e.g., cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles).

Terminal modifications can be added for a number of reasons, including as discussed elsewhere herein to modulate activity or to modulate resistance to degradation. Terminal modifications useful for modulating activity include modification of the 5' end with phosphate or phosphate analogs. E.g., in preferred embodiments iRNA agents, especially antisense strands, are 5' phosphorylated or include a phosphoryl analog at the 5' prime terminus. 5'-phosphate modifications include those which are compatible with RISC mediated gene silencing. Suitable modifications include: 5'-monophosphate ((HO)2(O)P—O-5); 5'-diphosphate ((HO)2(O)P—O—P(HO)(O)—O-5'); 5'-triphosphate ((HO)2(O)P—O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5'); 5'-adenosine cap (Appp), and any modified or unmodified nucleotide cap structure (N—O-5'-(HO)(O)P—O—(HO)(O)P—O—P(HO)(O)—O-5'); 5'-monothiophosphate (phosphorothioate; (HO)2(S)P—O-5'); 5'-monodithiophosphate (phosphorodithioate; (HO)(HS)(S)P—O-5'), 5'-phosphorothiolate ((HO)2(O)P—S-5'); any additional combination of oxygen/sulfur replaced monophosphate, diphosphate and triphosphates (e.g. 5'-alpha-thiotriphosphate, 5'-gamma-thiotriphosphate, etc.), 5'-phosphoramidates ((HO)2(O)P—NH-5', (HO)(NH2)(O)P—O-5'), 5'-alkylphosphonates (R=alkyl=methyl, ethyl, isopropyl, propyl, etc., e.g. RP(OH)(O)—O-5'-, (OH)2(O)P-5'-CH2-), 5'-alkyletherphosphonates (R=alkylether=methoxymethyl (MeOCH2-), ethoxymethyl, etc., e.g. RP(OH)(O)—O-5'—).

Terminal modifications can also be useful for monitoring distribution, and in such cases the preferred groups to be added include fluorophores, e.g., fluorescein or an Alexa dye, e.g., Alexa 488. Terminal modifications can also be useful for enhancing uptake, useful modifications for this include cholesterol. Terminal modifications can also be useful for cross-linking an RNA agent to another moiety; modifications useful for this include mitomycin C.

Candidate modifications can be evaluated as described below.

The Bases

Adenine, guanine, cytosine and uracil are the most common bases found in RNA. These bases can be modified or replaced to provide RNA's having improved properties. E.g., nuclease resistant oligoribonucleotides can be prepared with these bases or with synthetic and natural nucleobases (e.g., inosine, thymine, xanthine, hypoxanthine, nubularine, isoguanisine, or tubercidine) and any one of the above modifications. Alternatively, substituted or modified analogs of any of the above bases, e.g., "unusual bases" and "universal bases" described herein, can be employed. Examples include without limitation 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 5-halouracil, 5-(2-aminopropyl)uracil, 5-amino allyl uracil, 8-halo, amino, thiol, thioalkyl, hydroxyl and other 8-substituted adenines and guanines, 5-trifluoromethyl and other 5-substituted uracils and cytosines, 7-methylguanine, 5-substituted pyrimidines, 6-azapyrimidines and N-2, N-6 and O-6 substituted purines, including 2-aminopropyladenine, 5-propynyluracil and 5-propynylcytosine, dihydrouracil, 3-deaza-5-azacytosine, 2-aminopurine, 5-alkyluracil, 7-alkylguanine, 5-alkyl cytosine, 7-deazaadenine, N6, N6-dimethyladenine, 2,6-diaminopurine, 5-amino-allyl-uracil, N3-methyluracil, substituted 1,2,4-triazoles, 2-pyridinone, 5-nitroindole, 3-nitropyrrole, 5-methoxyuracil, uracil-5-oxyacetic acid, 5-methoxycarbonylmethyluracil, 5-methyl-2-thiouracil, 5-methoxycarbonylmethyl-2-thiouracil, 5-methylaminomethyl-2-thiouracil, 3-(3-amino-3-carboxypropyl)uracil, 3-methylcytosine, 5-methylcytosine, $N^4$-acetyl cytosine, 2-thiocytosine, N6-methyladenine, N6-isopentyladenine, 2-methylthio-N6-isopentenyladenine, N-methylguanines, or O-alkylated bases. Further purines and pyrimidines include those disclosed in U.S. Pat. No. 3,687,808, those disclosed in the Concise Encyclopedia Of Polymer Science And Engineering, pages 858-859, Kroschwitz, J. I., ed. John Wiley & Sons, 1990, and those disclosed by Englisch et al., Angewandte Chemie, International Edition, 1991, 30, 613.

Generally, base changes are less preferred for promoting stability, but they can be useful for other reasons, e.g., some, e.g., 2,6-diaminopurine and 2 amino purine, are fluorescent. Modified bases can reduce target specificity. This should be taken into consideration in the design of iRNA agents.

An iRNA agent can have a ZXY structure, such as is described in co-owned PCT Application No. PCT/US2004/07070 filed on Mar. 8, 2004.

An iRNA agent can be complexed with an amphipathic moiety. Exemplary amphipathic moieties for use with iRNA agents are described in co-owned PCT Application No. PCT/US2004/07070 filed on Mar. 8, 2004.

In another embodiment, the iRNA agent can be complexed to a delivery agent that features a modular complex. The complex can include a carrier agent linked to one or more of (preferably two or more, more preferably all three of): (a) a condensing agent (e.g., an agent capable of attracting, e.g., binding, a nucleic acid, e.g., through ionic or electrostatic interactions); (b) a fusogenic agent (e.g., an agent capable of fusing and/or being transported through a cell membrane); and (c) a targeting group, e.g., a cell or tissue targeting agent, e.g., a lectin, glycoprotein, lipid or protein, e.g., an antibody, that binds to a specified cell type. iRNA agents complexed to a delivery agent are described in co-owned PCT Application No. PCT/US2004/07070 filed on Mar. 8, 2004.

An iRNA agent can have non-canonical pairings, such as between the sense and antisense sequences of the iRNA duplex. Exemplary features of non-canonical iRNA agents are described in co-owned PCT Application No. PCT/US2004/07070 filed on Mar. 8, 2004.

Candidate modifications can be evaluated as described below.

Evaluation of Candidate iRNA Agents

A candidate iRNA agent can be evaluated for its ability to downregulate target gene expression. For example, a candidate iRNA agent can be provided, and contacted with a cell that expresses the target gene either endogenously or because it has been transfected with a construct from which the target gene can be expressed. The level of target gene expression prior to and following contact with the candidate iRNA agent can be compared, e.g. on an mRNA or protein level. If it is determined that the amount of RNA or protein expressed from the target gene is lower following contact with the iRNA agent, then it can be concluded that the iRNA agent downregulates target gene expression. The level of target RNA or protein in the cell can be determined by any method desired. For example, the level of target RNA can be determined by Northern blot analysis, reverse transcription coupled with polymerase chain reaction (RT-PCR), or RNAse protection assay. The level of protein can be determined, for example, by Western blot analysis.

Stability Testing, Modification, and Retesting of iRNA Agents

A candidate iRNA agent can be evaluated with respect to stability, e.g., its susceptibility to cleavage by an endonuclease or exonuclease, such as when the iRNA agent is introduced into the body of a subject. Methods can be employed to identify sites that are susceptible to modification, particularly cleavage, e.g., cleavage by a component found in the body of a subject.

When sites susceptible to cleavage are identified, a further iRNA agent can be designed and/or synthesized wherein the potential cleavage site is made resistant to cleavage, e.g. by introduction of a 2'-modification on the site of cleavage, e.g. a 2'-O-methyl group. This further iRNA agent can be retested for stability, and this process may be iterated until an iRNA agent is found exhibiting the desired stability.

In Vivo Testing

An iRNA agent identified as being capable of inhibiting target gene expression can be tested for functionality in vivo in an animal model (e.g., in a mammal, such as in mouse or rat). For example, the iRNA agent can be administered to an animal, and the iRNA agent evaluated with respect to its biodistribution, stability, and its ability to inhibit target gene expression.

The iRNA agent can be administered directly to the target tissue, such as by injection, or the iRNA agent can be administered to the animal model in the same manner that it would be administered to a human.

The iRNA agent can also be evaluated for its intracellular distribution. The evaluation can include determining whether the iRNA agent was taken up into the cell. The evaluation can also include determining the stability (e.g., the half-life) of the iRNA agent. Evaluation of an iRNA agent in vivo can be facilitated by use of an iRNA agent conjugated to a traceable marker (e.g., a fluorescent marker such as fluorescein; a radioactive label, such as $^{35}S$, $^{32}P$, $^{33}P$, or $^3H$; gold particles; or antigen particles for immunohistochemistry).

An iRNA agent useful for monitoring biodistribution can lack gene silencing activity in vivo. For example, the iRNA agent can target a gene not present in the animal (e.g., an iRNA agent injected into mouse can target luciferase), or an iRNA agent can have a non-sense sequence, which does not target any gene, e.g., any endogenous gene). Localization/biodistribution of the iRNA can be monitored, e.g. by a traceable label attached to the iRNA agent, such as a traceable agent described above The iRNA agent can be evaluated with respect to its ability to down regulate target gene expression. Levels of target gene expression in vivo can be measured, for example, by in situ hybridization, or by the isolation of RNA from tissue prior to and following exposure to the iRNA agent. Where the animal needs to be sacrificed in order to harvest the tissue, an untreated control animal will serve for comparison. Target mRNA can be detected by any desired method, including but not limited to RT-PCR, Northern blot, branched-DNA assay, or RNAase protection assay. Alternatively, or additionally, target gene expression can be monitored by performing Western blot analysis on tissue extracts treated with the iRNA agent.

References

General References

The oligoribonucleotides and oligoribonucleosides used in accordance with this invention may be with solid phase synthesis, see for example "Oligonucleotide synthesis, a practical approach", Ed. M. J. Gait, IRL Press, 1984; "Oligonucleotides and Analogues, A Practical Approach", Ed. F. Eckstein, IRL Press, 1991 (especially Chapter 1, Modern machine-aided methods of oligodeoxyribonucleotide synthesis, Chapter 2, Oligoribonucleotide synthesis, Chapter 3,2'-O-Methyloligoribonucleotide-s: synthesis and applications, Chapter 4, Phosphorothioate oligonucleotides, Chapter 5, Synthesis of oligonucleotide phosphorodithioates, Chapter 6, Synthesis of oligo-2'-deoxyribonucleoside methylphosphonates, and. Chapter 7, Oligodeoxynucleotides containing modified bases. Other particularly useful synthetic procedures, reagents, blocking groups and reaction conditions are described in Martin, P., Helv. Chim. Acta, 1995, 78, 486-504; Beaucage, S. L. and Iyer, R. P., Tetrahedron, 1992, 48, 2223-2311 and Beaucage, S. L. and Iyer, R. P., Tetrahedron, 1993, 49, 6123-6194, or references referred to therein.

Modification described in WO 00/44895, WO01/75164, or WO02/44321 can be used herein.

The disclosure of all publications, patents, and published patent applications listed herein are hereby incorporated by reference.

Phosphate Group References

The preparation of phosphinate oligoribonucleotides is described in U.S. Pat. No. 5,508,270. The preparation of alkyl phosphonate oligoribonucleotides is described in U.S. Pat. No. 4,469,863. The preparation of phosphoramidite oligoribonucleotides is described in U.S. Pat. No. 5,256,775 or U.S. Pat. No. 5,366,878. The preparation of phosphotriester oligoribonucleotides is described in U.S. Pat. No. 5,023,243. The preparation of borano phosphate oligoribonucleotide is described in U.S. Pat. Nos. 5,130,302 and 5,177,198. The preparation of 3'-Deoxy-3'-amino phosphoramidate oligoribonucleotides is described in U.S. Pat. No. 5,476,925. 3'-Deoxy-3'-methylenephosphonate oligoribonucleotides is described in An, H, et al. J. Org. Chem. 2001, 66, 2789-2801. Preparation of sulfur bridged nucleotides is described in Sproat et al. Nucleosides Nucleotides 1988, 7, 651 and Crosstick et al. Tetrahedron Lett. 1989, 30, 4693.

Sugar Group References

Modifications to the 2' modifications can be found in Verma, S. et al. Annu. Rev. Biochem. 1998, 67, 99-134 and all references therein. Specific modifications to the ribose can be found in the following references: 2'-fluoro (Kawasaki et. al., J. Med. Chem., 1993, 36, 831-841), 2'-MOE (Martin, P. Helv. Chim. Acta 1996, 79, 1930-1938), "LNA" (Wengel, J. Acc. Chem. Res. 1999, 32, 301-310).

Replacement of the Phosphate Group References

Methylenemethylimino linked oligoribonucleosides, also identified herein as MMI linked oligoribonucleosides, methylenedimethylhydrazo linked oligoribonucleosides, also identified herein as MDH linked oligoribonucleosides, and methylenecarbonylamino linked oligonucleosides, also identified herein as amide-3 linked oligoribonucleosides, and methyleneaminocarbonyl linked oligonucleosides, also identified herein as amide-4 linked oligoribonucleosides as well as mixed backbone compounds having, as for instance, alternating MMI and PO or PS linkages can be prepared as is described in U.S. Pat. Nos. 5,378,825, 5,386,023, 5,489,677 and in published PCT applications PCT/US92/04294 and PCT/US92/04305 (published as WO 92/20822 WO and 92/20823, respectively). Formacetal and thioformacetal linked oligoribonucleosides can be prepared as is described in U.S. Pat. Nos. 5,264,562 and 5,264,564. Ethylene oxide linked oligoribonucleosides can be prepared as is described in U.S. Pat. No. 5,223,618. Siloxane replacements are described in Cormier, J. F. et al. Nucleic Acids Res. 1988, 16, 4583. Carbonate replacements are described in Tittensor, J. R. J. Chem. Soc. C 1971, 1933. Carboxymethyl replacements are described in Edge, M. D. et al. J. Chem. Soc. Perkin Trans. 1 1972, 1991. Carbamate replacements are described in Stirchak, E. P. Nucleic Acids Res. 1989, 17, 6129.

Replacement of the Phosphate-Ribose Backbone References

Cyclobutyl sugar surrogate compounds can be prepared as is described in U.S. Pat. No. 5,359,044. Pyrrolidine sugar surrogate can be prepared as is described in U.S. Pat. No. 5,519,134. Morpholino sugar surrogates can be prepared as is described in U.S. Pat. Nos. 5,142,047 and 5,235,033, and other related patent disclosures. Peptide Nucleic Acids (PNAs) are known per se and can be prepared in accordance with any of the various procedures referred to in Peptide Nucleic Acids (PNA): Synthesis, Properties and Potential Applications, Bioorganic & Medicinal Chemistry, 1996, 4, 5-23. They may also be prepared in accordance with U.S. Pat. No. 5,539,083.

Terminal Modification References

Terminal modifications are described in Manoharan, M. et al. Antisense and Nucleic Acid Drug Development 12, 103-128 (2002) and references therein.

Bases References

N-2 substituted purine nucleoside amidites can be prepared as is described in U.S. Pat. No. 5,459,255. 3-Deaza purine nucleoside amidites can be prepared as is described in U.S. Pat. No. 5,457,191. 5,6-Substituted pyrimidine nucleoside amidites can be prepared as is described in U.S. Pat. No. 5,614,617. 5-Propynyl pyrimidine nucleoside amidites can be prepared as is described in U.S. Pat. No. 5,484,908. Additional references can be disclosed in the above section on base modifications.

Preferred iRNA Agents

Preferred RNA agents have the following structure (see Formula 2 below):

FORMULA 2

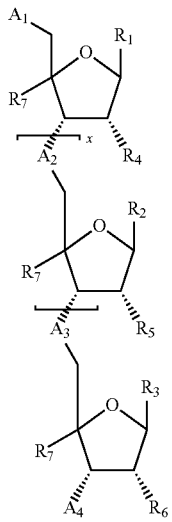

Referring to Formula 2 above, $R^1$, $R^2$, and $R^3$ are each, independently, H, (i.e. abasic nucleotides), adenine, guanine, cytosine and uracil, inosine, thymine, xanthine, hypoxanthine, nubularine, tubercidine, isoguanisine, 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 5-halouracil, 5-(2-aminopropyl)uracil, 5-amino allyl uracil, 8-halo, amino, thiol, thioalkyl, hydroxyl and other 8-substituted adenines and guanines, 5-trifluoromethyl and other 5-substituted uracils and cytosines, 7-methylguanine, 5-substituted pyrimidines, 6-azapyrimidines and N-2, N-6 and O-6 substituted purines, including 2-aminopropyladenine, 5-propynyluracil and 5-propynylcytosine, dihydrouracil, 3-deaza-5-azacytosine, 2-aminopurine, 5-alkyluracil, 7-alkylguanine, 5-alkyl cytosine, 7-deazaadenine, 7-deazaguanine, N6, N6-dimethyladenine, 2,6-diaminopurine, 5-amino-allyl-uracil, N3-methyluracil, substituted 1,2,4-triazoles, 2-pyridinone, 5-nitroindole, 3-nitropyrrole, 5-methoxyuracil, uracil-5-oxyacetic acid, 5-methoxycarbonylmethyluracil, 5-methyl-2-thiouracil, 5-methoxycarbonylmethyl-2-thiouracil, 5-methylaminomethyl-2-thiouracil, 3-(3-amino-3-carboxypropyl)uracil, 3-methylcytosine, 5-methylcytosine, $N^4$-acetyl cytosine, 2-thiocytosine, N6-methyladenine, N6-isopentyladenine, 2-methylthio-N6-isopentenyladenine, N-methylguanines, or O-alkylated bases.

$R^4$, $R^5$, and $R^6$ are each, independently, $OR^8$, $O(CH_2CH_2O)_mCH_2CH_2OR^8$; $O(CH_2)_nR^9$; $O(CH_2)_nOR^9$, H; halo; $NH_2$; $NHR^8$; $N(R^8)_2$; $NH(CH_2CH_2NH)_mCH_2CH_2NHR^9$; $NHC(O)R^8$; cyano; mercapto, $SR^8$; alkylthio-alkyl; alkyl, aralkyl, cycloalkyl, aryl, heteroaryl, alkenyl, alkynyl, each of which may be optionally substituted with halo, hydroxy, oxo, nitro, haloalkyl, alkyl, alkaryl, aryl, aralkyl, alkoxy, aryloxy, amino, alkylamino, dialkylamino, heterocyclyl, arylamino, diaryl amino, heteroaryl amino, diheteroaryl amino, acylamino, alkoxycarbonyl, carboxy, hydroxyalkyl, alkanesulfonyl, alkanesulfonamido, arenesulfonamido, aralkylsulfonamido, alkylcarbonyl, acyloxy, cyano, or ureido; or $R^4$, $R^5$, or $R^6$ together combine with $R^7$ to form an [—O—CH$_2$—] covalently bound bridge between the sugar 2' and 4' carbons.

$A^1$ is:

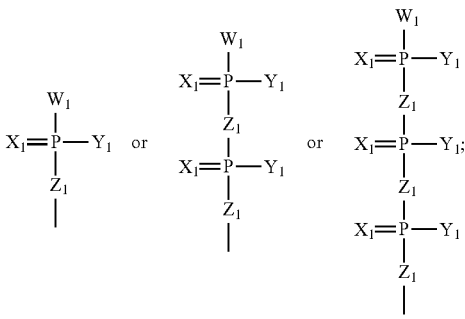

H; OH; OCH$_3$; $W^1$; an abasic nucleotide; or absent;

(a preferred A1, especially with regard to anti-sense strands, is chosen from 5'-monophosphate ((HO)2(O)P—O-5'), 5'-diphosphate ((HO)$_2$(O)P—O—P(HO)(O)—O-5'), 5'-triphosphate ((HO)$_2$(O)P—O—(HO)(O)P—O—P(HO)(O)—O-5'), 5'-guanosine cap (7-methylated or non-methylated) (7m-G-O-5'-(HO)(O)P—O—(HO)(O)P—O—P(HO)(O)—O-5'), 5'-adenosine cap (Appp), and any modified or unmodified nucleotide cap structure (N—O-5'-(HO)(O)P—O—(HO)(O)P—O—P(HO)(O)—O-5'), 5'-monothiophosphate (phosphorothioate; (HO)$_2$(S)P—O-5'), 5'-monodithiophosphate (phosphorodithioate; (HO)(HS)(S)P—O-5'), 5'-phosphorothiolate ((HO)$_2$(O)P—S-5'); any additional combination of oxygen/sulfur replaced monophosphate, diphosphate and triphosphates (e.g. 5'-alpha-thiotriphosphate, 5'-gamma-thiotriphosphate, etc.), 5'-phosphoramidates ((HO)$_2$(O)P—NH-5', (HO)(NH$_2$)(O)P—O-5'), 5'-alkylphosphonates (R=alkyl=methyl, ethyl, isopropyl, propyl, etc., e.g. RP(OH)(O)—O-5'-, (OH)$_2$(O)P-5'-CH$_2$—), 5'-alkyletherphosphonates (R=alkylether=methoxymethyl (MeOCH$_2$—), ethoxymethyl, etc., e.g. RP(OH)(O)—O-5'—)).

$A^2$ is:

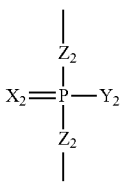

$A^3$ is:

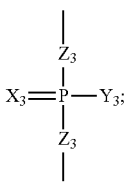

and
$A^4$ is:

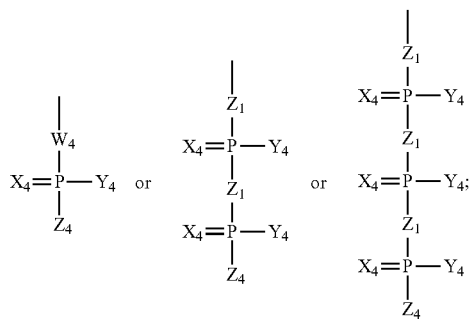

H; $Z^4$; an inverted nucleotide; an abasic nucleotide; or absent.

$W^1$ is OH, $(CH_2)_nR^{10}$, $(CH_2)_nNHR^{10}$, $(CH_2)_nOR^{10}$, $(CH_2)_nSR^{10}$; $O(CH_2)_nR^{10}$; $O(CH_2)_nOR^{10}$, $O(CH_2)_nNR^{10}$, $O(CH_2)_nSR^{10}$; $O(CH_2)_nSS(CH_2)_nOR^{10}$, $O(CH_2)_nC(O)OR^{10}$, $NH(CH_2)_nR^{10}$; $NH(CH_2)_nNR^{10}$; $NH(CH_2)_nOR^{10}$, $NH(CH_2)_nSR^{10}$; $S(CH_2)_nR^{10}$, $S(CH_2)_nNR^{10}$, $S(CH_2)_nOR^{10}$, $S(CH_2)_nSR^{10}O(CH_2CH_2O)_mCH_2CH_2OR^{10}$; $O(CH_2CH_2O)_mCH_2CH_2NHR^{10}$, $NH(CH_2CH_2NH)_mCH_2CH_2NHR^{10}$; $Q-R^{10}$; $O-Q-R^{10}N-Q-R^{10}$, $S-Q-R^{10}$ or —O—. $W^4$ is O, $CH_2$, NH, or S.

$X^1$, $X^2$, $X^3$, and $X^4$ are each, independently, O or S.

$Y^1$, $Y^2$, $Y^3$, and $Y^4$ are each, independently, OH, O⁻, $OR^8$, S, Se, $BH_3^-$, H, $NHR^9$, $N(R^9)_2$ alkyl, cycloalkyl, aralkyl, aryl, or heteroaryl, each of which may be optionally substituted.

$Z^1$, $Z^2$, and $Z^3$ are each independently O, $CH_2$, NH, or S. $Z^4$ is OH, $(CH_2)_nR^{10}$, $(CH_2)_nNHR^{10}$, $(CH_2)_nOR^{10}$, $(CH_2)_nSR^{10}$; $O(CH_2)_nR^{10}$; $O(CH_2)_nOR^{10}$, $O(CH_2)_nNR^{10}$, $O(CH_2)_nSR^{10}$, $O(CH_2)_nSS(CH_2)_nOR^{10}$, $O(CH_2)_nC(O)OR^{10}$; $NH(CH_2)_nR^{10}$; $NH(CH_2)_nNR^{10}$; $NH(CH_2)_nOR^{10}$, $NH(CH_2)_nSR^{10}$; $S(CH_2)_nR^{10}$, $S(CH_2)_nNR^{10}$, $S(CH_2)_nOR^{10}$, $S(CH_2)_nSR^{10}O(CH_2CH_2O)_mCH_2CH_2OR^{10}$, $O(CH_2CH_2O)_mCH_2CH_2NHR^{10}$, $NH(CH_2CH_2NH)_mCH_2CH_2NHR^{10}$; $Q-R^{10}$, $O-Q-R^{10}N-Q-R^{10}$, $S-Q-R^{10}$.

x is 5-100, chosen to comply with a length for an RNA agent described herein.

$R^7$ is H; or is together combined with $R^4$, $R^5$, or $R^6$ to form an [—O—$CH_2$—] covalently bound bridge between the sugar 2' and 4' carbons.

$R^8$ is alkyl, cycloalkyl, aryl, aralkyl, heterocyclyl, heteroaryl, amino acid, or sugar; $R^9$ is $NH_2$, alkylamino, dialkylamino, heterocyclyl, arylamino, diaryl amino, heteroaryl amino, diheteroaryl amino, or amino acid; and $R^{10}$ is H; fluorophore (pyrene, TAMRA, fluorescein, Cy3 or Cy5 dyes); sulfur, silicon, boron or ester protecting group; intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipohilic carriers (cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]₂, polyamino; alkyl, cycloalkyl, aryl, aralkyl, heteroaryl; radiolabelled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles); or an RNA agent. m is 0-1,000,000, and n is 0-20. Q is a spacer selected from the group consisting of abasic sugar, amide, carboxy, oxyamine, oxyimine, thioether, disulfide, thiourea, sulfonamide, or morpholino, biotin or fluorescein reagents.

Preferred RNA agents in which the entire phosphate group has been replaced have the following structure (see Formula 3 below):

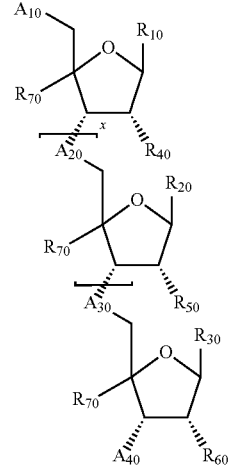

FORMULA 3

Referring to Formula 3, $A^{10}$-$A^{40}$ is L-G-L; $A^{10}$ and/or $A^{40}$ may be absent, in which L is a linker, wherein one or both L may be present or absent and is selected from the group consisting of $CH_2(CH_2)_g$; $N(CH_2)_g$; $O(CH_2)_g$; $S(CH_2)_g$. G is a functional group selected from the group consisting of siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino.

$R^{10}$, $R^{20}$, and $R^{30}$ are each, independently, H, (i.e. abasic nucleotides), adenine, guanine, cytosine and uracil, inosine, thymine, xanthine, hypoxanthine, nubularine, tubercidine, isoguanisine, 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 5-halouracil, 5-(2-aminopropyl)uracil, 5-amino allyl uracil, 8-halo, amino, thiol, thioalkyl, hydroxyl and other 8-substituted adenines and guanines, 5-trifluoromethyl and other 5-substituted uracils and cytosines, 7-methylguanine, 5-substituted pyrimidines, 6-azapyrimidines and N-2, N-6 and O-6 substituted purines, including 2-aminopropyladenine, 5-propynyluracil and 5-propynylcytosine, dihydrouracil, 3-deaza-5-azacytosine, 2-aminopurine, 5-alkyluracil, 7-alkylguanine, 5-alkyl cytosine, 7-deazaadenine, 7-deazaguanine, N6, N6-dimethyladenine, 2,6-diaminopurine, 5-amino-allyl-uracil, N3-methyluracil substituted 1,2,4-triazoles, 2-pyridinone, 5-nitroindole, 3-nitropyrrole, 5-methoxyuracil, uracil-5-oxyacetic acid, 5-methoxycarbonylmethyluracil, 5-methyl-2-thiouracil, 5-methoxycarbonylmethyl-2-thiouracil, 5-methylaminomethyl-2-thiouracil, 3-(3-amino-3-carboxypropyl)uracil, 3-methylcytosine, 5-methylcytosine, $N^4$-acetyl cytosine, 2-thiocytosine, N6-methyladenine, N6-isopentyladenine, 2-methylthio-N6-isopentenyladenine, N-methylguanines, or O-alkylated bases.

$R^{40}$, $R^{50}$, and $R^{60}$ are each, independently, $OR^8$, $O(CH_2CH_2O)_mCH_2CH_2OR^8$; $O(CH_2)_nR^9$; $O(CH_2)_nOR^9$, H; halo; $NH_2$; $NHR^8$; $N(R^8)_2$; $NH(CH_2CH_2NH)_mCH_2CH_2R^9$; $NHC(O)R^8$; cyano; mercapto, $SR^7$; alkyl-thio-alkyl; alkyl, aralkyl, cycloalkyl, aryl, heteroaryl, alkenyl, alkynyl, each of which may be optionally substituted with halo, hydroxy, oxo, nitro, haloalkyl, alkyl, alkaryl, aryl, aralkyl, alkoxy, aryloxy, amino, alkylamino, dialkylamino, heterocyclyl, arylamino, diaryl amino, heteroaryl amino, diheteroaryl amino, acylamino, alkylcarbamoyl, arylcarbamoyl, aminoalkyl, alkoxycarbonyl, carboxy, hydroxyalkyl, alkanesulfonyl, alkanesulfonamido, arenesulfonamido, aralkylsulfonamido, alkylcarbonyl, acyloxy, cyano, and ureido groups; or $R^{40}$, $R^{50}$, or $R^{60}$ together combine with $R^{70}$ to form an [—O—CH₂—] covalently bound bridge between the sugar 2' and 4' carbons.

x is 5-100 or chosen to comply with a length for an RNA agent described herein.

$R^{70}$ is H; or is together combined with $R^{40}$, $R^{50}$, or $R^{60}$ to form an [—O—CH₂—] covalently bound bridge between the sugar 2' and 4' carbons.

$R^8$ is alkyl, cycloalkyl, aryl, aralkyl, heterocyclyl, heteroaryl, amino acid, or sugar; and $R^9$ is $NH_2$, alkylamino, dialkylamino, heterocyclyl, arylamino, diaryl amino, heteroaryl amino, diheteroaryl amino, or amino acid. m is 0-1,000,000, n is 0-20, and g is 0-2.

Preferred nucleoside surrogates have the following structure (see Formula 4 below):

  FORMULA 4

S is a nucleoside surrogate selected from the group consisting of mophilino, cyclobutyl, pyrrolidine and peptide nucleic acid. L is a linker and is selected from the group consisting of $CH_2(CH_2)_g$; $N(CH_2)_g$; $O(CH_2)_g$; $S(CH_2)_g$; —C(O)(CH₂)ₙ— or may be absent. M is an amide bond; sulfonamide; sulfinate; phosphate group; modified phosphate group as described herein; or may be absent.

$R^{100}$, $R^{200}$, and $R^{300}$ are each, independently, H (i.e., abasic nucleotides), adenine, guanine, cytosine and uracil, inosine, thymine, xanthine, hypoxanthine, nubularine, tubercidine, isoguanisine, 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 5-halouracil, 5-(2-aminopropyl)uracil, 5-amino allyl uracil, 8-halo, amino, thiol, thioalkyl, hydroxyl and other 8-substituted adenines and guanines, 5-trifluoromethyl and other 5-substituted uracils and cytosines, 7-methylguanine, 5-substituted pyrimidines, 6-azapyrimidines and N-2, N-6 and O-6 substituted purines, including 2-aminopropyladenine, 5-propynyluracil and 5-propynylcytosine, dihydrouracil, 3-deaza-5-azacytosine, 2-aminopurine, 5-alkyluracil, 7-alkylguanine, 5-alkyl cytosine, 7-deazaadenine, 7-deazaguanine, N6, N6-dimethyladenine, 2,6-diaminopurine, 5-amino-allyl-uracil, N3-methyluracil substituted 1,2,4-triazoles, 2-pyridinones, 5-nitroindole, 3-nitropyrrole, 5-methoxyuracil, uracil-5-oxyacetic acid, 5-methoxycarbonylmethyluracil, 5-methyl-2-thiouracil, 5-methoxycarbonylmethyl-2-thiouracil, 5-methylaminomethyl-2-thiouracil, 3-(3-amino-3-carboxypropyl)uracil, 3-methylcytosine, 5-methylcytosine, $N^4$-acetyl cytosine, 2-thiocytosine, N6-methyladenine, N6-isopentyladenine, 2-methylthio-N6-isopentenyladenine, N-methylguanines, or O-alkylated bases.

x is 5-100, or chosen to comply with a length for an RNA agent described herein; and g is 0-2.

Nuclease Resistant Monomers

The monomers and methods described herein can be used to prepare an RNA, e.g., an iRNA agent, that incorporates a nuclease resistant monomer (NRM), such as those described herein and those described in copending, co-owned U.S. Provisional Application Ser. No. 60/469,612, filed on May 9, 2003, and International Application No. PCT/US04/07070, both of which are hereby incorporated by reference.

An iRNA agent can include monomers which have been modified so as to inhibit degradation, e.g., by nucleases, e.g., endonucleases or exonucleases, found in the body of a subject. These monomers are referred to herein as NRMs, or nuclease resistance promoting monomers or modifications. In many cases these modifications will modulate other properties of the iRNA agent as well, e.g., the ability to interact with a protein, e.g., a transport protein, e.g., serum albumin, or a member of the RISC(RNA-induced Silencing Complex), or the ability of the first and second sequences to form a duplex with one another or to form a duplex with another sequence, e.g., a target molecule.

While not wishing to be bound by theory, it is believed that modifications of the sugar, base, and/or phosphate backbone in an iRNA agent can enhance endonuclease and exonuclease resistance, and can enhance interactions with transporter proteins and one or more of the functional components of the RISC complex. Preferred modifications are those that increase exonuclease and endonuclease resistance and thus prolong the half-life of the iRNA agent prior to interaction with the RISC complex, but at the same time do not render the iRNA agent resistant to endonuclease activity in the RISC complex. Again, while not wishing to be bound by any theory, it is believed that placement of the modifications at or near the 3' and/or 5' end of antisense strands can result in iRNA agents that meet the preferred nuclease resistance criteria delineated above. Again, still while not wishing to be bound by any theory, it is believed that placement of the modifications at e.g., the middle of a sense strand can result in iRNA agents that are relatively less likely to undergo off-targeting.

Modifications described herein can be incorporated into any double-stranded RNA and RNA-like molecule described herein, e.g., an iRNA agent. An iRNA agent may include a duplex comprising a hybridized sense and antisense strand, in which the antisense strand and/or the sense strand may include one or more of the modifications described herein. The anti sense strand may include modifications at the 3' end and/or the 5' end and/or at one or more positions that occur 1-6 (e.g., 1-5, 1-4, 1-3, 1-2) nucleotides from either end of the strand. The sense strand may include modifications at the 3' end and/or the 5' end and/or at any one of the intervening positions between the two ends of the strand. The iRNA agent may also include a duplex comprising two hybridized antisense strands. The first and/or the second antisense strand may include one or more of the modifications described herein. Thus, one and/or both anti-sense strands may include modifications at the 3' end and/or the 5' end and/or at one or more positions that occur 1-6 (e.g., 1-5, 1-4, 1-3, 1-2) nucleotides from either end of the strand. Particular configurations are discussed below.

Modifications that can be useful for producing iRNA agents that meet the preferred nuclease resistance criteria delineated above can include one or more of the following chemical and/or stereochemical modifications of the sugar, base, and/or phosphate backbone:

(i) chiral ($S_P$) thioates. Thus, preferred NRMs include nucleotide dimers with an enriched or pure for a particular chiral form of a modified phosphate group containing a heteroatom at the nonbridging position, e.g., Sp or Rp, at the position X, where this is the position normally occupied by the oxygen. The atom at X can also be S, Se, $Nr_2$, or $Br_3$. When X is S, enriched or chirally pure Sp linkage is preferred. Enriched means at least 70, 80, 90, 95, or 99% of the preferred form. Such NRMs are discussed in more detail below;

(ii) attachment of one or more cationic groups to the sugar, base, and/or the phosphorus atom of a phosphate or modified phosphate backbone moiety. Thus, preferred NRMs include monomers at the terminal position derivatized at a cationic group. As the 5' end of an antisense sequence should have a terminal —OH or phosphate group this NRM is preferably not used at the 5' end of an anti-sense sequence. The group should be attached at a position on the base which minimizes interference with H bond formation and hybridization, e.g., away form the face which interacts with the complementary base on the other strand, e.g., at the 5' position of a pyrimidine or a 7-position of a purine. These are discussed in more detail below;

(iii) nonphosphate linkages at the termini. Thus, preferred NRMs include Non-phosphate linkages, e.g., a linkage of 4 atoms which confers greater resistance to cleavage than does a phosphate bond. Examples include 3' $CH2-NCH_3$—O—CH2-5' and 3' CH2-NH—(O═)—CH2-5';

(iv) 3'-bridging thiophosphates and 5'-bridging thiophosphates. Thus, preferred NRM's can included these structures;

(v) L-RNA, 2'-5' linkages, inverted linkages, a-nucleosides. Thus, other preferred NRM's include: L nucleosides and dimeric nucleotides derived from L-nucleosides; 2'-5' phosphate, non-phosphate and modified phosphate linkages (e.g., thiophosphates, phosphoramidates and boronophosphates); dimers having inverted linkages, e.g., 3'-3' or 5'-5' linkages; monomers having an alpha linkage at the 1' site on the sugar, e.g., the structures described herein having an alpha linkage;

(vi) conjugate groups. Thus, preferred NRM's can include e.g., a targeting moiety or a conjugated ligand described herein conjugated with the monomer, e.g., through the sugar, base, or backbone;

(vi) abasic linkages. Thus, preferred NRM's can include an abasic monomer, e.g., an abasic monomer as described herein (e.g., a nucleobaseless monomer); an aromatic or heterocyclic or polyheterocyclic aromatic monomer as described herein; and (vii) 5'-phosphonates and 5'-phosphate prodrugs. Thus, preferred NRM's include monomers, preferably at the terminal position, e.g., the 5' position, in which one or more atoms of the phosphate group is derivatized with a protecting group, which protecting group or groups, are removed as a result of the action of a component in the subject's body, e.g., a carboxyesterase or an enzyme present in the subject's body. E.g., a phosphate prodrug in which a carboxy esterase cleaves the protected molecule resulting in the production of a thioate anion which attacks a carbon adjacent to the O of a phosphate and resulting in the production of an unprotected phosphate.

One or more different NRM modifications can be introduced into an iRNA agent or into a sequence of an iRNA agent. An NRM modification can be used more than once in a sequence or in an iRNA agent. As some NRM's interfere with hybridization the total number incorporated, should be such that acceptable levels of iRNA agent duplex formation are maintained.

In some embodiments NRM modifications are introduced into the terminal the cleavage site or in the cleavage region of a sequence (a sense strand or sequence) which does not target a desired sequence or gene in the subject. This can reduce off-target silencing.

Chiral $S_P$ Thioates

A modification can include the alteration, e.g., replacement, of one or both of the non-linking (X and Y) phosphate oxygens and/or of one or more of the linking (W and Z) phosphate oxygens. Formula X below depicts a phosphate moiety linking two sugar/sugar surrogate-base moieties, $SB_1$ and $SB_2$.

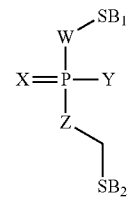

FORMULA X

In certain embodiments, one of the non-linking phosphate oxygens in the phosphate backbone moiety (X and Y) can be replaced by any one of the following: S, Se, $BR_3$ (R is hydrogen, alkyl, aryl, etc.), C (i.e., an alkyl group, an aryl group, etc.), H, $NR_2$ (R is hydrogen, alkyl, aryl, etc.), or OR (R is alkyl or aryl). The phosphorus atom in an unmodified phosphate group is achiral. However, replacement of one of the non-linking oxygens with one of the above atoms or groups of atoms renders the phosphorus atom chiral; in other words a phosphorus atom in a phosphate group modified in this way is a stereogenic center. The stereogenic phosphorus atom can possess either the "R" configuration (herein $R_P$) or the "S" configuration (herein $S_P$). Thus if 60% of a population of stereogenic phosphorus atoms have the $R_P$ configuration, then the remaining 40% of the population of stereogenic phosphorus atoms have the $S_P$ configuration.

In some embodiments, iRNA agents, having phosphate groups in which a phosphate non-linking oxygen has been replaced by another atom or group of atoms, may contain a population of stereogenic phosphorus atoms in which at least about 50% of these atoms (e.g., at least about 60% of these atoms, at least about 70% of these atoms, at least about 80% of these atoms, at least about 90% of these atoms, at least about 95% of these atoms, at least about 98% of these atoms, at least about 99% of these atoms) have the $S_P$ configuration. Alternatively, iRNA agents having phosphate groups in which a phosphate non-linking oxygen has been replaced by another atom or group of atoms may contain a population of stereogenic phosphorus atoms in which at least about 50% of these atoms (e.g., at least about 60% of these atoms, at least about 70% of these atoms, at least about 80% of these atoms, at least about 90% of these atoms, at least about 95% of these atoms, at least about 98% of these atoms, at least about 99% of these atoms) have the $R_P$ configuration. In other embodiments, the population of stereogenic phosphorus atoms may have the $S_P$ configuration and may be substantially free of stereogenic phosphorus atoms having the $R_P$ configuration. In still other embodiments, the population of stereogenic phosphorus atoms may have the $R_P$ configuration and may be substantially free of stereogenic phosphorus atoms having the $S_P$ configuration. As used herein, the phrase "substantially free of stereogenic phosphorus atoms having the $R_P$ configuration" means that moieties containing stereogenic phosphorus atoms having the $R_P$ configuration cannot be detected by conventional methods known in the art (chiral HPLC, $^1$H NMR analysis using chiral shift reagents, etc.). As used herein, the phrase "substantially free of stereogenic phosphorus atoms having the $S_P$ configuration" means that moieties containing stereogenic phosphorus atoms having the $S_P$ configuration cannot be detected by conventional methods known in the art (chiral HPLC, $^1$H NMR analysis using chiral shift reagents, etc.).

In a preferred embodiment, modified iRNA agents contain a phosphorothioate group, i.e., a phosphate groups in which a phosphate non-linking oxygen has been replaced by a sulfur atom. In an especially preferred embodiment, the population of phosphorothioate stereogenic phosphorus atoms may have the $S_P$ configuration and be substantially free of stereogenic phosphorus atoms having the $R_P$ configuration.

Phosphorothioates may be incorporated into iRNA agents using dimers e.g., formulas X-1 and X-2. The former can be used to introduce phosphorothioate

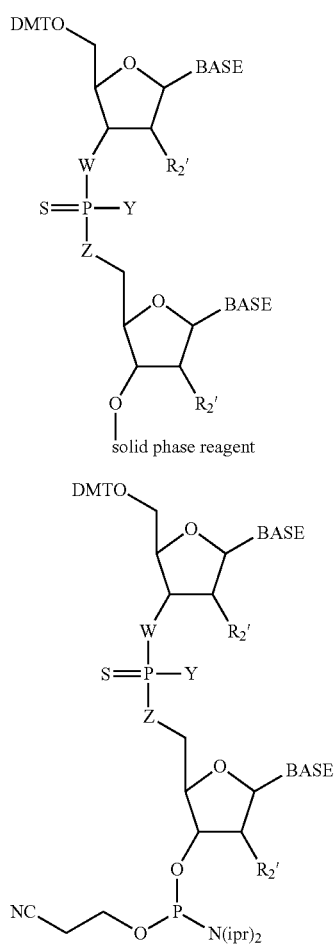

at the 3' end of a strand, while the latter can be used to introduce this modification at the 5' end or at a position that occurs e.g., 1, 2, 3, 4, 5, or 6 nucleotides from either end of the strand. In the above formulas, Y can be 2-cyanoethoxy, W and Z can be O, $R_2$, can be, e.g., a substituent that can impart the C-3 endo configuration to the sugar (e.g., OH, F, $OCH_3$), DMT is dimethoxytrityl, and "BASE" can be a natural, unusual, or a universal base.

X-1 and X-2 can be prepared using chiral reagents or directing groups that can result in phosphorothioate-containing dimers having a population of stereogenic phosphorus atoms having essentially only the $R_P$ configuration (i.e., being substantially free of the $S_P$ configuration) or only the $S_P$ configuration (i.e., being substantially free of the $R_P$ configuration). Alternatively, dimers can be prepared having a population of stereogenic phosphorus atoms in which about 50% of the atoms have the $R_P$ configuration and about 50% of the atoms have the $S_P$ configuration. Dimers having stereogenic phosphorus atoms with the $R_P$ configuration can be identified and separated from dimers having stereogenic phosphorus atoms with the $S_P$ configuration using e.g., enzymatic degradation and/or conventional chromatography techniques.

Cationic Groups

Modifications can also include attachment of one or more cationic groups to the sugar, base, and/or the phosphorus atom of a phosphate or modified phosphate backbone moiety. A cationic group can be attached to any atom capable of substitution on a natural, unusual or universal base. A preferred position is one that does not interfere with hybridization, i.e., does not interfere with the hydrogen bonding interactions needed for base pairing. A cationic group can be attached e.g., through the C2' position of a sugar or analogous position in a cyclic or acyclic sugar surrogate. Cationic groups can include e.g., protonated amino groups, derived from e.g., O-AMINE (AMINE=$NH_2$; alkylamino, dialkylamino, heterocyclyl, arylamino, diaryl amino, heteroaryl amino, or diheteroaryl amino, ethylene diamine, polyamino); aminoalkoxy, e.g., $O(CH_2)_n$AMINE, (e.g., AMINE=$NH_2$; alkylamino, dialkylamino, heterocyclyl, arylamino, diaryl amino, heteroaryl amino, or diheteroaryl amino, ethylene diamine, polyamino); amino (e.g. $NH_2$; alkylamino, dialkylamino, heterocyclyl, arylamino, diaryl amino, heteroaryl amino, diheteroaryl amino, or amino acid); or $NH(CH_2CH_2NH)_nCH_2CH_2$-AMINE (AMINE=$NH_2$; alkylamino, dialkylamino, heterocyclyl, arylamino, diaryl amino, heteroaryl amino, or diheteroaryl amino).

Nonphosphate Linkages

Modifications can also include the incorporation of nonphosphate linkages at the 5' and/or 3' end of a strand. Examples of nonphosphate linkages which can replace the phosphate group include methyl phosphonate, hydroxylamino, siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino. Preferred replacements include the methyl phosphonate and hydroxylamino groups.

3'-Bridging Thiophosphates and 5'-Bridging Thiophosphates; Locked-RNA, 2'-5' Linkages, Inverted Linkages, α-Nucleosides; Conjugate Groups; Abasic Linkages; and 5'-Phosphonates and 5'-Phosphate Prodrugs Referring to formula X above, modifications can include replacement of one of the bridging or linking phosphate oxygens in the phosphate backbone moiety (W and Z). Unlike the situation where only one of X or Y is altered, the phosphorus center in the phosphorodithioates is achiral which precludes the formation of iRNA agents containing a stereogenic phosphorus atom.

Modifications can also include linking two sugars via a phosphate or modified phosphate group through the 2' position of a first sugar and the 5' position of a second sugar. Also contemplated are inverted linkages in which both a first and second sugar are eached linked through the respective 3' positions. Modified RNA's can also include "abasic" sugars, which lack a nucleobase at C-1'. The sugar group can also contain one or more carbons that possess the opposite stereochemical configuration than that of the corresponding carbon in ribose. Thus, a modified iRNA agent can include nucleotides containing e.g., arabinose, as the sugar. In another subset of this modification, the natural, unusual, or universal base may have the α-configuration. Modifications can also include L-RNA.

Modifications can also include 5'-phosphonates, e.g., $P(O)(O^-)_2$—X—$C^{5'}$-sugar (X=CH2, CF2, CHF and 5'-phosphate prodrugs, e.g., $P(O)[OCH2CH2SC(O)R]_2CH_2C^{5'}$-sugar. In the latter case, the prodrug groups may be decomposed via reaction first with carboxy esterases. The remaining ethyl thiolate group via intramolecular $S_N2$ displacement can depart as episulfide to afford the underivatized phosphate group.

Modification can also include the addition of conjugating groups described elsewhere herein, which are preferably attached to an iRNA agent through any amino group available for conjugation.

Nuclease resistant modifications include some which can be placed only at the terminus and others which can go at any position. Generally the modifications that can inhibit hybridization so it is preferably to use them only in terminal regions, and preferable to not use them at the cleavage site or in the cleavage region of an sequence which targets a subject sequence or gene. The can be used anywhere in a sense sequence, provided that sufficient hybridization between the two sequences of the iRNA agent is maintained. In some embodiments it is desirable to put the NRM at the cleavage site or in the cleavage region of a sequence which does not target a subject sequence or gene, as it can minimize off-target silencing.

In addition, an iRNA agent described herein can have an overhang which does not form a duplex structure with the other sequence of the iRNA agent—it is an overhang, but it does hybridize, either with itself, or with another nucleic acid, other than the other sequence of the iRNA agent.

In most cases, the nuclease-resistance promoting modifications will be distributed differently depending on whether the sequence will target a sequence in the subject (often referred to as an anti-sense sequence) or will not target a sequence in the subject (often referred to as a sense sequence). If a sequence is to target a sequence in the subject, modifications which interfere with or inhibit endonuclease cleavage should not be inserted in the region which is subject to RISC mediated cleavage, e.g., the cleavage site or the cleavage region (As described in Elbashir et al., 2001, Genes and Dev. 15: 188, hereby incorporated by reference, cleavage of the target occurs about in the middle of a 20 or 21 nt guide RNA, or about 10 or 11 nucleotides upstream of the first nucleotide which is complementary to the guide sequence. As used herein cleavage site refers to the nucleotide on either side of the cleavage site, on the target or on the iRNA agent strand which hybridizes to it. Cleavage region means an nucleotide with 1, 2, or 3 nucleotides of the cleave site, in either direction.)

Such modifications can be introduced into the terminal regions, e.g., at the terminal position or with 2, 3, 4, or 5 positions of the terminus, of a sequence which targets or a sequence which does not target a sequence in the subject.

An iRNA agent can have a first and a second strand chosen from the following:

a first strand which does not target a sequence and which has an NRM modification at or within 1, 2, 3, 4, 5, or 6 positions from the 3' end;

a first strand which does not target a sequence and which has an NRM modification at or within 1, 2, 3, 4, 5, or 6 positions from the 5' end;

a first strand which does not target a sequence and which has an NRM modification at or within 1, 2, 3, 4, 5, or 6 positions from the 3' end and which has a NRM modification at or within 1, 2, 3, 4, 5, or 6 positions from the 5' end;

a first strand which does not target a sequence and which has an NRM modification at the cleavage site or in the cleavage region;

a first strand which does not target a sequence and which has an NRM modification at the cleavage site or in the cleavage region and one or more of an NRM modification at or within 1, 2, 3, 4, 5, or 6 positions from the 3' end, a NRM modification at or within 1, 2, 3, 4, 5, or 6 positions from the 5' end, or NRM modifications at or within 1, 2, 3, 4, 5, or 6 positions from both the 3' and the 5' end; and a second strand which targets a sequence and which has an NRM modification at or within 1, 2, 3, 4, 5, or 6 positions from the 3' end;

a second strand which targets a sequence and which has an NRM modification at or within 1, 2, 3, 4, 5, or 6 positions from the 5' end (5' end NRM modifications are preferentially not at the terminus but rather at a position 1, 2, 3, 4, 5, or 6 away from the 5' terminus of an antisense strand);

a second strand which targets a sequence and which has an NRM modification at or within 1, 2, 3, 4, 5, or 6 positions from the 3' end and which has a NRM modification at or within 1, 2, 3, 4, 5, or 6 positions from the 5' end;

a second strand which targets a sequence and which preferably does not have an NRM modification at the cleavage site or in the cleavage region;

a second strand which targets a sequence and which does not have an NRM modification at the cleavage site or in the cleavage region and one or more of an NRM modification at or within 1, 2, 3, 4, 5, or 6 positions from the 3' end, a NRM modification at or within 1, 2, 3, 4, 5, or 6 positions from the 5' end, or NRM modifications at or within 1, 2, 3, 4, 5, or 6 positions from both the 3' and the 5' end (5' end NRM modifications are preferentially not at the terminus but rather at a position 1, 2, 3, 4, 5, or 6 away from the 5' terminus of an antisense strand).

An iRNA agent can also target two sequences and can have a first and second strand chosen from:

a first strand which targets a sequence and which has an NRM modification at or within 1, 2, 3, 4, 5, or 6 positions from the 3' end;

a first strand which targets a sequence and which has an NRM modification at or within 1, 2, 3, 4, 5, or 6 positions from the 5' end (5' end NRM modifications are preferentially not at the terminus but rather at a position 1, 2, 3, 4, 5, or 6 away from the 5' terminus of an antisense strand);

a first strand which targets a sequence and which has an NRM modification at or within 1, 2, 3, 4, 5, or 6 positions from the 3' end and which has a NRM modification at or within 1, 2, 3, 4, 5, or 6 positions from the 5' end;

a first strand which targets a sequence and which preferably does not have an NRM modification at the cleavage site or in the cleavage region;

a first strand which targets a sequence and which does not have an NRM modification at the cleavage site or in the cleavage region and one or more of an NRM modification at or within 1, 2, 3, 4, 5, or 6 positions from the 3' end, a NRM modification at or within 1, 2, 3, 4, 5, or 6 positions from the 5' end, or NRM modifications at or within 1, 2, 3, 4, 5, or 6 positions from both the 3' and the 5' end (5' end NRM modifications are preferentially not at the terminus but rather at a position 1, 2, 3, 4, 5, or 6 away from the 5' terminus of an antisense strand) and a second strand which targets a sequence and which has an NRM modification at or within 1, 2, 3, 4, 5, or 6 positions from the 3' end;

a second strand which targets a sequence and which has an NRM modification at or within 1, 2, 3, 4, 5, or 6 positions from the 5' end (5' end NRM modifications are preferentially not at the terminus but rather at a position 1, 2, 3, 4, 5, or 6 away from the 5' terminus of an antisense strand);

a second strand which targets a sequence and which has an NRM modification at or within 1, 2, 3, 4, 5, or 6 positions from the 3' end and which has a NRM modification at or within 1, 2, 3, 4, 5, or 6 positions from the 5' end;

a second strand which targets a sequence and which preferably does not have an NRM modification at the cleavage site or in the cleavage region;

a second strand which targets a sequence and which does not have an NRM modification at the cleavage site or in the cleavage region and one or more of an NRM modification at or within 1, 2, 3, 4, 5, or 6 positions from the 3' end, a NRM modification at or within 1, 2, 3, 4, 5, or 6 positions from the 5' end, or NRM modifications at or within 1, 2, 3, 4, 5, or 6 positions from both the 3' and the 5' end (5' end NRM modifications are preferentially not at the terminus but rather at a position 1, 2, 3, 4, 5, or 6 away from the 5' terminus of an antisense strand).

Ribose Mimics

The monomers and methods described herein can be used to prepare an RNA, e.g., an iRNA agent, that incorporates a ribose mimic, such as those described herein and those described in copending co-owned U.S. Provisional Application Ser. No. 60/454,962, filed on Mar. 13, 2003, and International Application No. PCT/US04/07070, both of which are hereby incorporated by reference.

Thus, an aspect of the invention features an iRNA agent that includes a secondary hydroxyl group, which can increase efficacy and/or confer nuclease resistance to the agent. Nucleases, e.g., cellular nucleases, can hydrolyze nucleic acid phosphodiester bonds, resulting in partial or complete degradation of the nucleic acid. The secondary hydroxy group confers nuclease resistance to an iRNA agent by rendering the iRNA agent less prone to nuclease degradation relative to an iRNA which lacks the modification. While not wishing to be bound by theory, it is believed that the presence of a secondary hydroxyl group on the iRNA agent can act as a structural mimic of a 3' ribose hydroxyl group, thereby causing it to be less susceptible to degradation.

The secondary hydroxyl group refers to an "OH" radical that is attached to a carbon atom substituted by two other carbons and a hydrogen. The secondary hydroxyl group that confers nuclease resistance as described above can be part of any acyclic carbon-containing group. The hydroxyl may also be part of any cyclic carbon-containing group, and preferably one or more of the following conditions is met (1) there is no ribose moiety between the hydroxyl group and the terminal phosphate group or (2) the hydroxyl group is not on a sugar moiety which is coupled to a base. The hydroxyl group is located at least two bonds (e.g., at least three bonds away, at least four bonds away, at least five bonds away, at least six bonds away, at least seven bonds away, at least eight bonds away, at least nine bonds away, at least ten bonds away, etc.) from the terminal phosphate group phosphorus of the iRNA agent. In preferred embodiments, there are five intervening bonds between the terminal phosphate group phosphorus and the secondary hydroxyl group.

Preferred iRNA agent delivery modules with five intervening bonds between the terminal phosphate group phosphorus and the secondary hydroxyl group have the following structure (see formula Y below):

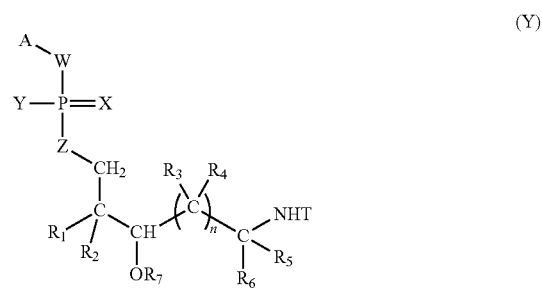

(Y)

Referring to formula Y, A is an iRNA agent, including any iRNA agent described herein. The iRNA agent may be connected directly or indirectly (e.g., through a spacer or linker) to "W" of the phosphate group. These spacers or linkers can include e.g., —(CH$_2$)$_n$—, —(CH$_2$)$_n$N—, —(CH$_2$)$_n$O—, —(CH$_2$)$_n$S—, O(CH$_2$CH$_2$O)$_n$CH$_2$CH$_2$OH (e.g., n=3 or 6), abasic sugars, amide, carboxy, amine, oxyamine, oxyimine, thioether, disulfide, thiourea, sulfonamide, or morpholino, or biotin and fluorescein reagents.

The iRNA agents can have a terminal phosphate group that is unmodified (e.g., W, X, Y, and Z are O) or modified. In a modified phosphate group, W and Z can be independently NH, O, or S; and X and Y can be independently S, Se, BH$_3^-$, C$_1$-C$_6$ alkyl, C$_6$-C$_{10}$ aryl, H, O, O$^-$, alkoxy or amino (including alkylamino, arylamino, etc.). Preferably, W, X and Z are O and Y is S.

R$_1$ and R$_3$ are each, independently, hydrogen; or C$_1$-C$_{100}$ alkyl, optionally substituted with hydroxyl, amino, halo, phosphate or sulfate and/or may be optionally inserted with N, O, S, alkenyl or alkynyl.

R$_2$ is hydrogen; C$_1$-C$_{100}$ alkyl, optionally substituted with hydroxyl, amino, halo, phosphate or sulfate and/or may be optionally inserted with N, O, S, alkenyl or alkynyl; or, when n is 1, R$_2$ may be taken together with R$_4$ or R$_6$ to form a ring of 5-12 atoms.

R$_4$ is hydrogen; C$_1$-C$_{100}$ alkyl, optionally substituted with hydroxyl, amino, halo, phosphate or sulfate and/or may be optionally inserted with N, O, S, alkenyl or alkynyl; or, when n is 1, R$_4$ may be taken together with R$_2$ or R$_5$ to form a ring of 5-12 atoms.

R$_5$ is hydrogen, C$_1$-C$_{100}$ alkyl optionally substituted with hydroxyl, amino, halo, phosphate or sulfate and/or may be optionally inserted with N, O, S, alkenyl or alkynyl; or, when n is 1, R$_5$ may be taken together with R$_4$ to form a ring of 5-12 atoms.

R$_6$ is hydrogen, C$_1$-C$_{100}$ alkyl, optionally substituted with hydroxyl, amino, halo, phosphate or sulfate and/or may be optionally inserted with N, O, S, alkenyl or alkynyl, or, when n is 1, R$_6$ may be taken together with R$_2$ to form a ring of 6-10 atoms;

$R_7$ is hydrogen, $C_1$-$C_{100}$ alkyl, or $C(O)(CH_2)_qC(O)NHR_9$; T is hydrogen or a functional group; n and q are each independently 1-100; $R_8$ is $C_1$-$C_{10}$ alkyl or $C_6$-$C_{10}$ aryl; and $R_9$ is hydrogen, C1-C10 alkyl, C6-C10 aryl or a solid support agent.

Preferred embodiments may include one of more of the following subsets of iRNA agent delivery modules.

In one subset of RNAi agent delivery modules, A can be connected directly or indirectly through a terminal 3' or 5' ribose sugar carbon of the RNA agent.

In another subset of RNAi agent delivery modules, X, W, and Z are O and Y is S.

In still yet another subset of RNAi agent delivery modules, n is 1, and $R_2$ and $R_6$ are taken together to form a ring containing six atoms and $R_4$ and $R_5$ are taken together to form a ring containing six atoms. Preferably, the ring system is a trans-decalin. For example, the RNAi agent delivery module of this subset can include a compound of Formula (Y-1):

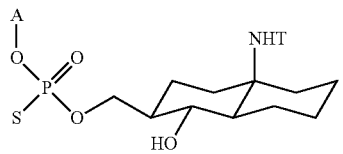

The functional group can be, for example, a targeting group (e.g., a steroid or a carbohydrate), a reporter group (e.g., a fluorophore), or a label (an isotopically labelled moiety). The targeting group can further include protein binding agents, endothelial cell targeting groups (e.g., RGD peptides and mimetics), cancer cell targeting groups (e.g., folate Vitamin B12, Biotin), bone cell targeting groups (e.g., bisphosphonates, polyglutamates, polyaspartates), multivalent mannose (for e.g., macrophage testing), lactose, galactose, N-acetyl-galactosamine, monoclonal antibodies, glycoproteins, lectins, melanotropin, or thyrotropin.

As can be appreciated by the skilled artisan, methods of synthesizing the compounds of the formulae herein will be evident to those of ordinary skill in the art. The synthesized compounds can be separated from a reaction mixture and further purified by a method such as column chromatography, high pressure liquid chromatography, or recrystallization. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

Physiological Effects

The iRNA agents described herein can be designed such that determining therapeutic toxicity is made easier by the complementarity of the iRNA agent with both a human and a non-human animal sequence. By these methods, an iRNA agent can consist of a sequence that is fully complementary to a nucleic acid sequence from a human and a nucleic acid sequence from at least one non-human animal, e.g., a non-human mammal, such as a rodent, ruminant or primate. For example, the non-human mammal can be a mouse, rat, dog, pig, goat, sheep, cow, monkey, *Pan paniscus, Pan troglodytes, Macaca mulatto,* or Cynomolgus monkey. The sequence of the iRNA agent could be complementary to sequences within homologous genes, e.g., oncogenes or tumor suppressor genes, of the non-human mammal and the human. By determining the toxicity of the iRNA agent in the non-human mammal, one can extrapolate the toxicity of the iRNA agent in a human. For a more strenuous toxicity test, the iRNA agent can be complementary to a human and more than one, e.g., two or three or more, non-human animals.

The methods described herein can be used to correlate any physiological effect of an iRNA agent on a human, e.g., any unwanted effect, such as a toxic effect, or any positive, or desired effect.

iRNA Conjugates

An iRNA agent can be coupled, e.g., covalently coupled, to a second agent. For example, an iRNA agent used to treat a particular disorder can be coupled to a second therapeutic agent, e.g., an agent other than the iRNA agent. The second therapeutic agent can be one which is directed to the treatment of the same disorder. For example, in the case of an iRNA used to treat a disorder characterized by unwanted cell proliferation, e.g., cancer, the iRNA agent can be coupled to a second agent which has an anti-cancer effect. For example, it can be coupled to an agent which stimulates the immune system, e.g., a CpG motif, or more generally an agent that activates a toll-like receptor and/or increases the production of gamma interferon.

iRNA Production

An iRNA can be produced, e.g., in bulk, by a variety of methods. Exemplary methods include: organic synthesis and RNA cleavage, e.g., in vitro cleavage.

Organic Synthesis.

An iRNA can be made by separately synthesizing each respective strand of a double-stranded RNA molecule. The component strands can then be annealed.

A large bioreactor, e.g., the OligoPilot II from Pharmacia Biotec AB (Uppsala Sweden), can be used to produce a large amount of a particular RNA strand for a given iRNA. The OligoPilotII reactor can efficiently couple a nucleotide using only a 1.5 molar excess of a phosphoramidite nucleotide. To make an RNA strand, ribonucleotides amidites are used. Standard cycles of monomer addition can be used to synthesize the oligonucleotide strands for the iRNA. Typically, the two complementary strands are produced separately and then annealed, e.g., after release from the solid support and deprotection.

Organic synthesis can be used to produce a discrete iRNA species. The complementarity of the species to the target gene can be precisely specified. For example, the species may be complementary to a region that includes a polymorphism, e.g., a single nucleotide polymorphism. Further the location of the polymorphism can be precisely defined. In some embodiments, the polymorphism is located in an internal region, e.g., at least 4, 5, 7, or 9 nucleotides from one or both of the termini.

dsRNA Cleavage.

iRNAs can also be made by cleaving a larger ds iRNA. The cleavage can be mediated in vitro or in vivo. For example, to produce iRNAs by cleavage in vitro, the following method can be used:

In vitro transcription. dsRNA is produced by transcribing a nucleic acid (DNA) segment in both directions. For example, the HiScribe™ RNAi transcription kit (New England Biolabs) provides a vector and a method for producing a dsRNA for a nucleic acid segment that is cloned into the vector at a position flanked on either side by a T7 promoter. Separate templates are generated for T7 transcription of the two complementary strands for the dsRNA. The templates are transcribed in vitro by addition of T7 RNA polymerase and dsRNA is produced. Similar methods using PCR and/or other RNA polymerases (e.g., T3 or SP6 polymerase) can also be used. In one embodiment, RNA generated by this method is carefully purified to remove endotoxins that may contaminate preparations of the recombinant enzymes.

In vitro cleavage. dsRNA is cleaved in vitro into iRNAs, for example, using a Dicer or comparable RNAse III-based activity. For example, the dsRNA can be incubated in an in vitro extract from Drosophila or using purified components, e.g. a purified RNAse or RISC complex. See, e.g., Ketting et al. *Genes Dev* 2001 Oct. 15; 15(20):2654-9. and Hammond *Science* 2001 Aug. 10; 293(5532):1146-50.

dsRNA cleavage generally produces a plurality of iRNA species, each being a particular 21 to 23 nt fragment of a source dsRNA molecule. For example, iRNAs that include sequences complementary to overlapping regions and adjacent regions of a source dsRNA molecule may be present.

Regardless of the method of synthesis, the iRNA preparation can be prepared in a solution (e.g., an aqueous and/or organic solution) that is appropriate for formulation. For example, the iRNA preparation can be precipitated and redissolved in pure double-distilled water, and lyophilized. The dried iRNA can then be resuspended in a solution appropriate for the intended formulation process.

Synthesis of modified and nucleotide surrogate iRNA agents is discussed below.

Formulation

The iRNA agents described herein can be formulated for administration to a subject.

For ease of exposition, the formulations, compositions, and methods in this section are discussed largely with regard to unmodified iRNA agents. It should be understood, however, that these formulations, compositions, and methods can be practiced with other iRNA agents, e.g., modified iRNA agents, and such practice is within the invention.

A formulated iRNA composition can assume a variety of states. In some examples, the composition is at least partially crystalline, uniformly crystalline, and/or anhydrous (e.g., less than 80, 50, 30, 20, or 10% water). In another example, the iRNA is in an aqueous phase, e.g., in a solution that includes water.

The aqueous phase or the crystalline compositions can, e.g., be incorporated into a delivery vehicle, e.g., a liposome (particularly for the aqueous phase) or a particle (e.g., a microparticle as can be appropriate for a crystalline composition). Generally, the iRNA composition is formulated in a manner that is compatible with the intended method of administration.

In particular embodiments, the composition is prepared by at least one of the following methods: spray drying, lyophilization, vacuum drying, evaporation, fluid bed drying, or a combination of these techniques; or sonication with a lipid, freeze-drying, condensation and other self-assembly.

An iRNA preparation can be formulated in combination with another agent, e.g., another therapeutic agent or an agent that stabilizes a iRNA, e.g., a protein that complexes with iRNA to form an iRNP. Still other agents include chelators, e.g., EDTA (e.g., to remove divalent cations such as $Mg^{2+}$), salts, RNAse inhibitors (e.g., a broad specificity RNAse inhibitor such as RNAsin) and so forth.

In one embodiment, the iRNA preparation includes another iRNA agent, e.g., a second iRNA agent that can mediate RNAi with respect to a second gene, or with respect to the same gene. Still other preparations can include at least three, five, ten, twenty, fifty, or a hundred or more different iRNA species. Such iRNAs can mediated RNAi with respect to a similar number of different genes.

In one embodiment, the iRNA preparation includes at least a second therapeutic agent (e.g., an agent other than an RNA or a DNA).

In some embodiments, an iRNA agent, e.g., a double-stranded iRNA agent, or siRNA agent, (e.g., a precursor, e.g., a larger iRNA agent which can be processed into an siRNA agent, or a DNA which encodes an iRNA agent, e.g., a double-stranded iRNA agent, or siRNA agent, or precursor thereof) is formulated to target a particular cell. For example, a liposome or particle or other structure that includes a iRNA can also include a targeting moiety that recognizes a specific molecule on a target cell. The targeting moiety can be a molecule with a specific affinity for a target cell. Targeting moieties can include antibodies directed against a protein found on the surface of a target cell, or the ligand or a receptor-binding portion of a ligand for a molecule found on the surface of a target cell.

In one embodiment, the targeting moiety is attached to a liposome. For example, U.S. Pat. No. 6,245,427 describes a method for targeting a liposome using a protein or peptide. In another example, a cationic lipid component of the liposome is derivatized with a targeting moiety. For example, WO 96/37194 describes converting N-glutaryldioleoylphosphatidyl ethanolamine to a N-hydroxysuccinimide activated ester. The product was then coupled to an RGD peptide. Additional targeting methods are described elsewhere herein.

Pharmaceutical Compositions

In one embodiment, the invention relates to a pharmaceutical composition containing a modified iRNA agent, as described in the preceding sections, and a pharmaceutically acceptable carrier, as described below. A pharmaceutical composition including the modified iRNA agent is useful for treating a disease caused by expression of a target gene. In this aspect of the invention, the iRNA agent of the invention is formulated as described below. The pharmaceutical composition is administered in a dosage sufficient to inhibit expression of the target gene.

The pharmaceutical compositions of the present invention are administered in dosages sufficient to inhibit the expression or activity of the target gene. Exemplary dosages and routes of administration are described below.

The pharmaceutical compositions can include encapsulated formulations to protect the iRNA agent against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811; PCT publication WO 91/06309; and European patent publication EP-A-43075, which are incorporated by reference herein.

Toxicity and therapeutic efficacy of iRNA agent can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. iRNA agents that exhibit high therapeutic indices are preferred.

Advances in mouse genetics have generated a number of mouse models for the study of various human diseases. For example, mouse repositories can be found at The Jackson Laboratory, Charles River Laboratories, Taconic, Harlan, Mutant Mouse Regional Resource Centers (MMRRC) National Network and at the European Mouse Mutant Archive. Such models may be used for in vivo testing of iRNA agent, as well as for determining a therapeutically effective dose.

The data obtained from cell culture assays and animal studies can be used in formulating a range of dosage for use in humans. The dosages of compositions of the invention are preferably within a range of circulating concentrations that include the ED50 with little or no toxicity. The dosage may vary within this range depending upon the dosage form employed and the route of administration utilized. For any iRNA agent used in the method of the invention, the therapeutically effective dose can be estimated initially from cell culture assays. A dose may be formulated in animal models to achieve a circulating plasma concentration range of the iRNA agent or, when appropriate, of the polypeptide product of a target sequence (e.g., achieving a decreased concentration of the polypeptide) that includes the IC50 (i.e., the concentration of the test iRNA agent which achieves a half-maximal inhibition of symptoms) as determined in cell culture. Such information can be used to more accurately determine useful doses in humans. Levels in plasma may be measured, for example, by high performance liquid chromatography.

In addition to their administration individually or as a plurality, iRNA agents relating to the invention can be administered in combination with other known agents effective in treating viral infections and diseases. In any event, the administering physician can adjust the amount and timing of iRNA agent administration on the basis of results observed using standard measures of efficacy known in the art or described herein.

Methods for Treating Diseases Caused by Expression of a Target Gene

In one embodiment, the invention relates to a method for treating a subject having a disease or at risk of developing a disease caused by the expression of a target gene. In this embodiment, iRNA agents can act as novel therapeutic agents for controlling one or more of cellular proliferative and/or differentiative disorders, disorders associated with bone metabolism, immune disorders, hematopoietic disorders, cardiovascular disorders, liver disorders, viral diseases, or metabolic disorders. The method includes administering a pharmaceutical composition of the invention to the patient (e.g., a human), such that expression of the target gene is silenced. Because of their high efficiency and specificity, the iRNA agent of the present invention specifically target mRNA of target genes of diseased cells and tissues, as described below, and at surprisingly low dosages. The pharmaceutical compositions are formulated as described in the preceding section, which is hereby incorporated by reference herein.

Examples of genes which can be targeted for treatment include, without limitation, an oncogene (Hanahan, D. and R. A. Weinberg, *Cell* (2000) 100:57; and Yokota, J., *Car-cinogenesis* (2000) 21(3):497-503); a cytokine gene (Rubinstein, M., et al., *Cytokine Growth Factor Rev.* (1998) 9(2): 175-81); a idiotype (Id) protein gene (Benezra, R., et al., *Oncogene* (2001) 20(58):8334-41; Norton, J. D., *J. Cell Sci.* (2000) 113(22):3897-905); a prion gene (Prusiner, S. B., et al., *Cell* (1998) 93(3):337-48; Safar, J., and S. B. Prusiner, *Prog. Brain Res.* (1998) 117:421-34); a gene that expresses molecules that induce angiogenesis (Gould, V. E. and B. M. Wagner, *Hum. Pathol.* (2002) 33(11):1061-3); adhesion molecules (Chothia, C. and E. Y. Jones, *Annu. Rev. Biochem.* (1997) 66:823-62; Parise, L. V., et al., *Semin. Cancer Biol.* (2000) 10(6):407-14); cell surface receptors (Deller, M. C., and Y. E. Jones, *Curr. Opin. Struct. Biol.* (2000) 10(2):213-9); genes of proteins that are involved in metastasizing and/or invasive processes (Boyd, D., *Cancer Metastasis Rev.* (1996) 15(1):77-89; Yokota, J., *Carcinogenesis* (2000) 21(3):497-503); genes of proteases as well as of molecules that regulate apoptosis and the cell cycle (Matrisian, L. M., *Curr. Biol.* (1999) 9(20):R776-8; Krepela, E., *Neoplasma* (2001) 48(5):332-49; Basbaum and Werb, *Curr. Opin. Cell Biol.* (1996) 8:731-738; Birkedal-Hansen, et al., *Crit. Rev. Oral Biol. Med.* (1993) 4:197-250; Mignatti and Rifkin, *Physiol. Rev.* (1993) 73:161-195; Stetler-Stevenson, et al., *Annu. Rev. Cell Biol.* (1993) 9:541-573; Brinkerhoff, E., and L. M. Matrisan, *Nature Reviews* (2002) 3:207-214; Strasser, A., et al., *Annu. Rev. Biochem.* (2000) 69:217-45; Chao, D. T. and S. J. Korsmeyer, *Annu. Rev. Immunol.* (1998) 16:395-419; Mullauer, L., et al., *Mutat. Res.* (2001) 488(3):211-31; Fotedar, R., et al., *Prog. Cell Cycle Res.* (1996) 2:147-63; Reed, J. C., *Am. J. Pathol.* (2000) 157(5):1415-30; D'Ari, R., *Bioassays* (2001) 23(7):563-5); genes that express the EGF receptor; Mendelsohn, J. and J. Baselga, *Oncogene* (2000) 19(56):6550-65; Normanno, N., et al., *Front. Biosci.* (2001) 6:D685-707); and the multi-drug resistance 1 gene, MDR1 gene (Childs, S., and V. Ling, *Imp. Adv. Oncol.* (1994) 21-36).

In the prevention of disease, the target gene may be one which is required for initiation or maintenance of the disease, or which has been identified as being associated with a higher risk of contracting the disease. In the treatment of disease, the iRNA agent can be brought into contact with the cells or tissue exhibiting the disease. For example, iRNA agent substantially identical to all or part of a mutated gene associated with cancer, or one expressed at high levels in tumor cells, may be brought into contact with or introduced into a cancerous cell or tumor gene.

Examples of cellular proliferative and/or differentiative disorders include cancer, e.g., a carcinoma, sarcoma, metastatic disorder or hematopoietic neoplastic disorder, such as a leukemia. A metastatic tumor can arise from a multitude of primary tumor types, including but not limited to those of prostate, colon, lung, breast and liver origin. As used herein, the terms "cancer," "hyperproliferative," and "neoplastic" refer to cells having the capacity for autonomous growth, i.e., an abnormal state or condition characterized by rapidly proliferating cell growth. These terms are meant to include all types of cancerous growths or oncogenic processes, metastatic tissues or malignantly transformed cells, tissues, or organs, irrespective of histopathologic type or stage of invasiveness. Proliferative disorders also include hematopoietic neoplastic disorders, including diseases involving hyperplastic/neoplastic cells of hematopoietic origin, e.g., arising from myeloid, lymphoid or erythroid lineages, or precursor cells thereof.

The pharmaceutical compositions of the present invention can also be used to treat a variety of immune disorders, in particular those associated with overexpression or aberrant expression of a gene or expression of a mutant gene. Examples of hematopoietic disorders or diseases include, without limitation, autoimmune diseases (including, for example, diabetes mellitus, arthritis (including rheumatoid arthritis, juvenile rheumatoid arthritis, osteoarthritis, psoriatic arthritis), multiple sclerosis, encephalomyelitis, myasthenia gravis, systemic lupus erythematosis, autoimmune thyroiditis, dermatitis (including atopic dermatitis and eczematous dermatitis), psoriasis, Sjogren's Syndrome, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing, loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis), graft-versus-host disease, cases of transplantation, and allergy.

In another embodiment, the invention relates to methods for treating viral diseases, including but not limited to hepatitis C, hepatitis B, herpes simplex virus (HSV), HIV-AIDS, poliovirus, and smallpox virus. iRNA agent of the invention are prepared as described herein to target expressed sequences of a virus, thus ameliorating viral activity and replication. The iRNA agents can be used in the treatment and/or diagnosis of viral infected tissue, both animal and plant. Also, such iRNA agent can be used in the treatment of virus-associated carcinoma, such as hepatocellular cancer.

For example, the iRNA agent of the present invention are useful for treating a subject having an infection or a disease associated with the replication or activity of a (+) strand RNA virus having a 3'-UTR, such as HCV. In this embodiment, the iRNA agent can act as novel therapeutic agents for inhibiting replication of the virus. The method includes administering a pharmaceutical composition of the invention to the patient (e.g., a human), such that viral replication is inhibited. Examples of (+) strand RNA viruses which can be targeted for inhibition include, without limitation, picornaviruses, caliciviruses, nodaviruses, coronaviruses, arteriviruses, flaviviruses, and togaviruses. Examples of picornaviruses include enterovirus (poliovirus 1), rhinovirus (human rhinovirus 1A), hepatovirus (hepatitis A virus), cardiovirus (encephalomyocarditis virus), aphthovirus (foot-and-mouth disease virus O), and parechovirus (human echovirus 22). Examples of caliciviruses include vesiculovirus (swine vesicular exanthema virus), lagovirus (rabbit hemorrhagic disease virus), "Norwalk-like viruses" (Norwalk virus), "Sapporo-like viruses" (Sapporo virus), and "hepatitis E-like viruses" (hepatitis E virus). Betanodavirus (striped jack nervous necrosis virus) is the representative nodavirus. Coronaviruses include coronavirus (avian infections bronchitis virus) and torovirus (Berne virus). Arterivirus (equine arteritis virus) is the representative arteriviridus. Togavirises include alphavirus (Sindbis virus) and rubivirus (Rubella virus). Finally, the flaviviruses include flavivirus (Yellow fever virus), pestivirus (bovine diarrhea virus), and hepacivirus (hepatitis C virus). In a preferred embodiment, the virus is hepacivirus, the hepatitis C virus. Although the foregoing list exemplifies vertebrate viruses, the present invention encompasses the compositions and methods for treating infections and diseases caused by any (+) strand RNA virus having a 3'-UTR, regardless of the host. For example, the invention encompasses the treatment of plant diseases caused by sequiviruses, comoviruses, potyviruses, sobemovirus, luteoviruses, tombusviruses, tobaviruses, tobravirus, bromoviruses, and closteroviruses.

Treatment Methods and Routes of Delivery

A composition that includes an iRNA agent can be delivered to a subject by a variety of routes. Exemplary routes include intrathecal, parenchymal, intravenous, nasal, oral, and ocular delivery.

An iRNA agent can be incorporated into pharmaceutical compositions suitable for administration. For example, compositions can include one or more species of an iRNA agent and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The pharmaceutical compositions featured in the present invention may be administered in a number of ways depending upon whether local or systemic treatment is desired and upon the area to be treated. Administration may be topical (including ophthalmic, intranasal, transdermal), oral or parenteral. Parenteral administration includes intravenous drip, subcutaneous, intraperitoneal or intramuscular injection, or intrathecal or intraventricular administration.

The route of delivery can be dependent on the disorder of the patient. In general, the delivery of the iRNA agents can achieve systemic delivery into the subject.

Formulations for parenteral administration may include sterile aqueous solutions which may also contain buffers, diluents and other suitable additives. For intravenous use, the total concentration of solutes should be controlled to render the preparation isotonic.

Administration can be provided by the subject or by another person, e.g., a another caregiver. A caregiver can be any entity involved with providing care to the human: for example, a hospital, hospice, doctor's office, outpatient clinic; a healthcare worker such as a doctor, nurse, or other practitioner; or a spouse or guardian, such as a parent. The medication can be provided in measured doses or in a dispenser which delivers a metered dose.

The subject can also be monitored for an improvement or stabilization of disease symptoms.

The term "therapeutically effective amount" is the amount present in the composition that is needed to provide the desired level of drug in the subject to be treated to give the anticipated physiological response.

The term "physiologically effective amount" is that amount delivered to a subject to give the desired palliative or curative effect.

The term "pharmaceutically acceptable carrier" means that the carrier can be taken into the lungs with no significant adverse toxicological effects on the lungs.

The types of pharmaceutical excipients that are useful as carrier include stabilizers such as human serum albumin (HSA), bulking agents such as carbohydrates, amino acids and polypeptides; pH adjusters or buffers; salts such as sodium chloride; and the like. These carriers may be in a crystalline or amorphous form or may be a mixture of the two.

Bulking agents that are particularly valuable include compatible carbohydrates, polypeptides, amino acids or combinations thereof. Suitable carbohydrates include monosaccharides such as galactose, D-mannose, sorbose, and the like; disaccharides, such as lactose, trehalose, and the like; cyclodextrins, such as 2-hydroxypropyl-.beta.-cyclodextrin; and polysaccharides, such as raffinose, maltodextrins, dextrans, and the like; alditols, such as mannitol, xylitol, and the like. A preferred group of carbohydrates includes lactose, threhalose, raffinose maltodextrins, and mannitol. Suitable polypeptides include aspartame. Amino acids include alanine and glycine, with glycine being preferred.

Suitable pH adjusters or buffers include organic salts prepared from organic acids and bases, such as sodium citrate, sodium ascorbate, and the like; sodium citrate is preferred.

Dosage.

An iRNA agent can be administered at a unit dose less than about 75 mg per kg of bodyweight, or less than about 70, 60, 50, 40, 30, 20, 10, 5, 2, 1, 0.5, 0.1, 0.05, 0.01, 0.005, 0.001, or 0.0005 mg per kg of bodyweight, and less than 200 nmole of RNA agent (e.g., about $4.4 \times 10^{16}$ copies) per kg of bodyweight, or less than 1500, 750, 300, 150, 75, 15, 7.5, 1.5, 0.75, 0.15, 0.075, 0.015, 0.0075, 0.0015, 0.00075, 0.00015 nmole of RNA agent per kg of bodyweight. The unit dose, for example, can be administered by injection (e.g., intravenous or intramuscular, intrathecally, or directly into an organ), an inhaled dose, or a topical application.

Delivery of an iRNA agent directly to an organ (e.g., directly to the liver) can be at a dosage on the order of about 0.00001 mg to about 3 mg per organ, or preferably about 0.0001-0.001 mg per organ, about 0.03-3.0 mg per organ, about 0.1-3.0 mg per eye or about 0.3-3.0 mg per organ.

The dosage can be an amount effective to treat or prevent a disease or disorder.

In one embodiment, the unit dose is administered less frequently than once a day, e.g., less than every 2, 4, 8 or 30 days. In another embodiment, the unit dose is not administered with a frequency (e.g., not a regular frequency). For example, the unit dose may be administered a single time.

In one embodiment, the effective dose is administered with other traditional therapeutic modalities.

In one embodiment, a subject is administered an initial dose, and one or more maintenance doses of an iRNA agent, e.g., a double-stranded iRNA agent, or siRNA agent, (e.g., a precursor, e.g., a larger iRNA agent which can be processed into an siRNA agent, or a DNA which encodes an iRNA agent, e.g., a double-stranded iRNA agent, or siRNA agent, or precursor thereof). The maintenance dose or doses are generally lower than the initial dose, e.g., one-half less of the initial dose. A maintenance regimen can include treating the subject with a dose or doses ranging from 0.01 µg to 75 mg/kg of body weight per day, e.g., 70, 60, 50, 40, 30, 20, 10, 5, 2, 1, 0.5, 0.1, 0.05, 0.01, 0.005, 0.001, or 0.0005 mg per kg of bodyweight per day. The maintenance doses are preferably administered no more than once every 5, 10, or 30 days. Further, the treatment regimen may last for a period of time which will vary depending upon the nature of the particular disease, its severity and the overall condition of the patient. In preferred embodiments the dosage may be delivered no more than once per day, e.g., no more than once per 24, 36, 48, or more hours, e.g., no more than once every 5 or 8 days. Following treatment, the patient can be monitored for changes in his condition and for alleviation of the symptoms of the disease state. The dosage of the compound may either be increased in the event the patient does not respond significantly to current dosage levels, or the dose may be decreased if an alleviation of the symptoms of the disease state is observed, if the disease state has been ablated, or if undesired side-effects are observed.

The effective dose can be administered in a single dose or in two or more doses, as desired or considered appropriate under the specific circumstances. If desired to facilitate repeated or frequent infusions, implantation of a delivery device, e.g., a pump, semi-permanent stent (e.g., intravenous, intraperitoneal, intracisternal or intracapsular), or reservoir may be advisable.

In one embodiment, the iRNA agent pharmaceutical composition includes a plurality of iRNA agent species. The iRNA agent species can have sequences that are non-overlapping and non-adjacent with respect to a naturally occurring target sequence. In another embodiment, the plurality of iRNA agent species is specific for different naturally occurring target genes. In another embodiment, the iRNA agents are specific for different alleles.

Following successful treatment, it may be desirable to have the patient undergo maintenance therapy to prevent the recurrence of the disease state, wherein the compound of the invention is administered in maintenance doses, ranging from 0.01 µg to 100 g per kg of body weight (see U.S. Pat. No. 6,107,094).

The concentration of the iRNA agent composition is an amount sufficient to be effective in treating or preventing a disorder or to regulate a physiological condition in humans. The concentration or amount of iRNA agent administered will depend on the parameters determined for the agent and the method of administration, e.g. nasal, buccal, or pulmonary. For example, nasal formulations tend to require much lower concentrations of some ingredients in order to avoid irritation or burning of the nasal passages. It is sometimes desirable to dilute an oral formulation up to 10-100 times in order to provide a suitable nasal formulation.

Certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an iRNA agent, e.g., a double-stranded iRNA agent, or siRNA agent (e.g., a precursor, e.g., a larger iRNA agent which can be processed into an siRNA agent, or a DNA which encodes an iRNA agent, e.g., a double-stranded iRNA agent, or siRNA agent, or precursor thereof) can include a single treatment or, preferably, can include a series of treatments. It will also be appreciated that the effective dosage of an iRNA agent such as an siRNA agent used for treatment may increase or decrease over the course of a particular treatment. Changes in dosage may result and become apparent from the results of diagnostic assays as described herein. For example, the subject can be monitored after administering an iRNA agent composition. Based on information from the monitoring, an additional amount of the iRNA agent composition can be administered.

Dosing is dependent on severity and responsiveness of the disease condition to be treated, with the course of treatment lasting from several days to several months, or until a cure is effected or a diminution of disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual compounds, and can generally be estimated based on EC50s found to be effective in in vitro and in vivo animal models. In some embodiments, the animal models include transgenic animals that express a human gene, e.g., a gene that produces a target RNA. The transgenic animal can be deficient for the corresponding endogenous RNA. In another embodiment, the composition for testing includes an iRNA agent that is complementary, at least in an internal region, to a sequence that is conserved between the target RNA in the animal model and the target RNA in a human.

The invention is further illustrated by the following examples, which should not be construed as further limiting.

EXAMPLES

Bio-Cleavable Oligonucleotide-Ligand Conjugates for Therapeutic Applications

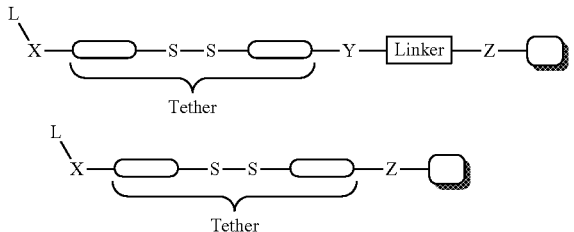

Oligonucleotide Ligand Conjugate

NA is a chemically modified or unmodified oligonucleotide (or a nucleic acid) comprising of either RNA or DNA or chimeric RNA-DNA, DNA-RNA, RNA-DNA-RNA or DNA-RNA-DNA. L is ligand (Table 2), X is chemical linkage between the ligand and tether (see Table 3); Y is chemical linkage between tether and linker (see Table 3), and Z is chemical linkage between linker and oligonucleotide (see Table 3). Also see Table 3 for definition of tether.

TABLE 2

Definition of ligand L.

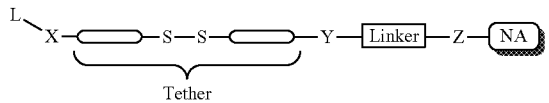

L = Cholesterol
Thiocholesterol

TABLE 2-continued

Definition of ligand L.

5β-Cholanic Acid
Cholic acid
Lithocholic acid
Biotin
Vitamin E
Naproxen
Ibuprofen
Amines (mono, di, tri, tetraalkyl or aryl)
Folate
Sugar (N-Acetylgalactosamine, galactosamine, galactose, Mannose)
—$(CH_2)_n NQ_1Q_2$, where n = 0-40, $Q_1$, $Q_2$ = H, Me or Et; $Q_1$ = H, $Q_2$ = H, Me, Et or aryl
—$(CH_2)_p CH=CH(CH_2)_q NQ_1Q_2$, where p and/or q = 0-40, $Q_1$, $Q_2$ = H, Me or Et; $Q_1$ = H, $Q_2$ = H, Me, Et or aryl with E and/or Z configuration
—$(CH_2)_p CH=CH(CH_2)_q NQ_1Q_2$, where p and/or q = 0-40, $Q_1$, $Q_2$ = H, Me or Et; $Q_1$ = H, $Q_2$ = H, Me, Et or aryl
—$(CH_2)_p CH=CH(CH_2)_q CH=CH(CH_2)_r NQ_1Q_2$, where p, q and/or r = 0-40, $Q_1$, $Q_2$ = H, Me or Et; $Q_1$ = H, $Q_2$ = H, Me, Et or aryl with E and/or Z configuration
—$O(CH_2)_m(OCH_2CH_2)_n$—OR, where m, n = 0-40 and R = H, Me, $NQ_1Q_2$, —C(O)NR'R" —C(S)NR'R"
—$NH(CH_2)_m(OCH_2CH_2)_n$—OR, where m, n = 0-40 and R = H, Me, $NQ_1Q_2$, —C(O)NR'R"—C(S)NR'R"
—$O(CH_2)_m(NHCH_2CH_2)_n$—R, where m, n = 0-40 and R = H, OH, Me, $NQ_1Q_2$, —C(O)R'R"—C(S)NR'R"
—$NH(CH_2)_m(NHCH_2CH_2)_n$—R, where m, n = 0-40 and R = H, OH, Me, $NQ_1Q_2$, —C(O)NR'R" —C(S)NR'R"
Dialkylglycerol (sn3, sn1, sn2 and racemic) with number of methylene varies from 0-40
Diacyglycerol (sn3, sn1, sn2 and racemic) with number of methylene varies from 0-40
Dialkylglycerol (sn3, sn1, sn2 and racemic) with number of methylene varies from 0-40
and the alkyl chian contains one or more double bonds with E and/or Z isomers
Dlacylglycerol (sn3, sn1, sn2 and racemic) with number of methylene varies from 0-40
and the alkyl chain contains one or more double bonds with E and/or isomers
Lipids

TABLE 3

Definition of tether.

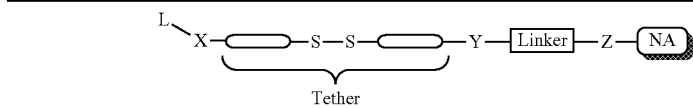

| X = | Y = | Z = |
|---|---|---|
| —NHC(O)— | —NHC(O)— | —NHC(O)— |
| —C(O)NH— | —C(O)NH— | —C(O)NH— |
| —OC(O)NH— | —OC(O)NH— | —OC(O)NH— |
| —NHC(O)O— | —NHC(O)O— | —NHC(O)O— |
| —O— | —O— | —O— |
| —S— | —S— | —S— |
| —SS— | —SS— | —SS— |
| —S(O)— | —S(O)— | —S(O)— |
| —S($O_2$)— | —S($O_2$)— | —S($O_2$)— |
| —NHC(O)NH— | —NHC(O)NH— | —NHC(O)NH— |
| —NHC(S)NH— | —NHC(S)NH— | —NHC(S)NH— |
| —C(O)O— | —C(O)O— | —C(O)O— |
| —OC(O)— | —OC(O)— | —OC(O)— |
| —NHC(S)— | —NHC(S)— | —NHC(S)— |
| —NHC(S)O— | —NHC(S)O— | —NHC(S)O— |
| —C(S)NH— | —C(S)NH— | —C(S)NH— |
| —OC(S)NH— | —OC(S)NH— | —OC(S)NH— |
| —NHC(S)O— | —NHC(S)O— | —NHC(S)O— |
| —$CH_2$— | —$CH_2$— | —$CH_2$— |
| —$CH_2$CH=CH— | —$CH_2$CH=CH— | —$CH_2$CH=CH— |
| —C(O)CH=CH— | —C(O)CH=CH— | —C(O)CH=CH— |
| —NH—$CH_2$CH=CH— | —NH—$CH_2$CH=CH— | —NH—$CH_2$CH=CH— |
| —O—P(O)(OH)—O— | —O—P(O)(OH)—O— | —O—P(O)(OH)—O— |

TABLE 3-continued

Definition of tether.

| | | |
|---|---|---|
| —O—P(S)(OH)—O— | —O—P(S)(OH)—O— | —O—P(S)(OH)—O— |
| —O—P(S)(SH)—O— | —O—P(S)(SH)—O— | —O—P(S)(SH)—O— |
| —S—P(O)(OH)—O— | —S—P(O)(OH)—O— | —S—P(O)(OH)—O— |
| —O—P(O)(OH)—S— | —O—P(O)(OH)—S— | —O—P(O)(OH)—S— |
| —S—P(O)(OH)—S— | —S—P(O)(OH)—S— | —S—P(O)(OH)—S— |
| —O—P(S)(OH)—S— | —O—P(S)(OH)—S— | —O—P(S)(OH)—S— |
| —S—P(S)(OH)—O— | —S—P(S)(OH)—O— | —S—P(S)(OH)—O— |
| —O—P(O)(R)—O— | —O—P(O)(R)—O— | —O—P(O)(R)—O— |
| —O—P(S)(R)—O— | —O—P(S)(R)—O— | —O—P(S)(R)—O— |
| —S—P(O)(R)—O— | —S—P(O)(R)—O— | —S—P(O)(R)—O— |
| —S—P(S)(R)—O— | —S—P(S)(R)—O— | —S—P(S)(R)—O— |
| —S—P(O)(R)—S— | —S—P(O)(R)—S— | —S—P(O)(R)—S— |
| —O—P(S)(R)—S— | —O—P(S)(R)—S— | —O—P(S)(R)—S— |

R = Alkyl, fluroalkyl, aryl or aralkyl

Tether $\begin{cases} -(CH_2)_m-S-S-(CH_2)_n- \\ -(CH_2)_{m1}-(CH=CH)_{m2}-(CH_2)_{m3}-S-S-(CH_2)_{n1}-(CH=CH)_{n2}-(CH_2)_{n3}- \\ -(CH_2)_{m1}-(C\equiv C)_{m2}-(CH_2)_{m3}-S-S-(CH_2)_{n1}-(C\equiv C)_{n2}-(CH_2)_{n3}- \\ -(CH_2CH_2O)_{m1}-(CH)_{m2}-S-S-(CH)_{n1}-(OCH_2CH_2)_{n2}- \\ -(CH_2CH_2NH)_{m1}-(CH)_{m2}-S-S-(CH)_{n1}-(NHCH_2CH_2)_{n2}- \\ -(CH_2)_m-S-S-(CH_2)_n-X-(CH_2)_p-S-S-(CH_2)_p \\ m, m1, m2, m3, n, n1, n2, n3, p, q = 0\text{-}20 \end{cases}$ Scheme 1<sup>a</sup>

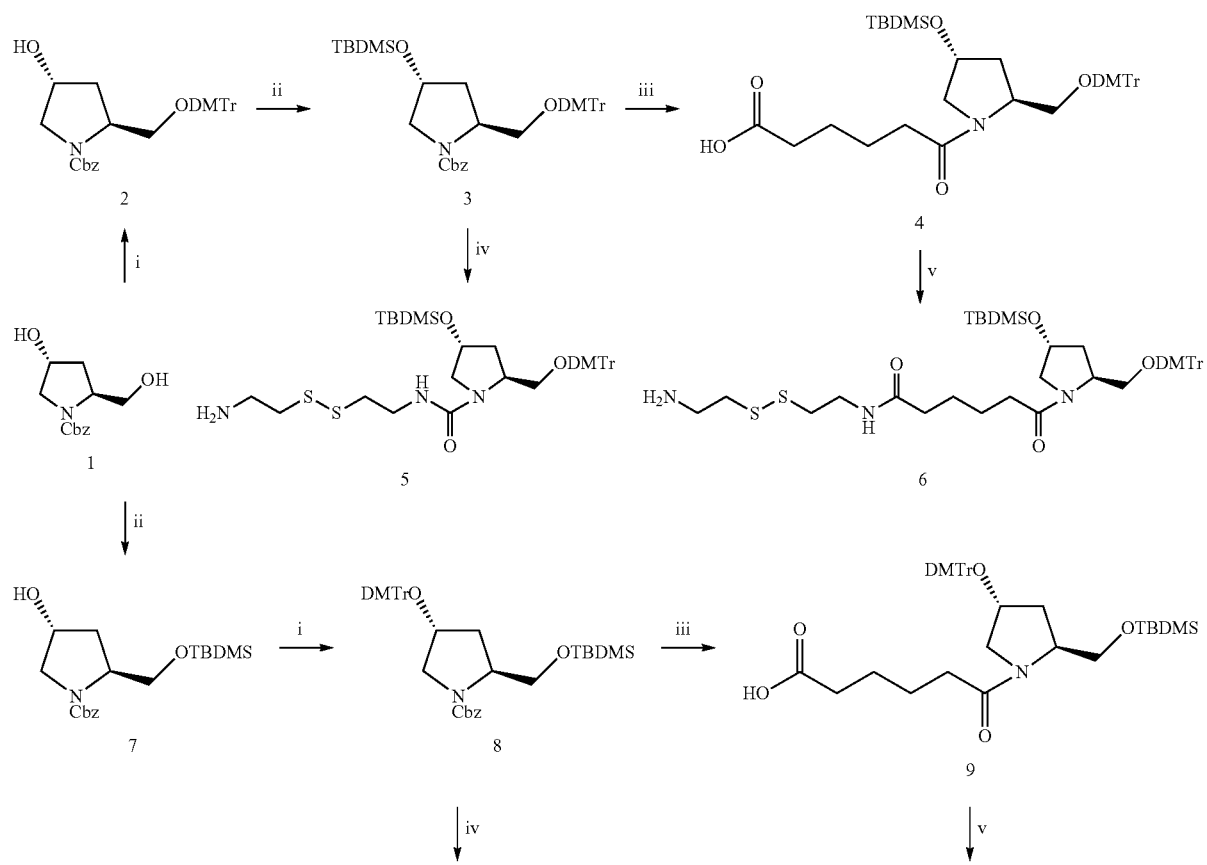

-continued

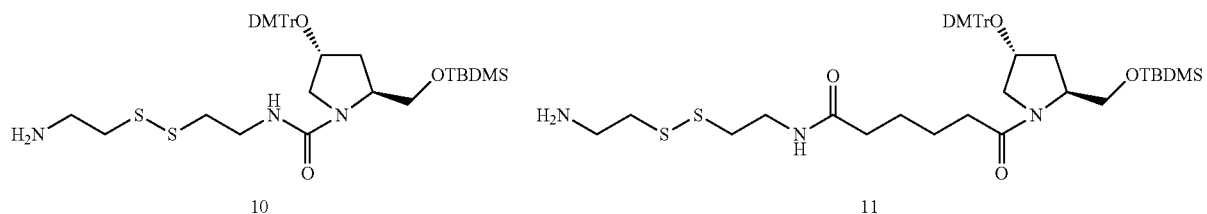

10

11

[a] (i), (DMTr—Cl, DMP/Py (ii) TBDMS—Cl, Imidazole/Py; (iii) (a) H₂/Pd—C, EtOAc, (b) Adipic acid monomethyl ester, DCC, DMAP, N-hydroxysuccinimide and (c) LiOH/THF—H₂O; (iv) N•N′-disuccinimidyl carbonate (DSC), TEA/DCM followed by addition of cystamine dihydrochloride; (v) DCC, DMAP, N-hydroxysuccinimide follwed by addition of cystamine dihydrochloride and TEA.

Scheme 2[a]

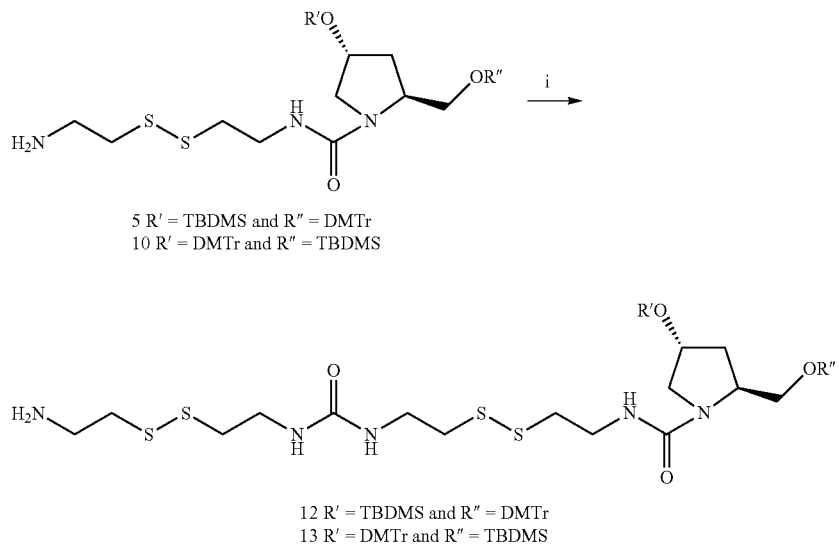

5 R' = TBDMS and R" = DMTr
10 R' = DMTr and R" = TBDMS

12 R' = TBDMS and R" = DMTr
13 R' = DMTr and R" = TBDMS

[a] (i) N•N′-disuccinimidyl carbonate (DSC), TEA/DCM followed by addition of cystamine dihydrochloride.

Scheme 3[a]

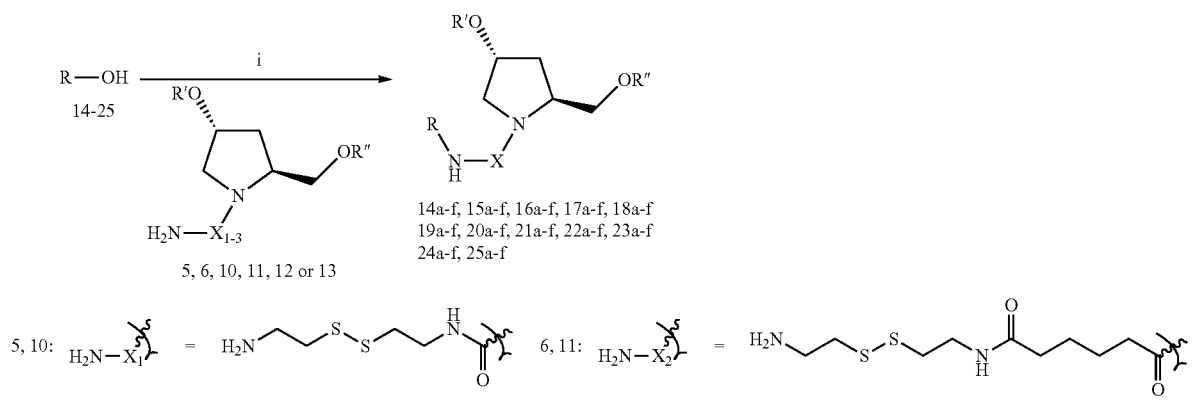

14-25

14a-f, 15a-f, 16a-f, 17a-f, 18a-f
19a-f, 20a-f, 21a-f, 22a-f, 23a-f
24a-f, 25a-f 5, 6, 10, 11, 12 or 13

-continued
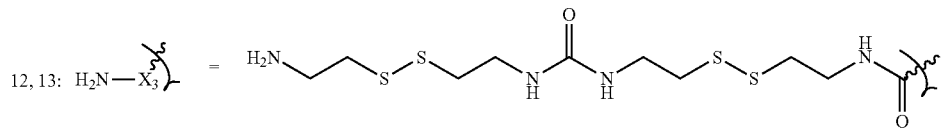
12, 13: H₂N—X₃⟩ =
5, 6, 12 R' = TBDMS and R" = DMTr; 10, 11, 13 R' = DMTr and R" = TBDMS
14a-25a: X = X₁, R' = TBDMS and R" = DMTr; 14b-25b: X = X₁, R' = DMTr and R" = TBDMS
14c-25c: X = X₂, R' = TBDMS and R" = DMTr; 14d-25d: X = X₂, R' = DMTr and R" = TBDMS
14e-25e: X = X₃, R' = TBDMS and R" = DMTr; 14f-25f: X = X₃, R' = DMTr and R" = TBDMS
R =
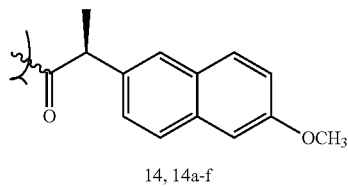
14, 14a-f
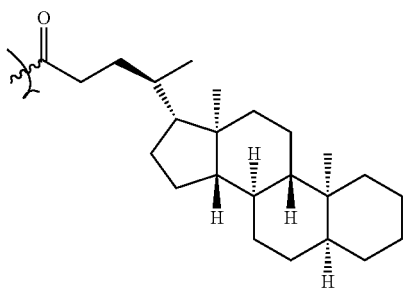
21, 21a-f
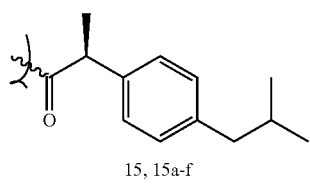
15, 15a-f
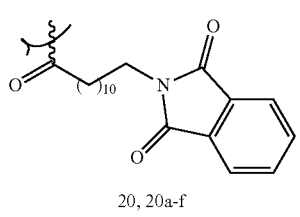
20, 20a-f
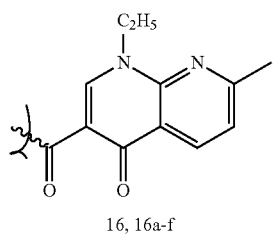
16, 16a-f
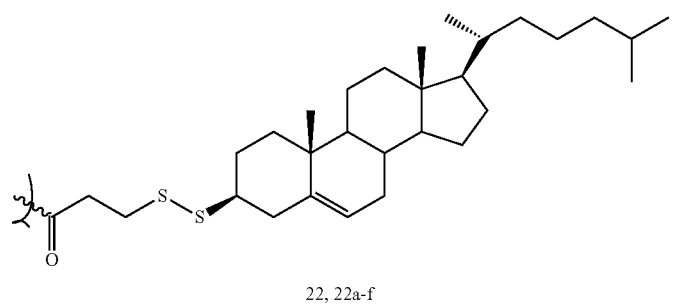
22, 22a-f
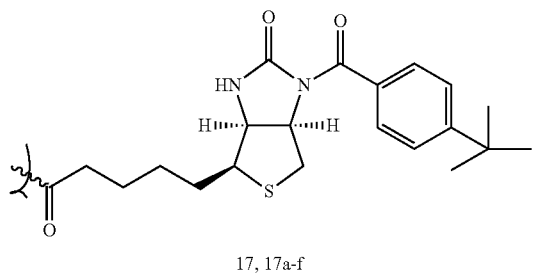
17, 17a-f
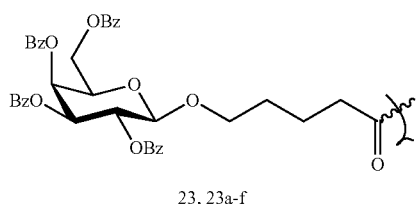
23, 23a-f
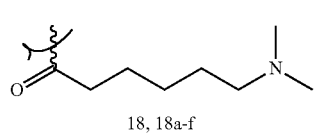
18, 18a-f
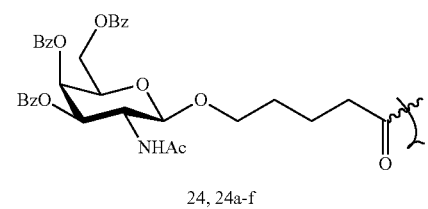
24, 24a-f -continued
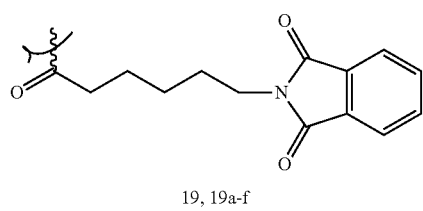
19, 19a-f
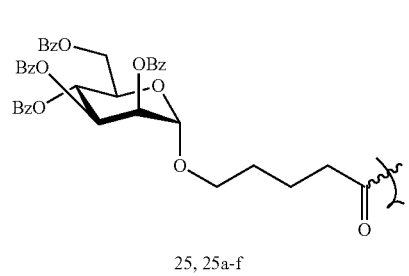
25, 25a-f
*a* (i) DCC, DMAP, N-hydroxysuccinimide followed by addition of 5, 6, 10, 11, 12 or 13/Dichloromethane or DMF
Scheme 4*a*
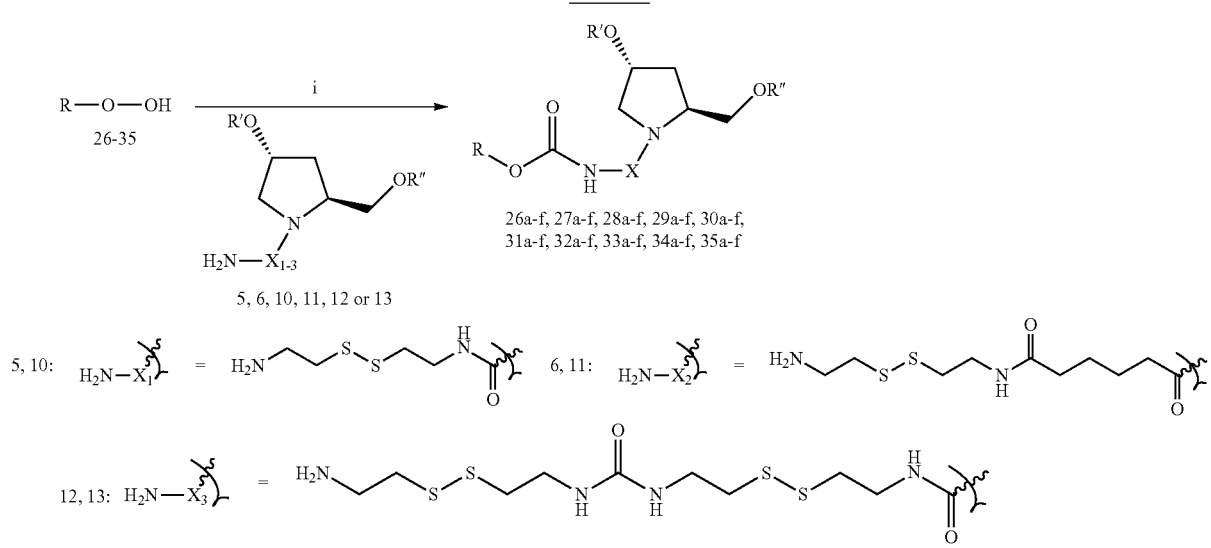
5, 6, 12 R' = TBDMS and R" = DMTr; 10, 11, 13 R' = DMTr and R" = TBDMS
26a-35a: X = X$_1$, R' = TBDMS and R" = DMTr; 26b-35b: X = X$_1$, R' = DMTr and R" = TBDMS
26c-35c: X = X$_2$, R' = TBDMS and R" = DMTr; 26d-35d: X = X$_2$, R' = DMTr and R" = TBDMS
26e-35e: X = X$_3$, R' = TBDMS and R" = DMTr; 26f-35f: X = X$_3$, R' = DMTr and R" = TBDMS
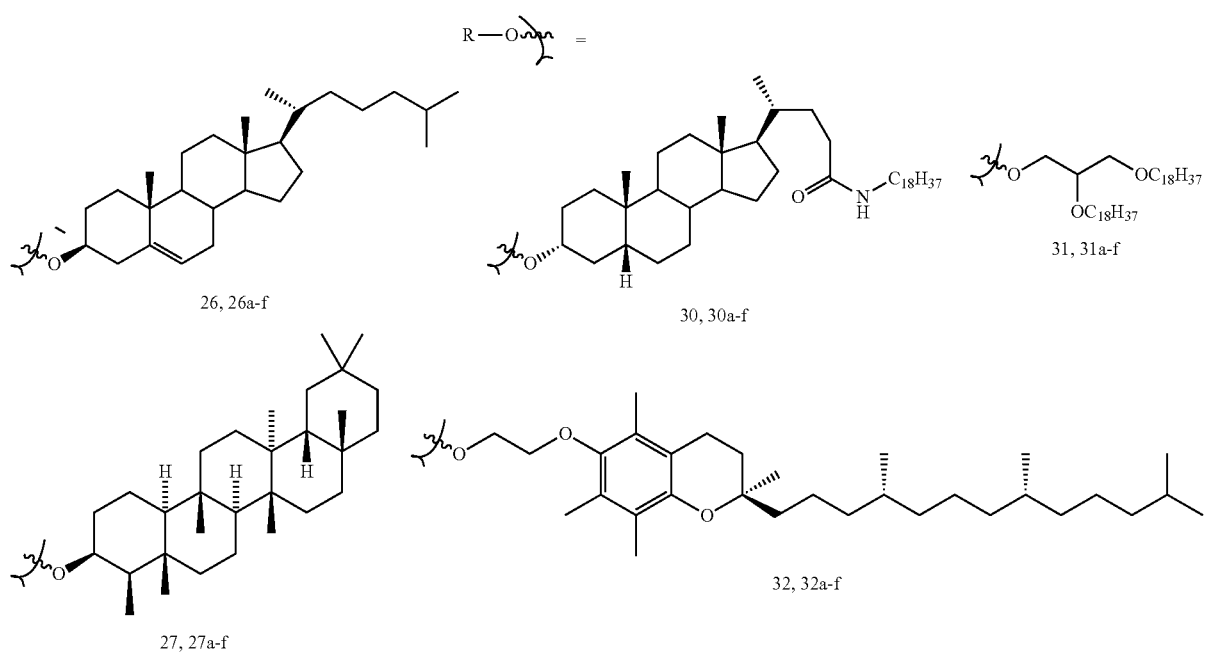

-continued
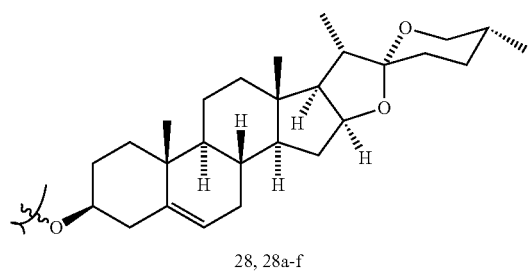
28, 28a-f
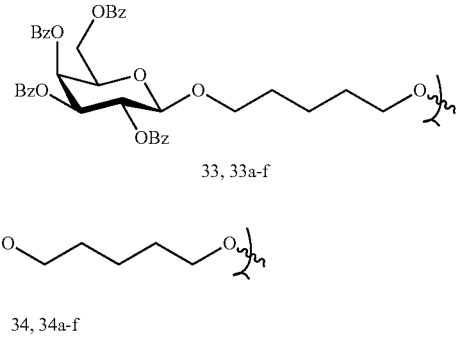
33, 33a-f
34, 34a-f
35, 35a-f
29, 29a-f
*a* (i) N•N′-disuccinimidyl carbonate (DSC), TEA/DCM followed by addition of 5, 6, 10, 11, 12 or 13/Dichloromethane or DMF
Scheme 5*a*
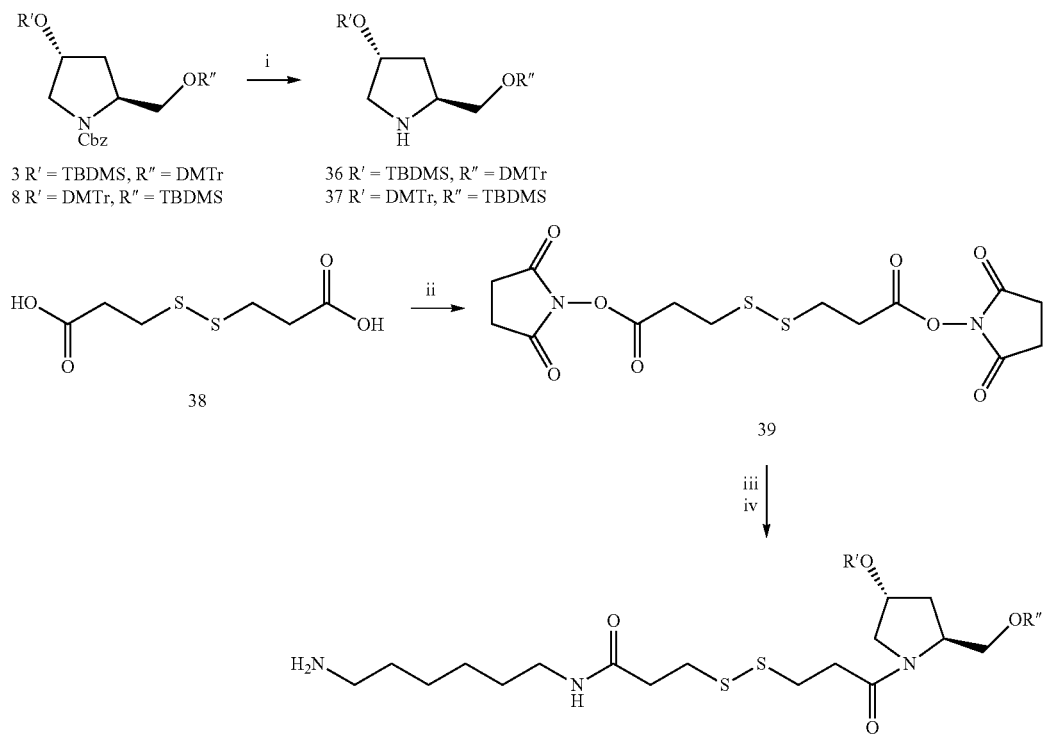
3 R′ = TBDMS, R″ = DMTr
8 R′ = DMTr, R″ = TBDMS
36 R′ = TBDMS, R″ = DMTr
37 R′ = DMTr, R″ = TBDMS
38
39
40 R′ = TBDMS, R″ = DMTr
41 R′ = DMTr, R″ = TBDMS
*a* (i) H$_2$, Pd—C /Ethyl acetate-MeOH; (ii) DCC, DMAP, N-hydroxysuccinimide; (iii) 36 or 37 (1 mol eq.), TEA/DCM and (iv) 1,6-Diaminohexane

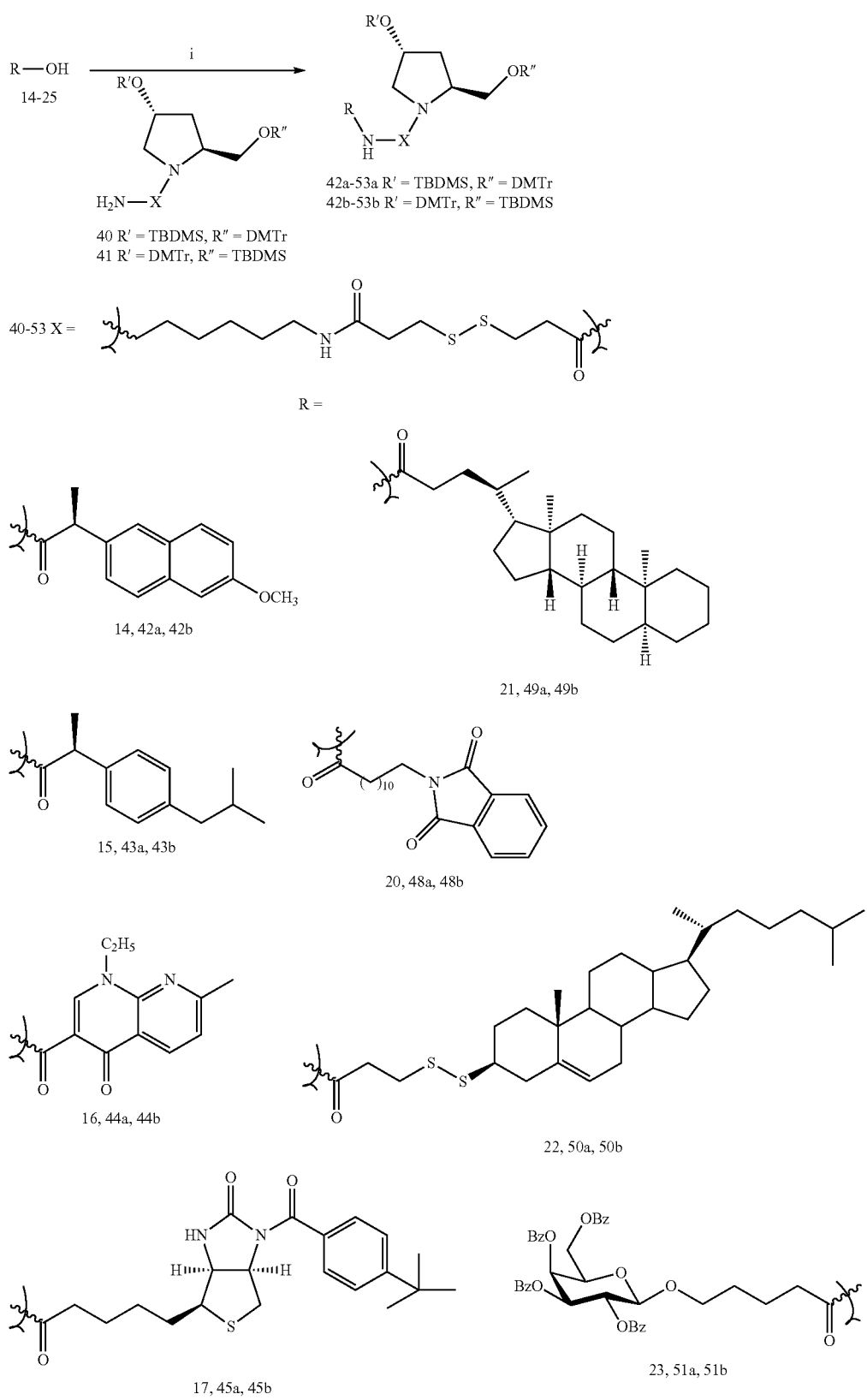

-continued
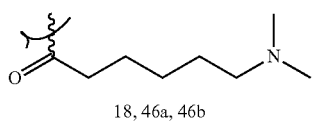
18, 46a, 46b
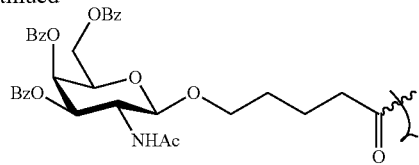
24, 52a, 52b
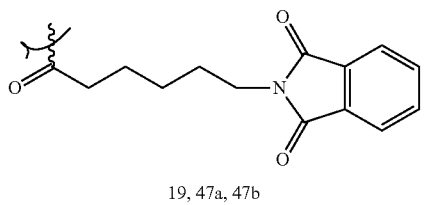
19, 47a, 47b
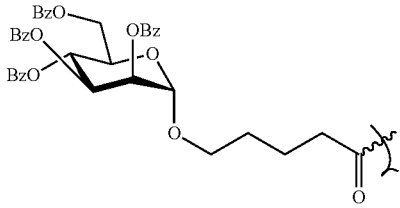
25, 53a, 53b
*a* (i) DCC, DMAP, N-hydroxysuccinimide followed by addition of 40 or 41/Dichloromethane or DMF
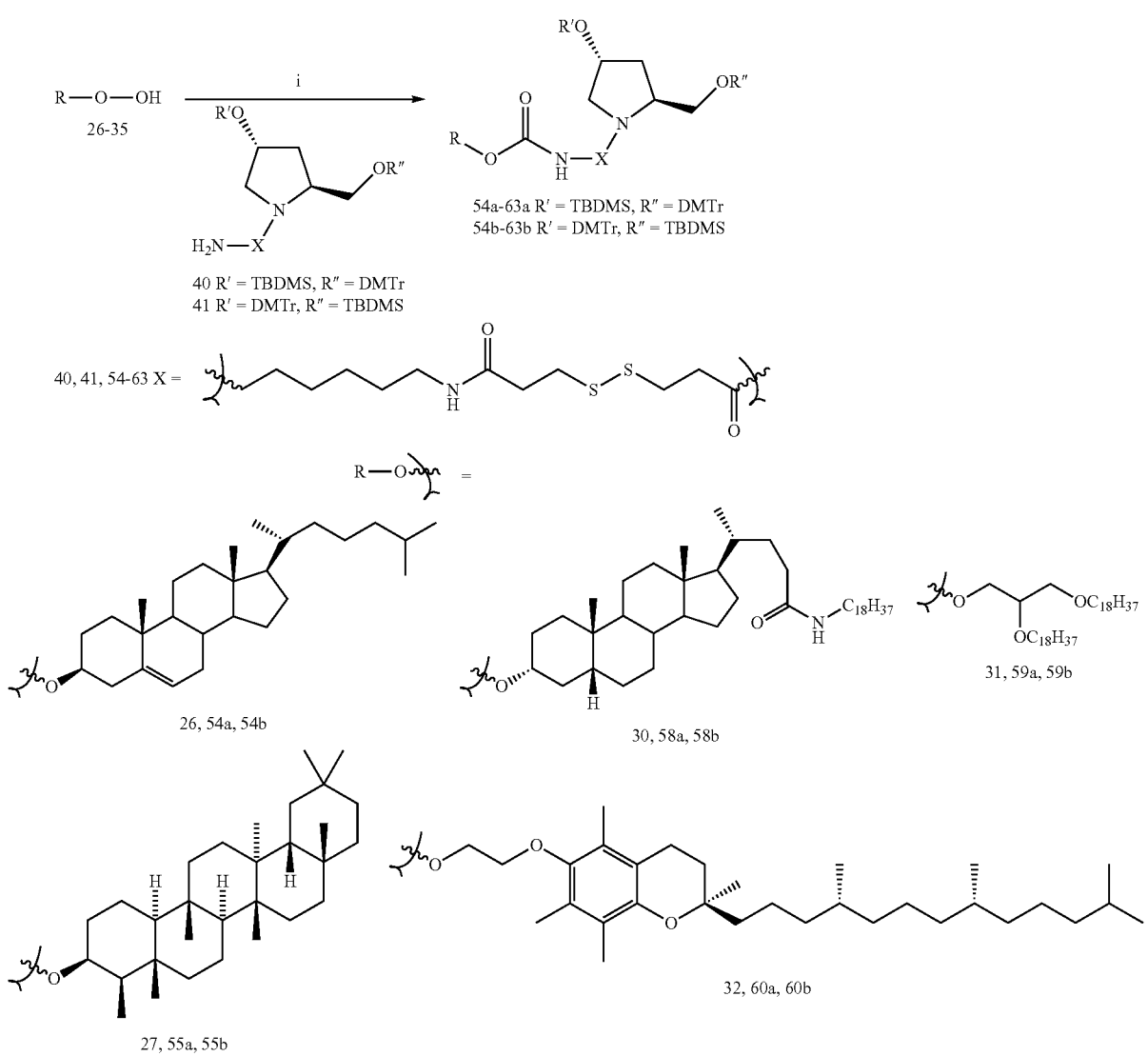

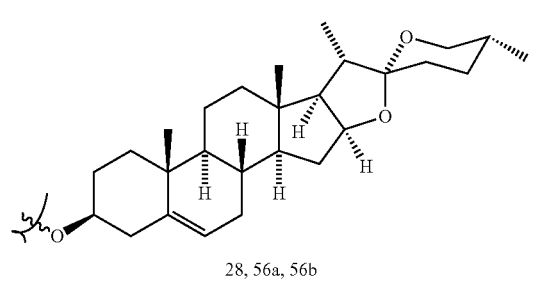
28, 56a, 56b
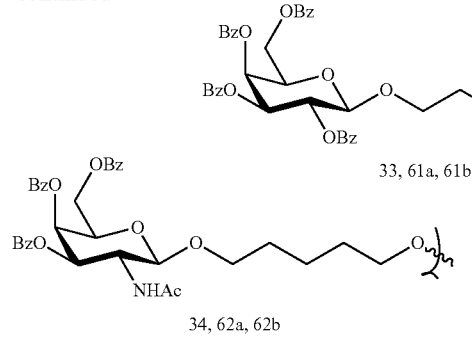
33, 61a, 61b
34, 62a, 62b
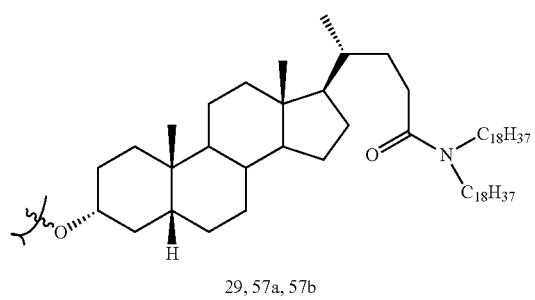
29, 57a, 57b
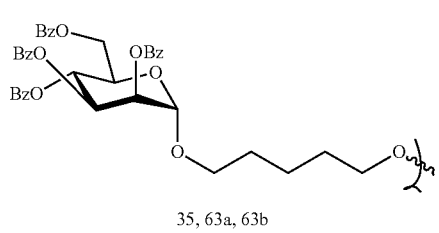
35, 63a, 63b
[a] (i) N•N'-disuccinimidyl carbonate (DSC), TEA/DCM followed by addition of 40 or 41/Dichloromethane or DMF
Scheme 8[a]
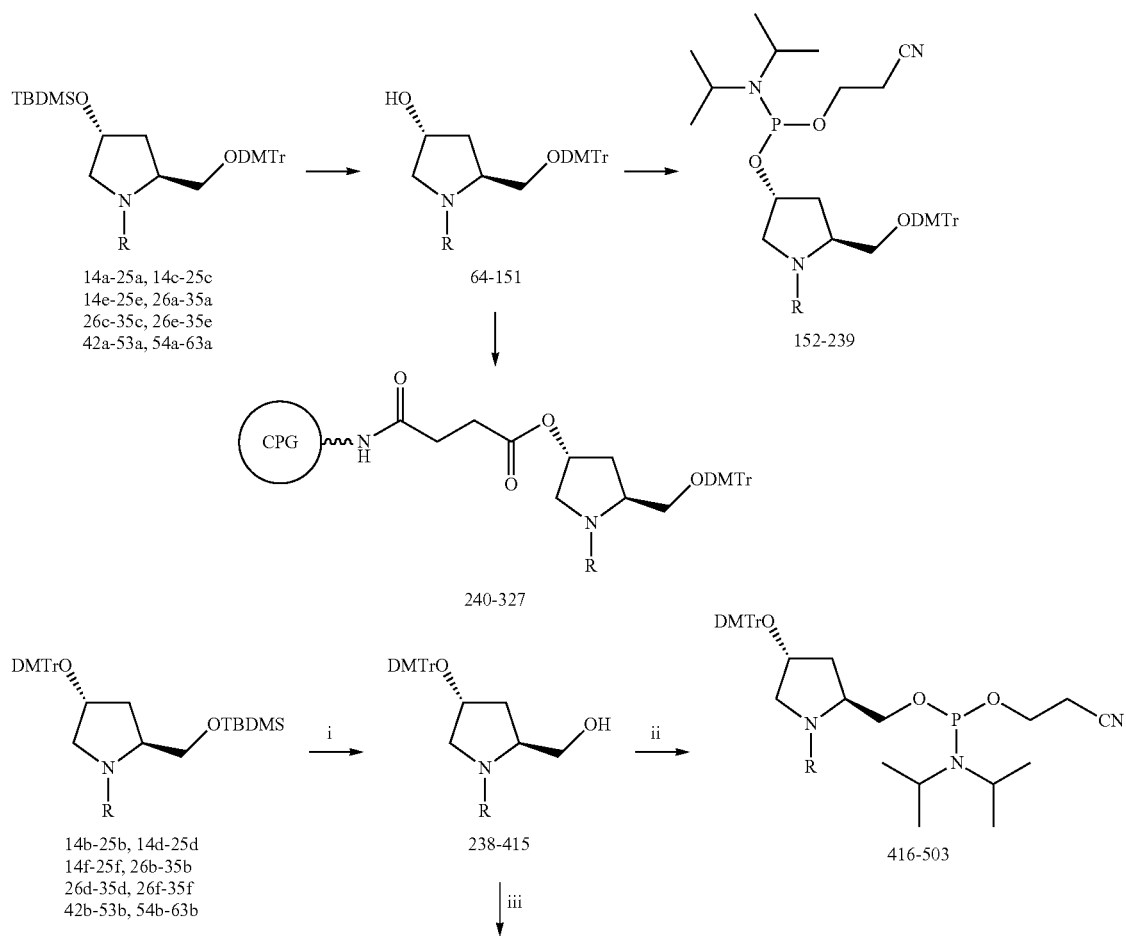

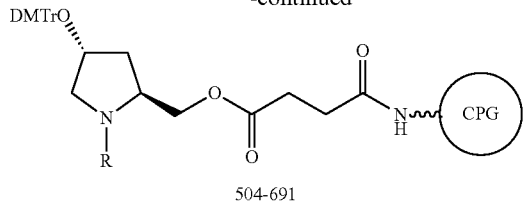

504-691

*a* (i)TBAF/THF; (ii) N,N-diisopropylamino β-cyanoethylphosphonamidic chloride{[(CH₃)₂CH]₂N—P(Cl)—OCH₂CH₂CN}, DIEA/Dichloromethane or 2-Cyanoethyl-N,N,N′,N′-tetraisopropylphosphane, tetrazole (or tetrazolediisopropylammonium salt)/Acetonitrile; (iii) (a) Succinic anhydride, DMAP/Dichloroethane and (b) DTNP, DMAP, Ph₃P, Aminoalkyl solid support Scheme 9ᵃ

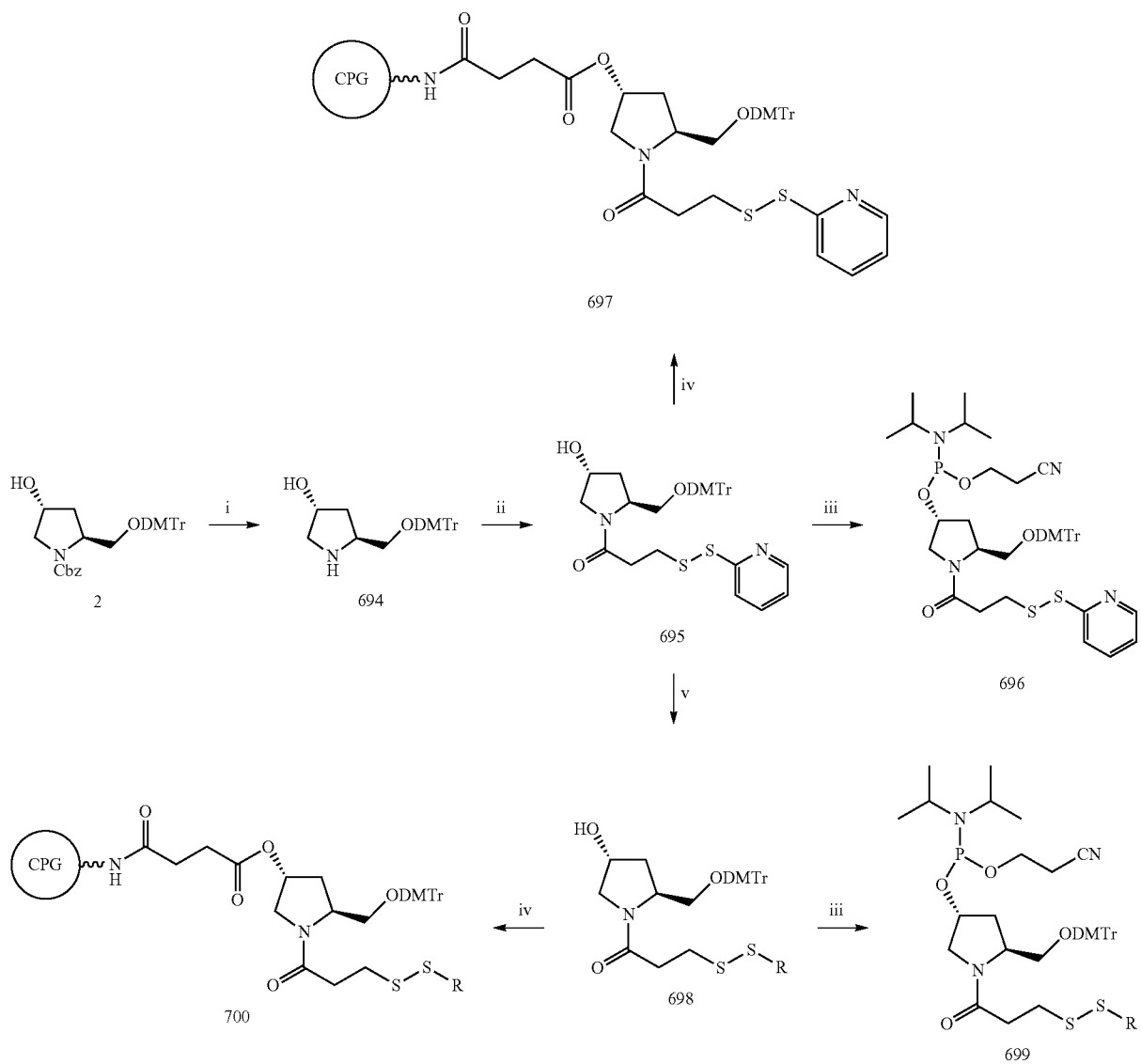

*a* (i) H₂, Pd—C/EtOH—MeOH; (ii) 3-(2-pyridyldithio)propionic acid NHS ester, TEA/dichloromethane; (iii) N,N-diisopropylamino β-cyanoethylphosphonamidic chloride {[(CH₃)₂CH]₂N—P(Cl)—OCH₂CH₂CN}, DIEA/Dichloromethane or 2-Cyanoethyl-N,N,N′,N′-tetraisopropylphosphane, tetrazole (or tetrazolediisopropylammonium salt)/Acetonitrile (iv) (a) Succinic anhydride, DMAP/Dichloroethane and (b) DTNP, DMAP, Ph₃P, Aminoalkyl solid support (v) R—SH, TEA/dichloromethane Scheme 10$^a$
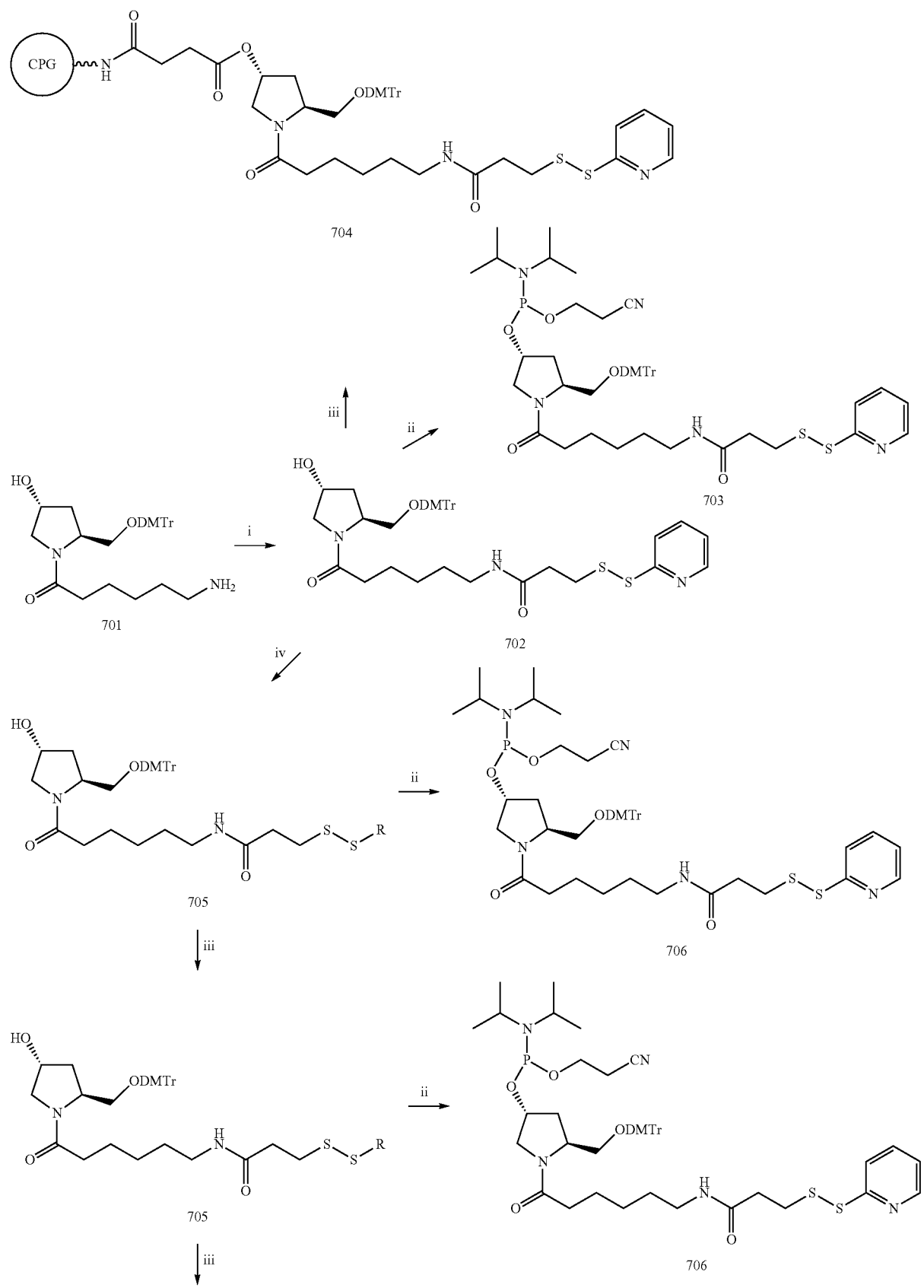

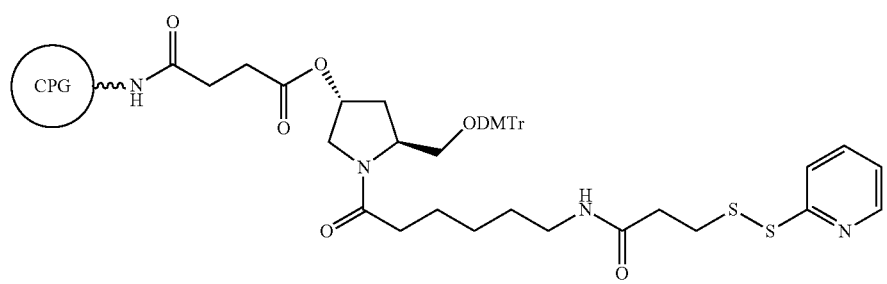

707

*a* (i) 3-(2-pyridyldithio)propionic acid NHS ester, TEA/dichlormethane; (ii) N,N-diisopropylamino β-cyanoethylphosphonamidic chloride{[(CH₃)₂CH]₂N—P(Cl)—OCH₂CH₂CN}, DIEA/Dichloromethane or 2-Cyanoethyl-N,N,N',N'-tetraisopropylphosphane, tetrazole (or tetrazolediisopropylammonium salt)/Acetonitrile; (iii) (a) Succinic anhydride, DMAP/Dichloroethane and (b) DTNP, DMAP, Ph₃P, Aminoalkyl solid support; (iv) R—SH, TEA/dichloromethane Scheme 11: Synthesis of Thiocholesterol-Hydroxyprolinol Building Blocks containing a disulfide linkage

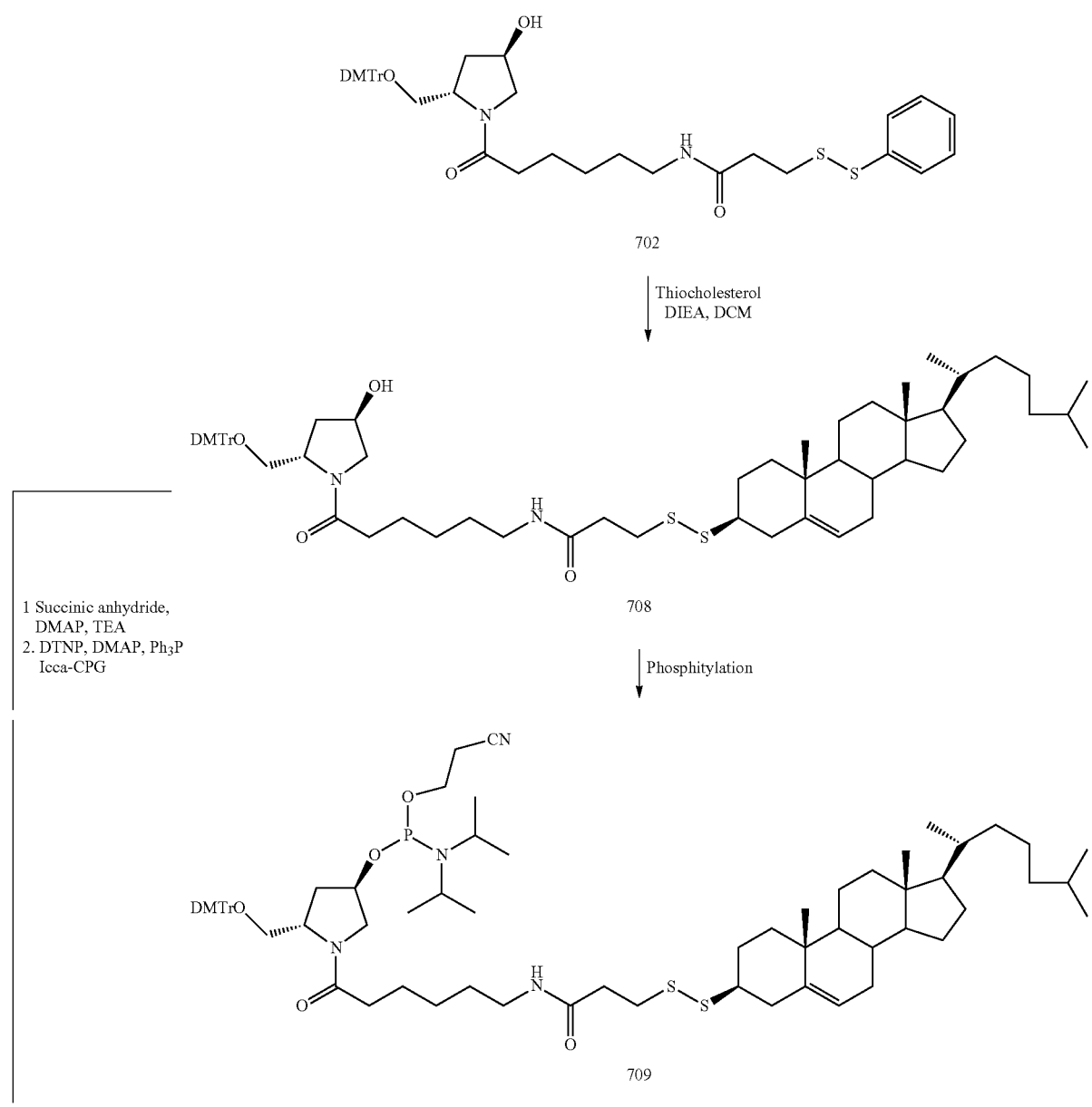

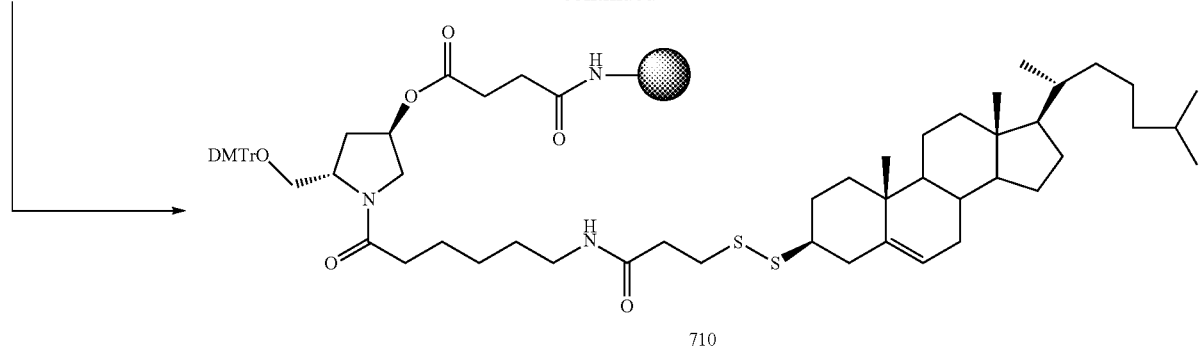

Example 1

Synthesis of Compound 5

Scheme 1

Step 1, Compound 2: Compound 1 (20.37 g, 86.64 mmol, purchased from Aldrich) and 4-(dimethylamino)pyridine (DMAP, 1.40 g, 11.46 mmol) were dried over anhydrous $P_2O_5$ under vacuum overnight. After releasing vacuum under argon, the mixture was then taken into anhydrous pyridine (150 mL) and to this DMTr-Cl (36.7 g, 108.3 mmol) was added at ambient temperature. The reaction mixture was stirred at ambient temperature overnight. After removing pyridine in vacuo, the product was extracted into ethyl acetate (600 mL), washed with water and sodium bicarbonate solution followed by standard workup. Compound 2 was purified by flash silica gel column chromatography, eluent: 3-4% methanol in dichloromethane, yield: 26.76 g (55.9%). $^1$H NMR (400 MHz, [D$_6$]DMSO, 25° C.): δ 7.38-7.04 (m, 14H); 6.86-6.84 (d, 4H); 5.06 (bs, 1H, exchangeable with $D_2O$); 4.97-4.89 (m, 2H); 4.33-4.28 (bm, 1H); 4.02-3.97 (bm, 1H); 3.68 S, 6H); 3.47-3.38 (m, 2H); 3.21-3.02 (m, 2H); 2.03-1.79 (m, 2H).

Step 2, Compound 3: Compound 2 (12.1 g, 21.87 mmol) in anhydrous pyridine (60 mL) was stirred with TBDMS-Cl (4.90 g, 32.51 mmol) in the presence of imidazole (6.0 g, 88.13 mmol) at ambient temperature overnight. Pyridine was removed form the reaction mixture in vacuo and the product was extracted into ethyl acetate (200 mL), washed with sodium bicarbonate solution followed by standard workup. Compound 3 was purified by flash silica gel column chromatography, eluent: 1-2% methanol in dichloromethane; yield: 14.40 g (95.9%) (Corey and Venkkateswarlu, *J. Am. Chem. Soc.,* 1972, 94, 6190)

Step 3, Compound 5: Compound 3 and 10% palladium on carbon (wet, Degussa type, 10% by weight with respect to 3) are suspended in a 9:1 mixture of ethyl acetate-methanol and hydrogenated at 1 atm pressure to remove the benzyl carbamate protection from compound 3 (Step 3a). After complete deprotection, the product is separated from the catalyst by filtration. Solvent is removed from the filtrate in vacuo and the product is co-evaporated with anhydrous dichloromethane and re-dissolved in anhydrous dichloromethane. To this one molar equivalent of N,N'-disuccinimidyl carbonate (DSC) and anhydrous triethylamine (TEA) are added the reaction mixture is stirred for overnight (Takeda et al., *Tetrahedron Lett.,* 1983, 24, 4569). After overnight stirring cystamine dihydrochloride (purchased from Aldrich) and excess of anhydrous TEA are added to the stirring solution, continued stirring to obtain compound 5 (Step 3b).

Example 2

Synthesis of Compound 6

Scheme 1

Step 1, Compound 4: Adipic acid monomethyl ester is treated with one molar equivalent of DCC, DMAP and N-hydroxysuccinimide in DMF for 30 min. To this a molar equivalent of the compound obtained from Step 3a (Example 1) is added and stirred at ambient temperature for 8 h. Dicylcohexylurea formed during the course of the reaction is filtered off and the product is extracted into ethyl acetate, washed with sodium bicarbonate solution followed by standard workup. The methyl ester thus obtained is treated with LiOH in THF/water to obtain compound 4.

Step 2, Compound 6: Compound 4 is treated with DCC, DMAP and N-hydroxysuccinimide as described in step 1 above and subsequently reacted with cystamine dihydrochloride in the presence of TEA to obtain compound 6.

Example 3

Synthesis of Compound 10

Scheme 1

Step 1, Compound 7: Compound 1 in pyridine in reacted with TBDMS-Cl (1 mol eq.) in the presence of imidazole (2 mol eq.) to obtain compound 7.

Step 2, Compound 8: Compound 7 is reacted with DMTr-Cl in anhydrous pyridine in the presence of DMAP to obtain compound 7.

Step 3, Compound 10: The benzyl carbamate protection on compound 7 is removed as described in Step 3a in Example 1. The product thus obtained is reacted with cystamine dihydrochloride as described in Step 3b in Example 1 to obtain compound 10.

Example 4

Synthesis of Compound 11

Scheme 1

Compound 11 is prepared from compound 8 as described in Example 2.

Example 5

Synthesis of Compound 12

Scheme 2

Compound 5 is treated with DSC (1 mol eq.) in the presence of TEA in dichloromethane and subsequently with cystamine dihydrochloride in the presence of excess of TEA as described in step 3, Example 1 to obtain compound 12.

Example 6

Synthesis of Compound 13

Scheme 2

Compound 10 is treated with DSC (1 mol eq.) in the presence of TEA in dichloromethane and subsequently with cystamine dihydrochloride in the presence of excess of TEA as described in step 3, Example 1 to obtain compound 13.

Example 7

Syntheses of Compounds 14a-f

Scheme 3

Step 1, Compound 14a: Naproxen (14, purchased from Aldrich) is stirred with DCC (1 mol eq.), DMAP (0.1 mol eq.) and N-hydroxysuccinimide (2 mol eq.) in dichloromethane for 30 min and to this compound 5 and TEA are added to obtain compound 14a.

Step 2, Compound 14b-f are prepared from 14 as described in step 1 by subsequent reaction of the activated carboxylate obtained by the reaction of DCC and N-hydroxysuccinimide in the presence of DMAP with compound 6, 10, 11, 12 and 13 respectively.

Example 8

Syntheses of Compounds 15a-f

Scheme 3

Step 1, Compound 15a: Compound 15 (purchased from Aldrich) is stirred with DCC (1 mol eq.), DMAP (0.1 mol eq.) and N-hydroxysuccinimide (2 mol eq.) in dichloromethane for 30 min and to this compound 5 and TEA are added to obtain compound 15a.

Step 2, Compound 15b-f are prepared from 15 as described in step 1 by subsequent reaction of the activated carboxylate obtained by the reaction of DCC and N-hydroxysuccinimide in the presence of DMAP with compound 6, 10, 11, 12 and 13 respectively.

Example 9

Syntheses of Compounds 16a-f

Scheme 3

Step 1, Compound 16a: Compound 16 (purchased from Aldrich) is stirred with DCC (1 mol eq.), DMAP (0.1 mol eq.) and N-hydroxysuccinimide (2 mol eq.) in dichloromethane for 30 min and to this compound 5 and TEA are added to obtain compound 16a.

Step 2, Compound 16b-f are prepared from 16 as described in step 1 by subsequent reaction of the activated carboxylate obtained by the reaction of DCC and N-hydroxysuccinimide in the presence of DMAP with compound 6, 10, 11, 12 and 13 respectively.

Example 10

Syntheses of Compounds 17a-f

Scheme 3

Step 1, Compound 17a: Compound 17 is prepared as reported in the literature (Fang and Bergstrom, *Nucleic Acids Res.*, 2003, 31, 708). Compound 17 is stirred with DCC (1 mol eq.), DMAP (0.1 mol eq.) and N-hydroxysuccinimide (2 mol eq.) in dichloromethane for 30 min and to this compound 5 and TEA are added to obtain compound 17a.

Step 2, Compound 17b-f are prepared from 17 as described in step 1 by subsequent reaction of the activated carboxylate obtained by the reaction of DCC and N-hydroxysuccinimide in the presence of DMAP with compound 6, 10, 11, 12 and 13 respectively.

Example 11

Syntheses of Compounds 18a-f

Scheme 3

Step 1, Compound 18a: Compound 18 is prepared as reported in the literature (Rahal and Badache, *Journal de la Societe Algerienne de Chemie*, 1994, 4, 75). Compound 18 is stirred with DCC (1 mol eq.), DMAP (0.1 mol eq.) and N-hydroxysuccinimide (2 mol eq.) in dichloromethane for 30 min and to this compound 5 and TEA are added to obtain compound 18a.

Step 2, Compound 18b-f are prepared from 18 as described in step 1 by subsequent reaction of the activated carboxylate obtained by the reaction of DCC and N-hydroxysuccinimide in the presence of DMAP with compound 6, 10, 11, 12 and 13 respectively.

Example 12

Syntheses of Compounds 19a-f

Scheme 3

Step 1, Compound 19a: Commercially available compound 19 is stirred with DCC (1 mol eq.), DMAP (0.1 mol eq.) and N-hydroxysuccinimide (2 mol eq.) in dichloromethane for 30 min and to this compound 5 and TEA are added to obtain compound 19a.

Step 2, Compound 19b-f are prepared from 19 as described in step 1 by subsequent reaction of the activated carboxylate obtained by the reaction of DCC and N-hydroxysuccinimide in the presence of DMAP with compound 6, 10, 11, 12 and 13 respectively.

Example 13

Syntheses of Compounds 20a-f

Scheme 3

Step 1, Compound 20a: Compound 20 is prepared as reported in the literature (De et al., 1998, 41, 4918). Compound 20 is stirred with DCC (1 mol eq.), DMAP (0.1 mol eq.) and N-hydroxysuccinimide (2 mol eq.) in dichloromethane for 30 min and to this compound 5 and TEA are added to obtain compound 20a.

Step 2, Compound 20b-f are prepared from 20 as described in step 1 by subsequent reaction of the activated carboxylate obtained by the reaction of DCC and N-hydroxysuccinimide in the presence of DMAP with compound 6, 10, 11, 12 and 13 respectively.

Example 14

Syntheses of Compounds 21a-f

Scheme 3

Step 1, Compound 21a: Commercially available 5β-cholanic acid 21 is stirred with DCC (1 mol eq.), DMAP (0.1 mol eq.) and N-hydroxysuccinimide (2 mol eq.) in dichloromethane for 30 min and to this compound 5 and TEA are added to obtain compound 21a.

Step 2, Compound 21b-f are prepared from 21 as described in step 1 by subsequent reaction of the activated carboxylate obtained by the reaction of DCC and N-hydroxysuccinimide in the presence of DMAP with compound 6, 10, 11, 12 and 13 respectively.

Example 15

Syntheses of Compounds 22a-f

Scheme 3

Step 1, Compound 22a: Compound 22 is stirred with DCC (1 mol eq.), DMAP (0.1 mol eq.) and N-hydroxysuccinimide (2 mol eq.) in dichloromethane for 30 min and to this compound 5 and TEA are added to obtain compound 22a.

Step 2, Compound 22b-f are prepared from 22 as described in step 1 by subsequent reaction of the activated carboxylate obtained by the reaction of DCC and N-hydroxysuccinimide in the presence of DMAP with compound 6, 10, 11, 12 and 13 respectively.

Example 16

Syntheses of Compounds 22a-f

Scheme 3

Step 1, Compound 23a: Compound 23 is obtained as reported in the literature (Valentijn et al., *Tetrahedron*, 1997, 53, 759). Compound 23 is stirred with DCC (1 mol eq.), DMAP (0.1 mol eq.) and N-hydroxysuccinimide (2 mol eq.) in dichloromethane for 30 min and to this compound 5 and TEA are added to obtain compound 23a.

Step 2, Compound 23b-f are prepared from 23 as described in step 1 by subsequent reaction of the activated carboxylate obtained by the reaction of DCC and N-hydroxysuccinimide in the presence of DMAP with compound 6, 10, 11, 12 and 13 respectively.

Example 17

Syntheses of Compounds 24a-f

Scheme 3

Step 1, Compound 24a: Compound 24 is obtained as reported in the literature (Valentijn et al., *Tetrahedron*, 1997, 53, 759). Compound 24 is stirred with DCC (1 mol eq.), DMAP (0.1 mol eq.) and N-hydroxysuccinimide (2 mol eq.) in dichloromethane for 30 min and to this compound 5 and TEA are added to obtain compound 24a.

Step 2, Compound 24b-f are prepared from 24 as described in step 1 by subsequent reaction of the activated carboxylate obtained by the reaction of DCC and N-hydroxysuccinimide in the presence of DMAP with compound 6, 10, 11, 12 and 13 respectively.

Example 18

Syntheses of Compounds 25a-f

Scheme 3

Step 1, Compound 25a: Compound 25 is stirred with DCC (1 mol eq.), DMAP (0.1 mol eq.) and N-hydroxysuccinimide (2 mol eq.) in dichloromethane for 30 min and to this compound 5 and TEA are added to obtain compound 25a.

Step 2, Compound 25b-f are prepared from 25 as described in step 1 by subsequent reaction of the activated carboxylate obtained by the reaction of DCC and N-hydroxysuccinimide in the presence of DMAP with compound 6, 10, 11, 12 and 13 respectively.

Example 19

Syntheses of Compounds 26a-f

Scheme 4

Step 1, Compound 26a: Compound 26 (Cholesterol) is stirred with DSC (1 mol eq.) in dichloromethane in the presence of TEA overnight. Compound 5 is added into the reaction mixture, after over night stirring and continued stirring to form compound 26a. Standard synthetic organic chemistry purification procedures yields compound 26a.

Step 2, Compound 26b-f: Compound 26 is initially reacted with DSC in the presence of TEA and subsequently with compounds 6, 10, 11, 12 and 13 in the presence of TEA to obtain their respective carbamates 26b-f.

Example 20

Syntheses of Compounds 27a-f

Scheme 4

Step 1, Compound 27a: Commercially available compound 27 is stirred with DSC (1 mol eq.) in dichloromethane in the presence of TEA overnight. Compound 5 is added into the reaction mixture, after over night stirring and continued stirring to form compound 27a. Standard synthetic organic chemistry purification procedures yields compound 27a.

Step 2, Compound 27b-f: Compound 27 is initially reacted with DSC in the presence of TEA and subsequently with compounds 6, 10, 11, 12 and 13 in the presence of TEA to obtain their respective carbamates 27b-f.

Example 21

Syntheses of Compounds 28a-f

Scheme 4

Step 1, Compound 28a: Commercially available compound 28 is stirred with DSC (1 mol eq.) in dichloromethane in the presence of TEA overnight. Compound 5 is added into the reaction mixture, after over night stirring and continued stirring to form compound 28a. Standard synthetic organic chemistry purification procedures yields compound 28a.

Step 2, Compound 28b-f: Compound 28 is initially reacted with DSC in the presence of TEA and subsequently with compounds 6, 10, 11, 12 and 13 in the presence of TEA to obtain their respective carbamates 28b-f.

Example 22

Syntheses of Compounds 29a-f

Scheme 4

Step 1, Compound 29a: Compound 29 is stirred with DSC (1 mol eq.) in dichloromethane in the presence of TEA overnight. Compound 5 is added into the reaction mixture, after over night stirring and continued stirring to form compound 29a. Standard synthetic organic chemistry purification procedures yields compound 29a.

Step 2, Compound 29b-f: Compound 29 is initially reacted with DSC in the presence of TEA and subsequently with compounds 6, 10, 11, 12 and 13 in the presence of TEA to obtain their respective carbamates 29b-f.

Example 23

Syntheses of Compounds 30a-f

Scheme 4

Step 1, Compound 30a: Compound 30 is stirred with DSC (1 mol eq.) in dichloromethane in the presence of TEA overnight. Compound 5 is added into the reaction mixture, after over night stirring and continued stirring to form compound 30a. Standard synthetic organic chemistry purification procedures yields compound 30a.

Step 2, Compound 30b-f: Compound 30 is initially reacted with DSC in the presence of TEA and subsequently with compounds 6, 10, 11, 12 and 13 in the presence of TEA to obtain their respective carbamates 30b-f.

Example 24

Syntheses of Compounds 31a-f

Scheme 4

Step 1, Compound 31a: Compound 31 is stirred with DSC (1 mol eq.) in dichloromethane in the presence of TEA overnight. Compound 5 is added into the reaction mixture, after over night stirring and continued stirring to form compound 31a. Standard synthetic organic chemistry purification procedures yields compound 31a.

Step 2, Compound 31b-f: Compound 31 is initially reacted with DSC in the presence of TEA and subsequently with compounds 6, 10, 11, 12 and 13 in the presence of TEA to obtain their respective carbamates 31b-f.

Example 25

Syntheses of Compounds 32a-f

Scheme 4

Step 1, Compound 32a: Compound 32 is stirred with DSC (1 mol eq.) in dichloromethane in the presence of TEA overnight. Compound 5 is added into the reaction mixture, after over night stirring and continued stirring to form compound 32a. Standard synthetic organic chemistry purification procedures yields compound 32a.

Step 2, Compound 32b-f: Compound 32 is initially reacted with DSC in the presence of TEA and subsequently with compounds 6, 10, 11, 12 and 13 in the presence of TEA to obtain their respective carbamates 32b-f.

Example 26

Syntheses of Compounds 33a-f

Scheme 4

Step 1, Compound 33a: Compound 33 is obtained as reported in the literature (Valentijn et al., *Tetrahedron*, 1997, 53, 759). Compound 33 is stirred with DSC (1 mol eq.) in dichloromethane in the presence of TEA overnight. Compound 5 is added into the reaction mixture, after over night stirring and continued stirring to form compound 33a. Standard synthetic organic chemistry purification procedures yields compound 33a.

Step 2, Compound 33b-f: Compound 33 is initially reacted with DSC in the presence of TEA and subsequently with compounds 6, 10, 11, 12 and 13 in the presence of TEA to obtain their respective carbamates 33b-f.

Example 27

Syntheses of Compounds 34a-f

Scheme 4

Step 1, Compound 34a: Compound 34 is obtained as reported in the literature (Valentijn et al., *Tetrahedron*, 1997, 53, 759). Compound 34 is stirred with DSC (1 mol eq.) in dichloromethane in the presence of TEA overnight. Compound 5 is added into the reaction mixture, after over night stirring and continued stirring to form compound 34a. Standard synthetic organic chemistry purification procedures yields compound 34a.

Step 2, Compound 34b-f: Compound 34 is initially reacted with DSC in the presence of TEA and subsequently with compounds 6, 10, 11, 12 and 13 in the presence of TEA to obtain their respective carbamates 34b-f.

Example 28

Syntheses of Compounds 35a-f

Scheme 4

Step 1, Compound 35a: Compound 35 is obtained as reported in the literature (Wijsman et al., *Recueil des Travaux Chimiques des Pays-Bas*, 1996, 115, 397). Compound 35 is stirred with DSC (1 mol eq.) in dichloromethane in the presence of TEA overnight. Compound 5 is added into the reaction mixture, after over night stirring and continued stirring to form compound 35a. Standard synthetic organic chemistry purification procedures yields compound 35a.

Step 2, Compound 35b-f: Compound 35 is initially reacted with DSC in the presence of TEA and subsequently with compounds 6, 10, 11, 12 and 13 in the presence of TEA to obtain their respective carbamates 35b-f.

Example 29

Synthesis of Compound 40

Scheme 5

Step 1, Compound 39: Commercially available dicarboxylic acid 38 (purchased from Aldrich) in DMF is stirred with DCC (2 mol eq.), DMAP (0.1 mol eq.) and N-hydroxysuccinimide (3 mol eq.) to obtain the diester 39.

Step 2, Compound 40: Compound 3 and 10% palladium on carbon (wet, Degussa type, 10% by weight with respect to 3) are suspended in a 9:1 mixture of ethyl acetate-methanol and hydrogenated at 1 atm pressure to obtain compound 36 (step 2a). After complete deprotection, the product is separated from the catalyst by filtration. The free amine 36 (1 mol eq.) thus obtained is stirred with compound 39 (1 mol eq.) in the presence of TEA for 4 h and subsequently 1,6-diaminohexane and excess TEA are added into the stirring solution to obtain compound 40 (step 2b).

Example 30

Synthesis of Compound 41

Scheme 5

Step 1, Compound 39: Compound 38 (purchased from Aldrich) in DMF is stirred with DCC (2 mol eq.), DMAP (0.1 mol eq.) and N-hydroxysuccinimide (3 mol eq.) to obtain the diester 39.

Step 2, Compound 41: Compound 8 and 10% palladium on carbon (wet, Degussa type, 10% by weight with respect to 8) are suspended in a 9:1 mixture of ethyl acetate-methanol and hydrogenated at 1 atm pressure to obtain compound 37 (step 2a). After complete deprotection, the product is separated from the catalyst by filtration. The free amine 37 (1 mol eq.) thus obtained is stirred with compound 39 (1 mol eq.) in the presence of TEA for 4 h and subsequently 1,6-diaminohexane and excess TEA are added into the stirring solution to obtain compound 41 (step 2b).

Example 31

Syntheses of Compounds 42a-b

Scheme 6

Step 1, Compound 42a: Naproxen (14, purchased from Aldrich) is stirred with DCC (1 mol eq.), DMAP (0.1 mol eq.) and N-hydroxysuccinimide (2 mol eq.) in dichloromethane for 30 min and to this compound 40 and TEA are added to obtain compound 42a.

Step 2, Compound 42b is prepared from 14 as described in step 1 by subsequent reaction of the activated carboxylate obtained by the reaction of DCC and N-hydroxysuccinimide in the presence of DMAP with compound 41.

Example 32

Syntheses of Compounds 43a-b

Scheme 6

Step 1, Compound 43a: Compound 15 is stirred with DCC (1 mol eq.), DMAP (0.1 mol eq.) and N-hydroxysuccinimide (2 mol eq.) in dichloromethane for 30 min and to this compound 40 and TEA are added to obtain compound 43a.

Step 2, Compound 43b is prepared from 15 as described in step 1 by subsequent reaction of the activated carboxylate obtained by the reaction of DCC and N-hydroxysuccinimide in the presence of DMAP with compound 41.

Example 33

Syntheses of Compounds 44a-b

Scheme 6

Step 1, Compound 44a: Compound 16 is stirred with DCC (1 mol eq.), DMAP (0.1 mol eq.) and N-hydroxysuccinimide (2 mol eq.) in dichloromethane for 30 min and to this compound 40 and TEA are added to obtain compound 44a.

Step 2, Compound 44b is prepared from 16 as described in step 1 by subsequent reaction of the activated carboxylate obtained by the reaction of DCC and N-hydroxysuccinimide in the presence of DMAP with compound 41.

Example 34

Syntheses of Compounds 45a-b

Scheme 6

Step 1, Compound 45a: Compound 17 is stirred with DCC (1 mol eq.), DMAP (0.1 mol eq.) and N-hydroxysuccinimide (2 mol eq.) in dichloromethane for 30 min and to this compound 40 and TEA are added to obtain compound 45a.

Step 2, Compound 45b is prepared from 17 as described in step 1 by subsequent reaction of the activated carboxylate obtained by the reaction of DCC and N-hydroxysuccinimide in the presence of DMAP with compound 41.

Example 35

Syntheses of Compounds 46a-b

Scheme 6

Step 1, Compound 46a: Compound 18 is stirred with DCC (1 mol eq.), DMAP (0.1 mol eq.) and N-hydroxysuccinimide (2 mol eq.) in dichloromethane for 30 min and to this compound 40 and TEA are added to obtain compound 46a.

Step 2, Compound 46b is prepared from 18 as described in step 1 by subsequent reaction of the activated carboxylate obtained by the reaction of DCC and N-hydroxysuccinimide in the presence of DMAP with compound 41.

Example 36

Syntheses of Compounds 47a-b

Scheme 6

Step 1, Compound 47a: Compound 19 is stirred with DCC (1 mol eq.), DMAP (0.1 mol eq.) and N-hydroxysuccinimide (2 mol eq.) in dichloromethane for 30 min and to this compound 40 and TEA are added to obtain compound 47a.

Step 2, Compound 47b is prepared from 19 as described in step 1 by subsequent reaction of the activated carboxylate obtained by the reaction of DCC and N-hydroxysuccinimide in the presence of DMAP with compound 41.

Example 37

Syntheses of Compounds 48a-b

Scheme 6

Step 1, Compound 48a: Compound 20 is stirred with DCC (1 mol eq.), DMAP (0.1 mol eq.) and N-hydroxysuccinimide (2 mol eq.) in dichloromethane for 30 min and to this compound 40 and TEA are added to obtain compound 48a.

Step 2, Compound 48b is prepared from 20 as described in step 1 by subsequent reaction of the activated carboxylate obtained by the reaction of DCC and N-hydroxysuccinimide in the presence of DMAP with compound 41.

Example 38

Syntheses of Compounds 49a-b

Scheme 6

Step 1, Compound 49a: Compound 21 is stirred with DCC (1 mol eq.), DMAP (0.1 mol eq.) and N-hydroxysuccinimide (2 mol eq.) in dichloromethane for 30 min and to this compound 40 and TEA are added to obtain compound 49a.

Step 2, Compound 49b is prepared from 21 as described in step 1 by subsequent reaction of the activated carboxylate obtained by the reaction of DCC and N-hydroxysuccinimide in the presence of DMAP with compound 41.

Example 39

Syntheses of Compounds 50a-b

Scheme 6

Step 1, Compound 50a: Compound 22 is stirred with DCC (1 mol eq.), DMAP (0.1 mol eq.) and N-hydroxysuccinimide (2 mol eq.) in dichloromethane for 30 min and to this compound 40 and TEA are added to obtain compound 50a.

Step 2, Compound 50b is prepared from 22 as described in step 1 by subsequent reaction of the activated carboxylate obtained by the reaction of DCC and N-hydroxysuccinimide in the presence of DMAP with compound 41.

Example 40

Syntheses of Compounds 51a-b

Scheme 6

Step 1, Compound 51a: Compound 23 is stirred with DCC (1 mol eq.), DMAP (0.1 mol eq.) and N-hydroxysuccinimide (2 mol eq.) in dichloromethane for 30 min and to this compound 40 and TEA are added to obtain compound 51a.

Step 2, Compound 51b is prepared from 23 as described in step 1 by subsequent reaction of the activated carboxylate obtained by the reaction of DCC and N-hydroxysuccinimide in the presence of DMAP with compound 41.

Example 41

Syntheses of Compounds 52a-b

Scheme 6

Step 1, Compound 52a: Compound 24 is stirred with DCC (1 mol eq.), DMAP (0.1 mol eq.) and N-hydroxysuccinimide (2 mol eq.) in dichloromethane for 30 min and to this compound 40 and TEA are added to obtain compound 52a.

Step 2, Compound 52b is prepared from 24 as described in step 1 by subsequent reaction of the activated carboxylate obtained by the reaction of DCC and N-hydroxysuccinimide in the presence of DMAP with compound 41.

Example 42

Syntheses of Compounds 53a-b

Scheme 6

Step 1, Compound 53a: Compound 25 is stirred with DCC (1 mol eq.), DMAP (0.1 mol eq.) and N-hydroxysuccinimide (2 mol eq.) in dichloromethane for 30 min and to this compound 40 and TEA are added to obtain compound 52a.

Step 2, Compound 53b is prepared from 25 as described in step 1 by subsequent reaction of the activated carboxylate obtained by the reaction of DCC and N-hydroxysuccinimide in the presence of DMAP with compound 41.

Example 43

Syntheses of Compounds 54a-b

Scheme 7

Step 1, Compound 54a: Compound 26 is stirred with DSC (1 mol eq.) in dichloromethane in the presence of TEA overnight. Compound 40 is added into the reaction mixture, after over night stirring and continued stirring to form compound 54a. Standard synthetic organic chemistry purification procedures yields compound 54a.

Step 2, Compound 54b: Compound 26 is initially reacted with DSC in the presence of TEA and subsequently with compound 41 in the presence of excess TEA to obtain 54b.

Example 44

Syntheses of Compounds 55a-b

Scheme 7

Step 1, Compound 55a: Compound 27 is stirred with DSC (1 mol eq.) in dichloromethane in the presence of TEA overnight. Compound 40 is added into the reaction mixture, after over night stirring and continued stirring to form compound 55a. Standard synthetic organic chemistry purification procedures yields compound 55a.

Step 2, Compound 55b: Compound 27 is initially reacted with DSC in the presence of TEA and subsequently with compound 41 in the presence of excess TEA to obtain 55b.

Example 45

Syntheses of Compounds 56a-b

Scheme 7

Step 1, Compound 56a: Compound 28 is stirred with DSC (1 mol eq.) in dichloromethane in the presence of TEA overnight. Compound 40 is added into the reaction mixture, after over night stirring and continued stirring to form compound 56a. Standard synthetic organic chemistry purification procedures yields compound 56a.

Example 46

Syntheses of Compounds 57a-b

Scheme 7

Step 1, Compound 57a: Compound 29 is stirred with DSC (1 mol eq.) in dichloromethane in the presence of TEA overnight. Compound 40 is added into the reaction mixture, after over night stirring and continued stirring to form compound 57a. Standard synthetic organic chemistry purification procedures yields compound 57a.

Step 2, Compound 57b: Compound 29 is initially reacted with DSC in the presence of TEA and subsequently with compound 41 in the presence of excess TEA to obtain 57b.

Example 47

Syntheses of Compounds 58a-b

Scheme 7

Step 1, Compound 58a: Compound 30 is stirred with DSC (1 mol eq.) in dichloromethane in the presence of TEA overnight. Compound 40 is added into the reaction mixture, after over night stirring and continued stirring to form compound 58a. Standard synthetic organic chemistry purification procedures yields compound 58a.

Step 2, Compound 58b: Compound 30 is initially reacted with DSC in the presence of TEA and subsequently with compound 41 in the presence of excess TEA to obtain 58b.

Example 48

Syntheses of Compounds 58a-b

Scheme 7

Step 1, Compound 58a: Compound 31 is stirred with DSC (1 mol eq.) in dichloromethane in the presence of TEA overnight. Compound 40 is added into the reaction mixture, after over night stirring and continued stirring to form compound 58a. Standard synthetic organic chemistry purification procedures yields compound 58a.

Step 2, Compound 58b: Compound 31 is initially reacted with DSC in the presence of TEA and subsequently with compound 41 in the presence of excess TEA to obtain 58b.

Example 49

Syntheses of Compounds 60a-b

Scheme 7

Step 1, Compound 60a: Compound 32 is stirred with DSC (1 mol eq.) in dichloromethane in the presence of TEA overnight. Compound 40 is added into the reaction mixture, after over night stirring and continued stirring to form compound 60a. Standard synthetic organic chemistry purification procedures yields compound 60a.

Step 2, Compound 60b: Compound 32 is initially reacted with DSC in the presence of TEA and subsequently with compound 41 in the presence of excess TEA to obtain 60b.

Example 50

Syntheses of Compounds 61a-b

Scheme 7

Step 1, Compound 61a: Compound 33 is stirred with DSC (1 mol eq.) in dichloromethane in the presence of TEA overnight. Compound 40 is added into the reaction mixture, after over night stirring and continued stirring to form compound 61a. Standard synthetic organic chemistry purification procedures yields compound 61a.

Step 2, Compound 61b: Compound 33 is initially reacted with DSC in the presence of TEA and subsequently with compound 41 in the presence of excess TEA to obtain 61b.

Example 51

Syntheses of Compounds 62a-b

Scheme 7

Step 1, Compound 62a: Compound 34 is stirred with DSC (1 mol eq.) in dichloromethane in the presence of TEA overnight. Compound 40 is added into the reaction mixture, after over night stirring and continued stirring to form compound 62a. Standard synthetic organic chemistry purification procedures yields compound 62a.

Step 2, Compound 62b: Compound 34 is initially reacted with DSC in the presence of TEA and subsequently with compound 41 in the presence of excess TEA to obtain 62b.

Example 52

Syntheses of Compounds 63a-b

Scheme 7

Step 1, Compound 63a: Compound 35 is stirred with DSC (1 mol eq.) in dichloromethane in the presence of TEA overnight. Compound 40 is added into the reaction mixture, after over night stirring and continued stirring to form compound 63a. Standard synthetic organic chemistry purification procedures yields compound 63a.

Step 2, Compound 63b: Compound 34 is initially reacted with DSC in the presence of TEA and subsequently with compound 41 in the presence of excess TEA to obtain 63b.

Example 53

Syntheses of Compounds 64-151

Scheme 8

Step 1, Compound 64: Compound 14a is stirred with excess tetrabutylammonium fluoride in THF as reported in the literature to obtain compound 64 (Nakaba et al., *Tetrahedron Lett.*, 1988, 29, 2219, 2223).

Step 2, Compounds 65-151: The desired compounds 65-151 are obtained from their corresponding precursor 15a-25a, 14c-25c, 14e-25e, 26a-35a, 26c-35c, 26e-35e, 42a-

53a and 54a-63a respectively as described in step 1 for the synthesis of compound 64 from 14a.

Example 54

Syntheses of Compounds 152-239

Scheme 8

Step 1, Compound 152: Compound 64 is reacted with 2-cyanoethyl-N,N,N',N'-tetraisopropylphosphine in the presence of tetrazolediisopropylammonium salt in anhydrous acetonitrile or in a mixture of acetonitrile-dichloromethane as reported in the literature to obtain compound 152 (Rajeev et al., *Org. Lett.*, 2003, 5, 3005).

Step 2, Compounds 153-239: The phosphoramidites 153-239 are prepared from their corresponding precursor 65-151 as described above for the preparation compound 152 from 64.

Example 55

Syntheses of Compounds 240-327

Step 1, Compound 240: Treatment of compound 64 with succinic anhydride in the presence of DMAP as reported in the literature (Rajeev et al., *Org. Lett.*, 2003, 5, 3005) yields the corresponding succinate. The succinate thus obtained is treated with 2,2'-dithiobis(5-nitropyridine) (purchased from Aldrich) and triphenylphosphine in the presence of DMAP followed by addition of long chain aminoalkyl CPG (from Millipore) as reported in the literature yields compound 240 (Kumar et al., *Nucleosides Nucleotides,* 1996, 15, 879).

Step 2, Compounds 241-327: The solid supports 241-327 are obtained from their corresponding precursor 65-151 as described above for the preparation of compound 240 from compound 64.

Example 56

Syntheses of Compounds 328-415

Scheme 8

Step 1, Compound 328: Compound 14b is stirred with excess tetrabutylammonium fluoride in THF as reported in the literature to obtain compound 328 (Nakaba et al., *Tetrahedron Lett.,* 1988, 29, 2219, 2223).

Step 2, Compounds 329-415: The desired compounds 329-415 are obtained from their corresponding precursor 15b-25b, 14d-25d, 14f-25f, 26b-35b, 26d-35d, 26f-35f, 42b-53b and 54b-63b respectively as described in step 1 for the synthesis of compound 328 from 14b.

Example 56

Syntheses of Compounds 416-503

Scheme 8

Step 1, Compound 416: Compound 328 is reacted with 2-cyanoethyl-N,N,N',N'-tetraisopropylphosphine in the presence of tetrazolediisopropylammonium salt in anhydrous acetonitrile or in a mixture of acetonitrile-dichloromethane as reported in the literature to obtain compound 416 (Rajeev et al., *Org. Lett.*, 2003, 5, 3005).

Step 2, Compounds 417-503: The phosphoramidites 417-503 are prepared from their corresponding precursor 329-415 as described above for the preparation compound 416 from 328.

Example 57

Syntheses of Compounds 504-691

Step 1, Compound 504: Treatment of compound 328 with succinic anhydride in the presence of DMAP as reported in the literature (Rajeev et al., *Org. Lett.*, 2003, 5, 3005) yields the corresponding succinate. The succinate thus obtained is treated with 2,2'-dithiobis(5-nitropyridine) (purchased from Aldrich) and triphenylphosphine in the presence of DMAP followed by addition of long chain aminoalkyl CPG (from Millipore) as reported in the literature yields compound 504 (Kumar et al., *Nucleosides Nucleotides,* 1996, 15, 879).

Step 2, Compounds 505-691: The solid supports 505-691 are obtained from their corresponding precursor 329-415 as described above for the preparation of compound 504 from compound 328.

Example 58

Synthesis of Compound 695

Scheme 9

Step 1, Compound 694: Compound 2 and 10% palladium on carbon (wet, Degussa type, 10% by weight with respect to 2) are suspended in a 9:1 mixture of ethyl acetate-methanol and hydrogenated at 1 atm pressure to obtain compound 694.

Step 2, Compound 695: Compound 694 is stirred with commercially available 3-(2-pyridyldithio)propionic acid N-hydroyxysuccinimide ester (available from Bachem) in the presence of TEA in dichloromethane to obtain compound 695.

Example 59

Synthesis of Compound 696

Scheme 9

Phosphitylation of compound 695 as described in Example 56 yields the desired phosphoramidite 696.

Example 60

Synthesis of Compound 697

Scheme 9

Compound 697 is obtained from compound 695 and long chain aminoalkyl CPG (from Millipore) as described in Example 57 for the preparation of compound 504 from compound 328.

Example 61

Synthesis of Compound 698

Scheme 9

Compound 695 is stirred with R—SH (any thiol or mercaptan, where R is any organic functional group or moiety) in the presence of TEA to obtain compound 698.

Example 62

Synthesis of Compound 699

Scheme 9

Phosphitylation of compound 698 as described in Example 56 yields the desired phosphoramidite 699.

Example 63

Synthesis of Compound 700

Scheme 9

Compound 700 is obtained from compound 698 and long chain aminoalkyl CPG (from Millipore) as described in Example 57 for the preparation of compound 504 from compound 328.

Example 64

Synthesis of Compound 702

Scheme 10

Compound 701 (7.7 g, 14.5 mmol) was dissolved in anhydrous dichloromethane (40 mL) and cooled to 0° C. To the solution were added triethylamine (3.0 g, 4.2 mL, 30 mmol) and 3-(Pyridin-2-yldisulfanyl)-propionic succiate ester (SPDP) (4.5 g, 14.4 mmol) successively. The reaction temperature was brought to ambient temperature and stirred further for 16 h. The completion of the reaction was ascertained by TLC (10% MeOH/CHCl$_3$, R$_f$=0.6). The reaction mixture was diluted with dichloromethane and washed with saturated NaHCO$_3$, water followed by brine. The organic layer was dried over sodium sulfate, filtered and concentrated under vacuum to afford the crude product. Compound 702 (10.58 g, 78%) was obtained as a white foamy solid after column chromatography over silica gel.

$^1$H NMR (400 MHz, DMSO-d$_6$): δ 8.45 (d, 1H), 7.9 (m, 1H), 7.8 (m, 1H), 7.76 (m, 1H), 7.3 (m, 4H), 7.18 (m, 5H), 6.86 (m, 4H), 4.98 (d, —OH, 1H), 4.38 (m, 1H), 4.1 (m, 1H) (s, 6H), 3.56 (m, 1H), 3.46 (m, 1H), 3.21-3.34 (m, 3H), 3.14 (m, 1H), 3 (m, 2H), 2.48 (m, 2H), 2.2 (m, 2H), 1.8-2.02 (m, 2H), 1.1-1.5 (4H).

$^{13}$C NMR (100 MHz, DMSO-d$_6$): δ 171.32, 169.97, 159.36, 158.31, 158.18, 149.80, 145.27, 138.08, 136.1, 135.9, 129.8, 128.0, 127.7, 121.4, 119.3, 113.3, 85.338, 68.7, 55.3, 34.75, 34.28, 29.1, 26.3, 24.36.

Example 65

Synthesis of Compound 703

Scheme 10

Phosphitylation of compound 702 as described in Example 56 yields the desired phosphoramidite 703.

Example 66

Synthesis of Compound 704

Scheme 10

Compound 704 is obtained from compound 702 and long chain aminoalkyl CPG (from Millipore) as described in Example 57 for the preparation of compound 504 from compound 328.

Example 67

Synthesis of Compound 705

Scheme 10

Compound 702 is stirred with R—SH (any thiol or mercaptan, where R is any organic functional group or moiety) in the presence of TEA to obtain compound 705.

Example 68

Synthesis of Compound 706

Scheme 10

Phosphitylation of compound 705 as described in Example 56 yields the desired phosphoramidite 706.

Example 69

Synthesis of Compound 700

Scheme 9

Compound 707 is obtained from compound 705 and long chain aminoalkyl CPG (from Millipore) as described in Example 57 for the preparation of compound 504 from compound 328.

Example 70

Synthesis of Compound 708

Scheme 11

Compound 702 (7.5 g, 10.28 mmol) was dissolved in anhydrous dichloromethane (75 mL) under argon and cooled to 0° C. To this solution were added diisopropylethyl amine (2.71 g, 3.66 mL, 21 mmol) followed by thiocholesterol (4.145 g, 10.28 mmol). The reaction mixture was brought to ambient temperature and stirred further for 16 h. The completion of the reaction was ascertained by TLC (100% ethyl acetate, R$_f$=0.6). The reaction mixture was concentrated under reduced pressure and the residue was subjected to column chromatography on silica gel. Even though there was good separation in hexane/ethyl acetate system, compound precipitates in that mixture. After eluting with 4 L of ethyl acetate, the column was eluted with 5% MeOH/dichloromethane (2 L) to obtain compound 708 as white foamy solid (8 g, 76%).

$^1$H NMR (400 MHz, DMSO-$d_6$): δ 7.88 (m, 1H), 7.3 (m, 4H), 7.17 (m, 5H), 6.84 (m, 4H), 5.3 (bs, 1H), 4.89 (d, —OH), 4.38 (m, 1H), 4.1 (m, 1H), 3.72 (s, 6H), 3.56 (m, 1H), 3.32 (m, 1H), 3.14 (m, 1H), 3 (m, 3H), 2.84 (m, 2H), 2.64 (m, 1H), 2.42 (m, 2H), 2.2 (m, 3H), 1.8-2.0 (m, 7H), 0.8-1.54 (m, 35H), 0.62 (s, 3H).

$^{13}$C NMR (100 MHz, DMSO-$d_6$): δ 170.8, 158.0, 157.9, 155.6, 145.0, 139.7, 135.8, 135.7, 129.5, 127.7, 127.5, 121.7, 113.1, 113.0, 85.7, 85.1, 72.7, 68.5, 63.3, 60.72, 56.1, 55.5, 55.28, 54.9, 49.4, 41.8, 36.5, 35.2, 31.3, 30.35, 27.7, 27.3, 26.0, 24.1, 23.8, 23.2, 22.6, 22.3, 21.11, 20.5, 19.43, 18.9, 18.5, 14.4, 11.6.

Example 71

Synthesis of Compound 709

Scheme 11

Compound 708 (5.7 g, 5.58 mmol) was coevaporated with anhydrous toluene (50 mL). To the residue N,N-tetraisopropylammonium tetrazolide (0.315 g, 2.79 mmol) was added and the mixture was dried over $P_2O_5$ in a vacuum oven for overnight at 40° C. The reaction mixture was dissolved in dichloromethane (20 mL) and 2-cyanoethyl-N,N,N',N'-tetraisopropylphosphorodiamidite (2.48 g, 2.72 mL, 8.25 mmol) was added. The reaction mixture was stirred at ambient temperature for overnight. The completion of the reaction was ascertained by TLC ($R_f$=0.9 in ethyl acetate). The reaction mixture was diluted with dichloromethane (50 mL) and washed with 5% $NaHCO_3$ (50 mL) and brine (50 mL). The organic layer was dried over anhydrous $Na_2SO_4$ filtered and concentrated under reduced pressure. The residue was purified over silica gel (50:49:1, EtOAc:Hexane:triethylamine) to afford 709 as white foamy solid (6.1 g, 89%).

$^1$H NMR (400 MHz, $C_6D_6$): δ 7.62 (m, 2H), 7.45 (m, 5H), 7.24 (m, 2H), 7.1 (m, 1H), 6.82 (m, 4H), 5.64 (m, 1H), 5.38 (m, 1H), 4.7 (m, 1H), 4.54 (m, 2H), 3.78 (m, 2H), 3.5 (m, 3H), 3.36 (m, 9H), 3.22 (m, 4H), 3.06 (m, 3H), 2.72 (m, 1H), 2.32-2.54 (m, 5H), 1.8-2.2 (m, 10H), 1.08-1.74 (m, 28H), 1.3 (m, 6H), 0.94 (m, 12H), 0.67 (s, 3H).

$^{31}$P NMR (161.82 MHz, $C_6D_6$): δ 146.05, 145.91, 145.66, 145.16

$^{13}$C NMR (100 MHz, $C_6D_6$): δ 171.43, 171.25, 169.87, 159.25, 159.11, 146.08, 141.59, 136.66, 136.6, 130.62, 130.54, 128.63, 127.53, 127.02, 121.53, 117.73, 117.57, 113.66, 113.57, 86.59, 86.54, 64.36, 58.56, 58.37, 58.30, 56.96, 56.51, 56.07, 54.86, 54.77, 50.57, 50.27, 43.48, 43.35, 42.55, 40.13, 39.9, 39.75, 39.56, 38.70, 36.94, 36.64, 36.29, 36.19, 35.90, 34.58, 32.24, 32.08, 29.48, 29.03, 28.98, 28.6, 28.38, 26.54, 24.68, 24.61, 24.54, 23.6, 23.0, 22.74, 21.26, 20.03, 19.9, 19.38, 19.01, 12.06.

Example 72

Synthesis of Compound 710

Scheme 11

Step 1, Synthesis of succinate of compound 708: Compound 708 (2.2 g, 2.15 mmol) was mixed with succinic anhydride (0.323 g, 3.23 mmol) and DMAP (0.026 g, 0.215 mmol) and dried in a vacuum at 40° C. overnight. The mixture was dissolved in anhydrous dichloromethane (10 mL), triethylamine (0.708 g, 0.976 mL, 7 mmol) was added and the solution was stirred at room temperature under argon atmosphere for 16 h. It was then diluted with dichloromethane (50 mL) and washed with ice cold aqueous citric acid (5% wt., 25 mL) and water (2×25 mL). The organic phase was dried over anhydrous sodium sulfate and concentrated to dryness. The crude product was purified by column chromatography to afford the succinate derivative as white foamy solid (2.2 g, 92% yield; $R_f$=0.6 s in 10% MeOH/$CHCl_3$).

$^1$H NMR (400 MHz, DMSO-$d_6$): δ 12.22 (bs, 1H), 7.84 (m, 1H), 7.25 (m, 4H), 7.2 (m, 5H), 6.86 (m, 4H), 5.36 (m, 2H), 4.18 (bs, 1H), 3.72 (s, 6H), 3.4-3.6 (m, 2H), 3.2 (m, 1H), 3.0 (m, 4H), 2.84 (m, 2H), 2.64 (m, 2H), 2.4-2.52 (m, 12H), 2.2 (m, 6H), 1.9 (m, 8H), 0.8-1.52 (m, 28H), 0.65 (s, 3H).

$^{13}$C NMR (100 MHz, DMSO-$d_6$): δ 173.35, 171.94, 170.63, 169.64, 157.99, 144.96, 141.02, 135.72, 129.61, 127.81, 127.55, 113.12, 56.15, 54.99, 52.28, 49.58, 49.06, 41.82, 36.17, 34.97, 33.41, 33.09, 31.32, 27.39, 23.16, 22.68, 22.39, 20.56, 18.95, 18.54, 11.66, 6.02, 5.0

Step 2, Synthesis of compound 710 from the succinate: The succinate (2.1 g, 1.9 mmol) thus obtained was dissolved in dichloroethane (8 mL). To that solution DMAP (0.228 g, 1.9 mmol) was added. 2,2'-Dithio-bis(5-nitropyridine) (0.58 g, 1.9 mmol) in acetonitrile/dichloroethane (3:1, 8 mL) was added successively. To the resulting solution triphenylphosphine (0.49 g, 1.9 mmol) in acetonitrile (4 ml) was added. The reaction mixture turned bright orange in color. The solution was agitated briefly using wrist-action shaker (5 mins). Long chain alkyl amine-CPG (LCAA-CPG) (12 g, 1860 μmoles, 155 μm/g) was added. The suspension was agitated for 4 h. The CPG was filtered through a sintered funnel and washed with acetonitrile, dichloromethane and ether successively. Unreacted amino groups were masked using acetic anhydride/pyridine. The loading capacity of the CPG 710 was measured by taking UV measurement. (57 μM/g).

Example 73

Oligonucleotide Synthesis, Purification and Analysis

Synthesis:

The RNA molecules were synthesized on a 394 ABI machine using the standard 93 step cycle written by the manufacturer with modifications to a few wait steps as described below. The solid support was available in house and the monomers were RNA phosphoramidites with fast protecting groups (5'-O-dimethoxytrityl N6-phenoxyacetyl-2'-O-t-butyldimethylsilyladenosine-3'-O—N,N'-diisopropyl-cyanoethylphosphoramidite, 5'-O-dimethoxytrityl-N4-acetyl-2'-O-t-butyldimethylsilylcytidine-3'-O—N,N'-diisopropyl-2-cyanoethylphosphoramidite, 5'-O-dimethoxytrityl-N2-p-isopropylphenoxyacetyl-2'-O-t-butyldimethylsilylguanosine-3'-O—N,N'-diisopropyl-2-cyanoethylphosphoramidite, and 5'-O-dimethoxytrityl-2'-O-t-butyldimethylsilyluridine-3'-O—N,N'-diisopropyl-2-cyanoethylphosphoramidite from Pierce Nucleic Acids Technologies. All 2'-O-Me amidites were received from Glen Research. All amidites were used at a concentration of 0.15M in acetonitrile ($CH_3CN$) and a coupling time of 12-15 min. The activator was 5-(ethylthio)-1H-tetrazole (0.25M), for the PO-oxidation Iodine/Water/Pyridine was used and for PS-oxidation, 2% Beaucage reagent (Iyer et al., *J. Am. Chem. Soc.*, 1990, 112, 1253) in anhydrous acetonitrile was used. The sulphurization time was about 6 min.

Deprotection-I (Nucleobase Deprotection)

After completion of synthesis the support was transferred to a screw cap vial (VWR Cat #20170-229) or screw caps RNase free microfuge tube. The oligonucleotide was cleaved from the support with simultaneous deprotection of base and phosphate groups with 1.0 mL of a mixture of ethanolic ammonia [ammonia:ethanol (3:1)] for 15 h at 55° C. The vial was cooled briefly on ice and then the ethanolic ammonia mixture was transferred to a new microfuge tube. The CPG was washed with 2×0.1 mL portions of RNase free deionised water. Combined washings, cooled over a dry ice bath for 10 min and subsequently dried in speed vac.

Deprotection-II (Removal of 2' TBDMS Group)

The white residue obtained was resuspended in 400 μl of triethylamine, triethylamine trihydrofluoride (TEA.3HF) and NMP (4:3:7) and heated at 50° C. for overnight to remove the tert-butyldimethylsilyl (TBDMS) groups at the 2' position (Wincott et al., *Nucleic Acids Res.*, 1995, 23, 2677). The reaction was then quenched with 400 μl of isopropoxytrimethylsilane (iPrOMe$_3$Si, purchased from Aldrich) and further incubated on the heating block leaving the caps open for 10 min; (This causes the volatile isopropxytrimethylsilylfluoride adduct to vaporize). The residual quenching reagent was removed by drying in a speed vac. Added 1.5 ml of 3% triethylamine in diethyl ether and pelleted by centrifuging. The supernatant was pipetted out without disturbing the pellet and the pellet was dried in speed vac. The crude RNA was obtained as a white fluffy material in the microfuge tube.

Quantitation of Crude Oligomer or Raw Analysis

Samples were dissolved in RNase free deionized water (1.0 mL) and quantitated as follows: Blanking was first performed with water alone (1 mL) 20 μL of sample and 980 μL of water were mixed well in a microfuge tube, transferred to cuvette and absorbance reading obtained at 260 nm. The crude material is dried down and stored at −20° C.

5. Purification of Oligomers:

PAGE Purification

PAGE purification of oligomers synthesized was performed as reported by Sambrook et al. (Molecular Cloning: a Laboratory Manual, Second Edition, Cold Spring Harbor Laboratory Press, Cold Spring Harbor, N.Y., 1989). The 12% denaturing gel was prepared for purification of unmodified and modified oligoribonucleotides. Took 120 mL Concentrate+105 mL Diluents+25 mL Buffer (National Diagnostics) then added 50 μL TEMED and 1.5 mL 10% APS. Pour the gel and leave it for ½ h to polymerize. Suspended the RNA in 20 μL water and 80 μL formamide. Load the gel tracking dye on left lane followed by the sample slowly on to the gel. Run the gel on 1×TBE buffer at 36 W for 4-6 h. Once run is completed, Transfer the gel on to preparative TLC plates and see under UV light. Cut the bands. Soak and crushed in Water. Leave in shaker for overnight. Remove the eluent, Dry in speed vac.

Desalting of Purified Oligomer

The purified dry oligomer was then desalted using Sephadex G-25 M (Amersham Biosciences). The cartridge was conditioned with 10 mL of RNase free deionised water thrice. Finally the purified oligomer was dissolved in 2.5 mL RNasefree water and passed through the cartridge with very slow drop wise elution. The salt free oligomer was eluted with 3.5 mL of RNase free water directly into a screw cap vial. All oligonucleotides were finally analyzed by LC-MS and capillary gel electrophoresis.

TABLE 4

List of ligand oligonucleotides (sense and antisense strand).

| Sequence ID | Sequence | Cal Mass amu | Found Mass amu | CGE (%) |
|---|---|---|---|---|
| 20 | 5' CUU ACG CUG AGU ACU UCG A dTdT 3' | 6606.00 | 6606.45 | 99.25 |
| 21 | 5' UCG AAG UAC UCA GCG UAA G dT dT 3' | 6696.32 | 6693.0 | 89.0 |
| 22 | 5' CUU ACG CUG AGU ACU UCG A dTdT L$_1$ 3' | 7312.96 | 7311.39 | 88.0 |
| 23 | 5' UCG AAG UAC UCA GCG UAA G dT dT L$_1$ 3' | 7399.00 | 7399.06 | 92.00 |
| 24 | 5' L$_1$ CUU ACG CUG AGU ACU UCG A dT dT 3' | 7311.88 | 7311.6 | 88.0 |
| 25 | 5' L$_1$ UCG AAG UAC UCA GCG UAA G dT dT 3' | 7397.98 | 7396.2 | 95.2 |
| 26 | 5' CUU ACG CUG AGU ACU UCG A dTdT L$_2$ 3' | 7387.39 | 7386.6 | 96.90 |
| 27 | 5' UCG AAG UAC UCA GCG UAA G dT dT L$_2$ 3' | 7473.49 | 7474.0 | 92.00 |
| 28 | 5' L$_2$ CUU ACG CUG AGU ACU UCG A dT dT 3' | 7387.39 | 7787.53 | 90.00 |
| 29 | 5' L$_2$ UCG AAG UAC UCA GCG UAA G dT dT 3' | 7473.49 | 7473.54 | 96.34 |

L$_1$ = Cholesterol 6-aminohexanoic acid with trans-4-hydroxy-L-prolinol linker
L$_2$ = Thiocholesterol with trans-4-hydroxy-L-prolinol linker

Example 74

In Vitro Cell Culture Activities of Aromatic Ligand Conjugated siRNA Duplex

Dual Luciferase Gene Silencing Assays

In vitro activity of siRNAs was determined using a high-throughput 96-well plate format luciferase silencing assay. Assays were performed in one of two possible formats. In the first format, HeLa SS6 cells were first transiently transfected with plasmids encoding firefly (target) and renilla (control) luciferase. DNA transfections were performed using Lipofectamine 2000 (Invitrogen) and the plasmids gWiz-Luc (Aldevron, Fargo, N. Dak.) (200 ng/well) and pRL-CMV (Promega, Madison, Wis.) (200 ng/well). After 2 h, the plasmid transfection medium was removed, and the firefly luciferase targeting siRNAs were added to the cells at various concentrations. In the second format, HeLa Dual-luc cells (stably expressing both firefly and renilla luciferase) were directly transfected with firefly luciferase targeting siRNAs. SiRNA transfections were performed using either TransIT-TKO (Minis, Madison, Wis.) or Lipofectamine 2000 according to manufacturer protocols. After 24 h, cells were analyzed for both firefly and renilla luciferase expression using a plate luminometer (VICTOR$^2$, PerkinElmer, Boston, Mass.) and the Dual-Glo Luciferase Assay kit (Promega). Firefly/renilla luciferase expression ratios were used to determine percent gene silencing relative to mock-treated (no siRNA) controls.

TABLE 5

RNAi silencing by siRNA in stable Hela Dual Luc Cell Line: IC$_{50}$'s (nM) of duplexes tested with transfection agent.

| AS Strand | S Strand | | | | |
|---|---|---|---|---|---|
| | 20 | 22 | 24 | 26 | 28 |
| 21 | 0.09 | 0.1 | 0.04 | 0.04 | 0.05 |
| 23 | 1.00 | 24 | | | |
| 25 | >30.0 | | >30.00 | | |
| 27 | 0.08 | | | 0.20 | 2.0 |
| 29 | 0.04 | | | 2.0 | 0.13 |

TABLE 6

RNAi silencing by siRNA in transiently transfectd Hela Dual Luc Cell Line: IC$_{50}$'s (nM) of duplexes tested without transfection agent.

| AS Strand | S Strand | | | | |
|---|---|---|---|---|---|
| | 20 | 22 | 24 | 26 | 28 |
| 21 | >2000 | 30 | 20 | <30.0 | 20.0 |
| 23 | 260 | >2000 | | | |
| 25 | >1500 | | >1500 | | |
| 27 | <30.0 | | | 80.0 | 200 |
| 29 | 20. | | | 200 | 40.0 |

A number of embodiments of the invention have been described. Nevertheless, it will be understood that various modifications may be made without departing from the spirit and scope of the invention. Accordingly, other embodiments are within the scope of the following claims.

What is claimed is:

1. A bio-cleavable oligonucleotide-ligand conjugate represented by the following formula:

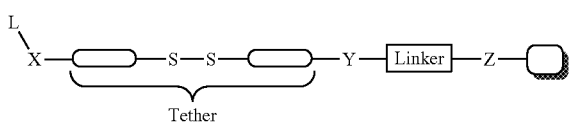

wherein:

NA is a chemically modified or unmodified oligonucleotide;

L is a ligand selected from the group consisting of a multivalent galactose and a multivalent N-acetyl-galactosamine;

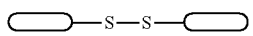

represents a tether comprising one or more linking groups having a cleavable disulfide group (—SS—), wherein each

linking group is either present or absent;

is a cyclic carrier selected from the group consisting of hydroxyproline, piperidine, morpholine, piperazine, and decalin or acyclic carrier moiety containing a serinol backbone or a diethanolamine backbone;

X is a chemical linkage between the ligand L and the tether;

Y is a chemical linkage between the tether and the

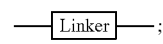

and

Z is a chemical linkage between the

and the oligonucleotide NA.

2. The bio-cleavable oligonucleotide-ligand conjugate of claim 1, wherein the oligonucleotide NA is a double-stranded RNA (dsRNA) agent comprising a sense strand and an antisense strand, and wherein each strand has at least 21 nucleotides in length and the duplex region of the dsRNA agent is about 19 nucleotides in length.

3. The bio-cleavable oligonucleotide-ligand conjugate of claim 1, wherein the oligonucleotide NA is a double-stranded RNA having a duplex region of about 20-21 nucleotides in length and one or two 3' overhangs of about 2 nucleotides in length.

4. The bio-cleavable oligonucleotide-ligand conjugate of claim 1, wherein the oligonucleotide NA is a double-stranded RNA (dsRNA) agent comprising a sense strand and an antisense strand, and wherein the ligand is attached to the sense strand.

5. The bio-cleavable oligonucleotide-ligand conjugate of claim 4, wherein the ligand is attached to position 1, 2, or 3 of the 3' end of the sense strand.

6. The bio-cleavable oligonucleotide-ligand conjugate of claim 1, wherein the oligonucleotide NA is a double-stranded RNA (dsRNA) agent comprising a sense strand and an antisense strand, and wherein the ligand is attached to the antisense strand.

7. The bio-cleavable oligonucleotide-ligand conjugate of claim 6, wherein the ligand is attached to the 3'-end of the antisense strand.

8. The bio-cleavable oligonucleotide-ligand conjugate of claim 1, wherein each of X, Y, and Z is independently selected from the group consisting of —NHC(O)—, —C(O)NH—, —OC(O)NH—, —NHC(O)O—, —O—, —S—, —SS—, —S(O)—, —S(O$_2$)—, —NHC(O)NH—, —NHC(S)NH—, —C(O)O—, —OC(O), —NHC(S)—, —NHC(S)O—, —C(S)NH—, —OC(S)NH—, —NHC(S)O—, —CH$_2$—, —CH$_2$CH=CH—, —C(O)CH=CH—, —NH—CH$_2$CH=CH—, —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(R)—O—, —O—P(S)(R)—O—, —S—P(O)(R)—O—, —S—P(S)(R)—O—, —S—P(O)(R)—S—, and —O—P(S)(R)—S—; wherein R is alkyl, fluoroalkyl, aryl, or aralkyl.

9. The bio-cleavable oligonucleotide-ligand conjugate of claim 1, wherein the tether is selected from the group consisting of —(CH$_2$)$_m$—S—S—(CH$_2$)$_n$—, (CH$_2$)$_{m1}$—(CH=CH)$_{m2}$—(CH$_2$)$_{m3}$—S—S—(CH$_2$)$_{n1}$—(CH=CH)$_{n2}$—(CH$_2$)$_{n3}$, (CH$_2$)$_{m1}$—(C≡C)$_{m2}$—(CH$_2$)$_{m3}$—S—S—(CH$_2$)$_{n1}$—(C≡C)$_{n2}$—(CH$_2$)$_{n3}$, —(CH$_2$CH$_2$O)$_{m1}$—(CH$_2$)$_{m2}$—S—S—(CH$_2$)$_{n1}$—(OCH$_2$CH$_2$)$_{n2}$, —(CH$_2$CH$_2$NH)$_{m1}$—(CH$_2$)$_{m2}$—S—S—(CH$_2$)$_{n1}$—(NHCH$_2$CH$_2$)$_{n2}$, and —(CH$_2$)$_m$—S—S—(CH$_2$)$_n$—X—(CH$_2$)$_p$—S—S—(CH$_2$)$_q$—; wherein each of m, m1, m2, m3, n, n1, n2, n3, p, and q is independently 0-20.

10. A bio-cleavable oligonucleotide-ligand conjugate represented by the following formula:

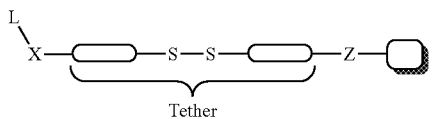

Tether wherein:
NA is a chemically modified or unmodified oligonucleotide;

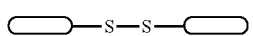

represents a tether comprising one or more linking groups having a cleavable disulfide group (—SS—), wherein each

linking group is either present or absent;

L is a ligand selected from the group consisting of a multivalent galactose and a multivalent N-acetyl-galactosamine;

X is a chemical linkage between the ligand L and the tether;

Z is a chemical linkage between the tether and the oligonucleotide NA;

each of X and Z is independently selected from the group consisting of —NHC(O)—, —C(O)NH—, —OC(O)NH—, —NHC(O)O—, —O—, —S—, —SS—, —S(O)—, —S(O$_2$)—, —NHC(O)NH—, —NHC(S)NH—, —C(O)O—, —OC(O)—, —NHC(S)—, —NHC(S)O—, —C(S)NH—, —OC(S)NH—, —NHC(S)O—, —CH$_2$—, —CH$_2$CH=CH—, —C(O)CH=CH—, —NH—CH$_2$CH=CH—, —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, P(S)(OH)—O—, —O—P(O)(R)—O—, —O—P(S)(R)—O—, —S—P(O)(R)—O—, —S—P(S)(R)—O—, —S—P(O)(R)—R—, and —O—P(S)(R)—S—; wherein R is alkyl, fluoroalkyl, aryl, or aralkyl; and the tether is a cleavable linking group selected from the group consisting of —(CH$_2$)$_m$—S—S—(CH$_2$)$_n$—, (CH$_2$)$_{m1}$—(CH=CH)$_{m2}$—(CH$_2$)$_{m3}$—S—S—(CH$_2$)$_{n1}$—(CH=CH)$_{n2}$—(CH$_2$)$_{n3}$, (CH$_2$)$_{m1}$—(C≡C)$_{m2}$—(CH$_2$)$_{m3}$—S—S—(CH$_2$)$_{n1}$—(C≡C)$_{n2}$—(CH$_2$)$_{n3}$, —(CH$_2$CH$_2$O)$_{m1}$—(CH$_2$)$_{m2}$—S—S—(CH$_2$)$_{n1}$—(OCH$_2$CH$_2$)$_{n2}$, —(CH$_2$CH$_2$NH)$_{m1}$—(CH$_2$)$_{m2}$—S—S—(CH$_2$)$_{n1}$—(NHCH$_2$CH$_2$)$_{n2}$, and —(CH$_2$)$_m$—S—S—(CH$_2$)$_p$—S—S—(CH$_2$)$_q$—; wherein each of m, m1, m2, m3, n, n1, n2, n3, p, and q is independently 0-20.

11. The bio-cleavable oligonucleotide-ligand conjugate of claim 10, wherein the oligonucleotide NA is a double-stranded RNA (dsRNA) agent comprising a sense and antisense strands, wherein each strand has at least 21 nucleotides in length, and the duplex region of the dsRNA agent is about 19 nucleotides in length.

12. The bio-cleavable oligonucleotide-ligand conjugate of claim 10, wherein the oligonucleotide NA is a double-stranded RNA having a duplex region of about 20-21 nucleotides in length and one or two 3' overhangs of about 2 nucleotides in length.

13. The bio-cleavable oligonucleotide-ligand conjugate of claim 10, wherein the oligonucleotide NA is a double-stranded RNA (dsRNA) agent comprising a sense strand and an antisense strand, and wherein the ligand is attached to the sense strand.

14. The bio-cleavable oligonucleotide-ligand conjugate of claim 10, wherein the oligonucleotide NA is a double-stranded RNA (dsRNA) agent comprising a sense strand and an antisense strand, and wherein the ligand is attached to position 1, 2, or 3 of the 3' end of the sense strand.

15. The bio-cleavable oligonucleotide-ligand conjugate of claim 10, wherein the oligonucleotide NA is a double-stranded RNA (dsRNA) agent comprising a sense strand and an antisense strand, and wherein the ligand is attached to the antisense strand.

16. The bio-cleavable oligonucleotide-ligand conjugate of claim 15, wherein the ligand is attached to the 3'-end of the antisense strand.

* * * * *

UNITED STATES PATENT AND TRADEMARK OFFICE
CERTIFICATE OF CORRECTION

PATENT NO. : 9,476,045 B2
APPLICATION NO. : 14/485255
DATED : October 25, 2016
INVENTOR(S) : Muthiah Manoharan and Kallanthottathil G. Rajeev It is certified that error appears in the above-identified patent and that said Letters Patent is hereby corrected as shown below:

In the Claims

In Claim 1, Column 159, between Lines 45 and 50, delete

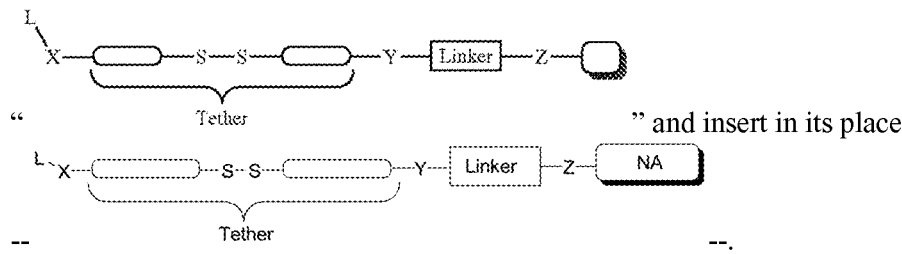

" and insert in its place

-- --.

In Claim 1, Column 159, Line 65, delete " " and insert in its place -- --.

In Claim 10, Column 161, between Lines 51 and 60, delete

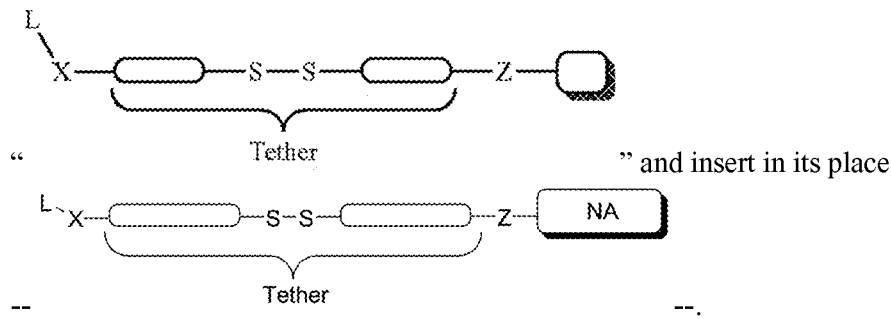

" and insert in its place

-- --.

In Claim 10, Column 162, Line 5, delete " " and insert in its place -- --.

In Claim 10, Column 162, Line 29, delete "P(S)(OH)—O—".

Signed and Sealed this
Ninth Day of January, 2018

Joseph Matal
*Performing the Functions and Duties of the
Under Secretary of Commerce for Intellectual Property and
Director of the United States Patent and Trademark Office*

In Claim 10, Column 162, Lines 41-42, delete "— $(CH_2)_m$-S-S-$(CH_2)_p$-S-S-$(CH_2)_q$—" and insert in its place -- — $(CH_2)_m$-S-S-$(CH_2)_n$-X-$(CH_2)_p$-S-S-$(CH_2)_q$— --.